United States Patent
Tanabe et al.

(10) Patent No.: US 10,173,997 B2
(45) Date of Patent: *__Jan. 8, 2019__

(54) BIPYRIDINE COMPOUND AND USE OF SAME FOR NOXIOUS ARTHROPOD CONTROL

(71) Applicant: Sumitomo Chemical Company, Limited, Tokyo (JP)

(72) Inventors: Takamasa Tanabe, Takarazuka (JP); Yoshihiko Nokura, Takarazuka (JP); Ryota Maehata, Takarazuka (JP); Yuji Nakajima, Takarazuka (JP); Kohei Orimoto, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/547,162

(22) PCT Filed: Jan. 29, 2016

(86) PCT No.: PCT/JP2016/052787
§ 371 (c)(1),
(2) Date: Jul. 28, 2017

(87) PCT Pub. No.: WO2016/121969
PCT Pub. Date: Aug. 4, 2016

(65) Prior Publication Data
US 2018/0009778 A1  Jan. 11, 2018

(30) Foreign Application Priority Data
Jan. 30, 2015 (JP) ................. 2015-016525
Sep. 30, 2015 (JP) ................. 2015-192862

(51) Int. Cl.
| | |
|---|---|
| C07D 401/04 | (2006.01) |
| C07D 401/14 | (2006.01) |
| A61K 31/44 | (2006.01) |
| A01N 25/04 | (2006.01) |
| A01N 43/40 | (2006.01) |
| A01N 43/56 | (2006.01) |
| A01N 43/60 | (2006.01) |
| A01N 43/653 | (2006.01) |
| A01N 43/78 | (2006.01) |
| A01N 43/84 | (2006.01) |
| A01N 47/02 | (2006.01) |
| A01N 51/00 | (2006.01) |
| C07D 213/71 | (2006.01) |
| C07D 213/70 | (2006.01) |
| C07D 417/14 | (2006.01) |

(52) U.S. Cl.
CPC .......... *C07D 401/04* (2013.01); *A01N 25/04* (2013.01); *A01N 43/40* (2013.01); *A01N 43/56* (2013.01); *A01N 43/60* (2013.01); *A01N 43/653* (2013.01); *A01N 43/78* (2013.01); *A01N 43/84* (2013.01); *A01N 47/02* (2013.01); *A01N 51/00* (2013.01); *A61K 31/44* (2013.01); *C07D 213/70* (2013.01); *C07D 213/71* (2013.01); *C07D 401/14* (2013.01); *C07D 417/14* (2013.01)

(58) Field of Classification Search
None
See application file for complete search history.

(56) References Cited

U.S. PATENT DOCUMENTS

2003/0069242 A1  4/2003  Toriyabe et al.

FOREIGN PATENT DOCUMENTS

| | | |
|---|---|---|
| JP | 2000-026421 A | 1/2000 |
| JP | 2000198768 A | 7/2000 |
| JP | 201360420 A | 4/2013 |
| WO | 2006059103 A2 | 6/2006 |
| WO | 2012106495 A1 | 8/2012 |
| WO | 2013027660 A1 | 2/2013 |

OTHER PUBLICATIONS

U.S. Appl. No. 15/547,112, filed Jul. 28, 2017 by Tanabe.
Int'l Search Report dated Apr. 5, 2016 in Int'l Application No. PCT/JP2016/052787.
Int'l Preliminary Report on Patentability dated Aug. 1, 2017 in Int'l Application No. PCT/JP2016/052787.
Extended European Search Report dated Jun. 21, 2018 in EP Application No. 16743572.6.

*Primary Examiner* — Seepak R Rao
*Assistant Examiner* — Laura M Daniel
(74) *Attorney, Agent, or Firm* — Panitch Schwarze Belisario & Nadel LLP

(57) ABSTRACT

Provided is a bipyridine compound that exhibits an excellent controlling effect against noxious arthropods. In particular, provided is a bipyridine compound of formula (I) or an N-oxide thereof in which the variable groups are as defined in the specification. Also provided are compositions containing the biypridine compound or an N-oxide thereof, and methods of using such compounds and compositions to control noxious arthropods.

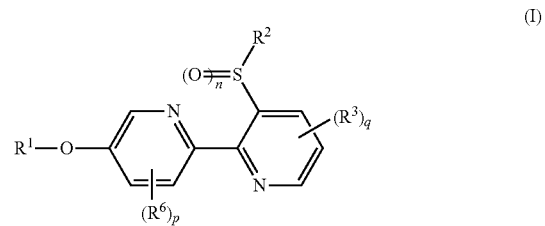

(I)

16 Claims, No Drawings

BIPYRIDINE COMPOUND AND USE OF SAME FOR NOXIOUS ARTHROPOD CONTROL

CROSS-REFERENCE TO RELATED APPLICATION

This application is a Section 371 of International Application No. PCT/JP2016/052787, filed Jan. 29, 2016, which was published in the Japanese language on Aug. 4, 2016 under International Publication No. WO 2016/121969 A1, and the disclosure of which is incorporated herein by reference.

TECHNICAL FIELD

This application claims priority to and the benefit of Japanese Patent Application Nos. 2015-016525 filed Jan. 30, 2015, and 2015-192862 filed Sep. 30, 2015, the entire contents of which are incorporated herein by reference.

The present invention is related to a certain class of bipyridine compound and its use for controlling harmful arthropods.

BACKGROUND ART

To date, some compounds for controlling harmful arthropods have been developed and come into practical use. Also, a certain class of heterocyclic compound has been known (see Patent Documents 1 and 2).

CITATION LIST

Patent Document

Patent Document 1: JP 2000-26421 A
Patent Document 2: WO 2006/059103 pamphlet

SUMMARY OF THE INVENTION

Problems to be Solved by Invention

An object of the present invention is to provide a compound having an excellent efficacy for controlling harmful arthropods.

Means to Solve Problems

[1] A bipyridine compound represented by formula (I) or its N oxide compound:

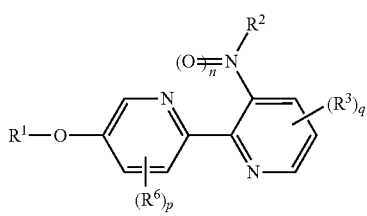

(I)

[wherein
$R^1$ represents a C2-C10 haloalkyl group, a C3-C10 haloalkenyl group, a C3-C10 haloalkynyl group, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G;

$R^2$ represents a C1-C6 alkyl group optionally having one or more halogen atoms, a cyclopropylmethyl group, or a cyclopropyl group;

$R^3$ represents a C1-C6 chain hydrocarbon group optionally having one or more substituents selected from Group B, a phenyl group optionally having one or more substituents selected from Group D, a 5 or 6 membered aromatic heterocyclic group optionally having one or more substituents selected from Group D, a $OR^{12}$, a $NR^{11}R^{12}$, a $NR^{11a}R^{12a}$, a $NR^{24}NR^{11}R^{12}$, a $NR^{11}C(O)R^{13}$, a $NR^{24}NR^{11}C(O)R^{13}$, a $NR^{11}C(O)OR^{14}$, a $NR^{24}NR^{11}C(O)OR^{14}$, a $NR^{11}C(O)NR^{15}R^{16}$, a $NR^{24}NR^{11}C(O)NR^{15}R^{16}$, a $N=CHNR^{15}R^{16}$, a $N=S(O)_xR^{15}R^{16}$, a $S(O)_yR^{15}$, a $C(O)OR^{17}$, a $C(O)NR^{11}R^{12}$, a cyano group, a nitro group, or a halogen atom;

$R^6$ represents a C1-C6 alkyl group optionally having one or more halogen atoms, a $OR^{18}$, a $NR^{18}R^{19}$, a $C(O)OR^{25}$, a $OC(O)R^{20}$, a cyano group, a nitro group, or a halogen atom;

$R^{11}$, $R^{17}$, $R^{18}$, $R^{19}$, $R^{20}$, $R^{24}$ and $R^{25}$ represent independently of each other a hydrogen atom, or a C1-C6 chain hydrocarbon group optionally having one or more halogen atoms;

$R^{12}$ represents a hydrogen atom, a C1-C6 chain hydrocarbon group optionally having one or more halogen atoms, a C1-C6 alkyl group having one substituent selected from Group F, or a $S(O)_2R^{23}$;

$R^{23}$ represents a C1-C6 chain hydrocarbon group optionally having one or more halogen atoms, or a phenyl group optionally having one or more substituents selected from Group D, $R^{11a}$ and $R^{12a}$ combine together with a nitrogen atom to which they are attached to form a 3 to 7 membered nonaromatic heterocyclic group {the 3 to 7 membered nonaromatic heterocyclic group represents aziridine, azetidine, pyrrolidine, imidazoline, imidazolidine, piperidine, tetrahydropyrimidine, hexahydropyrimidine, piperazine, azepane, oxazolidine, isooxazolidine, 1,3-oxazinane, morpholine, 1,4-oxazepane, thiazolidine, isothiazolidine, 1,3-thiazinane, thiomorpholine, or 1,4-thiazepane, which may optionally have one or more substituents selected from Group E};

$R^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, or a 5 or 6 membered aromatic heterocyclic group optionally having one or more substituents selected from Group D;

$R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenylC1-C3 alkyl group {the phenyl group in the group may optionally have one or more substituents selected from Group D};

$R^{15}$ and $R^{16}$ represent independently of each other, a C1-C6 alkyl group optionally having one or more halogen atoms;

n and y represent independently of each other 0, 1 or 2;
x represents 0 or 1;
p and q represent independently of each other 0, 1, 2, or 3, and when p is 2 or 3, a plurality of $R^6$ may be identical or different, and when q is 2 or 3, a plurality of $R^3$ may be identical or different;

Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen atom;

Group D: a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, a $NHR^{21}$, a $NR^{21}R^{22}$, a $C(O)R^{21}$, a $OC(O)R^{21}$, a $C(O)OR^{21}$, a cyano group, a nitro group, and a halogen atom {$R^{21}$ and $R^{22}$ represent independently of each other a C1-C6 alkyl group optionally having one or more halogen atoms};

Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group;

Group F: a group consisting of a C1-C6 alkoxy group optionally having one or more halogen atoms, a $NHR^{21}$, a $NR^{21}R^{22}$, a cyano group, a phenyl group optionally having one or more substituents selected from Group D, a 5 or 6 membered aromatic heterocyclic group optionally having one or more substituents selected from Group D, a C3-C7 cycloalkyl group optionally having one or more halogen atoms, and a 3 to 7 membered nonaromatic heterocyclic group optionally having one or more substituents selected from Group C;

Group C: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom;

Group G: a group consisting of a halogen atom, and a C1-C6 haloalkyl group]
(hereinafter, a bipyridine compound represented by formula (I) or its N oxide compound is referred to as Present compound).

[2] The compound described in [1] wherein q is 0, 1, 2 or 3, $R^3$ represents a C1-C6 chain hydrocarbon group optionally having one or more halogen atoms, a 5 or 6 membered aromatic heterocyclic group optionally having one or more substituents selected from Group D, a $OR^{12}$, a $NR^{11}R^{12}$, a $NR^{24}NR^{11}R^{12}$, or a halogen atom.

[3] The compound described in [1] wherein q is 0, 1, 2 or 3, $R^3$ represents a C1-C6 chain hydrocarbon group optionally having one or more halogen atoms, or a 5 membered aromatic heterocyclic group containing one to four nitrogen atoms (the 5 membered aromatic heterocyclic group may optionally have one or more substituents selected from Group D), a $OR^{12}$, a $NR^{11}R^{12}$, a $NR^{24}NR^{11}R^{12}$, or a halogen atom.

[4] The compound described in [1] wherein q is 0, 1 or 2, $R^3$ represents a C1-C6 alkyl group optionally having one or more halogen atoms, a 1,2,4-triazol-1-yl group optionally having one or more halogen atoms, a $NR^{11}R^{12}$, or a halogen atom, and $R^{11}$ and $R^{12}$ represent independently of each other a hydrogen atom, or a C1-C3 alkyl group optionally having one or more halogen atoms.

[5] The compound described in any one of [1] to [4] wherein p is 0 or 1, and $R^5$ represents a C1-C6 alkyl group optionally having one or more halogen atoms, or a halogen atom.

[6] The compound described in any one of [1] to [5] wherein $R^1$ represents a C2-C10 haloalkyl group, or a (C1-C5 alkoxy)C2-C5 alkyl group having one or more halogen atoms.

[7] The compound described in any one of [1] to [5] wherein $R^1$ represents a C2-C10 fluoroalkyl group, or a (C1-C5 alkoxy)C2-C5 alkyl group having one or more fluorine atoms.

[8] The compound described in any one of [1] to [5] wherein $R^1$ represents a C2-C10 alkyl group having two or more fluorine atoms, or a (C1-C5 alkoxy)C2-C5 alkyl group having two or more fluorine atoms.

[9] The compound described in any one of [1] to [5] wherein $R^1$ represents a C3-C5 alkyl group having four or more fluorine atoms.

[10] The compound described in any one of [1] to [9] wherein $R^2$ represents a C1-C6 alkyl group optionally having one or more halogen atoms.

[11] The compound described in any one [1] to [9] wherein $R^2$ represents an ethyl group.

[12] The compound described in [1] wherein $R^1$ represents a C2-C10 haloalkyl group, or a (C1-C5 alkoxy)C2-C5 alkyl group having one or more halogen atoms;

$R^2$ represents a C1-C6 alkyl group optionally having one or more halogen atoms;

q is 0, 1 or 2, $R^3$ represents a halogen atom, or a C1-C6 alkyl group optionally having one or more halogen atoms, p is 0 or 1, and $R^6$ represents a halogen atom, or a C1-C6 alkyl group optionally having one or more halogen atoms.

[13] The compound described in [1] wherein $R^1$ represents a C3-C5 alkyl group having four or more fluorine atoms, or a 1,1,2-trifluoro-2-(trifluoromethoxy)ethyl group;

$R^2$ represents an ethyl group;

q is 0, 1 or 2, $R^3$ represents a C1-C6 alkyl group optionally having one or more halogen atoms, a 1,2,4-triazol-1-yl group optionally having one or more halogen atoms, a $NR^{11}R^{12}$, or a halogen atom, and $R^{11}$ and $R^{12}$ represent independently of each other a hydrogen atom, or a C1-C3 alkyl group optionally having one or more halogen atoms; and p is 0 or 1, and $R^6$ represents a halogen atom.

[14] The compound described in [1] wherein $R^1$ represents a C3-C5 alkyl group having four or more fluorine atoms;

$R^2$ represents an ethyl group, q is 0 or 1, $R^3$ represents a halogen atom, or a C1-C6 alkyl group optionally having one or more halogen atoms, and p is 0.

[15] A composition for controlling a harmful arthropod comprising the compound described in any one of [1] to [14] and an inert carrier.

[16] A method for controlling a harmful arthropod which comprises applying an effective amount of the compound described in any one of [1] to [14] to a harmful arthropod or a habitat where a harmful arthropod lives.

Effect of Invention

The present compound has an excellent control efficacy against harmful arthropods, and is thus useful as an active ingredient for an agent for controlling harmful arthropods.

MODE FOR CARRYING OUT THE INVENTION

The substituent(s) as described herein is/are explained.

The term of "optionally having one or more halogen atoms" represents that when two or more halogen atoms are present, these halogen atoms may be identical to or different from each other.

The expression of "CX-CY" as used herein represents that the number of carbon atom is from X to Y. For example, the expression of "C1-C6" represents that the number of carbon atom is from 1 to 6.

The term "halogen atom" represents fluorine atom, chlorine atom, bromine atom, or iodine atom.

Example of "N oxide compound" includes a compound represented by formula (Id), a compound represented by formula (Ie), and a compound represented by formula (If).

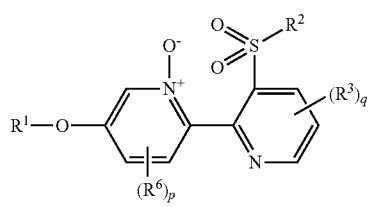

(Id)

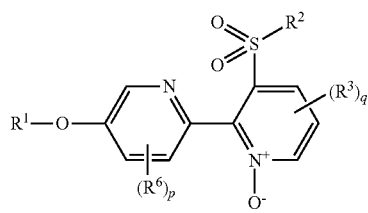

(Ie)

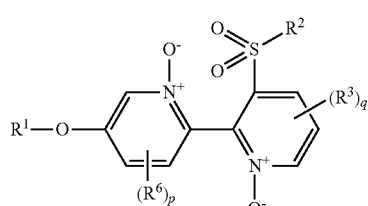

(If)

Example of the term of "$R^{11a}$ and $R^{12a}$ combine together with a nitrogen atom to which they are attached to form a 3 to 7 membered nonaromatic heterocyclic group" {the 3 to 7 membered nonaromatic heterocyclic group represents aziridine, azetidine, pyrrolidine, imidazoline, imidazolidine, piperidine, tetrahydropyrimidine, hexahydropyrimidine, piperazine, azepane, oxazolidine, isooxazolidine, 1,3-oxazinane, morpholine, 1,4-oxazepane, thiazolidine, isothiazolidine, 1,3-thiazinane, thiomorpholine, or 1,4-thiazepane, which may optionally have one or more substituents selected from Group E}" includes the following groups:

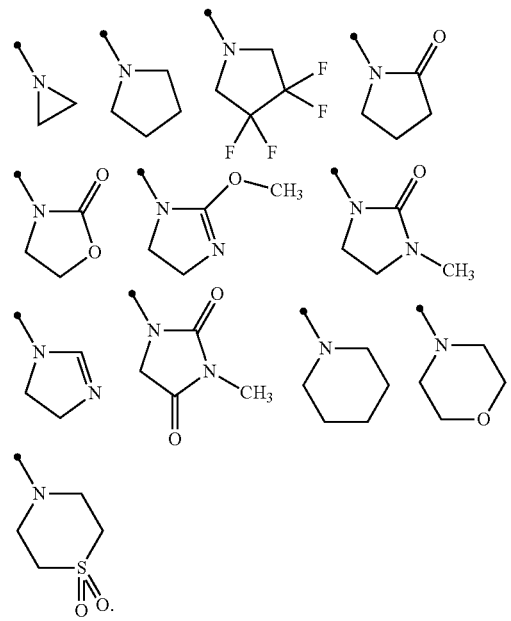

Example of the term of "cycloalkyl group" includes cyclopropyl group, cyclobutyl group, cyclopentyl group, cyclohexyl group, and cycloheptyl group.

Example of the term of "phenylC1-C3 alkyl group {the phenyl group in the group may optionally have one or more substituents selected from Group D}] includes benzyl group, 2-fluorobenzyl group, 4-chlorobenzyl group, 4-(trifluoromethyl)benzyl group, and 2-[4-(trifluoromethyl)phenyl]ethyl group.

The term of "chain hydrocarbon group" represents an alkyl group, an alkenyl group, or an alkynyl group.

Example of the term of "alkyl group" include methyl group, ethyl group, propyl group, isopropyl group, 1,1-dimethylpropyl group, 2,2-dimethylpropyl group, 1,2-dimethylpropyl group, 1-ethylpropyl group, butyl group, sec-butyl group, isobutyl group, tert-butyl group, 1-methylbutyl group, 2-methylbutyl group, 3-methylbutyl group, 1,1-dimethylbutyl group, 2,2-dimethylbutyl group, 3,3-dimethylbutyl group, 1-ethylbutyl group, 2-ethylbutyl group, pentyl group, 1-methylpentyl group, 2-methylpentyl group, 3-methylpentyl group, 4-methylpentyl group, hexyl group, heptyl group, octyl group, nonyl group, and decyl group.

Example of the term of "alkenyl group" include vinyl group, 1-propenyl group, 2-propenyl group, 1-methyl-1-propenyl group, 1-methyl-2-propenyl group, 1,2-dimethyl-1-propenyl group, 1,1-dimethyl-2-propenyl group, 1-ethyl-1-propenyl group, 1-ethyl-2-propenyl group, 3-butenyl group, 4-pentenyl group, and 5-hexenyl group, heptenyl group, octenyl group, nonenyl group, and decenyl group.

Example of the term of "alkynyl group" includes ethynyl group, 1-propynyl group, 2-propynyl group, 1-methyl-2-propynyl group, 1,1-dimethyl-2-propynyl group, 1-ethyl-2-propynyl group, 2-butynyl group, 4-pentynyl group, 5-hexynyl group, heptynyl group, octinyl group, nonynyl group, and decynyl group.

The term of "(C1-C5 alkoxy)C2-C5 alkyl group having one or more halogen atoms" represents a group wherein the (C1-C5 alkoxy) and/or the (C2-C5 alkyl) have/has one or more halogen atoms, and, for example, includes a (C1-C5 haloalkoxy)C2-C5 haloalkyl group such as 2,2-difluoro-3-(2,2,2-trichloroethoxy)propyl group, a (C1-C5 haloalkoxy)C2-C5 alkyl group such as 2-(2,2,2-trichloroethoxy)ethyl group, a (C1-C5 alkoxy)C2-C5 haloalkyl group such as 2,2-difluoro-3-methoxypropyl group, a (C1-C5 fluoroalkoxy)C2-C5 fluoroalkyl group such as 1,1,2-trifluoro-2-(trifluoromethoxy)ethyl group, 2,2-difluoro-3-(2,2,2-trifluoroethoxy)propyl group, a (C1-C5 fluoroalkoxy)C2-C5 alkyl group such as 2-(2,2,2-trifluoroethoxy)ethyl group, and a (C1-C5 alkoxy)C2-C5 fluoroalkyl group such as 2,2-difluoro-3-methoxypropyl group.

The term of "C1-C10 haloalkyl group" represents that a group wherein one or more hydrogen atoms in the C1-C10 alkyl group is/are substituted by a halogen atom, and includes, for example, 2,2,2-trifluoroethyl group, 2,2,2-trichloroethyl group, and 2,2,3,3-tetrafluoropropyl group.

The term of "C1-C10 fluoroalkyl group" represents a group wherein one or more hydrogen atom(s) in the C1-C10 alkyl group is/are substituted by a fluorine atom, and includes, for example, 2,2,2-trifluoroethyl group, and 2,2,3,3-tetrafluoropropyl group.

The term of "C3-C10 haloalkenyl group" represents that a group wherein one or more hydrogen atoms in the C3-C10 alkenyl group is/are substituted by a halogen atom, and includes, for example, 3,3,3-trifluoro-1-propeny group, 3,3,3-trichloro-1-propeny group, and 2,2,3,3-tetrafluoro-1-propeny group.

The term of "C3-C10 haloalkynyl group" represents that a group wherein one or more hydrogen atoms in the C3-C10 alkynyl group is/are substituted by a halogen atom, and includes, for example, 3,3,3-trifluoro-1-propynyl group, and 3,3,3-trichloro-1-propynyl group.

The term of "(C1-C5 fluoroalkoxy)C2-C5 fluoroalkyl group" represents a group wherein one hydrogen atom in the C2-C5 fluoroalkyl group is substituted by a C1-C5 fluoroalkoxy group, and includes, for example, 1,1,2-trifluoro-2-(trifluoromethoxy)ethyl group.

The term of "C1-C5 fluoroalkoxy group" represents a group wherein one or more hydrogen atoms in C1-C5 alkoxy group is/are substituted by a fluorine atom, and includes, for example, trifluoromethoxy group, difluoromethoxy group, and 2,2,2-trifluoroethoxy.

The term of "(C1-C5 haloalkoxy)C2-C5 haloalkyl group" represents a group wherein one hydrogen atom in the C2-C5 haloalkyl group is substituted by a C1-C5 haloalkoxy group, and includes, for example, 1,1,2-trifluoro-2-(trifluoromethoxy)ethyl group.

The term of "C1-C6 haloalkoxy group" represents a group wherein one or more hydrogen atoms in the C1-C6 alkoxy group is/are substituted by halogen atoms, and includes, for example, trifluoromethoxy group, difluoromethoxy group, 2,2,2-trichloroethoxy group, and 2,2,2-trifluoroethoxy.

The term of "C3-C6 haloalkenyloxy group" represents a group wherein one or more hydrogen atoms in the C3-C6 alkenyloxy group is/are substituted by halogen atoms, and includes, for example, 3,3,3-trifluoro-1-propenyloxy group, 3,3,3-trichloro-1-propenyloxy group, and 2,3,3,3-tetrafluoro-1-propenyloxy group.

The term of "C3-C6 haloalkynyloxy group" represents a group wherein one or more hydrogen atoms in the C3-C6 alkynyloxy group is/are substituted by halogen atoms, and includes, for example, 3,3,3-trifluoro-1-propynyloxy group, and 3,3,3-trichloro-1-propynyloxy group.

The terms of "alkylsulfanyl", "alkylsulfinyl", and "alkylsulfonyl" represent an alkyl group containing a S(O)z moiety, respectively.

For example, example of the "alkylsulfanyl" when z is 0 includes methylsulfanyl group, ethylsulfanyl group, propylsulfanyl group, and isopropylsulfanyl group.

For example, example of the "alkylsulfinyl" when z is 1 includes methylsulfinyl group, ethylsulfinyl group, propylsulfinyl group, and isopropylsulfinyl group.

For example, example of the "alkylsulfonyl" when z is 2 includes methylsulfonyl group, ethylsulfonyl group, propylsulfonyl group, and isopropylsulfonyl group.

The term of "(C1-C5 alkylsulfanyl)C2-C5 alkyl group having one or more halogen atoms" represents a group wherein the (C1-C5 alkylsulfanyl) and/or the (C2-C5 alkyl) have/has one or more halogen atoms, and includes, for example, 2,2-difluoro-2-(trifluoromethylthio))ethyl group.

The term of "(C1-C5 alkylsulfinyl)C2-C5 alkyl group having one or more halogen atoms" represents a group wherein the (C1-C5 alkylsulfinyl) and/or the (C2-C5 alkyl) have/has one or more halogen atoms, and includes, for example, 2,2-difluoro-2-(trifluoromethansulfinyl)ethyl group.

The term of "(C1-C5 alkylsulfonyl) C2-C5 alkyl group optionally having one or more halogen atoms" represents a group wherein the (C1-C5 alkylsulfonyl) and/or the (C2-C5 alkyl) group have/has one or more halogen atoms, and includes, for example, 2,2-difluoro-2-(trifluoromethansulfonyl)ethyl group.

The term of "(C3-C6 cycloalkyl)C1-C3 alkyl group having one or more halogen atoms" represents a group wherein the (C3-C6 cycloalkyl) and/or the (C1-C3 alkyl) has/have one or more substituents selected from Group G, and includes, for example, (2,2-difluorocyclopropyl)methyl group, [1-(trifluoromethyl)cyclopropyl]methyl group, [2-(trifluoromethyl)cyclopropyl]methyl group, 2-cyclopropyl-1,1,2,2-tetrafluoroethyl group, and 2-cyclopropyl-3,3,3-trifluoropropyl group.

The term of "(C3-C7 cycloalkyl)C1-C3 alkyl group having one or more substituents selected from Group G" represents a group wherein the (C3-C7 cycloalkyl) and/or the (C1-C3 alkyl) has/have one or more substituents selected from Group G, and includes, for example, (2,2-difluorocyclopropyl)methyl group, [1-(trifluoromethyl)cyclopropyl]methyl group, [2-(trifluoromethyl)cyclopropyl]methyl group, 2-cyclopropyl-1,1,2,2-tetrafluoroethyl group, and 2-cyclopropyl-3,3,3-trifluoropropyl group.

The term of "C3-C7 cycloalkyl group having one or more halogen atoms" includes, for example, 2,2-difluorocyclopropyl group.

The term of "C3-C7 cycloalkyl group having one or more substituents selected from Group G" includes, for example, 2,2-difluorocyclopropyl group, 1-(2,2,2-trifluoroethyl)cyclopropyl group, and 4-(trifluoromethyl)cyclohexyl group.

The term of "5 or 6 membered aromatic heterocyclic group" represents pyrrolyl group, furyl group, thienyl group, pyrazolyl group, imidazolyl group, triazolyl group, tetrazolyl group, oxazolyl group, isoxazolyl group, thiazolyl group, oxadiazolyl group, thiadiazolyl group, pyridyl group, pyridazinyl group, pyrimidinyl group or pyrazinyl group.

The term of "5 membered aromatic heterocyclic group containing one to four nitrogen atoms" represents pyrrolyl group, pyrazolyl group, imidazolyl group, 1,2,4-triazolyl group, 1,2,3-triazolyl group, and tetrazolyl group.

Examples of the present compound include the following compounds.

a compound of the present invention wherein $R^2$ represents a C1-C3 alkyl group optionally having one or more halogen atoms;

a compound of the present invention wherein $R^2$ represents a C2-C6 alkyl group having optionally one or more halogen atoms;

a compound of the present invention wherein R represents a C2-C3 alkyl group optionally having one or more halogen atoms;

a compound of the present invention wherein $R^2$ represents a C1-C6 alkyl group;

a compound of the present invention wherein $R^2$ represents a C1-C3 alkyl group;

a compound of the present invention wherein $R^2$ represents a C2-C6 alkyl group;

a compound of the present invention wherein $R^2$ represents a C2-C3 alkyl group;

a compound of the present invention wherein $R^2$ represents a methyl group, an ethyl group, a propyl group, an isopropyl group, a trifluoromethyl group, or a 2,2,2-trifluoroethyl group;

a compound of the present invention wherein $R^2$ represents a methyl group, an ethyl group, or a 2,2,2-trifluoroethyl group;

a compound of the present invention wherein $R^2$ represents a methyl group or an ethyl group;

a compound of the present invention wherein R represents an ethyl group;

a compound of the present invention wherein n is 0, 1, or 2;

a compound of the present invention wherein n is 0;

a compound of the present invention wherein n is 1;

a compound of the present invention wherein n is 2;

a compound of the present invention wherein p is 0, 1, or 2, $R^6$ represents a C1-C6 alkyl group optionally having one or more halogen atoms, a $OR^{18}$, a $OC(O)R^{20}$, a cyano group, or a halogen atom;

a compound of the present invention wherein p is 0, 1, or 2, $R^6$ represents a $OR^{18}$, a $OC(O)R^{20}$, a cyano group, or a halogen atom;

a compound of the present invention wherein p is 0, 1, or 2, and $R^6$ represents a halogen atom;

a compound of the present invention wherein p is 0 or 1, and $R^6$ represents a C1-C6 alkyl group optionally having one or more halogen atoms, a $OR^{18}$, a $OC(O)R^{20}$, a cyano group, or a halogen atom;

a compound of the present invention wherein p is 0 or 1, and $R^6$ represents a $OR^{18}$, a $OC(O)R^{20}$, a cyano group, or a halogen atom;

a compound of the present invention wherein p is 0 or 1, and $R^6$ represents a halogen atom;

a compound of the present invention wherein p is 0 or 1, and $R^6$ represents a C1-C6 alkyl group optionally having one or more halogen atoms, or a halogen atom;

a compound of the present invention wherein p is 0;

a compound of the present invention wherein q is 0, 1, 2 or 3, and $R^3$ represents a C1-C6 chain hydrocarbon group optionally having one or more substituents selected from Group B, a phenyl group optionally having one or more substituents selected from Group D, a 5 or 6 membered aromatic heterocyclic group optionally having one or more substituents selected from Group D, a $OR^{12}$, a $NR^{11}R^{12}$, a $NR^{11a}R^{12a}$, a $NR^{24}NR^{11}R^{12}$, or a halogen atom;

a compound of the present invention wherein q is 0, 1 or 2, and $R^3$ represents a C1-C6 chain hydrocarbon group optionally having one or more substituents selected from Group B, a phenyl group optionally having one or more substituents selected from Group D, a 5 or 6 membered aromatic heterocyclic group optionally having one or more substituents selected from Group D, a $OR^{12}$, a $NR^{11}R^{12}$, a $NR^{11a}R^{12a}$, a $NR^{24}NR^{11}R^{12}$, or a halogen atom;

a compound of the present invention wherein q is 0, 1 or 2, and $R^3$ represents a C1-C6 chain hydrocarbon group optionally having one or more substituents selected from Group B, a 5 membered aromatic heterocyclic group selected from Group Q (the 5 membered aromatic heterocyclic group may optionally have one or more substituents selected from Group D), a $OR^{12}$, a $NR^{11}R^{12}$, a $NR^{11a}R^{12a}$, a $NR^{24}NR^{11}R^{12}$, or a halogen atom, Group Q:

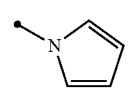
Q-1

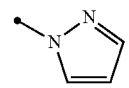
Q-2

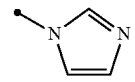
Q-3

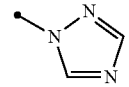
Q-4

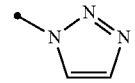
Q-5

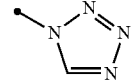
Q-6

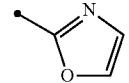
Q-7

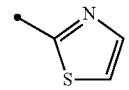
Q-8

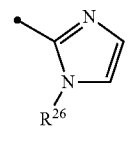
Q-9

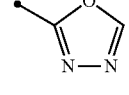
Q-10

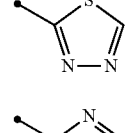
Q-11

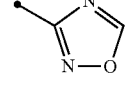
Q-12

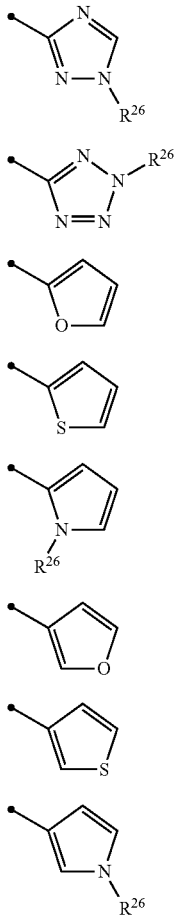

{wherein $R^{26}$ represents a C1-C6 alkyl group optionally having one or more halogen atoms};

a compound of the present invention wherein q is 0, 1 or 2, and $R^3$ represents a 5 membered aromatic heterocyclic group selected from Group Q (the 5 membered aromatic heterocyclic group may optionally have one or more substituents selected from Group D), a $OR^{12}$, a $NR^{11}R^{12}$, a $NR^{11a}R^{12a}$, a $NR^{24}NR^{11}R^{12}$, or a halogen atom;

a compound of the present invention wherein q is 0, 1, 2, or 3, and $R^3$ represents a C1-C6 chain hydrocarbon group optionally having one or more halogen atoms, a 5 or 6 membered aromatic heterocyclic group optionally having one or more substituents selected from Group D, a $OR^{12}$, a $NR^{11}R^{12}$, a $NR^{24}NR^{11}R^{12}$, or a halogen atom;

a compound of the present invention wherein q is 0, 1 or 2, and $R^3$ represents a C1-C6 chain hydrocarbon group optionally having one or more halogen atoms, a 5 membered aromatic heterocyclic group containing one to four nitrogen atoms (the 5 membered aromatic heterocyclic group may optionally have one or more substituents selected from Group D), a $OR^{12}$, a $NR^{11}R^{12}$, a $NR^{24}NR^{11}R^{12}$, or a halogen atom;

a compound of the present invention wherein q is 0, 1 or 2, $R^3$ represents a C1-C6 alkyl group optionally having one or more halogen atoms, a C2-C6 alkenyl group optionally having one or more halogen atoms, a 1,2,4-triazol-1-yl group optionally having one or more halogen atoms, a $NR^{11}R^{12}$, or a halogen atom, and $R^{11}$ and $R^{12}$ represent independently of each other a hydrogen atom, or a C1-C3 alkyl group optionally having one or more halogen atoms;

a compound of the present invention wherein q is 0, 1 or 2, and $R^3$ represents a 5 membered aromatic heterocyclic group containing one to four nitrogen atoms (the 5 membered aromatic heterocyclic group may optionally have one or more substituents selected from Group D), a $OR^{12}$, a $NR^{11}R^{12}$, a $NR^{24}NR^{11}R^{12}$, or a halogen atom;

a compound of the present invention wherein q is 0, 1 or 2, $R^3$ represents a 1,2,4-triazol-1-yl group optionally having one or more halogen atoms, a $NR^{11}R^{12}$, or a halogen atom, and $R^{11}$ and $R^{12}$ represent independently of each other a hydrogen atom, or a C1-C3 alkyl group optionally having one or more halogen atoms;

a compound of the present invention wherein q is 0, 1 or 2, and $R^3$ represents a C1-C6 alkyl group optionally having one or more halogen atoms, a C2-C6 alkenyl group optionally having one or more halogen atoms, or a halogen atom;

a compound of the present invention wherein q is 0 or 1, and $R^3$ represents a C1-C6 alkyl group having one or more halogen atoms;

a compound of the present invention wherein q is 0 or 1, and $R^3$ represents a 5 membered aromatic heterocyclic group optionally having one or more substituents selected from Group D, or a $NR^{11}R^{12}$;

a compound of the present invention wherein q is 0 or 1, and $R^3$ represents a 5 membered aromatic heterocyclic group selected from Group Q (the 5 membered aromatic heterocyclic group may optionally have one or more substituents selected from Group D), or a $NR^{11}R^{12}$;

a compound of the present invention wherein q is 0 or 1, and $R^3$ represents a 5 membered aromatic heterocyclic group containing one to four nitrogen atoms (the 5 membered aromatic heterocyclic group may optionally have one or more substituents selected from Group D), or a $NR^{11}R^{12}$;

a compound of the present invention wherein q is 0 or 1, and $R^3$ represents a triazole group optionally having one or more halogen atoms, or a $NR^{11}R^{12}$;

a compound of the present invention wherein q is 0 or 1, and $R^3$ represents a C1-C6 alkyl group optionally having one or more halogen atoms, a 5 membered aromatic heterocyclic group selected from Group Q (the 5 membered aromatic heterocyclic group may optionally have one or more substituents selected from Group D), or a $NR^{11}R^{12}$;

a compound of the present invention wherein q is 0 or 1, and $R^3$ represents a C1-C6 alkyl group optionally having one or more halogen atoms, a 5 membered aromatic heterocyclic group containing one to four nitrogen atoms (the 5 membered aromatic heterocyclic group may optionally have one or more substituents selected from Group D), or a $NR^{11}R^{12}$;

a compound of the present invention wherein q is 0 or 1, and $R^3$ represents a C1-C6 alkyl group optionally having one or more halogen atoms, a triazole group optionally having one or more halogen atoms, or a $NR^{11}R^{12}$;

a compound of the present invention wherein q is 0;

a compound of the present invention wherein q is 0, 1 or 2, and $R^3$ represents a $OR^{12}$, a $NR^{11}R^{12}$, a $NR^{11a}R^{12a}$, a $NR^{24}NR^{11}R^{12}$, a $NR^{11}C(O)R^{13}$, a $NR^{24}NR^{11}C(O)R^{13}$, a $NR^{11}C(O)OR^{14}$, a $NR^{24}NR^{11}C(O)OR^{14}$, a $NR^{11}C(O)NR^{15}R^{16}$, a $NR^{24}NR^{11}C(O)NR^{15}R^{16}$, a $N=CHNR^{15}R^{16}$, a $N=S(O)_xR^{15}R^{16}$, a $S(O)_yR^{15}$, a $C(O)OR^{17}$, or a $C(O)NR^{11}R^{12}$;

a compound of the present invention wherein q is 0, 1 or 2, and $R^3$ represents a $OR^{12}$, a $NR^{11}R^{12}$, a $NR^{11a}R^{12a}$, a $NR^{24}NR^{11}R^{12}$, a $NR^{11}C(O)R^{13}$, a $NR^{24}NR^{11}C(O)R^{13}$, a $NR^{11}C(O)OR^{14}$, a $NR^{24}NR^{11}C(O)OR^{14}$, a $NR^{11}C(O)NR^{15}R^{16}$, or a $NR^{24}NR^{11}C(O)NR^{15}R^{16}$;

a compound of the present invention wherein q is 0 or 1, and $R^3$ represents a $OR^1$, a $NR^{11}R^{12}$, a $NR^{11a}R^{12a}$, or a $NR^{24}NR^{11}R^{12}$;

a compound of the present invention wherein q is 0 or 1, and $R^3$ represents a $OR^{12}$, a $NR^{11}R^{12}$, or a $NR^{24}NR^{11}R^{12}$;

a compound of the present invention wherein q is 0 or 1, and $R^3$ represents a $NR^{11}R^{12}$, or a $NR^{24}NR^{11}R^{12}$;

a compound of the present invention wherein q is 0, 1 or 2, and $R^3$ represents a C1-C6 chain hydrocarbon group optionally having one or more halogen atoms, a $OR^{12}$, a $NR^{11}R^{12}$, a $NR^{11a}R^{12a}$, a $NR^{24}NR^{11}R^{12}$, a $NR^{11}C(O)R^{13}$, a $NR^{24}NR^{11}C(O)R^{13}$, a $NR^{11}C(O)OR^{14}$, a $NR^{24}NR^{11}C(O)OR^{14}$, a $NR^{11}C(O)NR^{15}R^{16}$, or a $NR^{24}NR^{11}C(O)NR^{15}R^{16}$;

a compound of the present invention wherein q is 0 or 1, and $R^3$ represents a C1-C6 chain hydrocarbon group optionally having one or more halogen atoms, a $OR^{12}$, a $NR^{11}R^{12}$, a $NR^{11a}R^{12a}$, or a $NR^{24}NR^{11}R^{12}$;

a compound of the present invention wherein q is 0 or 1, and $R^3$ represents a C1-C6 alkyl group optionally having one or more halogen atoms, a C2-C6 alkenyl group optionally having one or more halogen atoms, a $OR^{12}$, a $NR^{11}R^{12}$, or a $NR^{24}NR^{11}R^{12}$;

a compound of the present invention wherein q is 0 or 1, and $R^3$ represents a C1-C6 alkyl group optionally having one or more halogen atoms, a $NR^{11}R^{12}$, or a $NR^{24}NR^{11}R^{12}$;

a compound of the present invention wherein $R^1$ represents a C2-C10 haloalkyl group, a C3-C10 haloalkenyl group, a C3-C10 haloalkynyl group, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G;

a compound of the present invention wherein $R^1$ represents a C2-C10 haloalkyl group, a C3-C10 haloalkenyl group, a C3-C10 haloalkynyl group, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, or a (C1-C5 alkylsulfonyl)C2-C5 alkyl group having one or more halogen atoms;

a compound of the present invention wherein $R^1$ represents a C2-C10 haloalkyl group, a C3-C10 haloalkenyl group, or a C3-C10 haloalkynyl group;

a compound of the present invention wherein $R^1$ represents a C2-C10 alkyl group having two or more fluorine atoms, a C3-C10 alkenyl group having two or more fluorine atoms, or a C3-C10 alkynyl group having two or more fluorine atoms;

a compound of the present invention wherein $R^1$ represents a C2-C10 alkyl group having three or more fluorine atoms, a C3-C10 alkenyl group having three or more fluorine atoms, or a C3-C10 alkynyl group having three or more fluorine atoms;

a compound of the present invention wherein $R^1$ represents a C2-C10 alkyl group having four or more fluorine atoms, or a C3-C10 alkenyl group having four or more fluorine atoms;

a compound of the present invention wherein $R^1$ represents a C2-C10 alkyl group having one or more halogen atoms, a C3-C10 alkenyl group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, or a (C1-C5 alkylsulfonyl)C2-C5 alkyl group having one or more halogen atoms;

a compound of the present invention wherein $R^1$ represents a C2-C10 fluoroalkyl group, or a (C1-C5 fluoroalkoxy)C2-C5 fluoroalkyl group;

a compound of the present invention wherein $R^1$ represents a C2-C10 alkyl group having two or more fluorine atoms, or a (C1-C5 fluoroalkoxy)C2-C5 fluoroalkyl group;

a compound of the present invention wherein $R^1$ represents a C2-C6 alkyl group having two or more fluorine atoms, or a (C1-C3 fluoroalkoxy)C2-C4 fluoroalkyl group; a compound of the present invention wherein $R^1$ represents a C2-C6 fluoroalkyl group having three or more fluorine atoms, or a (C1-C3 fluoroalkoxy)C2-C4 fluoroalkyl group;

a compound of the present invention wherein $R^1$ represents a C3-C5 alkyl group having four or more fluorine atoms, or a (C1-C3 perfluoroalkoxy)C2-C4 fluoroalkyl group; a compound of the present invention wherein $R^1$ represents a C2-C10 haloalkyl group;

a compound of the present invention wherein $R^1$ represents a C2-C10 fluoroalkyl group;

a compound of the present invention wherein $R^1$ represents a C2-C10 alkyl group having two or more halogen atoms;

a compound of the present invention wherein $R^1$ represents a C2-C10 alkyl group having two or more fluorine atoms;

a compound of the present invention wherein $R^1$ represents a C2-C6 alkyl group having three or more fluorine atoms;

a compound of the present invention wherein $R^1$ represents a C3-C5 alkyl group having four or more fluorine atoms;

a compound of the present invention wherein $R^1$ represents a (C1-C5 alkoxy)C2-C5 alkyl group having one or more halogen atoms;

a compound of the present invention wherein $R^1$ represents a (C1-C5 alkoxy)C2-C5 alkyl group having two or more halogen atoms;

a compound of the present invention wherein $R^1$ represents a (C1-C5 alkoxy)C2-C5 alkyl group having one or more fluorine atoms;

a compound of the present invention wherein $R^1$ represents a (C1-C5 alkoxy)C2-C5 alkyl group having two or more fluorine atoms;

a compound of the present invention wherein $R^1$ represents a C2-C10 haloalkyl group, a (C1-C5 haloalkoxy)C2-C5 alkyl group, a (C1-C5 alkoxy)C2-C5 haloalkyl group, or a (C1-C5 haloalkoxy)C2-C5 haloalkyl group;

a compound of the present invention wherein $R^1$ represents a C2-C10 fluoroalkyl group, a (C1-C5 fluoroalkoxy)C2-C5 alkyl group, a (C1-C5 alkoxy)C2-C5 fluoroalkyl group, or a (C1-C5 fluoroalkoxy)C2-C5 fluoroalkyl group;

a compound of the present invention wherein $R^1$ represents a C2-C10 alkyl group having two or more fluorine atoms, a (C1-C5 fluoroalkoxy)C2-C5 alkyl group, a (C1-C5 alkoxy)C2-C5 fluoroalkyl group, or a (C1-C5 fluoroalkoxy)C2-C5 fluoroalkyl group;

a compound of the present invention wherein $R^1$ represents a C2-C6 alkyl group having three or more fluorine atoms, a (C1-C5 fluoroalkoxy)C2-C5 alkyl group, a (C1-C5 alkoxy)C2-C5 fluoroalkyl group, or a (C1-C5 fluoroalkoxy)C2-C5 fluoroalkyl group;

a compound of the present invention wherein $R^1$ represents a C3-C5 alkyl group having four or more fluorine atoms, a (C1-C5 fluoroalkoxy)C2-C5 alkyl group, a (C1-C5 alkoxy)C2-C5 fluoroalkyl group, or a (C1-C5 fluoroalkoxy)C2-C5 fluoroalkyl group;

a compound of the present invention wherein $R^1$ represents a C2-C10 alkyl group having two or more fluorine atoms, a (C1-C5 alkoxy)C2-C5 fluoroalkyl group, or a (C1-C5 fluoroalkoxy)C2-C5 fluoroalkyl group;

a compound of the present invention wherein $R^1$ represents a C2-C6 alkyl group having three or more fluorine atoms, a (C1-C5 alkoxy)C2-C5 fluoroalkyl group, or a (C1-C5 fluoroalkoxy)C2-C5 fluoroalkyl group; a compound of the present invention wherein $R^1$ represents a C3-C5 alkyl group having four or more fluorine atoms, a (C1-C5 alkoxy)C2-C5 fluoroalkyl group, or a (C1-C5 fluoroalkoxy)C2-C5 fluoroalkyl group;

a compound of the present invention wherein $R^1$ represents a (C1-C5 haloalkoxy)C2-C5 alkyl group;

a compound of the present invention wherein $R^1$ represents a (C1-C5 alkoxy)C2-C5 haloalkyl group;

a compound of the present invention wherein $R^1$ represents a (C1-C5 haloalkoxy)C2-C5 haloalkyl group;

a compound of the present invention wherein $R^1$ represents a (C1-C5 fluoroalkoxy)C2-C5 alkyl group;

a compound of the present invention wherein $R^1$ represents a (C1-C5 alkoxy)C2-C5 fluoroalkyl group;

a compound of the present invention wherein $R^1$ represents a (C1-C5 fluoroalkoxy)C2-C5 fluoroalkyl group;

a compound of the present invention wherein $R^1$ represents a 2,2,2-trifluoroethyl group, a 2,2,3,3-tetrafluoropropyl group, a 2,2,3,3,3-pentafluoropropyl group, a 1,1,2,3,3,3-hexafluoropropyl group, a 1,1,2-trifluoro-2-(trifluoromethoxy)ethyl group, or a 2,2,3,4,4,4-hexafluorobutyl group;

a compound of the present invention wherein q is 0, 1, or 2, and p is 0, 1, or 2;

a compound of the present invention wherein
$R^1$ represents a C2-C10 haloalkyl group, or a (C1-C5 alkoxy)C2-C5 alkyl group having one or more halogen atoms,
q is 0, 1 or 2, and p is 0, 1, or 2;

a compound of the present invention wherein
$R^1$ represents a C2-C10 haloalkyl group, or a (C1-C5 alkoxy)C2-C5 alkyl group having one or more halogen atoms,
$R^2$ represents a C2-C6 alkyl group,
q is 0, 1 or 2, and p is 0, 1, or 2;

a compound of the present invention wherein
$R^1$ represents a C2-C10 haloalkyl group or a (C1-C5 alkoxy)C2-C5 alkyl group having one or more halogen atoms,
$R^2$ represents an ethyl group,
q is 0, 1 or 2, and p is 0, 1, or 2;

a compound of the present invention wherein
$R^1$ represents a C2-C10 haloalkyl group, or a (C1-C5 alkoxy)C2-C5 alkyl group having one or more halogen atoms,
$R^2$ represents an ethyl group, q is 0, 1 or 2,
$R^3$ represents a C1-C6 alkyl group optionally having one or more substituents selected from Group B, a C2-C6 alkenyl group optionally having one or more substituents selected from Group B, a 5 membered aromatic heterocyclic group selected from Group Q (the 5 membered aromatic heterocyclic group may optionally have one or more substituents selected from Group D), a $OR^{12}$, a $NR^{11}R^{12}$, a $NR^{11a}R^{12a}$, a $NR^{24}NR^{11}R^{12}$, a $NR^{11}C(O)R^{13}$, a $NR^{24}NR^{11}C(O)R^{13}$, a $NR^{11}C(O)OR^{14}$, a $NR^{24}NR^{11}C(O)OR^{14}$, a $NR^{11}C(O)NR^{15}R^{16}$, a $NR^{24}NR^{11}C(O)NR^{15}R^{16}$, a $N=CHNR^{15}R^{16}$, a $N=S(O)_xR^{15}R^{16}$, a $S(O)_yR^{15}$, a $C(O)OR^{17}$, a $C(O)NR^{11}R^{12}$, a cyano group, a nitro group, or a halogen atom, and
p is 0, 1, or 2;

a compound of the present invention wherein
$R^1$ represents a C2-C10 haloalkyl group, or a (C1-C5 alkoxy)C2-C5 alkyl group having one or more halogen atoms,
$R^2$ represents an ethyl group, q is 0, 1, or 2,
$R^3$ represents a C1-C6 alkyl group optionally having one or more substituents selected from Group B, a C2-C6 alkenyl group optionally having one or more substituents selected from Group B, a 5 membered aromatic heterocyclic group containing one to four nitrogen atoms (the 5 membered aromatic heterocyclic group may optionally have one or more substituents selected from Group D), a $OR^{12}$, a $NR^{11}R^{12}$, a $NR^{11a}R^{12a}$, a $NR^{24}NR^{11}R^{12}$, or a halogen atom,
p is 0, 1, or 2, and
R represents a $OR^{18}$, a $NR^{18}R^{19}$, a $C(O)OR^{25}$, a $OC(O)R^{20}$, a cyano group, a nitro group, or a halogen atom;

a compound of the present invention wherein
$R^1$ represents a C2-C6 alkyl group having two or more fluorine atoms, a (C1-C5 alkoxy)C2-C5 alkyl group having one or more fluorine atoms,
$R^2$ represents an ethyl group, q is 0, 1 or 2,
$R^3$ represents a C1-C6 alkyl group optionally having one or more substituents selected from Group B, a C2-C6 alkenyl group optionally having one or more substituents selected from Group B, a 5 membered aromatic heterocyclic group containing one to four nitrogen atoms (the 5 membered aromatic heterocyclic group may optionally have one or more substituents selected from Group D), a $OR^{12}$, a $NR^{11}R^{12}$, a $NR^{11a}R^{12a}$, a $NR^{24}NR^{11}R^{12}$, or a halogen atom, and
p is 0, 1, or 2, and $R^6$ represents a cyano group, or a halogen atom;

a compound of the present invention wherein
$R^1$ represents a C3-C5 alkyl group having four or more fluorine atoms, or a 1,1,2-trifluoro-2-(trifluoromethoxy)ethyl group,
$R^2$ represents an ethyl group,
q is 0, 1, or 2,
$R^3$ represents a C1-C6 alkyl group optionally having one or more halogen atoms, a C2-C6 alkenyl group optionally having one or more halogen atoms, a triazole group optionally having one or more halogen atoms, a $NR^{11}R^{12}$, or a halogen atom,
$R^{11}$ and $R^{12}$ represent independently of each other a hydrogen atom, or a C1-C3 alkyl group optionally having one or more halogen atoms, and
p is 0.

a compound of the present invention wherein
$R^1$ represents a C2-C6 alkyl group having two or more fluorine atoms, a (C1-C5 alkoxy)C2-C5 alkyl group having one or more fluorine atoms, a (C3-C7 cycloalkyl)C1-C3 alkyl group optionally having one or more substituents selected from Group G, or a C3-C7 cycloalkyl group having one or more substituents selected from Group G,
$R^2$ represents a methyl group, an ethyl group, or a cyclopropylmethyl group, q is 0, 1, or 2,
$R^3$ represents a C1-C6 alkyl group optionally having one or more substituents selected from Group B, a C2-C6 alkenyl group optionally having one or more substituents selected from Group B, a pyrazol-1-yl group optionally having one or more halogens, a 1,2,4-triazol-1-yl group optionally having one or more halogens, a $OR^1$, a $NR^{11}R^{12}$, a $NR^{11a}R^{12a}$, a $NR^{24}NR^{11}R^{12}$, or a halogen atom, p is 0, 1 or 2, and $R^6$ represents a cyano group, or a halogen atom;

a compound of the present invention wherein $R^1$ represents a 2,2,3,3,3-pentafluoropropyl group, a 2,2,3,3,-tetrafluoropropyl group, a 1,1,2,3,3,3-hexafluoropropyl group, a 2,2,3,4,4,4-hexafluorobutyl group, or a 1,1,2-trifluoro-2-(trifluoromethoxy)ethyl group, $R^2$ represents an ethyl group, q is 0, 1 or 2, $R^3$ represents a trifluoromethyl group, a 1,2,4-triazole-1-yl group optionally having one or more halogen atoms, a $NR^{11}R^{12}$, or a halogen atom, and $R^{11}$ and $R^{12}$ represent independently of each other a hydrogen atom, or a C1-C3 alkyl group optionally having one or more halogen atoms, and p is 0;

a compound of the present invention wherein $R^1$ represents a C3-C5 alkyl group having four or more fluorine atoms, or a 1,1,2-trifluoro-2-(trifluoromethoxy)ethyl group, $R^2$ represents an ethyl group, q is 0, 1 or 2, $R^3$ represents a C1-C6 alkyl group having one or more halogen atoms, or a halogen atom, and p is 0 or 1, and $R^6$ represents a halogen atom;

a compound of the present invention wherein $R^1$ represents a C3-C5 alkyl group having four or more fluorine atoms, or a 1,1,2-trifluoro-2-(trifluoromethoxy)ethyl group, $R^2$ represents an ethyl group, q is 0, 1 or 2, $R^3$ represents a C1-C6 alkyl group having one or more halogen atoms, or a halogen atom, and p is 0;

a compound of the present invention wherein $R^1$ represents a C3-C5 alkyl group having four or more fluorine atoms, $R^2$ represents an ethyl group, q is 0 or 1, $R^3$ represents a C1-C6 alkyl group having one or more halogen atoms, a 1,2,4-triazol-1-yl group optionally having one or more halogen atoms, a $NR^{11}R^2$, or a halogen atom, $R^{11}$ and $R^{12}$ represent independently of each other a hydrogen atom, or a C1-C3 alkyl group optionally having one or more halogen atoms, and p is 0;

a bipyridine compound represented by formula (100):

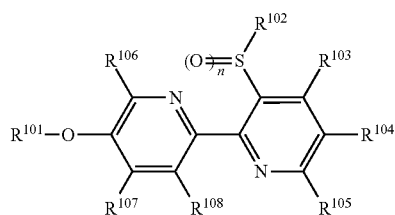

(100)

[wherein $R^{101}$ represents a C2-C10 haloalkyl group, or a (C1-C5 alkoxy)C2-C5 alkyl group having one or more halogen atoms, $R^{102}$ represents a C1-C6 alkyl group optionally having one or more halogen atoms, $R^{103}$, $R^{104}$, $R^{105}$, $R^{106}$, $R^{107}$, and $R^{108}$ represent independently of each other a hydrogen atom, a halogen atom, or a C1-C6 alkyl group optionally having one or more halogen atoms, and n is 0, 1, or 2.]

a compound represented by formula (100) wherein $R^{101}$ represents a C2-C10 fluoroalkyl group, or a (C1-C5 alkoxy)C2-C5 alkyl group having one or more fluorine atoms, $R^{102}$ represents a C1-C6 alkyl group optionally having one or more halogen atoms, $R^{103}$, $R^{104}$, $R^{105}$, $R^{106}$, $R^{107}$, and $R^{108}$ represent independently of each other a hydrogen atom, a halogen atom, or a C1-C6 alkyl group optionally having one or more halogen atoms, and n is 0, 1, or 2;

a compound represented by formula (100) wherein $R^{101}$ represents a C2-C10 fluoroalkyl group having two or more fluorine atoms, or a (C1-C5 alkoxy)C2-C5 alkyl group having two or more fluorine atoms, $R^{102}$ represents a C1-C6 alkyl group optionally having one or more halogen atoms, $R^{103}$, $R^{104}$, $R^{105}$, $R^{106}$, $R^{107}$, and $R^{108}$ represent independently of each other a hydrogen atom, a halogen atom, or a C1-C6 alkyl group optionally having one or more halogen atoms, and n is 0, 1, or 2;

a compound represented by formula (100) wherein $R^{101}$ represents a C2-C10 haloalkyl group, or a (C1-C5 alkoxy)C2-C5 alkyl group having one or more halogen atoms, $R^{102}$ represents an ethyl group, and $R^{103}$, $R^{104}$, $R^{105}$, $R^{106}$, $R^{107}$, and $R^{108}$ represent independently of each other a hydrogen atom, a halogen atom, or a C1-C6 alkyl group optionally having one or more halogen atoms, and n is 0, 1, or 2;

a compound represented by formula (100) wherein $R^{101}$ represents a C2-C10 fluoroalkyl group, or a (C1-C5 alkoxy)C2-C5 alkyl group having one or more fluorine atoms, $R^{102}$) represents an ethyl group, $R^{103}$, $R^{104}$, $R^{105}$, $R^{106}$, $R^{107}$, and $R^{108}$ represent independently of each other a hydrogen atom, a halogen atom, or a C1-C6 alkyl group optionally having one or more halogen atoms, and n is 0, 1, or 2;

a compound represented by formula (100) wherein $R^{101}$ represents a C2-C10 fluoroalkyl group having two or more fluorine atoms, or a (C1-C5 alkoxy)C2-C5 alkyl group having two or more fluorine atoms, $R^{102}$ represents an ethyl group, $R^{103}$, $R^{104}$, $R^{105}$, $R^{106}$, $R^{107}$, and $R^{108}$ represent independently of each other a hydrogen atom, a halogen atom, or a C1-C6 alkyl group optionally having one or more halogen atoms, and n is 0, 1, or 2;

a compound represented by formula (100) wherein $R^{101}$ represents a C2-C10 haloalkyl group, or a (C1-C5 alkoxy)C2-C5 alkyl group having one or more halogen atoms, $R^{102}$ represents an ethyl group, each of $R^{103}$, $R^{104}$, $R^{105}$, $R^{106}$, $R^{107}$, and $R^{108}$ represent a hydrogen atom, and n is 0, 1, or 2; a compound represented by formula (100) wherein $R^{101}$ represents a C2-C10 fluoroalkyl group, or a (C1-C5 alkoxy)C2-C5 alkyl group having one or more fluorine atoms, $R^{102}$ represents an ethyl group, each of $R^{103}$, $R^{104}$, $R^{105}$, $R^{106}$, $R^{107}$, and $R^{108}$ represent a hydrogen atom, and n is 0, 1, or 2;

a compound represented by formula (100) wherein $R^{101}$ represents a C2-C10 fluoroalkyl group having two or more fluorine atoms, or a (C1-C5 alkoxy)C2-C5 alkyl group having two or more fluorine atoms, $R^{102}$ represents an ethyl group, each of $R^{103}$, $R^{104}$, $R^{105}$, $R^{106}$, $R^{107}$, and $R^{108}$ represent a hydrogen atom, and n is 0, 1, or 2;

a compound represented by formula (100) wherein $R^{101}$ represents an C2-C10 fluoroalkyl group, or a (C1-C5 fluoroalkoxy)C2-C5 fluoroalkyl group, $R^{102}$ represents a C1-C6 alkyl group, $R^{104}$ represents a C1-C6 alkyl group optionally having one or more halogen atoms, or a hydrogen atom, and each of $R^{103}$, $R^{105}$, $R^{107}$, $R^{108}$, and $R^{108}$ represent a hydrogen atom;

a compound represented by formula (100) wherein $R^{101}$ represents a C2-C10 fluoroalkyl group, or a (C1-C5 fluoroalkoxy)C2-C5 fluoroalkyl group, $R^2$ represents a C1-C6 alkyl group, and each of $R^{103}$, $R^{104}$, $R^{105}$, $R^{106}$, $R^{107}$, and $R^{108}$ represents a hydrogen atom;

a compound represented by formula (100) wherein $R^{101}$ represents a C2-C6 fluoroalkyl group, or a (C1-C3 fluoroalkoxy)C2-C4 fluoroalkyl group, $R^2$ represents a C1-C3 alkyl group, $R^{104}$ represents a C1-C3 alkyl group optionally having one or more halogen atoms, or a hydrogen atom, and each of $R^{103}$, $R^{105}$, $R^{106}$, $R^{107}$, and $R^{108}$ represents a hydrogen atom;

a compound represented by formula (100) wherein $R^{101}$ represents a C2-C6 fluoroalkyl group, or a (C1-C3 fluoroalkoxy)C2-C4 fluoroalkyl group, $R^{102}$ represents a C1-C3 alkyl group, and each of $R^{103}$, $R^{104}$, $R^{105}$, $R^{106}$, $R^{107}$, and $R^{108}$ represents a hydrogen atom;

a compound represented by formula (100) wherein $R^{102}$ represents a C1-C6 alkyl group, each of $R^{103}$, $R^{104}$, $R^{105}$, $R^{106}$, $R^{107}$, and $R^{108}$ represents a hydrogen atom, and $R^1$ represents a C2-C6 fluoroalkyl group;

a compound represented by formula (100) wherein $R^{102}$ represents a C1-C6 alkyl group, each of $R^{103}$, $R^{104}$, $R^{105}$, $R^{106}$, $R^{107}$, and $R^{108}$ represents a hydrogen atom, and $R^1$ represents a (C1-C5 fluoroalkoxy)C2-C5 fluoroalkyl group;

a compound of the present invention wherein $R^1$ represents a C2-C10 haloalkyl group, or a (C1-C5 alkoxy)C2-C5 alkyl group having one or more halogen atoms, $R^1$ represents a C1-C6 alkyl group optionally having one or more halogen atoms, $R^3$ represents a C1-C6 chain hydrocarbon group having one or more substituents selected from Group B, a phenyl group optionally having one or more substituents selected from Group D, a 5 or 6 membered aromatic heterocyclic group optionally having one or more substituents selected from Group D, a $OR^{12}$, a $NR^{11}R^{12}$, a $NR^{11a}R^{12a}$, a $NR^{24}NR^{11}R^{12}$, a $NR^{11}C(O)R^{13}$, a $NR^{24}NR^{11}C(O)R^{13}$, a $NR^{11}C(O)OR^{14}$, a $NR^{24}NR^{11}C(O)OR^{14}$, or a halogen atom, $R^6$ represents a C1-C6 alkyl group optionally having one or more halogen atoms, a $OR^{18}$, a $NR^{18}R^{19}$, a $C(O)OR^{25}$, a $OC(O)R^{20}$, a cyano group, a nitro group, or a halogen atom, and p and q is independently of each other 0, 1, or 2;

a compound of the present invention wherein $R^1$ represents a C2-C10 haloalkyl group, or a (C1-C5 alkoxy)C2-C5 alkyl group having one or more halogen atoms, $R^2$ represents a C1-C6 alkyl group optionally having one or more halogen atoms, $R^3$ represents a C1-C6 chain hydrocarbon group optionally having one or more substituents selected from Group B, a 5 or 6 membered aromatic heterocyclic group optionally having one or more substituents selected from Group D, a $OR^{12}$, a $NR^{11}R^{12}$, a $NR^{24}NR^{11}R^{12}$, or a halogen atom, $R^6$ represents a $OR^{18}$, a $OC(O)R^{20}$, a cyano group, or a halogen atom, and p and q is independently of each other 0, 1, or 2;

a compound of the present invention wherein $R^1$ represents a C2-C10 fluoroalkyl group, or a (C1-C5 alkoxy)C2-C5 alkyl group having one or more fluorine atoms, $R^2$ represents a C1-C6 alkyl group optionally having one or more halogen atoms, $R^3$ represents a C1-C6 chain hydrocarbon group optionally having one or more substituents selected from Group B, a 5 membered aromatic heterocyclic group selected from Group Q (the 5 membered aromatic heterocyclic group may optionally have one or more substituents selected from Group D), a $OR^{12}$, a $NR^{11}R^{12}$, a $NR^{24}NR^{11}R^{12}$, or a halogen atom, $R^6$ represents a $OR^{18}$, a $OC(O)R^{20}$, a cyano group, or a halogen atom, and p and q is independently of each other 0, 1, or 2;

a compound of the present invention wherein $R^1$ represents a C2-C10 alkyl group having two or more fluorine atoms, or a (C1-C5 alkoxy)C2-C5 alkyl group having two or more fluorine atoms, $R^2$ represents a C1-C6 alkyl group, $R^1$ represents a C1-C6 alkyl group having one or more halogen atoms, a 5 membered aromatic heterocyclic group containing one to four nitrogen atoms (the 5 membered aromatic heterocyclic group may optionally have one or more substituents selected from Group D), a $OR^{12}$, a $NR^{11}R^{12}$, a $NR^{24}NR^{11}R^{12}$, or a halogen atom, $R^6$ represents a $OR^{18}$, a $OC(O)R^{20}$, a cyano group, or a halogen atom, and p and q is independently of each other 0, 1, or 2;

a compound of the present invention wherein $R^1$ represents a C3-C10 fluoroalkyl group having four or more fluorine atoms, or a (C1-C5 alkoxy)C2-C5 alkyl group having four or more fluorine atoms, $R^2$ represents an ethyl group, $R^3$ represents a C2-C6 alkenyl group optionally having one or more halogen atoms, a 1,2,4-triazol-1-yl group optionally having one or more halogen atoms, a $OR^{12}$, a $NR^{11}R^{12}$, a $NR^{24}NR^{11}R^{12}$, a C1-C6 alkyl group having one or more fluorine atoms, or a halogen atom, $R^{11}$ represents a hydrogen atom or a C1-C6 alkyl group, $R^{12}$ represents a hydrogen atom, or a C1-C6 alkyl group optionally having one or more fluorine atoms, $R^6$ represents a $OR^{18}$, a $OC(O)R^{20}$, a cyano group, or a halogen atom, $R^{18}$ represents a hydrogen atom or a methyl group, $R^{20}$ represents a methyl group, p is 0 or 1, and q is 0, 1, or 2; and a compound of the present invention wherein $R^1$ represents a C2-C10 haloalkyl group or a (C1-C5 alkoxy)C2-C5 alkyl group having one or more halogen atoms, $R^2$ represents a C1-C6 alkyl group optionally having one or more halogen atoms, $R^3$ represents a triazolyl group, a $OR^{12}$, a $NR^{11}R^{12}$, a $NR^{24}NR^{11}R^{12}$, a C1-C6 chain hydrocarbon group optionally having one or more halogen atoms, or a halogen atom, $R^6$ represents a C1-C6 alkyl group optionally having one or more halogen atoms, a $OR^{18}$, a $OC(O)R^{20}$, a cyano group, or a halogen atom, $R^{11}$ represents a hydrogen atom, or a C1-C6 alkyl group optionally having one or more halogen atoms, $R^{12}$ represents a hydrogen atom, a C1-C6 alkyl group optionally having one or more halogen atoms, a 2-chloro-5-thiazolylmethyl group, or a p-toluenesulfonyl group, $R^{24}$ represents a hydrogen atom, $R^{18}$ represents a hydrogen atom, or a C1-C6 alkyl group optionally having one or more halogen atoms, and $R^{20}$ represents a C1-C6 alkyl group optionally having one or more halogen atoms.

Next, a process for preparing the compound of the present invention is explained.

The compound of the present invention can be prepared, for example, according to the following processes.

Process 1

A compound of the present invention wherein n is 1 (hereinafter, referred to as Present compound (Ib)) and a compound of the invention wherein n is 2 (hereinafter, referred to as Present compound (Ic)) may be prepared by reacting a compound of the present invention wherein n is 0 (hereinafter, referred to as Present compound (Ia)) with an oxidizing agent.

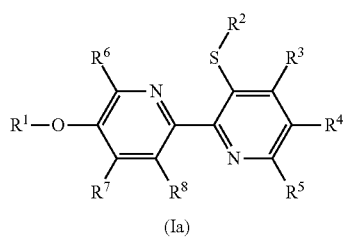

(Ia)

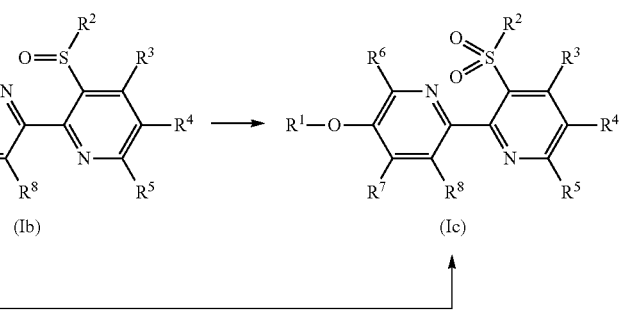

(Ib)          (Ic)

[wherein the symbols are the same as defined above]

First, a process for preparing the present compound (Ib) from the present compound (Ia) is described.

The reaction is usually carried out in a solvent.

Examples of the solvent to be used in the reaction include halogenated aliphatic hydrocarbons such as dichloromethane and chloroform (hereinafter, collectively referred to as halogenated aliphatic hydrocarbons); nitriles such as acetonitrile (hereinafter collectively referred to nitriles); esters such as ethyl acetate; alcohols such as methanol and ethanol (hereinafter, collectively referred to as alcohols); acetic acid; water; and mixed solvents thereof.

Examples of the oxidizing agent to be used in the reaction includes sodium periodate, m-chloroperoxybenzoic acid (hereinafter referred to as mCPBA), and hydrogen peroxide.

When hydrogen peroxide is used as the oxidizing agent, a base or a catalyst may be added as needed.

Examples of the base to be used in the reaction include sodium carbonate.

Examples of the catalyst to be used in the reaction include tungstic acid, and sodium tungstate.

In the reaction, the oxidizing agent is used usually within a range of 1 to 1.2 molar ratio(s) as opposed to 1 mole of the present compound (Ia).

In the reaction, the base is used usually within a range of 0.01 to 1 molar ratio(s) as opposed to 1 mole of the present compound (Ia).

In the reaction, the catalyst is used usually within a range of 0.01 to 0.5 molar ratios as opposed to 1 mole of the present compound (Ia).

The reaction temperature of the reaction is usually within a range of −20 to 80° C. The reaction period of the reaction is usually within a range of 0.1 to 12 hours.

When the reaction is completed, the reaction mixture is extracted with organic solvent(s), and the organic layers are washed with an aqueous solution of a reducing agent (such as sodium sulfite, and sodium thiosulfate) and an aqueous solution of a base (such as sodium hydrogen carbonate). The resulting organic layers are worked up (for example, drying and concentration) to give the present compound (Ib).

Next, a process for preparing the present compound (Ic) from the present compound (Ib) is explained.

The reaction is usually carried out in a solvent.

Examples of the solvent to be used in the reaction include halogenated aliphatic hydrocarbons, nitriles, alcohols, acetic acid, water, and mixed solvents thereof.

Examples of the oxidizing agent to be used in the reaction include mCPBA and hydrogen peroxide.

When hydrogen peroxide is used as oxidizing agent, a base or a catalyst may be added as needed.

Examples of the base to be used include sodium carbonate.

Examples of the catalyst to be used include sodium tungstate.

In the reaction, the oxidizing agent is used usually within a range of 1 to 4 molar ratio(s) as opposed to 1 mole of the present compound (Ib). Preferably, the oxidizing agent is used usually within a range of 1 to 2 molar ratio(s) as opposed to 1 mole of the present compound (Ib).

In the reaction, the base is used usually within a range of 0.01 to 1 molar ratio(s) as opposed to 1 mole of the present compound (Ib).

In the reaction, the base is used usually within a range of 0.01 to 0.5 molar ratios as opposed to 1 mole of the present compound (Ib).

The reaction temperature of the reaction is usually within a range of −20 to 120° C. The reaction period of the reaction is usually within a range of 0.1 to 12 hours.

When the reaction is completed, the reaction mixture is extracted with organic solvent(s), and the organic layers are washed with an aqueous solution of a reducing agent (such as sodium sulfite, and sodium thiosulfate) and an aqueous solution of a base (such as sodium hydrogen carbonate). The resulting organic layers are worked up (for example, drying and concentration) to give the present compound (Ic).

Also, the present compound (Ic) may be prepared in one step (one-spot) by reacting the present compound (Ia) with an oxidizing agent.

The reaction may be carried out by using the oxidizing agent usually in 2 to 5 molar ratios as opposed to 1 mole of the present compound (Ia) according to a method for preparing the present compound (Ic) from the present compound (Ib).

Process 2

A compound of the present invention represented by formula (Id) (hereinafter, referred to as Present compound (Id)), a compound of the present invention represented by formula (Ie) (hereinafter, referred to Present compound (Ie)), a compound of the present invention represented by formula (If) (hereinafter, referred to Present compound (If)) may be prepared by reacting the present compound (Ic) with an oxidizing agent.

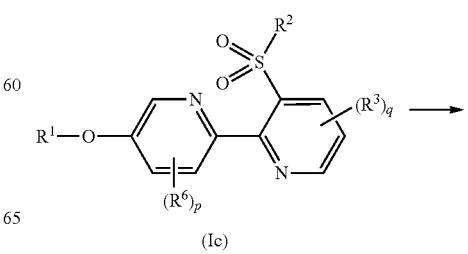

(Ic)

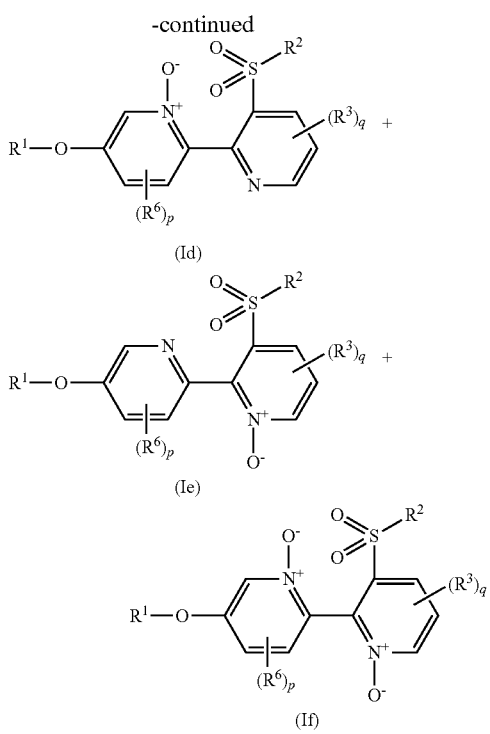

(Id)

(Ie)

(If)

[wherein the symbols are the same as defined above.]

The reaction is usually carried out in a solvent.

Examples of the solvent to be used in the reaction include halogenated aliphatic hydrocarbons; nitriles; esters such as ethyl acetate; alcohols; acetic acid; water; and mixed solvents thereof.

Examples of the oxidizing agent to be used in the reaction include mCPBA and hydrogen peroxide.

When hydrogen peroxide is used as the oxidizing agent, a base or a catalyst may be added as needed.

Examples of the base to be used include sodium carbonate.

Examples of the catalyst to be used include tungstic acid and sodium tungstate.

In the reaction, the oxidizing agent is used usually within a range of 1 to 10 molar ratio(s) as opposed to 1 mole of the present compound (Ic).

In the reaction, the base is used usually within a range of 0.01 to 1 molar ratio(s) as opposed to 1 mole of the present compound (Ic).

In the reaction, the base is used usually within a range of 0.01 to 0.5 molar ratios as opposed to 1 mole of the present compound (Ic).

The reaction temperature of the reaction is usually within a range of −20 to 80° C. The reaction period of the reaction is usually within a range of 0.1 to 24 hours.

When the reaction is completed, the reaction mixture is extracted with organic solvent(s), and the organic layers are washed with an aqueous solution of a reducing agent (such as sodium sulfite, and sodium thiosulfate) and an aqueous solution of a base (such as sodium hydrogen carbonate). The resulting organic layers are worked up (for example, drying and concentration) to give a mixture of the present compound (Id), the present compound (Ie) and the present compound (If). This mixture may be worked up (such as chromatography or recrystallization) to isolate the present compound (Id), the present compound (Ie) and the present compound (If), respectively.

Process 3

The present compound (Ia) may be prepared by reacting a compound represented by formula (M-1) (hereinafter, referred to Compound (M-1)) with a compound represented by formula (R-1) (hereinafter, referred to as Compound (R-1)) in the presence of a base.

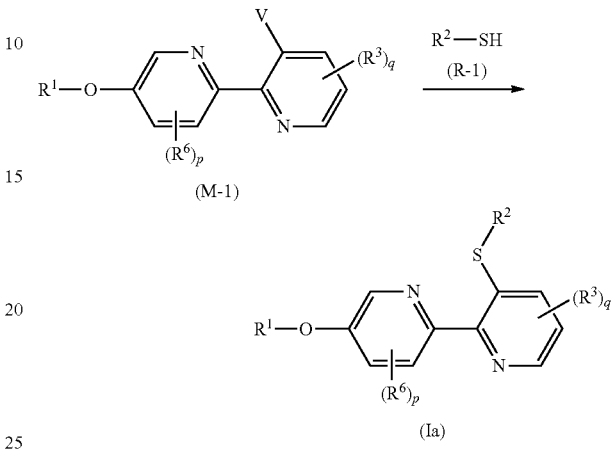

(M-1)

(Ia)

[wherein V represents a halogen atom, and the other symbols are the same as defined above.]

The reaction is usually carried out in a solvent.

Examples of the solvent to be used in the reaction include ethers such as tetrahydrofuran, ethyleneglycol dimethyl ether, methyl tert-butyl ether (hereinafter, referred to as MTBE), and 1,4-dioxane (hereinafter, collectively referred to as ethers); aromatic hydrocarbons such as toluene and xylene (hereinafter, collectively referred to as aromatic hydrocarbons); nitriles; polar aprotic solvents such as dimethylformamide, N-methyl pyrrolidone (hereinafter, referred to as NMP), dimethyl sulfoxide (hereinafter, referred to as DMSO) (hereinafter, collectively referred to as polar aprotic solvent); water; and mixed solvents thereof.

Examples of the base to be used in the reaction include alkali metal carbonates (such as sodium carbonate, and potassium carbonate) (hereinafter, collectively referred to as alkali metal carbonates); and alkali metal hydrides such as sodium hydride (hereinafter, collectively referred to as alkali metal hydrides).

In the reaction, the compound (R-1) is used usually within a range of 1 to 10 molar ratio(s), and the base is used usually within a range of 1 to 10 molar ratio(s), as opposed to 1 mole of the compound (M-1). Preferably, the compound (R-1) is used within a range of 1.0 to 1.1 molar ratio(s), and the base is used within a range of 1 to 2 molar ratio(s), as opposed to 1 mole of the compound (M-1).

The reaction temperature is usually within a range of −20 to 150° C. The reaction period of the reaction is usually within a range of 0.5 to 24 hours.

When the reaction is completed, the reaction mixtures are extracted with organic solvents, and the resulting organic layers are worked up (for example, drying and concentration) to give the present compound (Ia).

In the reaction, V is preferably a fluorine atom or a chlorine atom.

Process 4

The present compound (Ia) may be prepared by reacting a compound represented by formula (M-2) (hereinafter referred to as Compound (M-2)) with a compound represented by formula (R-2) (hereinafter, referred to as Compound (R-2)) in the presence of a base.

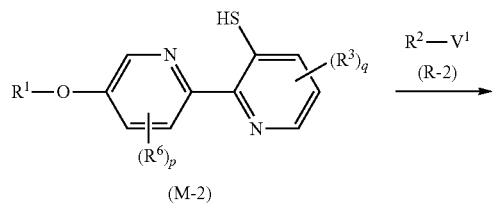

(M-2)

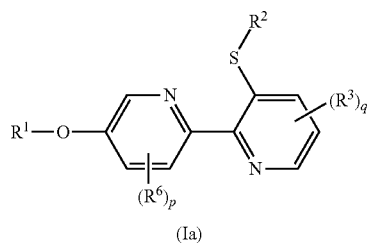

(Ia)

[wherein $V^1$ represents a halogen atom, a trifluoromethanesulfonyloxy group, a nonafluorobutanesulfonyloxy group, or a tosyloxy group, and the other symbols are the same as defined above.]

The reaction is usually carried out in a solvent.

Examples of the solvent to be used in the reaction include ethers, aromatic hydrocarbons, nitriles, and polar aprotic solvent.

Examples of the base to be used in the reaction include alkali metal carbonates and alkali metal hydrides.

In the reaction, the compound (R-2) is usually used within a range of in 1 to 10 molar ratio(s), and the base is usually used within a range of 1 to 10 molar ratio(s), as opposed to 1 mole of the compound (M-2). Preferably, the compound (R-2) is usually used within a range of in 1.0 to 1.1 molar ratio(s), and the base is usually used within a range of 1 to 2 molar ratio(s), as opposed to 1 mole of the compound (M-2).

The reaction temperature is usually within a range of −20 to 150° C. The reaction period of the reaction is usually within a range of 0.5 to 24 hours.

When the reaction is completed, the reaction mixtures are extracted with organic solvents, and the resulting organic layers are worked up (for example, drying and concentration) to give the present compound (Ia).

Process 5

A compound of the present invention represented by formula (I) (hereinafter, referred to Present compound (I)) may be prepared by reacting a compound represented by formula (M-3) (hereinafter, referred to Compound (M-3)) with a compound represented by formula (R-3) (hereinafter, referred to as Compound (R-3)) in the presence of a base.

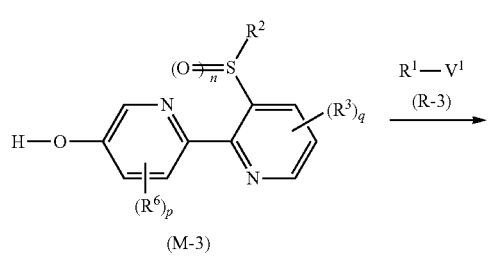

(M-3)

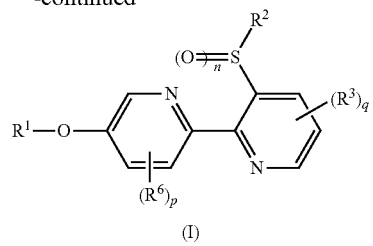

(I)

[wherein the symbols are the same as defined above.]

The reaction is usually carried out in a solvent.

Examples of the solvent to be used in the reaction include ethers, halogenated aliphatic hydrocarbons, aromatic hydrocarbons, polar aprotic solvent, and mixed solvents thereof.

Examples of the base to be used in the reaction include organic bases such as triethylamine, diisopropylethylamine, pyridine, 4-(dimethylamino)pyridine (hereinafter, collectively referred to as organic bases); alkali metal hydrides; and alkali metal carbonates.

In the reaction, the compound (R-3) is usually used within a range of 1 to 10 molar ratio(s), and the base is usually used within a range of 0.1 to 5 molar ratio(s), as opposed to 1 mole of the compound (M-3).

The reaction temperature is usually within a range of −20 to 120° C. The reaction period of the reaction is usually within a range of 0.1 to 24 hours.

When the reaction is completed, the reaction mixtures are extracted with organic solvents, and the resulting organic layers are worked up (for example, drying and concentration) to give the present compound (I).

Process 6

The present compound (I) may be prepared by reacting a compound represented by formula (M-4) (hereinafter, referred to as Compound (M-4)) with a compound represented by formula (R-4) (hereinafter, referred to as Compound (R-4)) in the presence of a base.

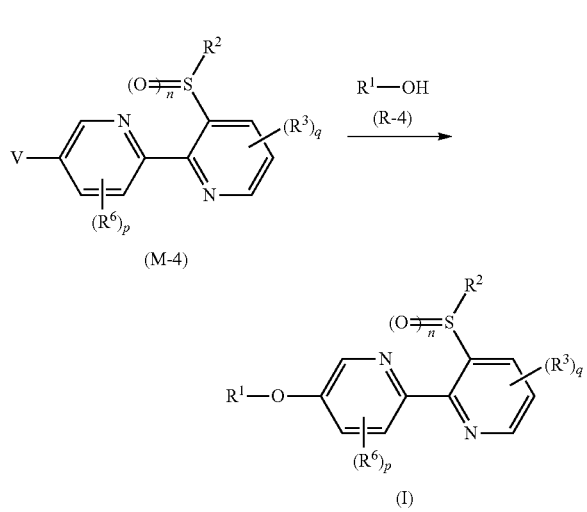

[wherein the symbols are the same as defined above.]

The reaction is usually carried out in a solvent.

Examples of the solvent to be used in the reaction include ethers, aromatic hydrocarbons, nitriles, polar aprotic solvent, and mixed solvents thereof.

Examples of the base to be used in the reaction include alkali metal carbonates and alkali metal hydrides.

In the reaction, the compound (R-4) is usually used within a range of 1 to 10 molar ratio(s), and the base is usually used within a range of 1 to 10 molar ratio(s), as opposed to 1 mole of the compound (R-4). Preferably, the compound (R-4) is usually used within a range of 1 to 1.1 molar ratio(s), and the base is usually used within a range of 1 to 2 molar ratio(s), as opposed to 1 mole of the compound (R-4).

The reaction temperature is usually within a range of −20 to 150° C. The reaction period of the reaction is usually within a range of 0.5 to 24 hours.

When the reaction is completed, the reaction mixtures are extracted with organic solvents, and the resulting organic layers are worked up (for example, drying and concentration) to give the present compound (I).

In the reaction, V is preferably a fluorine atom.

Process 7

A compound represented by formula (Ig) (hereinafter, referred to as Present Compound (Ig)) may be prepared according to a method described below.

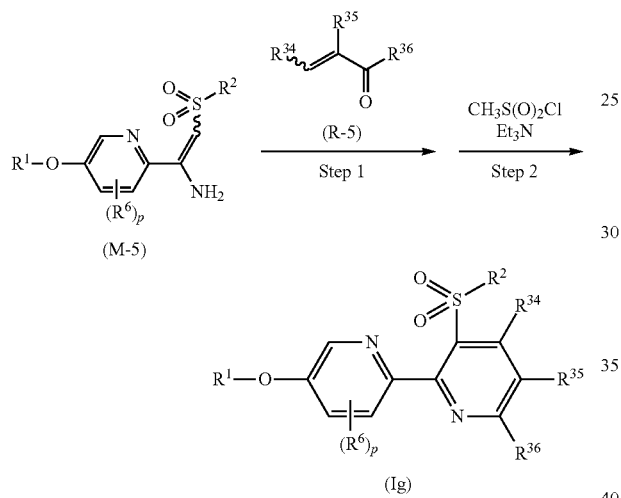

[$R^{34}$, $R^{35}$, and $R^{3C}$ represent independently of each other a hydrogen atom, a C1-C6 alkyl group optionally having one or more halogen atoms, a phenyl group optionally having one or more substituents selected from Group D, a 5 or 6 membered aromatic heterocyclic group optionally having one or more substituents selected from Group D; and the other symbols are the same as defined above.]

First, Step 1 is explained.

In the Step 1, a compound represented by formula (M-5) (hereinafter, referred to as Compound (M-5)) and a compound represented by formula (R-5) (hereinafter, referred to as Compound (R-5)) are reacted.

The reaction is usually carried out in a solvent.

Examples of the solvent to be used in the reaction include ethers, aliphatic hydrocarbons, aromatic hydrocarbons, halogenated aliphatic hydrocarbons, alcohols, esters, nitriles, polar aprotic solvent, pyridine, nitrogen-containing aromatic compounds such as 2,6-lutidine (hereinafter, collectively referred to as nitrogen-containing aromatic compounds), and mixed solvents thereof.

In the reaction, the compound (R-5) is usually used within a range of 1 to 10 molar ratio(s) as opposed to 1 mole of the compound (M-5).

The reaction temperature is usually within a range of 0 to 200° C. The reaction period of the reaction is usually within a range of 0.1 to 24 hours.

When the reaction is completed, the reaction mixtures are concentrated to obtain the residues, which are used as itself in the Step 2. Alternatively, to the reaction mixtures is added water and the mixtures are then extracted with organic solvents, and the organic layers are worked (for example, drying and concentration) to obtain the residues, which are used in Step 2.

Next, Step 2 is explained.

In the Step 2, the residue obtained in the Step 1 may be reacted with methansulfonyl chloride and triethylamine to give the present compound (Ig).

The reaction is usually carried out in a solvent.

Examples of the solvent to be used in the reaction include ethers, aliphatic hydrocarbons, aromatic hydrocarbons, halogenated aliphatic hydrocarbons, nitriles, polar aprotic solvent, nitrogen-containing aromatic compounds, and mixed solvents thereof.

In the reaction, methansulfonyl chloride is usually used within a range of 1 to 10 molar ratio(s), and triethylamine is usually used within a range of 1 to 10 molar ratio(s), as opposed to 1 mole of the compound (M-5).

The reaction temperature is usually within a range of 0 to 200° C. The reaction period of the reaction is usually within a range of 0.1 to 24 hours.

When the reaction is completed, to the reaction mixtures is added water. The resulting mixtures are extracted with organic solvents, and the organic layers are worked up (for example, drying and concentration) to give the present compound (Ig).

Process 8

A compound represented by formula (Ih) (hereinafter, referred to as Present compound (Ih)) may be prepared according to a method described above.

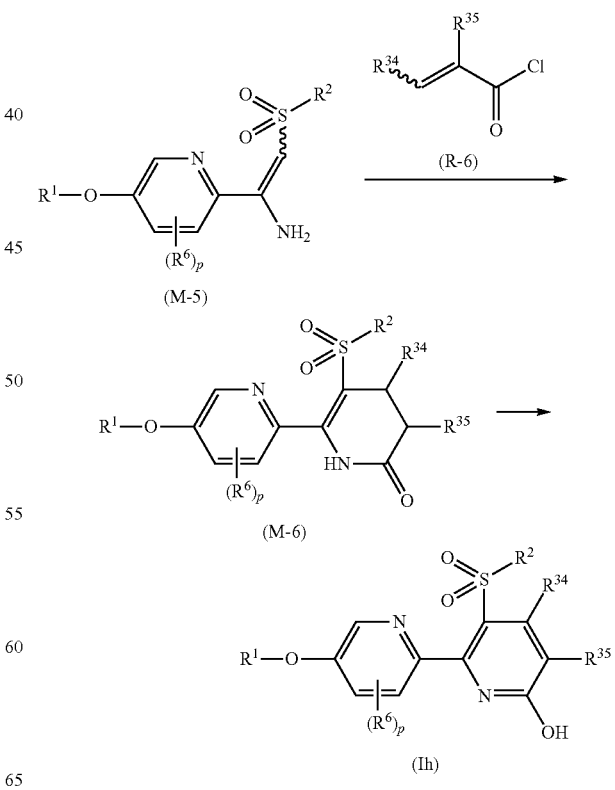

[wherein the symbols are the same as defined above.]

First, a method for preparing a compound represented by formula (M-6) (hereinafter, referred to as Compound (M-6)) from the compound (M-5) is described.

The compound (M-6) may be prepared by reacting the compound (M-5) with a compound represented formula (R-6) (hereinafter, referred to as Compound (R-6)).

The reaction is usually carried out in a solvent.

Examples of the solvent to be used in the reaction include ethers, aliphatic hydrocarbons, aromatic hydrocarbons, halogenated aliphatic hydrocarbons, nitriles, polar aprotic solvent, nitrogen-containing aromatic compounds, and mixed solvents thereof.

In the reaction, the compound (R-6) is usually used within a range of 1 to 10 molar ratio(s) as opposed to 1 mole of the compound (M-5).

The reaction temperature is usually within a range of 0 to 200° C. The reaction period of the reaction is usually within a range of 0.1 to 24 hours.

When the reaction is completed, to the reaction mixtures is added water. The resulting mixtures are extracted with organic solvents, and the organic layers are worked up (for example, drying and concentration) to isolate the compound (M-6).

Next, a method for preparing the present compound (Ih) from the compound (M-6) is explained. The present compound (Ih) may be prepared by reacting the compound (M-6) with a halogenating agent.

The reaction is usually carried out in a solvent.

Examples of the solvent to be used in the reaction include ethers, aliphatic hydrocarbons, aromatic hydrocarbons, halogenated aliphatic hydrocarbons, nitriles, polar aprotic solvent, nitrogen-containing aromatic compounds, and mixed solvents thereof.

Examples of the halogenating agent to be used in the reaction include N-bromosuccinimide, N-chlorosuccinimide, sulfuryl chloride, and bromine.

A catalyst may be added to the reaction as needed. Examples of the catalyst to be used in the reaction include benzoyl peroxide.

In the reaction, a halogenating agent is usually used within a range of 1 to 10 molar ratio(s), and the catalyst is usually used within a range of 0.1 to 0.5 molar ratio(s), as opposed to 1 mole of the compound (M-6).

The reaction temperature is usually within a range of 0 to 200° C. The reaction period of the reaction is usually within a range of 0.1 to 24 hours.

When the reaction is completed, to the reaction mixtures is added water. The resulting mixtures are extracted with organic solvents, and the organic layers are worked up (for example, drying and concentration) to isolate the present compound (Ih).

Process 9

A compound represented by formula (Ii) (hereinafter, referred to as Present compound (Ii)) may be prepared by reacting the compound (M-7) with a compound represented by formula (R-7) (hereinafter, referred to as Compound (R-7)) followed by reacting the resulting mixtures with ammonia.

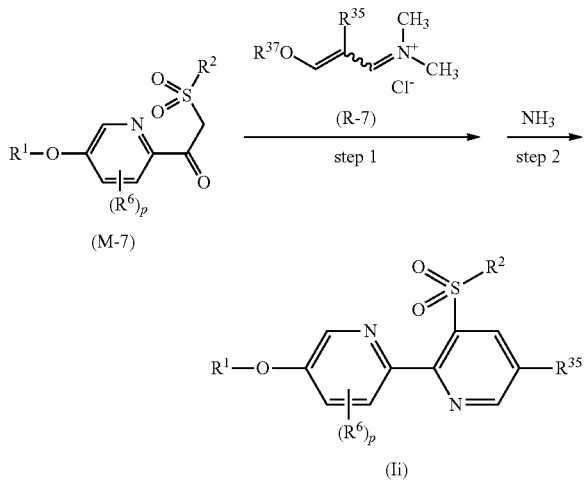

[wherein $R^{37}$ represents a C1-C6 alkyl group, and the other symbols are the same as defined above.]

First, Step 1 is explained.

The compound (R-7) may be prepared according to a similar method to that described in International Publication No. 2009/054742.

The reaction is usually carried out in a solvent.

Examples of the solvent to be used in the reaction include ethers, aliphatic hydrocarbons, aromatic hydrocarbons, halogenated aliphatic hydrocarbons, alcohols, esters, nitriles, polar aprotic solvent, nitrogen-containing aromatic compounds, and mixed solvents thereof.

In the reaction, the compound (R-7) is usually used within a range of 1 to 10 molar ratio(s) as opposed to 1 mole of the compound (M-7)).

The reaction temperature is usually within a range of −50 to 200° C. The reaction period of the reaction is usually within a range of 0.1 to 24 hours.

When the reaction is completed, the reaction mixtures are concentrated to obtain the residues, which are used as itself in the Step 2. Alternatively, to the reaction mixtures is added water and the mixtures are then extracted with organic solvents, and the organic layers are worked (for example, drying and concentration) to obtain the residues, which are used in Step 2.

Next, Step 2 is explained.

The residue obtained in the Step 1 may be reacted with ammonia to give the present compound (Ii).

The reaction is usually carried out in a solvent.

Examples of the solvent to be used in the reaction include ethers, nitriles, alcohols, polar aprotic solvent, nitrogen-containing aromatic compounds, and mixed solvents thereof.

Examples of the ammonia to be used in the reaction include aqueous ammonia solution and solution of ammonia in methanol.

In the reaction, ammonia is usually used within a range of 1 to 10 molar ratio(s) as opposed to 1 mole of the compound (M-7).

The reaction temperature is usually within a range of 0 to 100° C. The reaction period of the reaction is usually within a range of 0.1 to 24 hours.

When the reaction is completed, to the reaction mixtures is added water. The resulting mixtures are extracted with organic solvents, and the organic layers are worked up (for example, drying and concentration) to isolate the present compound (Ii).

Process 10

A compound represented by formula (Ij) (hereinafter, referred to as Present compound (Ij)) may be prepared by reacting the compound (M-5) with a compound represented by formula (R-8) (hereinafter, referred to as Compound (R-8)).

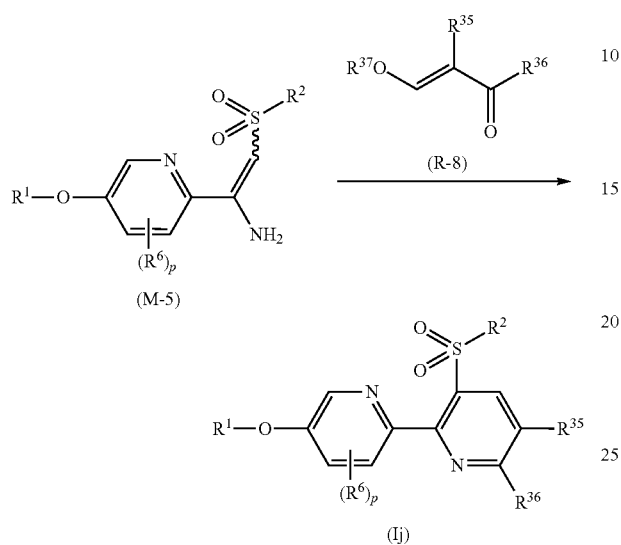

[wherein the symbols are the same as defined above.]

The reaction is usually carried out in a solvent.

Examples of the solvent to be used in the reaction include ethers, aliphatic hydrocarbons, aromatic hydrocarbons, halogenated aliphatic hydrocarbons, nitriles, alcohols, polar aprotic solvent, nitrogen-containing aromatic compounds, and mixed solvents thereof.

In the reaction, the compound (R-8) is usually used within a range of 1 to 10 molar ratio(s) as opposed to 1 mole of the compound (M-5).

The reaction temperature is usually within a range of 0 to 200° C. The reaction period of the reaction is usually within a range of 0.1 to 24 hours.

When the reaction is completed, to the reaction mixtures is added water. The resulting mixtures are extracted with organic solvents, and the organic layers are worked up (for example, drying and concentration) to isolate the present compound (Ij).

Process 11

A compound represented by formula (Ip) (hereinafter, referred to as Present compound (Ip)) may be prepared by reacting a compound represented by formula (Ik) (hereinafter, referred to as Present compound (Ik)) with a compound represented by formula (R-12) (hereinafter, referred to as Compound (R-12)) in the presence of a base.

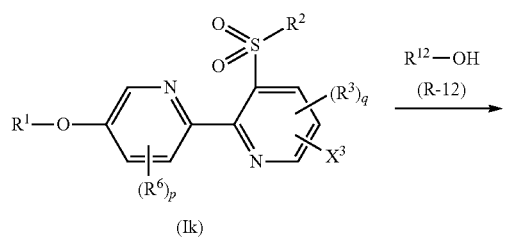

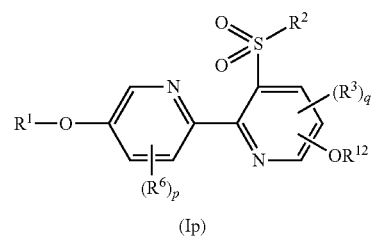

[wherein $X^3$ represents a fluorine atom, a chlorine atom, or a $S(O)_2R^{15}$, and the other symbols are the same as defined above.]

The reaction is usually carried out in a solvent.

Examples of the solvents to be used in the reaction include ethers, aliphatic hydrocarbons, aromatic hydrocarbons, halogenated aliphatic hydrocarbons, esters, nitriles, polar aprotic solvent, nitrogen-containing aromatic compounds, and mixed solvents thereof.

Examples of the base to be used in the reaction include alkali metal carbonates, alkali metal hydrides, and organic bases.

In the reaction, the compound (R-12) is usually used within a range of 1 to 10 molar ratio(s), and the base is usually used within a range of 1 to 10 molar ratio(s), as opposed to 1 mole of the compound (Ik).

The reaction temperature is usually within a range of 0 to 200° C. The reaction period of the reaction is usually within a range of 0.1 to 24 hours.

When the reaction is completed, to the reaction mixtures is added water. The resulting mixtures are extracted with organic solvents, and the organic layers are worked up (for example, drying and concentration) to isolate the present compound (Ip).

Process 12

A compound represented by formula (Im) (hereinafter, referred to as Present compound (Im)) may be reacting Present compound (Ik) with a compound represented by formula (R-9) (hereinafter, referred to as Compound (R-9)).

A compound represented by formula (In) (hereinafter, referred to as Present compound (In)) may be reacting Present compound (Ik) with a compound represented by formula (R-10) (hereinafter, referred to as Compound (R-10)).

A compound represented by formula (Io) (hereinafter, referred to as Present compound (Io)) may be reacting Present compound (Ik) with a compound represented by formula (R-11) (hereinafter, referred to as Compound (R-11)).

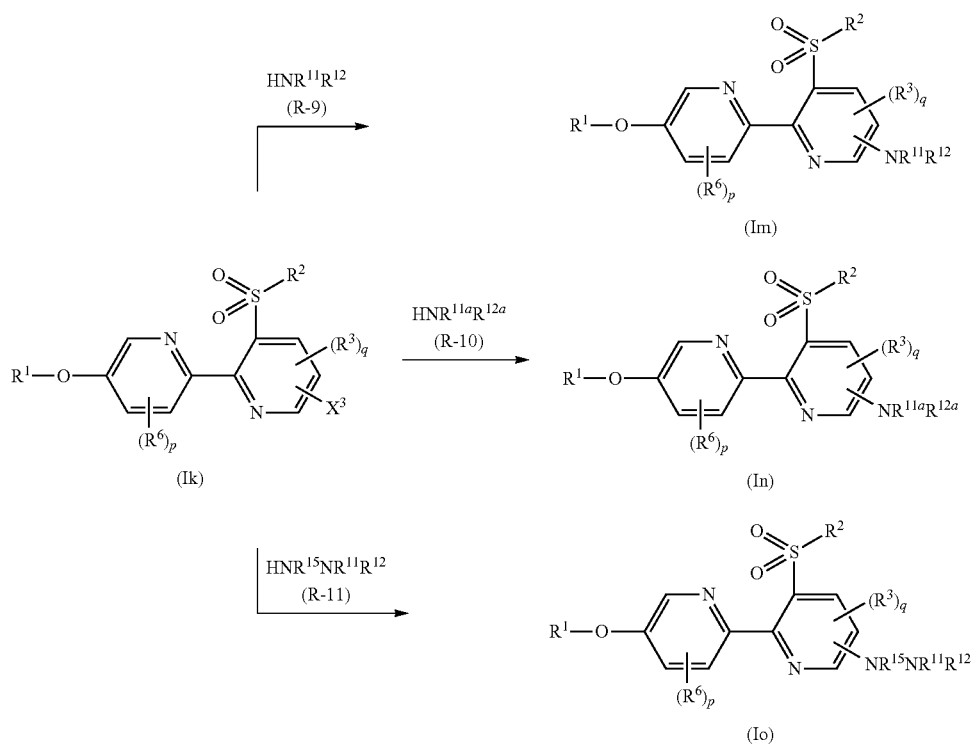

[wherein the symbols are the same as defined above.]

The reaction is usually carried out in a solvent.

Examples of the solvent to be used in the reaction include ethers, aliphatic hydrocarbons, aromatic hydrocarbons, halogenated aliphatic hydrocarbons, esters, nitriles, polar aprotic solvent, nitrogen-containing aromatic compounds, and mixed solvents thereof.

The reaction may be carried out by adding a base as needed.

Examples of the base to be used in the reaction include alkali metal carbonates, alkali metal hydrides, and organic bases.

In the reaction, when the present compound (Im) is prepared, the compound (R-9) is usually used within a range of 1 to 10 molar ratio(s), and the base is usually used within a range of 1 to 10 molar ratio(s), as opposed to 1 mole of the present compound (Ik).

In the reaction, when the present compound (In) is prepared, the compound (R-10) is usually used within a range of 1 to 10 molar ratio(s), and the base is usually used within a range of 1 to 10 molar ratio(s), as opposed to 1 mole of the present compound (Ik).

In the reaction, when the present compound (Io) is prepared, the compound (R-11) is usually used within a range of 1 to 10 molar ratio(s), and the base is usually used within a range of 1 to 10 molar ratio(s), as opposed to 1 mole of the present compound (Ik).

The reaction temperature is usually within a range of 0 to 200° C. The reaction period of the reaction is usually within a range of 0.1 to 24 hours.

When the reaction is completed, to the reaction mixtures is added water. The resulting mixtures are extracted with organic solvents, and the organic layers are worked up (for example, drying and concentration) to give the present compound (Im), the present compound (In), or the present compound (Io), respectively.

Process 13

A compound represented by formula (Iq) (hereinafter, referred to as Present compound (Iq)) may be prepared by reacting Present compound (Ik) with a compound represented by formula (R-13) (hereinafter, referred to as Compound (R-13)) in the presence of a base.

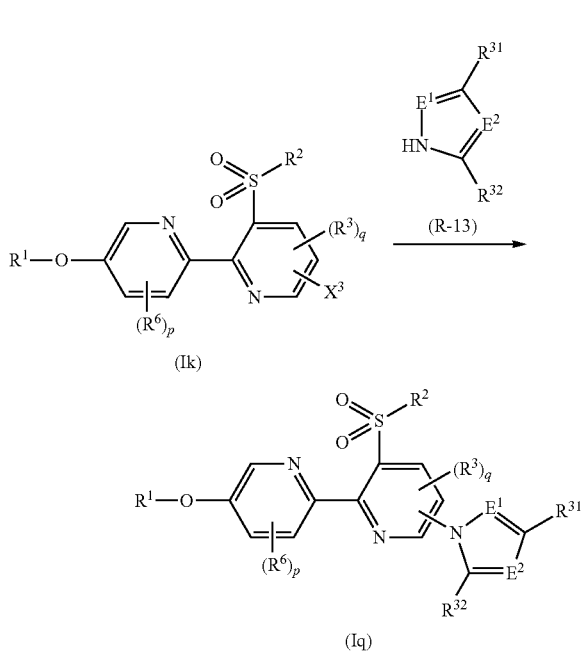

[wherein, $E^1$ and $E^2$ represent independently of each other a nitrogen atom, or a $CR^{33}$; $R^{31}$, $R^{32}$ and $R^{33}$ represent independently of each other a hydrogen atom or one substituent selected from Group D; and the other symbols are the same as defined above.]

The reaction may be carried out by using the compound (R-13) instead of the compound (R-12) according to a similar method to that described in Process 11.

Process 14

A compound represented by formula (Is) (hereinafter, referred to as Present compound (Is)), and a compound represented by formula (It) (hereinafter, referred to as Present compound (It)) may be prepared according to a method described below.

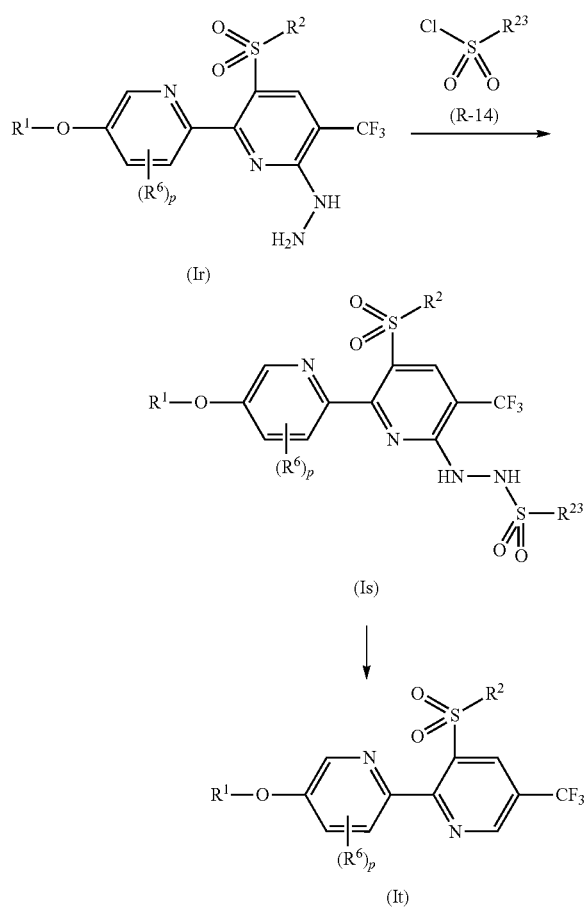

[wherein the symbols are the same as described above.]

First, a method for preparing Present compound (Is) by reacting a compound represented by formula (Ir) (hereinafter, referred to as Present compound (Ir)) with a compound represented by formula (R-14) (hereinafter, referred to as Compound (R-14)) is described.

The reaction is usually carried out in a solvent.

Examples of the solvents to be used in the reaction include ethers, aliphatic hydrocarbons, aromatic hydrocarbons, halogenated aliphatic hydrocarbons, nitriles, polar aprotic solvent, nitrogen-containing aromatic compounds, and mixed solvents thereof.

The reaction may be carried out by adding a base as needed.

Examples of the base include organic bases.

In the reaction, the compound (R-14) is usually used within a range of 1 to 5 molar ratio(s), and the base is usually used within a range of 0.1 to 5 molar ratio(s), as opposed to 1 mole of the present compound (Ir).

The reaction temperature is usually within a range of 0 to 200° C. The reaction period of the reaction is usually within a range of 0.1 to 24 hours.

When the reaction is completed, to the reaction mixtures is added water. The resulting mixtures are extracted with organic solvents, and the organic layers are worked up (for example, drying and concentration) to isolate the present compound (Is).

Next, a method for preparing the present compound (It) by reacting the present compound (Is) with a base is described.

The reaction is usually carried out in a solvent.

Examples of the solvents to be used in the reaction include ethers, aliphatic hydrocarbons, aromatic hydrocarbons, halogenated aliphatic hydrocarbons, nitriles, alcohols, polar aprotic solvent, nitrogen-containing aromatic compounds, and mixed solvents thereof.

Examples of the base to be used in the reaction include alkali metal hydroxides such as sodium hydroxide and potassium hydroxide; alkali metal carbonates; and alkali metal hydrides.

In the reaction, the base is usually used within a range of 0.1 to 5 molar ratio(s) as opposed to 1 mole of the present compound (Is).

The reaction temperature is usually within a range of 0 to 200° C. The reaction period of the reaction is usually within a range of 0.1 to 24 hours.

When the reaction is completed, to the reaction mixtures is added water. The resulting mixtures are extracted with organic solvents, and the organic layers are worked up (for example, drying and concentration) to isolate the present compound (It).

Process 15

The present compound (Ia) may be prepared by reacting a compound represented by formula (M-22) (hereinafter, referred to as Compound (M-22)) with the compound (R-2) in the presence of a base and a reducing agent.

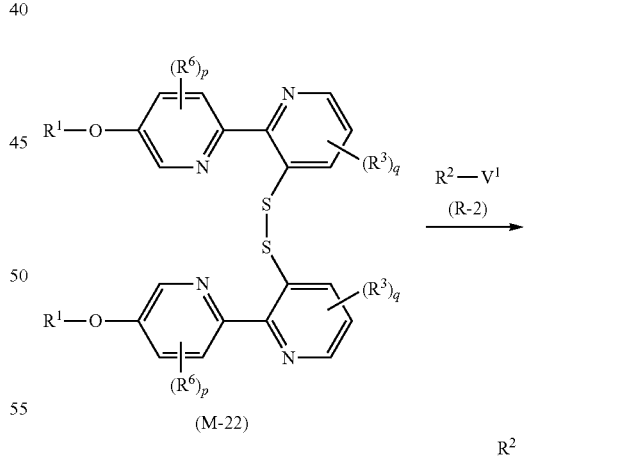

[wherein the symbols are the same as defined above.]

The reaction is usually carried out in a solvent.

Examples of the solvent to be used in the reaction include ethers, aromatic hydrocarbons, nitriles, and polar aprotic solvent.

Examples of the base to be used in the reaction include alkali metal carbonates, and alkali metal hydrides.

Examples of the reducing agent to be used in the reaction include hydroxymethanesulfinic acid sodium salt.

In the reaction, the compound (R-2) is usually used within a range of 1 to 10 molar ratio(s), the base is usually used within a range of 1 to 10 molar ratio(s), and the reducing agent is usually used within a range of 1 to 10 molar ratio(s), as opposed to 1 mole of the compound (M-22). Preferably, the compound (R-2) is usually used within a range of 1 to 1.1 molar ratio(s), the base is usually used within a range of 1 to 2 molar ratio(s), and the reducing agent is usually used within a range of 1 to 2 molar ratio(s), as opposed to 1 mole of the compound (M-22).

The reaction temperature is usually within a range of −20 to 150° C. The reaction period of the reaction is usually within a range of 0.1 to 24 hours.

When the reaction is completed, the reaction mixtures are extracted with organic solvents, and the resulting organic layers are worked up (for example, drying and concentration) to give the present compound (Ia).

Hereinafter, a process for preparing an intermediate compound is described.

Reference Process 1

The compound (M-1) may be prepared by reacting a compound represented by formula (M-8) (hereinafter referred to compound (M-8)) with a compound represented by formula (M-9) (hereinafter referred to compound (M-9)) in the presence of a metal catalyst.

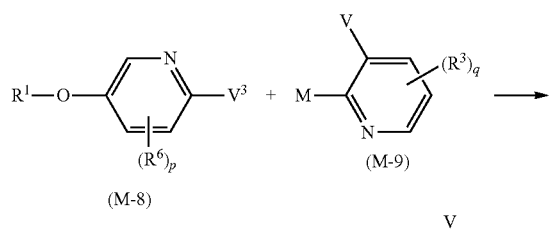

(M-8)     (M-9)

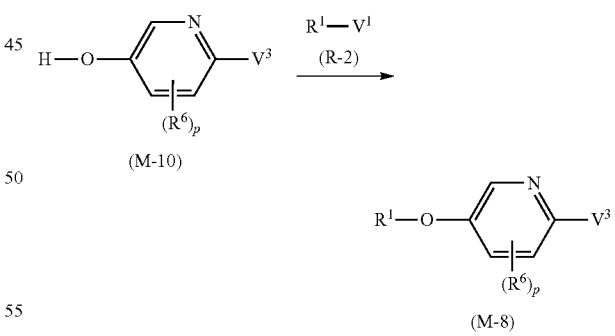

(M-1)

[wherein $V^3$ represents a chlorine atom, a bromine atom or an iodine atom; M represents $Sn(n-C_4H_9)_3$, ZnCl, or MgBr; and the other symbols are the same as defined above.]

The compound (M-9) may be prepared according to a similar method to that described in International Publication 03/024,961 or Organic Process Research & Development, 2004, 8, 192-200.

The reaction is usually carried out in a solvent.

Examples of the solvent to be used in the reaction include ethers, aromatic hydrocarbons, polar aprotic solvent, water, and mixed solvents thereof.

Examples of the metal catalyst to be used in the reaction include palladium catalysts such as tetrakis(triphenylphosphine)palladium(0), 1,1'-bis(diphenylphosphino)ferrocene palladium(II) chloride, tris(dibenzylideneacetone)dipalladium(0), and palladium(II) acetate; nickel catalysts such as bis(cyclooctadiene)nickel(0) and nickel(II) chloride; and copper catalyst such as copper(I) iodide and copper(I) chloride.

A ligand, a base and/or an inorganic halogenated compound may be added to the reaction as needed.

Examples of the ligand to be used in the reaction include triphenylphosphine, Xantphos, 2,2'-bis(diphenylphoshino)-1,1'-binaphthyl, 1,1'-bis(diphenylphoshino)ferrocene, 2-(dicyclohexylphosphino)-2',4',6'-triisopropyl-1,1'-biphenyl, 2-dicyclohexylphosphino-2',6'-dimethoxybiphenyl, 1,2-bis(diphenylphosphino)ethane, 2,2'-bipyridine, 2-aminoethanol, 8-hydroquinoline, and 1,10-phenanthroline.

Examples of the base to be used in the reaction include alkali metal hydrides, alkali metal carbonates, and organic bases.

Examples of the inorganic halogenated compounds include alkali metal fluorides such as potassium fluoride, and sodium fluoride; and alkali metal halides such as potassium chloride, and sodium chloride.

In the reaction, the compound (M-9) is usually used within a range of 1 to 10 molar ratio(s), the metal catalyst is usually used within a range of 0.01 to 0.5 molar ratios, the ligand is usually used within a range of 0.01 to 1 molar ratio(s), the base is usually used within a range of 0.1 to 5 molar ratios, and the inorganic halogenated compound is usually used within a range of 0.1 to 5 molar ratios, as opposed to 1 mole of the compound (M-8).

The reaction temperature is usually within a range of −20 to 200° C. The reaction period of the reaction is usually within a range of 0.1 to 24 hours.

When the reaction is completed, the reaction mixtures are extracted with organic solvent(s), and the organic solvents are worked up (for example, drying and concentration) to give the compound (M-1).

Reference Process 2

The compound (M-2) may be prepared by reacting a compound represented formula (M-10) (hereinafter, referred to Compound (M-10)) with the compound (R-2) in the presence of a base.

(M-10)

(M-8)

[wherein the symbols are the same as defined above.]

The reaction is usually carried out in a solvent.

Examples of the solvent to be used in the reaction include ethers, halogenated aliphatic hydrocarbons, aromatic hydrocarbons, polar aprotic solvent, and mixed solvents thereof.

Examples of the base to be used in the reaction include organic bases, alkali metal hydrides, and alkali metal carbonates.

In the reaction, the compound (R-2) is usually used within a range of 1 to 10 molar ratio(s), and the base is usually used within a range of 0.1 to 5 molar ratio(s), as opposed to 1 mole of the compound (M-10).

The reaction temperature is usually within a range of −20 to 120° C. The reaction period of the reaction is usually within a range of 0.1 to 24 hours.

When the reaction is completed, the reaction mixtures are extracted with organic solvent(s), and the organic solvents are worked up (for example, drying and concentration) to give the compound (M-8).

Reference Process 3

The compound (M-3) may be prepared by dealkylating a compound represented by formula (M-11) (hereinafter, referred to as Compound (M-11)) in the presence of an acid.

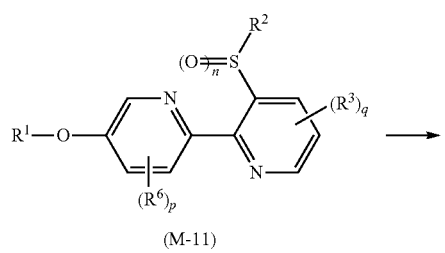

(M-11)

The reaction is usually carried out in a solvent.

Examples of a solvent to be used in the reaction include halogenated aliphatic hydrocarbons, aromatic hydrocarbons, nitriles, alcohols, acetic acid, water, and mixed solvents thereof.

Examples of the acid to be used in the reaction include mineral acids such as hydrochloric acid; boron halides such as boron chloride and boron bromide; metal chlorides such as titanium chloride, and aluminium chloride.

In the reaction, the acid is usually used within a range of 0.1 to 10 molar ratio(s) as opposed to 1 mole of the compound (M-11). In the reaction, when the mineral acids such as hydrochloric acid is used as the acid, the mineral acid may be used as a solvent.

The reaction temperature is usually within a range of −20 to 150° C. The reaction period of the reaction is usually within a range of 0.1 to 24 hours.

When the reaction is completed, the reaction mixtures are extracted with organic solvents, and the organic layers are worked up (for example, drying and concentration) to give the compound (M-3).

Reference Process 4

The compound (M-11) wherein n is 0 (hereinafter, referred to as Compound (M-11a)), the compound (M-11) wherein n is 1 (hereinafter, referred to as Compound (M-11b)), and the compound (M-11) wherein n is 2 (hereinafter, referred to as Compound (M-11c)) may be prepared according to a method described below.

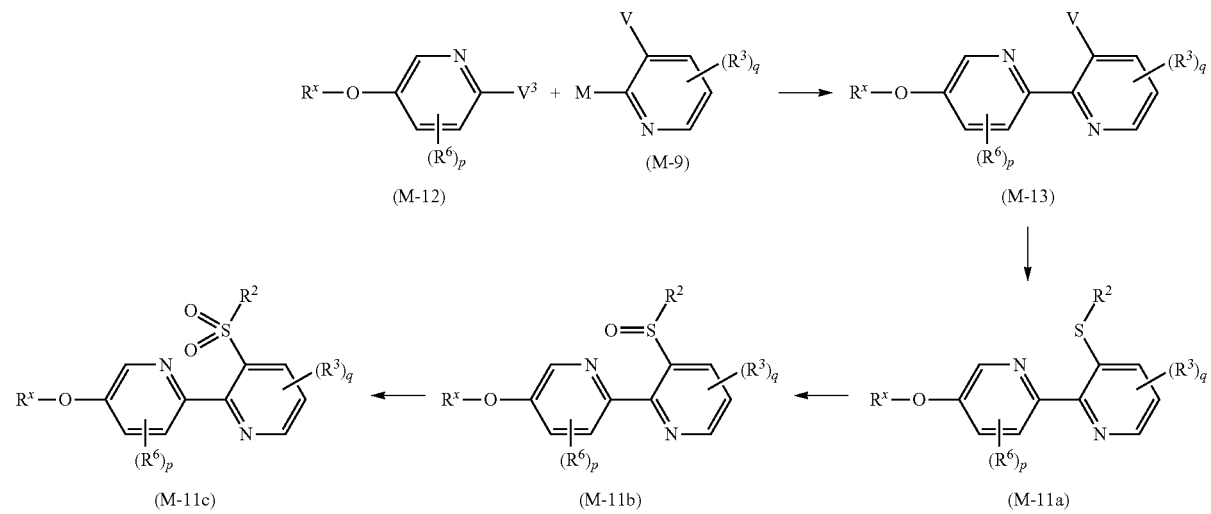

[wherein the symbols are the same as defined above.]

The compound (M-13) may be prepared by using a compound represented by formula (M-12) (hereinafter, referred to as Compound (M-12)) instead of the compound (M-8) according to the similar method to that described in Reference Process 1.

The compound (M-12) is a commercially available compound, or may be prepared according to the similar method described in that of Heterocycles, 1990, 30, 875 to 884.

The compound (M-11a) may be prepared by using the compound (M-13) instead of the compound (M-1) according to a method described in Process 3.

The compound (M-11b) and the compound (M-11c) may be prepared by using the compound (M-11a) instead of the compound (Ia) according to the similar method to that described in Process 1.

-continued

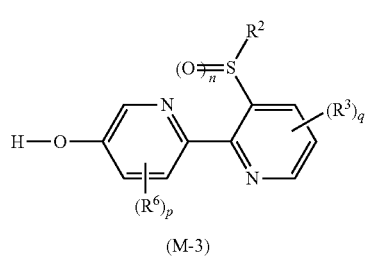

(M-3)

[wherein $R^x$ represents a methyl group or an ethyl group; and the other symbols are the same as defined above.]

Reference Process 5

A compound represented by formula (M-15) (hereinafter, Compound (M-15)) may be prepared according to the method described below.

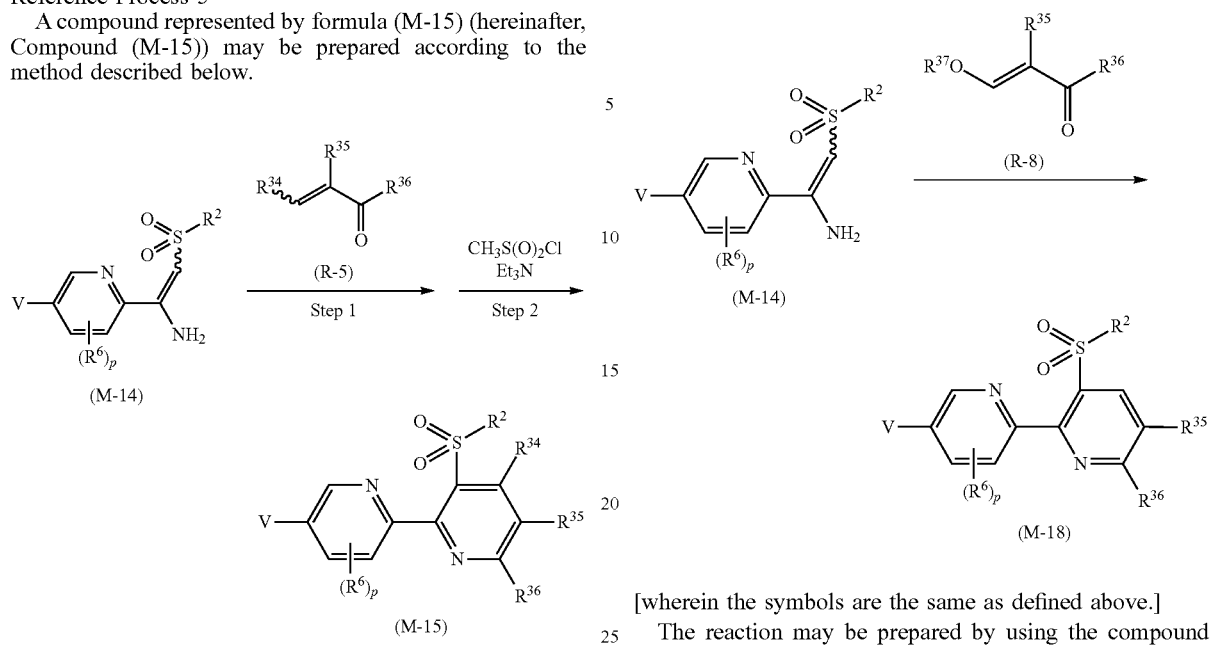

[wherein the symbols are the same as defined above.]

The reaction may be carried out by using a compound represented by formula (M-14) instead of the compound (M-15) according to the similar method to that described in Process 7.

Reference Process 6

A compound represented by formula (M-17) (hereinafter, referred to as Compound (M-17)) may be prepared by reacting a compound represented by formula (M-16) (hereinafter, referred to as Compound (M-16)) with the compound (R-12) followed by reacting the reaction mixtures with ammonia.

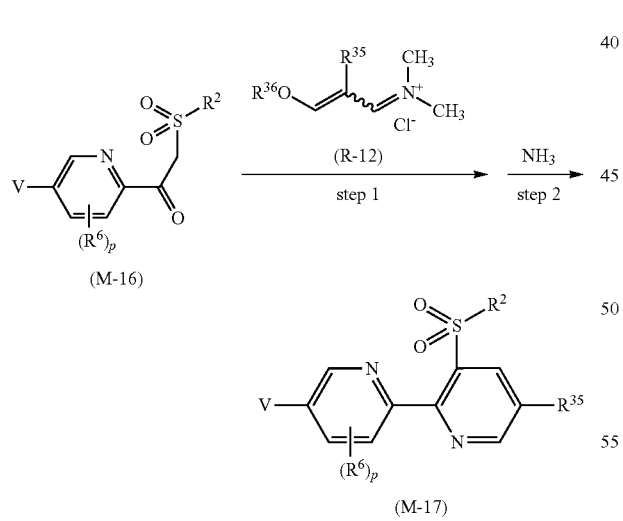

[wherein the symbols are the same as defined above.]

The reaction may be carried out by using the compound (M-16) instead of the compound (M-7) according to the similar method to that described in Process 9.

Reference Process 7

A compound represented by formula (M-18) (hereinafter, referred to as Compound (M-18)) may be prepared by reacting the compound (M-14) with the compound (R-8).

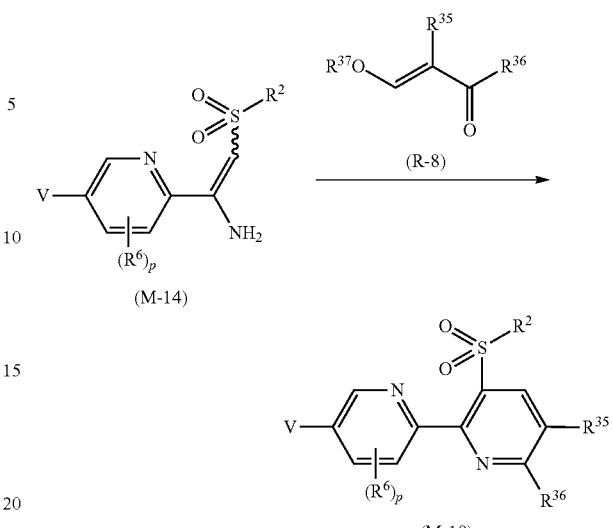

[wherein the symbols are the same as defined above.]

The reaction may be prepared by using the compound (M-14) instead of the compound (M-5) according to the similar method to that described in Process 10.

Reference Process 8

A compound represented by formula (M-19) (hereinafter, referred to as Compound (M-19)) may be prepared by reacting a compound represented by formula (M-20) (hereinafter, referred to as Compound (20)) in the presence of an acid.

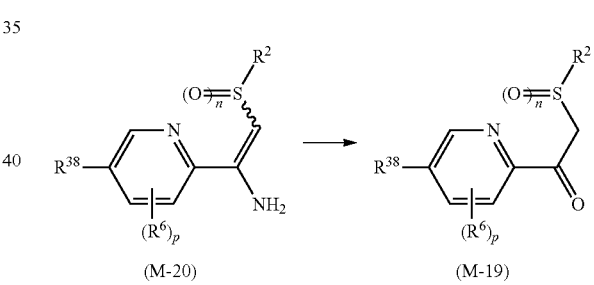

[wherein $R^{38}$ represents a halogen atom, or a $OR^1$, and the other symbols are the same as defined above.]

The reaction is usually carried out in a solvent.

Examples of the solvent to be used in the reaction include ethers, aromatic hydrocarbons, nitriles, alcohols, polar aprotic solvent, water, and mixed solvents thereof.

Examples of the acid to be used in the reaction include hydrochloric acid, sulfuric acid, trifluoroacetic acid, and acetic acid.

In the reaction, the acid is usually used within a range of 0.1 to 5 molar ratio(s) as opposed to 1 mole of the compound (M-18).

The reaction temperature is usually within a range of 0 to 100° C. The reaction period of the reaction is usually within a range of 0.5 to 12 hours.

When the reaction is completed, the reaction mixtures are extracted with organic solvents, and the organic layers are worked up (for example, drying and concentration) to give the compound (M-19). The obtained Compound (M-19) may be purified by chromatography and recrystallization.

Reference Process 9

The compound (M-20) may be prepared by reacting a compound represented by formula (M-21) (hereinafter, referred to as Compound (M-21)) with a compound represented by formula (R-16) (hereinafter, referred to as Compound (R-16)) in the presence of a base.

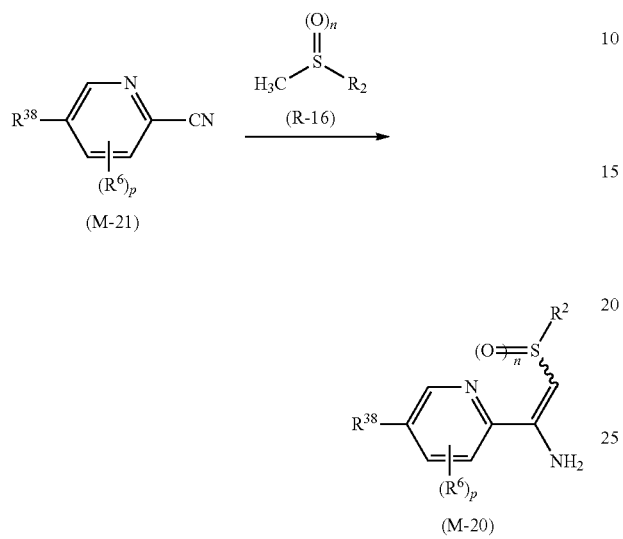

(M-21)

(R-16)

(M-20)

[wherein the symbols are the same as defined above.]

The reaction is usually carried out in a solvent.

Examples of the solvent to be used in the reaction include ethers, aromatic hydrocarbons, polar aprotic solvent, and mixed solvents thereof.

Examples of the base to be used in the reaction include n-butyl lithium, s-butyl lithium, t-butyl lithium, lithium diisopropylamide, sodium bis(trimethylsilyl)amide, potassium bis(trimethylsilyl)amide, potassium t-butoxide, and alkali metal hydrides.

In the reaction, the compound (R-16) is usually used within a range of 1 to 5 molar ratio(s), and the base is usually used within a range of 1 to 5 molar ratio(s), as opposed to 1 mole of the compound (M-21). Preferably, the compound (R-16) is usually used within a range of 1 to 1.1 molar ratio(s), and the base is usually used within a range of 1 to 2 molar ratio(s), as opposed to 1 mole of the compound (M-21).

The reaction temperature is usually within a range of −78 to 100° C. The reaction period of the reaction is usually within a range of 0.5 to 12 hours.

When the reaction is completed, the reaction mixtures are extracted with organic solvents, and the organic layers are worked up (for example, drying and concentration) to give the compound (M-20).

The obtained compound (M-19) may be further purified by chromatography and/or recrystallization.

The compound (M-20) is a commercially available compound or may be prepared by known methods.

Reference Process 10 The compound (M-2) and the compound (M-22) may be prepared according to a method described below.

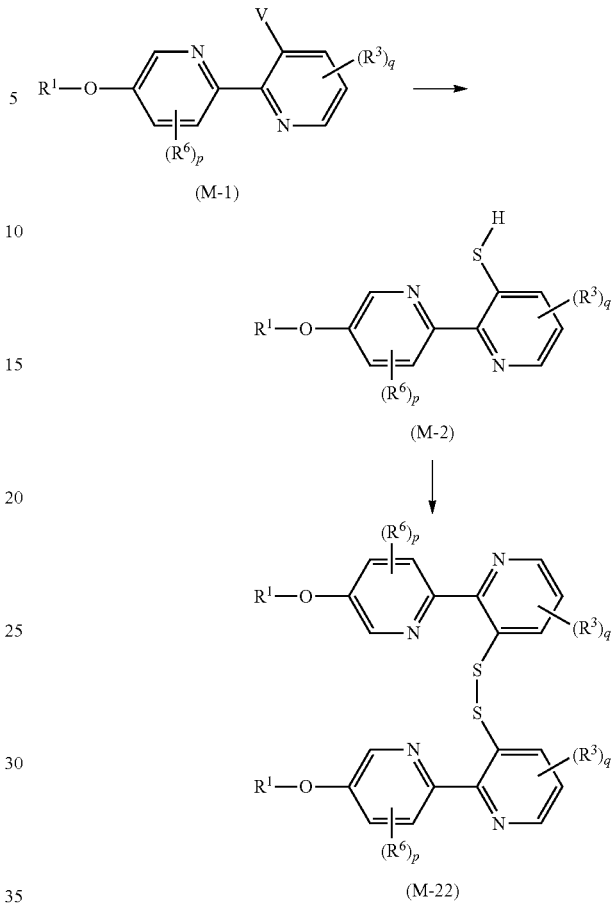

(M-1)

(M-2)

(M-22)

[wherein the symbols are the same as defined above.]

First, a method for preparing the compound (M-2) is described.

The compound (M-2) may be prepared by reacting the compound (M-1) with sulfating agent.

The reaction is usually carried out in a solvent.

Examples of the solvents to be used in the reaction include ethers, aromatic hydrocarbons, nitriles, polar aprotic solvent, and mixed solvents thereof.

Examples of the sulfating agent to be used in the reaction include sodium sulfide and sodium hydrogen sulfide.

In the reaction, the sulfating agent is usually used within a range of 1 to 10 molar ratio(s) as opposed to 1 mole of the compound (M-1).

The reaction temperature is usually within a range of −20 to 150° C. The reaction period of the reaction is usually within a range of 0.5 to 24 hours.

When the reaction is completed, the reaction mixtures are extracted with organic solvents, and the organic layers are worked up (for example, drying and concentration) to give the compound (M-2).

In the reaction, V is preferably a fluorine atom or a chlorine atom.

Next, a method for preparing the compound (M-22) is described.

The compound (M-22) may be prepared by reacting the compound (M-2) with an oxidizing agent.

The reaction is usually carried out in a solvent.

Examples of the solvent to be used in the reaction include ethers, aromatic hydrocarbons, nitriles, polar aprotic solvent, water, and mixed solvents thereof.

Examples of the oxidizing agent to be used in the reaction include oxygen, aqueous hydrogen peroxide, and potassium ferrocyanide.

A base may be added to the reaction as needed.

Examples of the base to be used in the reaction include alkali metal carbonates, alkali metal hydrides, and alkali metal hydroxides.

In the reaction, the oxidizing agent is usually used within a range of 1 to 100 molar ratio(s), and the base is usually used within a range of 1 to 10 molar ratio(s), as opposed to 1 mole of the compound (M-2). When oxygen is used as the oxidizing agent, oxygen that is present in air may be used as the oxidizing agent.

The reaction temperature is usually within a range of −20 to 150° C. The reaction period of the reaction is usually within a range of 0.5 to 24 hours.

When the reaction is completed, the reaction mixtures are extracted with organic solvents, and the organic layers are worked up (for example, drying and concentration) to give the compound (M-22).

Reference Process 11

The compound (M-4) wherein V represents a chlorine atom or a bromine atom (hereinafter, referred to as Compound (M-4a)) and the compound (M-4) (wherein V represents a fluorine atom or an iodine atom) (hereinafter, referred to as Compound (M-4b)) may be prepared according to the method described below.

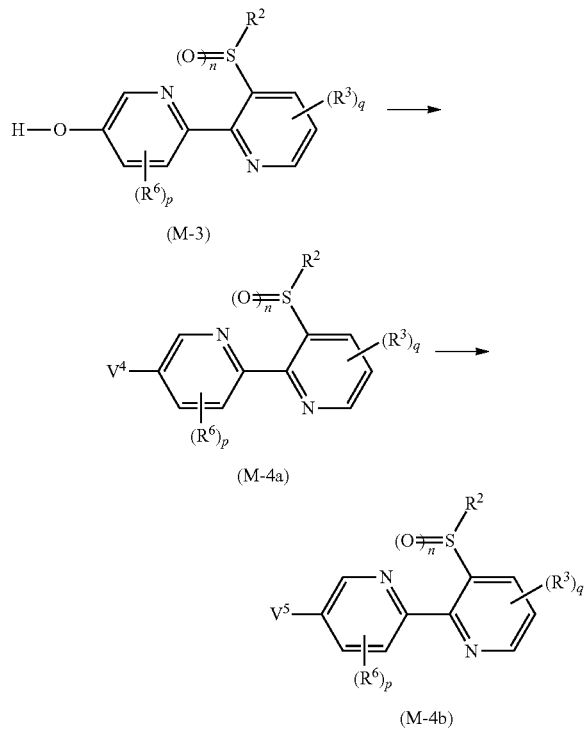

(M-3)

(M-4a)

(M-4b)

[wherein $V^4$ represents a chlorine atom or a bromine atom, $V^5$ represents a fluorine atom or an iodine atom; and the other symbols are the same as defined above.]

First, a method for preparing the compound (M-4a) from the compound (M-3) is described.

The compound (M-4a) may be prepared by reacting the compound (M-3) with phosphoryl chloride or phosphoryl bromide.

The reaction is usually carried out in a solvent.

Examples of the solvent to be used in the reaction include aromatic hydrocarbons. When phosphoryl chloride is used, phosphoryl chloride may be also used as a solvent.

In the reaction, phosphoryl chloride or phosphoryl bromide is usually used within a range of 1 to 10 molar ratio(s) as opposed to 1 mole of the compound (M-3).

The reaction temperature is usually within a range of 0 to 150° C. The reaction period of the reaction is usually within a range of 0.5 to 24 hours.

When the reaction is completed, the reaction mixtures are extracted with organic solvents, and the organic layers are worked up (for example, drying and concentration) to give the compound (M-4a).

Next, a method for preparing the compound (M-4b) from the compound (M-4a) is described.

The compound (4-b) may be prepared by reacting the compound (M-4a) with inorganic fluoride compound, or by reacting the compound (M-4a) with inorganic iodide compound.

Examples of the solvents to be used in the reaction include nitriles, polar aprotic solvent, nitrogen-containing aromatic compounds, and mixed solvents thereof.

Examples of the inorganic fluoride compound to be used in the reaction include potassium fluoride, sodium fluoride and cesium fluoride.

Examples of the inorganic iodide compound to be used in the reaction include potassium iodide and sodium iodide.

When the compound (M-4b) wherein $V^5$ represents a fluorine atom is prepared, the inorganic fluoride compound is usually used within a range of 1 to 10 molar ratio(s) as opposed to 1 mole of the compound (M-4a).

When the compound (M-4b) wherein $V^5$ represents an iodine atom is prepared, the inorganic iodide compound is usually within a range of 1 to 10 molar ratio(s) as opposed to 1 mole of the compound (M-4a).

The reaction temperature is usually within a range of 0 to 250° C. The reaction period of the reaction is usually within a range of 0.5 to 24 hours.

When the reaction is completed, the reaction mixtures are extracted with organic solvents, and the organic layers are worked up (for example, drying and concentration) to give the compound (M-4b).

Next, specific examples of the compound of the present invention are indicated below.

a compound represented by formula (200):

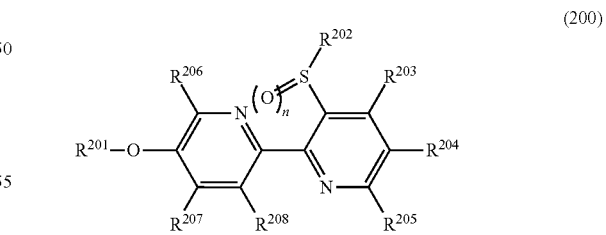

(200)

[wherein, $R^{201}$ represents $R^1$; $R^{202}$ represents $R^2$; $R^{203}$, $R^{204}$, and $R^{205}$ represent independently of each other a hydrogen atom, or $R^3$; $R^{206}$, $R^{207}$, and $R^{208}$ represent independently of each other a hydrogen atom, or $R^6$; and n is 0, 1, or 2.]

a compound represented by formula (200) wherein n is 2, each of $R^{203}$, $R^{204}$, $R^{205}$, $R^{206}$, $R^{207}$, and $R^{208}$ is a hydrogen atom, and $R^{201}$ and $R^{22}$ represent any combination of the groups indicated in Table 1 to Table 11.

TABLE 1

| $R^{201}$ | $R^{202}$ |
|---|---|
| $CF_2HCH_2$ | $CH_3CH_2$ |
| $CH_3CF_2$ | $CH_3CH_2$ |
| $CF_3CH_2$ | $CH_3CH_2$ |
| $CCl_3CH_2$ | $CH_3CH_2$ |
| $CF_2HCF_2$ | $CH_3CH_2$ |
| $CHClFCF_2$ | $CH_3CH_2$ |
| $CF_3CH_2CH_2$ | $CH_3CH_2$ |
| $CF_2HCF_2CH_2$ | $CH_3CH_2$ |
| $CF_3CF_2CH_2$ | $CH_3CH_2$ |
| $CBrF_2CF_2$ | $CH_3CH_2$ |
| $CF_3CFHCF_2$ | $CH_3CH_2$ |
| $CH_3CF_2CH_2$ | $CH_3CH_2$ |
| $CF_3CH(CH_3)$ | $CH_3CH_2$ |
| $CF_3C(CH_3)_2$ | $CH_3CH_2$ |
| $CH(CH_3)_2CH(CF_3)$ | $CH_3CH_2$ |
| $(CF_3)_2CH$ | $CH_3CH_2$ |
| $CH_3CH_2CH(CF_3)$ | $CH_3CH_2$ |
| $CF_3CCl_2CH_2$ | $CH_3CH_2$ |
| $CF_3CF_2CH(CH_3)$ | $CH_3CH_2$ |
| $CF_3CF_3CH(CH_2CH_3)$ | $CH_3CH_2$ |
| $C(CH_3)(CF_3)_2CH_2$ | $CH_3CH_2$ |
| $CF_3CFHCF_2CH_2$ | $CH_3CH_2$ |
| $CF_3(CF_2)_2CH_2$ | $CH_3CH_2$ |
| $CBrF_2CF_2CH_2CH_2$ | $CH_3CH_2$ |
| $CF_3CFHCF_2CH(CH_3)$ | $CH_3CH_2$ |

TABLE 2

| $R^{201}$ | $R^{202}$ |
|---|---|
| $CF_3CH=CHCH_2$ | $CH_3CH_2$ |
| $CF_3(CF_2)_3CH_2$ | $CH_3CH_2$ |
| $CF_3(CF_2)_4CH_2$ | $CH_3CH_2$ |
| $CF_3(CF_2)_3CH_2CH_2$ | $CH_3CH_2$ |
| $CF(CF_3)_2CF_2CF_2CH_2CH_2$ | $CH_3CH_2$ |
| $CF_2H(CF_2)_3CH_2$ | $CH_3CH_2$ |
| $CF_2H(CF_2)_5CH_2$ | $CH_3CH_2$ |
| $CF_3(CF_2)_3CH_2CH_2CH_2$ | $CH_3CH_2$ |
| $CF_3CF_2(CH_2)_5CH_2$ | $CH_3CH_2$ |
| $CF_3(CF_2)_5CH_2CH_2CH_2$ | $CH_3CH_2$ |
| $CF_3(CF_2)_3CH_2(CH_2)_4CH_2$ | $CH_3CH_2$ |
| $CF_3(CF_2)_5CH_2CH_2$ | $CH_3CH_2$ |
| $CF(CF_3)_2CH_2(CH_2)_4CH_2$ | $CH_3CH_2$ |
| $CF_3OCFHCF_2$ | $CH_3CH_2$ |
| $CH_3OCH_2CF_2CH_2$ | $CH_3CH_2$ |
| $CF_3CH_2OCH_2CF_2CH_2$ | $CH_3CH_2$ |
| $CH_2FCF_2CH_2$ | $CH_3CH_2$ |
| $CH_2ClCF_2CH_2$ | $CH_3CH_2$ |
| $CH_2BrCF_2CH_2$ | $CH_3CH_2$ |
| $CH_3OCH_2(CF_2)_2CH_2$ | $CH_3CH_2$ |
| $CF_3CH_2OCH_2(CF_2)_2CH_2$ | $CH_3CH_2$ |
| $CH_2F(CF_2)_2CH_2$ | $CH_3CH_2$ |
| $CH_2Cl(CF_2)_2CH_2$ | $CH_3CH_2$ |
| $CH_2Br(CF_2)_2CH_2$ | $CH_3CH_2$ |
| $CH_3OCH_2(CF_2)_3CH_2$ | $CH_3CH_2$ |

TABLE 3

| $R^{201}$ | $R^{202}$ |
|---|---|
| $CF_3CH_2OCH_2(CF_2)_3CH_2$ | $CH_3CH_2$ |
| $CH_3OCH_2(CF_2)_3CH_2$ | $CH_3CH_2$ |
| $CF_3CH_2OCH_2(CF_2)_3CH_2$ | $CH_3CH_2$ |
| $CH_2F(CF_2)_3CH_2$ | $CH_3CH_2$ |
| $CH_2Cl(CF_2)_3CH_2$ | $CH_3CH_2$ |
| $CH_2Br(CF_2)_3CH_2$ | $CH_3CH_2$ |
| $CH_3OCH_2(CF_2)_4CH_2$ | $CH_3CH_2$ |
| $CF_3CH_2OCH_2(CF_2)_4CH_2$ | $CH_3CH_2$ |
| $CH_2F(CF_2)_4CH_2$ | $CH_3CH_2$ |
| $CH_2Cl(CF_2)_4CH_2$ | $CH_3CH_2$ |
| $CH_2Br(CF_2)_4CH_2$ | $CH_3CH_2$ |
| $CF_3CF_2OCFHCF_2$ | $CH_3CH_2$ |
| $CF_3CF_2CF_2OCFHCF_2$ | $CH_3CH_2$ |

TABLE 3-continued

| $R^{201}$ | $R^{202}$ |
|---|---|
| $CF_3CF_2CF_2OCF(CF_3)CH_2$ | $CH_3CH_2$ |
| $CF_3CH_2OCH_2CH_2$ | $CH_3CH_2$ |

TABLE 4

| $R^{201}$ | $R^{202}$ |
|---|---|
| 2,2-difluorocyclopropylmethyl | $CH_3CH_2$ |
| 2-(trifluoromethyl)cyclopropylmethyl | $CH_3CH_2$ |
| (perfluorocyclohexyl)ethyl | $CH_3CH_2$ |
| (2,2,3,3-tetrafluorocyclobutyl)methyl | $CH_3CH_2$ |
| (4,4-difluorocyclohexyl)methyl | $CH_3CH_2$ |
| (4-(trifluoromethyl)cyclohexyl)methyl | $CH_3CH_2$ |
| (3-(trifluoromethyl)cyclohexyl)methyl | $CH_3CH_2$ |

TABLE 5

| $R_{201}$ | $R^{202}$ |
|---|---|
| $CH_3SCH_2CF_2CH_2$ | $CH_3CH_2$ |
| $CH_3S(O)CH_2CF_2CH_2$ | $CH_3CH_2$ |
| $CH_3S(O)_2CH_2CF_2CH_2$ | $CH_3CH_2$ |
| $CF_3CH_2SCH_2CF_2CH_2$ | $CH_3CH_2$ |
| $CF_3CH_2S(O)CH_2CF_2CH_2$ | $CH_3CH_2$ |
| $CF_3CH_2S(O)_2CH_2CF_2CH_2$ | $CH_3CH_2$ |
| $CF_3SCH_2CF_2CH_2$ | $CH_3CH_2$ |
| $CF_3S(O)CH_2CF_2CH_2$ | $CH_3CH_2$ |
| $CF_3S(O)_2CH_2CF_2CH_2$ | $CH_3CH_2$ |
| $CF_3SCH_2(CF_2)_2CH_2$ | $CH_3CH_2$ |
| $CF_3S(O)CH_2(CF_2)_2CH_2$ | $CH_3CH_2$ |
| $CF_3S(O)_2CH_2(CF_2)_2CH_2$ | $CH_3CH_2$ |
| $CF_3SCH_2(CF_2)_3CH_2$ | $CH_3CH_2$ |
| $CF_3S(O)CH_2(CF_2)_3CH_2$ | $CH_3CH_2$ |

TABLE 5-continued

| $R_{201}$ | $R^{202}$ |
|---|---|
| $CF_3S(O)_2CH_2(CF_2)_3CH_2$ | $CH_3CH_2$ |
| $CF_3SCH_2(CF_2)_4CH_2$ | $CH_3CH_2$ |
| $CF_3S(O)CH_2(CF_2)_4CH_2$ | $CH_3CH_2$ |
| $CF_3S(O)_2CH_2(CF_2)_4CH_2$ | $CH_3CH_2$ |
| $CF_3CH_2SCH_2CH_2$ | $CH_3CH_2$ |
| $CF_3CH_2S(O)CH_2CH_2$ | $CH_3CH_2$ |
| $CF_3CH_2S(O)_2CH_2CH_2$ | $CH_3CH_2$ |
| $CF_3SCH_2CH_2$ | $CH_3CH_2$ |
| $CF_3S(O)CH_2CH_2$ | $CH_3CH_2$ |
| $CF_3S(O)_2CH_2CH_2$ | $CH_3CH_2$ |

TABLE 6

| $R^{201}$ | $R^{202}$ |
|---|---|
| $CF_2HCF_2CH_2$ | $CH_3$ |
| $CF_3CF_2CH_2$ | $CH_3$ |
| $CBrF_2CF_2$ | $CH_3$ |
| $CF_3CFHCF_2$ | $CH_3$ |
| $CH_3CF_2CH_2$ | $CH_3$ |
| $CF_3CH(CH_3)$ | $CH_3$ |
| $CF_3C(CH_3)_2$ | $CH_3$ |
| $CH(CH_3)_2CH(CF_3)$ | $CH_3$ |
| $(CF_3)_2CH$ | $CH_3$ |
| $CH_3CH_2CH(CF_3)$ | $CH_3$ |
| $CF_3CCl_2CH_2$ | $CH_3$ |
| $CF_3CF_2CH(CH_3)$ | $CH_3$ |
| $CF_3CF_2CH(CH_2CH_3)$ | $CH_3$ |
| $C(CH_3)(CF_3)_2CH_2$ | $CH_3$ |
| $CF_3CFHCF_2CH_2$ | $CH_3$ |
| $CF_3(CF_2)_2CH_2$ | $CH_3$ |
| $CBrF_2CF_2CH_2CH_2$ | $CH_3$ |
| $CF_3CFHCF_2CH(CH_3)$ | $CH_3$ |

TABLE 7

| $R^{201}$ | $R^{202}$ |
|---|---|
| $CF_3(CF_2)_3CH_2$ | $CH_3$ |
| $CF_3(CF_2)_4CH_2$ | $CH_3$ |
| $CF_3(CF_2)_3CH_2CH_2$ | $CH_3$ |
| $CF(CF_3)_2CF_2CF_2CH_2CH_2$ | $CH_3$ |
| $CF_2H(CF_2)_3CH_2$ | $CH_3$ |
| $CF_3OCFHCF_2$ | $CH_3$ |
| $CH_3OCH_2CF_2CH_2$ | $CH_3$ |
| $CF_3CH_2OCH_2CF_2CH_2$ | $CH_3$ |
| $CH_2FCF_2CH_2$ | $CH_3$ |
| $CH_2ClCF_2CH_2$ | $CH_3$ |
| $CH_2BrCF_2CH_2$ | $CH_3$ |
| $CH_3OCH_2(CF_2)_2CH_2$ | $CH_3$ |
| $CF_3CH_2OCH_2(CF_2)_2CH_2$ | $CH_3$ |
| $CH_2F(CF_2)_2CH_2$ | $CH_3$ |
| $CH_2Cl(CF_2)_2CH_2$ | $CH_3$ |
| $CH_2Br(CF_2)_2CH_2$ | $CH_3$ |
| $CH_3OCH_2(CF_2)_3CH_2$ | $CH_3$ |

TABLE 8

| $R^{201}$ | $R^{202}$ |
|---|---|
| $CF_3CH_2OCH_2(CF_2)_3CH_2$ | $CH_3$ |
| $CH_3OCH_2(CF_2)_3CH_2$ | $CH_3$ |
| $CF_3CH_2OCH_2(CF_2)_3CH_2$ | $CH_3$ |
| $CH_2F(CF_2)_3CH_2$ | $CH_3$ |
| $CH_2Cl(CF_2)_3CH_2$ | $CH_3$ |
| $CH_2Br(CF_2)_3CH_2$ | $CH_3$ |
| $CH_3OCH_2(CF_2)_4CH_2$ | $CH_3$ |
| $CF_3CH_2OCH_2(CF_2)_4CH_2$ | $CH_3$ |
| $CH_2F(CF_2)_4CH_2$ | $CH_3$ |
| $CH_2Cl(CF_2)_4CH_2$ | $CH_3$ |
| $CH_2Br(CF_2)_4CH_2$ | $CH_3$ |

TABLE 8-continued

| $R^{201}$ | $R^{202}$ |
|---|---|
| $CF_3CF_2OCFHCF_2$ | $CH_3$ |
| $CF_3CF_2CF_2OCFHCF_2$ | $CH_3$ |
| $CF_3CF_2CF_2OCF(CF_3)CH_2$ | $CH_3$ |
| $CF_3CH_2OCH_2CH_2$ | $CH_3$ |

TABLE 9

| $R^{201}$ | $R^{202}$ |
|---|---|
| $CF_2HCF_2CH_2$ | $CF_3CH_2$ |
| $CF_3CF_2CH_2$ | $CF_3CH_2$ |
| $CBrF_2CF_2$ | $CF_3CH_2$ |
| $CF_3CFHCF_2$ | $CF_3CH_2$ |
| $CH_3CF_2CH_2$ | $CF_3CH_2$ |
| $CF_3CH(CH_3)$ | $CF_3CH_2$ |
| $CF_3C(CH_3)_2$ | $CF_3CH_2$ |
| $CH(CH_3)_2CH(CF_3)$ | $CF_3CH_2$ |
| $(CF_3)_2CH$ | $CF_3CH_2$ |
| $CH_3CH_2CH(CF_3)$ | $CF_3CH_2$ |
| $CF_3CCl_2CH_2$ | $CF_3CH_2$ |
| $CF_3CF_2CH(CH_3)$ | $CF_3CH_2$ |
| $CF_3CF_2CH(CH_2CH_3)$ | $CF_3CH_2$ |
| $C(CH_3)(CF_3)_2CH_2$ | $CF_3CH_2$ |
| $CF_3CFHCF_2CH_2$ | $CF_3CH_2$ |
| $CF_3(CF_2)_2CH_2$ | $CF_3CH_2$ |
| $CBrF_2CF_2CH_2CH_2$ | $CF_3CH_2$ |
| $CF_3CFHCF_2CH(CH_3)$ | $CF_3CH_2$ |

TABLE 10

| $R^{201}$ | $R^{202}$ |
|---|---|
| $CF_3(CF_2)_3CH_2$ | $CF_3CH_2$ |
| $CF_3(CF_2)_4CH_2$ | $CF_3CH_2$ |
| $CF_3(CF_2)_3CH_2CH_2$ | $CF_3CH_2$ |
| $CF(CF_3)_2CF_2CF_2CH_2CH_2$ | $CF_3CH_2$ |
| $CF_2H(CF_2)_3CH_2$ | $CF_3CH_2$ |
| $CF_3OCFHCF_2$ | $CF_3CH_2$ |
| $CH_3OCH_2CF_2CH_2$ | $CF_3CH_2$ |
| $CF_3CH_2OCH_2CF_2CH_2$ | $CF_3CH_2$ |
| $CH_2FCF_2CH_2$ | $CF_3CH_2$ |
| $CH_2ClCF_2CH_2$ | $CF_3CH_2$ |
| $CH_2BrCF_2CH_2$ | $CF_3CH_2$ |
| $CH_3OCH_2(CF_2)_2CH_2$ | $CF_3CH_2$ |
| $CF_3CH_2OCH_2(CF_2)_2CH_2$ | $CF_3CH_2$ |
| $CH_2F(CF_2)_2CH_2$ | $CF_3CH_2$ |
| $CH_2Cl(CF_2)_2CH_2$ | $CF_3CH_2$ |
| $CH_2Br(CF_2)_2CH_2$ | $CF_3CH_2$ |
| $CH_3OCH_2(CF_2)_3CH_2$ | $CF_3CH_2$ |

TABLE 11

| $R^{201}$ | $R^{202}$ |
|---|---|
| $CF_3CH_2OCH_2(CF_2)_3CH_2$ | $CF_3CH_2$ |
| $CH_3OCH_2(CF_2)_3CH_2$ | $CF_3CH_2$ |
| $CF_3CH_2OCH_2(CF_2)_3CH_2$ | $CF_3CH_2$ |
| $CH_2F(CF_2)_3CH_2$ | $CF_3CH_2$ |
| $CH_2Cl(CF_2)_3CH_2$ | $CF_3CH_2$ |
| $CH_2Br(CF_2)_3CH_2$ | $CF_3CH_2$ |
| $CH_3OCH_2(CF_2)_4CH_2$ | $CF_3CH_2$ |
| $CF_3CH_2OCH_2(CF_2)_4CH_2$ | $CF_3CH_2$ |
| $CH_2F(CF_2)_4CH_2$ | $CF_3CH_2$ |
| $CH_2Cl(CF_2)_4CH_2$ | $CF_3CH_2$ |
| $CH_2Br(CF_2)_4CH_2$ | $CF_3CH_2$ |
| $CF_3CF_2OCFHCF_2$ | $CF_3CH_2$ |
| $CF_3CF_2CF_2OCFHCF_2$ | $CF_3CH_2$ |
| $CF_3CF_2CF_2OCF(CF_3)CH_2$ | $CF_3CH_2$ |
| $CF_3CH_2OCH_2CH_2$ | $CF_3CH_2$ | a compound of the present invention represented by formula (200) wherein n is 1, each of $R^{203}$, $R^{204}$, $R^{205}$, $R^{206}$, $R^{207}$, and $R^{208}$ is a hydrogen atom, and $R^{201}$ and $R^{202}$ represent any combination of the groups indicated in [Table 1] to [Table 11];

a compound of the present invention represented by formula (200) wherein n is 0, each of $R^{203}$, $R^{204}$, $R^{205}$, $R^{206}$, $R^{207}$, and $R^{208}$ is a hydrogen atom, and $R^{201}$ and $R^{202}$ represent any combination of the groups indicated in [Table 1] to [Table 11];

a compound of the present invention represented by formula (200) wherein n is 2, $R^{201}$ represents a 2,2,3,3-tetrafluoropropyl group, $R^{202}$ represents an ethyl group, and $R^{203}$, $R^{204}$, $R^{205}$, $R^{206}$, $R^{207}$, and $R^{208}$ represent any combination of the groups indicated in [Table 12] to [Table 19];

TABLE 12

| $R^{206}$ | $R^{207}$ | $R^{208}$ | $R^{203}$ | $R^{204}$ | $R^{205}$ |
|---|---|---|---|---|---|
| H | H | H | H | $CH_2CH=CH_2$ | H |
| H | H | H | $OCH_3$ | H | H |
| H | H | H | H | $OCH_3$ | H |
| H | H | H | H | H | $OCH_3$ |
| H | H | H | H | $OCF_3$ | H |
| H | H | H | H | $SCF_3$ | H |
| H | H | H | H | $C(O)CF_3$ | H |
| H | H | H | H | $S(O)_2CF_3$ | H |
| H | H | H | Cl | H | H |
| H | H | H | H | Cl | H |
| H | H | H | H | H | Cl |
| H | H | H | $CF_3$ | H | H |
| H | H | H | $CF_2CF_3$ | H | H |
| H | H | H | $CF_2CF_2CF_3$ | H | H |
| H | H | H | $CF(CF_3)_2$ | H | H |
| H | H | H | H | $CF_3$ | H |
| H | H | H | H | $CF_2CF_3$ | H |
| H | H | H | H | $CF_2CF_2CF_3$ | H |
| H | H | H | H | $CF(CF_3)_2$ | H |
| H | H | H | H | H | $CF_3$ |
| H | H | H | H | H | $CF_2CF_3$ |
| H | H | H | H | H | $CF_2CF_2CF_3$ |
| H | H | H | H | H | $CF(CF_3)_2$ |

TABLE 13

| $R^{206}$ | $R^{207}$ | $R^{208}$ | $R^{203}$ | $R^{204}$ | $R^{205}$ |
|---|---|---|---|---|---|
| H | H | H | $NH_2$ | H | H |
| H | H | H | $NHCH_3$ | H | H |
| H | H | H | $N(CH_3)_2$ | H | H |
| H | H | H | $NHCH_2CF_3$ | H | H |
| H | H | H | H | $NH_2$ | H |
| H | H | H | H | $NHCH_3$ | H |
| H | H | H | H | $N(CH_3)_2$ | H |
| H | H | H | H | $NHCH_2CF_3$ | H |
| H | H | H | H | H | $NH_2$ |
| H | H | H | H | H | $NHCH_3$ |
| H | H | H | H | H | $N(CH_3)_2$ |
| H | H | H | H | H | $NHCH_2CF_3$ |
| H | H | H | H | $CF_3$ | $OCH_3$ |
| H | H | H | H | $CF_3$ | Cl |
| H | H | H | H | $CF_3$ | $NH_2$ |
| H | H | H | H | $CF_3$ | $NHCH_3$ |
| H | H | H | H | $CF_3$ | $N(CH_3)_2$ |

TABLE 14

| $R^{206}$ | $R^{207}$ | $R^{208}$ | $R^{203}$ | $R^{204}$ | $R^{205}$ |
|---|---|---|---|---|---|
| H | H | H | $NHC(O)CH_3$ | H | H |
| H | H | H | $NHNHC(O)CH_3$ | H | H |
| H | H | H | $NHC(O)OCH_3$ | H | H |

TABLE 14-continued

| $R^{206}$ | $R^{207}$ | $R^{208}$ | $R^{203}$ | $R^{204}$ | $R^{205}$ |
|---|---|---|---|---|---|
| H | H | H | $NHNHC(O)OCH_3$ | H | H |
| H | H | H | $NHC(O)N(CH_3)_2$ | H | H |
| H | H | H | $NHNHC(O)N(CH_3)_2$ | H | H |
| H | H | H | $N=CHN(CH_3)_2$ | H | H |
| H | H | H | $N=S(CH_3)_2$ | H | H |
| H | H | H | $N=S(O)(CH_3)_2$ | H | H |
| H | H | H | $C(O)OCH_3$ | H | H |
| H | H | H | $C(O)NH_2$ | H | H |
| H | H | H | $C(O)NHCH_3$ | H | H |

TABLE 15

| $R^{206}$ | $R^{207}$ | $R^{208}$ | $R^{203}$ | $R^{204}$ | $R^{205}$ |
|---|---|---|---|---|---|
| H | H | H | H | $NHC(O)CH_3$ | H |
| H | H | H | H | $NHNHC(O)CH_3$ | H |
| H | H | H | H | $NHC(O)OCH_3$ | H |
| H | H | H | H | $NHNHC(O)OCH_3$ | H |
| H | H | H | H | $NHC(O)N(CH_3)_2$ | H |
| H | H | H | H | $NHNHC(O)N(CH_3)_2$ | H |
| H | H | H | H | $N=CHN(CH_3)_2$ | H |
| H | H | H | H | $N=S(CH_3)_2$ | H |
| H | H | H | H | $N=S(O)(CH_3)_2$ | H |
| H | H | H | H | $C(O)OCH_3$ | H |
| H | H | H | H | $C(O)NH_2$ | H |
| H | H | H | H | $C(O)NHCH_3$ | H |

TABLE 16

| $R^{206}$ | $R^{207}$ | $R^{208}$ | $R^{203}$ | $R^{204}$ | $R^{205}$ |
|---|---|---|---|---|---|
| H | H | H | H | H | $NHC(O)CH_3$ |
| H | H | H | H | H | $NHNHC(O)CH_3$ |
| H | H | H | H | H | $NHC(O)OCH_3$ |
| H | H | H | H | H | $NHNHC(O)OCH_3$ |
| H | H | H | H | H | $NHC(O)N(CH_3)_2$ |
| H | H | H | H | H | $NHNHC(O)N(CH_3)_2$ |
| H | H | H | H | H | $N=CHN(CH_3)_2$ |
| H | H | H | H | H | $N=S(CH_3)_2$ |
| H | H | H | H | H | $N=S(O)(CH_3)_2$ |
| H | H | H | H | H | $C(O)OCH_3$ |
| H | H | H | H | H | $C(O)NH_2$ |
| H | H | H | H | H | $C(O)NHCH_3$ |
| H | H | H | H | H | 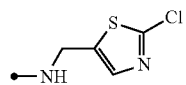 |
| H | H | H | H | H | 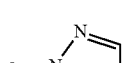 |
| H | H | H | H | H | 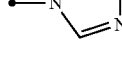 |
| H | H | H | H | H | 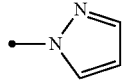 |

TABLE 17
| R206 | R207 | R208 | R203 | R204 | R205 |
|---|---|---|---|---|---|
| H | H | H | H | 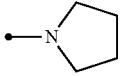 | H |
| H | H | H | H | 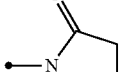 | H |
| H | H | H | H | 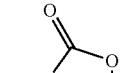 | H |
| H | H | H | H | 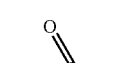 | H |
| H | H | H | H | 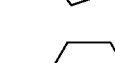 | H |
| H | H | H | H | H | 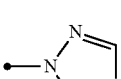 |
| H | H | H | H | H | 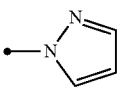 |
| H | H | H | H | H | 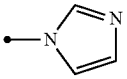 |
| H | H | H | H | H | 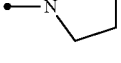 |
| H | H | H | H | H | 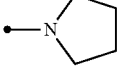 |
| H | H | H | H | H | 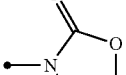 |
| H | H | H | H | H | 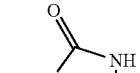 |
| H | H | H | H | H | 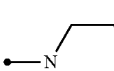 |
TABLE 18
| R206 | R207 | R208 | R203 | R204 | R205 |
|---|---|---|---|---|---|
| H | H | H | H | 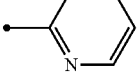 | H |
| H | H | H | H | 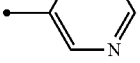 | H |
| H | H | H | H | 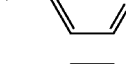 | H |
| H | H | H | H | 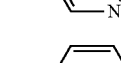 | H |
| H | H | H | H | 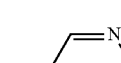 | H |
| H | H | H | H | 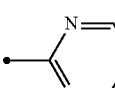 | H |
| H | H | H | H | 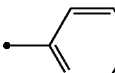 | H |
| H | H | H | H |  | H |
| H | H | H | H | H |  |
| H | H | H | H | H |  |
| H | H | H | H | H |  |
| H | H | H | H | H |  |
| H | H | H | H | H |  |
| H | H | H | H | H |  |
| H | H | H | H | H |  |

TABLE 18-continued

| $R^{206}$ | $R^{207}$ | $R^{208}$ | $R^{203}$ | $R^{204}$ | $R^{205}$ |
|---|---|---|---|---|---|
| H | H | H | H | H | ●—⟨pyrimidinyl⟩ |

TABLE 19

| $R^{206}$ | $R^{207}$ | $R^{208}$ | $R^{203}$ | $R^{204}$ | $R^{205}$ |
|---|---|---|---|---|---|
| H | H | H | H | $CF_3$ | ●—NH—CH₂—⟨2-chlorothiazol-5-yl⟩ |
| H | H | H | H | $CF_3$ | ●—N⟨1,2,4-triazol-1-yl⟩ |
| Cl | H | H | H | H | H |
| $CH_3$ | H | H | H | H | H |
| OH | H | H | H | H | H |
| $OCH_3$ | H | H | H | H | H |
| $OC(O)CH_3$ | H | H | H | H | H |
| CN | H | H | H | H | H |
| H | Cl | H | H | H | H |
| H | $CH_3$ | H | H | H | H |
| H | H | Cl | H | H | H |
| H | H | $CH_3$ | H | H | H | a compound of the present invention represented by formula (200) wherein n is 2, $R^{201}$ represents a 2,2,3,3,3-pentafluoropropyl group, $R^{202}$ represents an ethyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (200) wherein n is 2, $R^{201}$ represents a 1,1,2,3,3,3-hexafluoropropyl group, $R^{202}$ represents an ethyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (200) wherein n is 2, $R^{201}$ represents a 2,2,3,4,4,4-hexafluorobutyl group, $R^{202}$ represents an ethyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (200) wherein n is 2, $R^{201}$ represents a 1,1,2-trifluoro-2-(trifluoromethoxy)ethyl group, $R^{202}$ represents an ethyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (200) wherein n is 2, $R^{201}$ represents a 2,2,3,3-tetrafluoropropyl group, $R^{202}$ represents a methyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (200) wherein n is 2, $R^{201}$ represents a 2,2,3,3,3-pentafluoropropyl group, $R^{202}$ represents a methyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (200) wherein n is 2, $R^{201}$ represents a 1,1,2,3,3,3-hexafluoropropyl group, $R^{202}$ represents a methyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (200) wherein n is 2, $R^{201}$ represents a 2,2,3,4,4,4-hexafluorobutyl group, $R^{202}$ represents a methyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (200) wherein n is 2, $R^{201}$ represents a 1,1,2-trifluoro-2-(trifluoromethoxy)ethyl group, $R^{202}$ represents a methyl group, and $R^{203}$, $R^{204}$, $R^{205}$, $R^{206}$, $R^{207}$, and $R^{208}$ represent any combination of the groups indicated in [Table 12] to [Table 19];

a compound represented by formula (201):

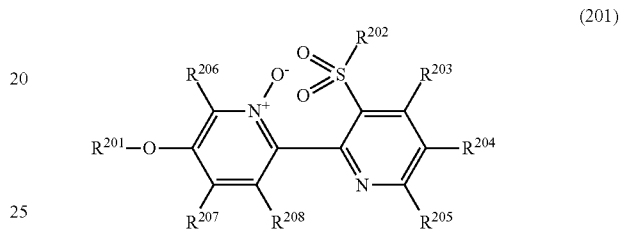

(201)

[wherein the symbols are the same as defined above.];

a compound of the present invention represented by formula (201) wherein each of $R^{203}$, $R^{204}$, $R^{205}$, $R^{206}$, $R^{207}$, and $R^{208}$ represent a hydrogen atom, and $R^{201}$ and $R^{202}$ represent any combination of the groups indicated in [Table 1] to [Table 11];

a compound of the present invention represented by formula (201) wherein n is 2, $R^{201}$ represents a 2,2,3,3-tetrafluoropropyl group, R represents an ethyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (201) wherein n is 2, $R^{201}$ represents a 2,2,3,3,3-pentafluoropropyl group, $R^{202}$ represents an ethyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (201) wherein n is 2, $R^{201}$ represents a 1,1,2,3,3,3-hexafluoropropyl group, $R^{202}$ represents an ethyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (201) wherein n is 2, $R^{201}$ represents a 2,2,3,4,4,4-hexafluorobutyl group, $R^{202}$ represents an ethyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (201) wherein n is 2, $R^{201}$ represents a 1,1,2-trifluoro-2-(trifluoromethoxy)ethyl group, $R^{202}$ represents an ethyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (201) wherein n is 2, $R^{201}$ represents a 2,2,3,3-tetrafluoropropyl group, $R^{202}$ represents a methyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (201) wherein n is 2, $R^{201}$ represents a 2,2,3,3,3-pentafluoropropyl group, $R^{202}$ represents a methyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (201) wherein n is 2, $R^{201}$ represents a 1,1,2,3,3,3-hexafluoropropyl group, $R^{202}$ represents a methyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (201) wherein n is 2, $R^{201}$ represents a 2,2,3,4,4,4-hexafluorobutyl group, $R^{202}$ represents a methyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (201) wherein n is 2, $R^{201}$ represents a 1,1,2-trifluoro-2-(trifluoromethoxy)ethyl group, $R^{202}$ represents a ethyl group, and $R^{203}$, $R^{204}$, $R^{205}$, $R^{206}$, $R^{207}$, and $R^{208}$ represent any combination of the groups indicated in [Table 12] to [Table 19];

a compound represented by formula (202):

(202)

[wherein the symbols are the same as defined above];

a compound of the present invention represented by formula (202) wherein each of $R^{203}$, $R^{204}$, $R^{205}$, $R^{206}$, $R^{207}$, and $R^{208}$ represents a hydrogen atom, and $R^{201}$ and $R^{202}$ represent any combination of the groups indicated in [Table 1] to [Table 11];

a compound of the preset invention represented by formula (202) wherein n is 2, $R^{201}$ represents a 2,2,3,3-tetrafluoropropyl group, R represents an ethyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (202) wherein n is 2, $R^{201}$ represents a 2,2,3,3,3-pentafluoropropyl group, $R^{202}$ represents an ethyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (202) wherein n is 2, $R^{201}$ represents a 1,1,2,3,3,3-hexafluoropropyl group, $R^{202}$ represents an ethyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (202) wherein n is 2, $R^{201}$ represents a 2,2,3,4,4,4-hexafluorobutyl group, $R^{202}$ represents an ethyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (202) wherein n is 2, $R^{201}$ represents a 1,1,2-trifluoro-2-(trifluoromethoxy)ethyl group, $R^{202}$ represents an ethyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (202) wherein n is 2, $R^{201}$ represents a 2,2,3,3-tetrafluoropropyl group, $R^{202}$ represents a methyl group, and $R^{203}$, $R^{204}$, $R^{205}$, $R^{206}$, $R^{207}$, and $R^{208}$ represent a combination of the groups indicated in [Table 12] to [Table 19];

a compound of the present invention represented by formula (202) wherein n is 2, $R^{201}$ represents a 2,2,3,3,3-pentafluoropropyl group, $R^{202}$ represents a methyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (202) wherein n is 2, $R^{201}$ represents a 1,1,2,3,3,3-hexafluoropropyl group, $R^{202}$ represents a methyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (202) wherein n is 2, $R^{201}$ represents a 2,2,3,4,4,4-hexafluorobutyl group, $R^{202}$ represents a methyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (202) wherein n is 2, $R^{201}$ represents a 1,1,2-trifluoro-2-(trifluoromethoxy)ethyl group, $R^{202}$ represents a methyl group, and $R^{203}$, $R^{204}$, $R^{205}$, $R^{206}$, $R^{207}$, and $R^{208}$ represent any combination of the groups indicated in [Table 12] to [Table 19];

a compound represented by formula (203):

(203)

[wherein the symbols are the same as defined above];

a compound of the present invention represented by formula (203) wherein each of $R^{203}$, $R^{204}$, $R^{205}$, $R^{206}$, $R^{207}$, and $R^{208}$ represent a hydrogen atom, and $R^{201}$ and $R^{202}$ represent any combination of the groups indicated in [Table 1] to [Table 11];

a compound of the present invention represented by formula (203) wherein n is 2, $R^{201}$ represents a 2,2,3,3-tetrafluoropropyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (203) wherein n is 2, $R^{201}$ represents a 2,2,3,3,3-pentafluoropropyl group, $R^{202}$ represents an ethyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (203) wherein n is 2, $R^{201}$ represents a 1,1,2,3,3,3-hexafluoropropyl group, $R^{202}$ represents an ethyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (203) wherein n is 2, $R^{201}$ represents a 2,2,3,4,4,4-hexafluorobutyl group, $R^{202}$ represents an ethyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (203) wherein n is 2, $R^{201}$ represents a 1,1,2- trifluoro-2-(trifluoromethoxy)ethyl group, $R^{202}$ represents an ethyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (203) wherein n is 2, $R^{201}$ represents a 2,2,3,3-tetrafluoropropyl group, $R^{202}$ represents a methyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (203) wherein n is 2, $R^{201}$ represents a 2,2,3,3,3-pentafluoropropyl group, $R^{202}$ represents a methyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (203) wherein n is 2, $R^{201}$ represents a 1,1,2,3,3,3-hexafluoropropyl group, $R^{202}$ represents a methyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (203) wherein n is 2, $R^{201}$ represents a 2,2,3,4,4,4-hexafluorobutyl group, $R^{202}$ represents a methyl group, and $R^{203}$, $R^{204}$, $R^{205}$, $R^{206}$, $R^{207}$, and $R^{208}$ represent any combination of the groups indicated in [Table 12] to [Table 19];

a compound of the present invention represented by formula (203) wherein n is 2, $R^{201}$ represents a 1,1,2-trifluoro-2-(trifluoromethoxy)ethyl group, $R^{202}$ represents a methyl group, and $R^{203}$, $R^{204}$, $R^{205}$, $R^{206}$, $R^{207}$, and $R^{208}$ represent any combination of the groups indicated in [Table 12] to [Table 19].

Examples of the compound (M-1) include the following compounds.

a compound represented by formula (M-1):

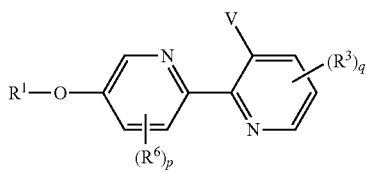

(M-1)

[wherein, V represents a halogen atom, and $R^1$, $R^3$, $R^6$, q, and p are the same as defined in formula (I)]

a compound (M-1) wherein V represents a halogen atom, $R^1$ represents a C2-C10 haloalkyl group, or a (C1-C5 alkoxy)C2-C5 alkyl group having one or more halogen atoms, q is 0, 1, 2, or 3, $R^3$ represents a C1-C6 chain hydrocarbon group optionally having one or more halogen atoms, a 5 or 6 membered aromatic heterocyclic group optionally having one or more substituents selected from Group D, a $OR^{12}$, a $NR^{11}R^{12}$, a $NR^{24}NR^{11}R^{12}$, or a halogen atom, p is 0, 1, 2, or 3, RE represents a C1-C6 alkyl group optionally having one or more halogen atoms, a $OR^{18}$, a $NR^{18}R^{19}$, a $C(O)OR^{25}$, a $OC(O)R^{20}$, a cyano group, a nitro group, or a halogen atom;

a compound (M-1) wherein V represents a fluorine atom or a chlorine atom, $R^1$ represents a C2-C10 haloalkyl group, or a (C1-C5 alkoxy)C2-C5 alkyl group having one or more halogen atoms, q is 0, 1, 2 or 3, $R^3$ represents a C1-C6 chain hydrocarbon group optionally having one or more halogen atoms, or a halogen atom, p is 0, 1, 2, or 3, and $R^6$ represents a C1-C6 alkyl group optionally having one or more halogen atoms, or a halogen atom;

a compound (M-1) wherein V represents a fluorine atom or a chlorine atom, $R^1$ represents a C2-C10 fluoroalkyl group having two or more fluorine atoms, q is 0, 1, 2, or 3, $R^3$ represents a C1-C6 chain hydrocarbon group optionally having one or more halogen atoms, or a halogen atom, and p is 0;

a compound (M-1) wherein V represents a fluorine atom, $R^1$ represents a C2-C10 haloalkyl group, or a (C1-C5 alkoxy)C2-C5 alkyl group having one or more halogen atoms, q is 0, and p is 0;

a compound (M-1) wherein V represents a fluorine atom or a chlorine atom, $R^1$ represents a C2-C6 alkyl group having two or more fluorine atoms, q is 0, 1, 2, or 3, $R^3$ represents a C1-C6 chain hydrocarbon group optionally having one or more halogen atoms, or a halogen atom, and p is 0; and a compound (M-1) wherein V represents a fluorine atom or a chlorine atom, $R^1$ represents a 2,2,2-trifluoroethyl group, a 2,2,3,3-tetrafluoropropyl group, a 2,2,3,3,3-pentafluoropropyl group, a 1,1,2,3,3,3-hexafluoropropyl group, a 1,1,2-trifluoro-2-(trifluoromethoxy)ethyl group, or a 2,2,3,4,4,4-hexafluorobutyl group, q is 0 or 1, $R^1$ represents a trifluoromethyl group, and p is 0.

Examples of compound (M-2) include the following compounds.

a compound represented by formula (M-2):

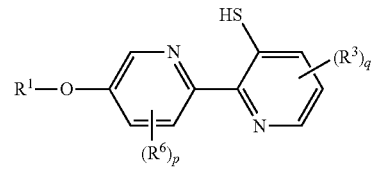

(M-2)

[wherein $R^1$, $R^3$, $R^6$, q and p are the same as defined in formula (I)]

a compound (M-2) wherein $R^1$ represents a C2-C10 haloalkyl group, or a (C1-C5 alkoxy)C2-C5 alkyl group having one or more halogen atoms, q is 0, 1, 2 or 3, $R^3$ represents a C1-C6 chain hydrocarbon group optionally having one or more halogen atoms, a 5 or 6 membered aromatic heterocyclic group having one or more substituents selected from Group D, a $OR^{12}$, a $NR^{11}R^{12}$, a $NR^{24}NR^{11}NR^{12}$, or a halogen atom, p is 0, 1, 2, or 3, and $R^6$ represents a C1-C6 alkyl group optionally having one or more halogen atoms, a $OR^{18}$, a $NR^{18}R^{19}$, a $C(O)OR^{25}$, a $OC(O)R^{20}$, a cyano group, a nitro group, or a halogen atom;

a compound (M-2) wherein $R^1$ represents a C2-C10 haloalkyl group, or a (C1-C5 alkoxy)C2-C5 alkyl group having one or more halogen atoms, q is 0, 1, 2 or 3, $R^3$ represents a C1-C6 chain hydrocarbon group optionally having one or more halogen atoms, or a halogen atom, p is 0, 1, 2, or 3, and $R^6$ represents a C1-C6 alkyl group optionally having one or more halogen atoms, or a halogen atom;

a compound (M-2) wherein $R^1$ represents a C2-C10 fluoroalkyl group having two or more fluorine atoms, q is 0, 1, 2 or 3, $R^1$ represents a C1-C6 chain hydrocarbon group optionally having one or more halogen atoms, or a halogen atom, and p is 0;

a compound (M-2) wherein $R^1$ represents a C2-C10 haloalkyl group, q is 0, and p is 0;

a compound (M-2) wherein $R^1$ represents a C2-C6 alkyl group having two or more fluorine atoms, q is 0, 1, 2 or 3, $R^3$ represents a C1-C6 chain hydrocarbon group optionally having one or more halogen atoms, or a halogen atom, and p is 0;

a compound (M-2) wherein $R^1$ represents a 2,2,2-trifluoroethyl group, a 2,2,3,3-tetrafluoropropyl group, a 2,2,3,3,3-pentafluoropropyl group, a 1,1,2,3,3,3-hexafluoropropyl group, a 1,1,2-trifluoro-2-(trifluoromethoxy)ethyl group, or a 2,2,3,4,4,4-hexafluorobutyl group, q is 0 or 1, $R^3$ represents a trifluoromethyl group, and p is 0.

Examples of the compound (M-3) include the following compounds.

a compound represented by formula (M-3):

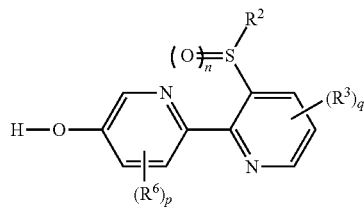

(M-3)

[wherein $R^2$, $R^3$, $R^6$, q, and p are the same as defined in formula (I)];

a compound (M-3) wherein $R^2$ represents a C1-C6 alkyl group optionally having one or more halogen atoms, q is 0, 1, 2 or 3, $R^3$ represents a C1-C6 chain hydrocarbon group optionally having one or more halogen atoms, a 5 or 6 membered aromatic heterocyclic group optionally having one or more substituents selected from Group D, a $OR^{12}$, a $NR^{11}R^{12}$, a $NR^{24}NR^{11}R^{12}$, or a halogen atom, p is 0, 1, 2, or 3, $R^6$ represents a C1-C6 alkyl group optionally having one or more halogen atoms, a $OR^{18}$, a $NR^{18}R^{19}$, a $C(O)OR^{25}$, a $OC(O)R^{20}$, a cyano group, a nitro group, or a halogen atom;

a compound (M-3) wherein $R^2$ represents an ethyl group, q is 0, 1, 2 or 3, $R^2$ represents a C1-C6 chain hydrocarbon group optionally having one or more halogen atoms, or a halogen atom, p is 0, 1, 2, or 3, and $R^6$ represents a C1-C6 alkyl group optionally having one or more halogen atoms, or a halogen atom;

a compound (M-2) wherein $R^2$ represents an ethyl group, q is 0, and p is 0.

Examples of the compound (M-4) include the following compounds.

a compound represented by formula (M-4):

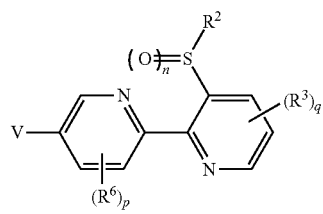

(M-4)

[wherein V represents a halogen atom, and $R^2$, $R^3$, $R^6$, q, and p are the same as defined in formula (I)];

a compound (M-4) wherein V represents a halogen atom, $R^2$ represents a C1-C6 alkyl group optionally having one or more halogen atoms, q is 0, 1, 2 or 3, $R^3$ represents a C1-C6 chain hydrocarbon group optionally having one or more halogen atoms, a 5 or 6 membered aromatic heterocyclic group optionally having one or more substituents selected from Group D, a $OR^{12}$, a $NR^{11}R^{12}$, a $NR^{24}NR^{11}R^{12}$, or a halogen atom, p is 0, 1, 2, or 3, $R^6$ represents a C1-C6 alkyl group optionally having one or more halogen atoms, a $OR^{18}$, a $NR^{18}R^{19}$, a $C(O)OR^{25}$, a $OC(O)R^{20}$, a cyano group, a nitro group, or a halogen atom;

a compound (M-4) wherein V represents a fluorine atom, a chlorine atom, or a bromine atom, $R^2$ represents an ethyl group, q is 0, 1, 2 or 3, $R^3$ represents a C1-C6 chain hydrocarbon group optionally having one or more halogen atoms, or a halogen atom, p is 0, 1, 2, or 3, $R^6$ represents a C1-C6 alkyl group optionally having one or more halogen atoms, or a halogen atom;

a compound (M-4) wherein V represents a fluorine atom, a chlorine atom, or a bromine atom, $R^2$ represents an ethyl group, q is 0, and p is 0.

Examples of the compound (M-19) include the following compounds.

a compound represented by formula (M-19):

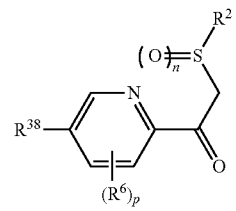

(M-19)

[wherein $R^{38}$ represents V, or $OR^1$, V represents a halogen atom, and $R^1$, $R^2$, $R^6$, and p are the same as defined in formula (I)];

a compound (M-19) wherein $R^P$ represents a halogen atom, or a $OR^1$, $R^1$ represents a C2-C10 haloalkyl group, or a (C1-C5 alkoxy)C2-C5 alkyl group having one or more halogen atoms, $R^2$ represents a C1-C6 alkyl group optionally having one or more halogen atoms, p is 0, 1, 2, or 3, $R^6$ represents a C1-C6 alkyl group optionally having one or more halogen atoms, a $OR^{18}$, a $NR^{18}R^{19}$, a $C(O)OR^{25}$, a $OC(O)R^{20}$, a cyano group, a nitro group, or a halogen atom;

a compound (M-19) wherein $R^{38}$ represents a halogen atom, $R^2$ represents a C1-C6 alkyl group optionally having one or more halogen atoms, p is 0, 1, 2, or 3, $R^6$ represents a C1-C6 alkyl group optionally having one or more halogen atoms, a $OR^{18}$, a $NR^{18}R^{19}$, a $C(O)OR^{25}$, a $OC(O)R^{20}$, a cyano group, a nitro group, or a halogen atom;

a compound (M-19) wherein $R^{38}$ represents a $OR^1$, $R^1$ represents a C2-C10 haloalkyl group, or a (C1-C5 alkoxy)C2-C5 alkyl group having one or more halogen atoms, $R^2$ represents an ethyl group, p is 0, 1, 2, or 3, $R^6$ represents a C1-C6 alkyl group optionally having one or more halogen atoms, a $OR^{18}$, a $NR^{18}R^{19}$, a $C(O)OR^{25}$, a $OC(O)R^{20}$, a cyano group, a nitro group, or a halogen atom;

a compound (M-19) wherein $R^{38}$ represents a $OR^1$, $R^1$ represents a C2-C10 haloalkyl group having two or more fluorine atoms, or a (C1-C5 alkoxy)C2-C5 alkyl group having one or more halogen atoms, $R^2$ represents an ethyl group, n is 2, and p is 0;

a compound (M-19) wherein $R^{18}$ represents a $OR^1$, $R^1$ represents a 2,2,2-trifluoroethyl group, a 2,2,3,3-tetrafluoropropyl group, a 2,2,3,3,3-pentafluoropropyl group, a 1,1,2,3,3,3-hexafluoropropyl group, a 1,1,2-trifluoro-2-(trifluoromethoxy)ethyl group, or a 2,2,3,4,4,4-hexafluorobutyl group, $R^2$ represents an ethyl group, n is 2, and p is 0;

a compound (M-19) wherein $R^{38}$ represents V, V represents a fluorine atom or a chlorine atom, $R^2$ represents an ethyl group, n is 2, and p is 0.

Examples of the compound (M-20) include the following compounds.

a compound represented by formula (M-20):

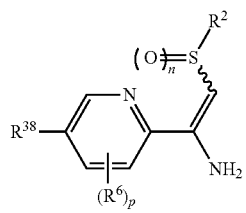

(M-20)

[wherein $R^{38}$ represents V, or $OR^1$, V represents a halogen atom, and $R^1$, $R^2$, $R^6$, and p are the same as defined in formula (I)];

a compound (M-20) wherein $R^{38}$ represents a halogen atom, or a $OR^1$, $R^1$ represents a C2-C10 haloalkyl group, or a (C1-C5 alkoxy)C2-C5 alkyl group having one or more halogen atoms, $R^2$ represents a C1-C6 alkyl group optionally having one or more halogen atoms, p is 0, 1, 2, or 3, $R^6$ represents a C1-C6 alkyl group optionally having one or more halogen atoms, a $OR^{18}$, a $NR^{18}R^{19}$, a $C(O)OR^{25}$, a $OC(O)R^{20}$, a cyano group, a nitro group, or a halogen atom;

a compound (M-20) wherein $R^{38}$ represents a halogen atom, $R^2$ represents a C1-C6 alkyl group optionally having one or more halogen atoms, p is 0, 1, 2, or 3, $R^6$ represents a C1-C6 alkyl group optionally having one or more halogen atoms, a $OR^{18}$, a $NR^{18}R^{19}$, a $C(O)OR^{25}$, a $OC(O)R^{20}$, a cyano group, a nitro group, or a halogen atom;

a compound (M-20) wherein $R^{38}$ represents a $OR^1$, $R^1$ represents a C2-C10 haloalkyl group, or a (C1-C5 alkoxy) C2-C5 alkyl group having one or more halogen atoms, $R^2$ represents an ethyl group, p is 0, 1, 2, or 3, $R^6$ represents a C1-C6 alkyl group optionally having one or more halogen atoms, a $OR^{18}$, a $NR^{18}R^{19}$, a $C(O)OR^{25}$, a $OC(O)R^{20}$, a cyano group, a nitro group, or a halogen atom;

a compound (M-20) wherein $R^{38}$ represents a $OR^1$, $R^1$ represents a C2-C10 haloalkyl group having two or more fluorine atoms, $R^2$ represents an ethyl group, p is 0;

a compound (M-20) wherein $R^{38}$ represents a $OR^1$, $R^1$ represents a 2,2,2-trifluoroethyl group, a 2,2,3,3-tetrafluoropropyl group, a 2,2,3,3,3-pentafluoropropyl group, a 1,1,2,3,3,3-hexafluoropropyl group, a 1,1,2-trifluoro-2-(trifluoromethoxy)ethyl group, or a 2,2,3,4,4,4-hexafluorobutyl group, $R^2$ represents an ethyl group, n is 2, and p is 0; and a compound (M-20) wherein $R^{38}$ represents V, V represents a chlorine atom or a bromine atom, $R^2$ represents an ethyl group, and p is 0.

Examples of the compound (M-22) include the following compounds.

a compound represented by formula (M-22):

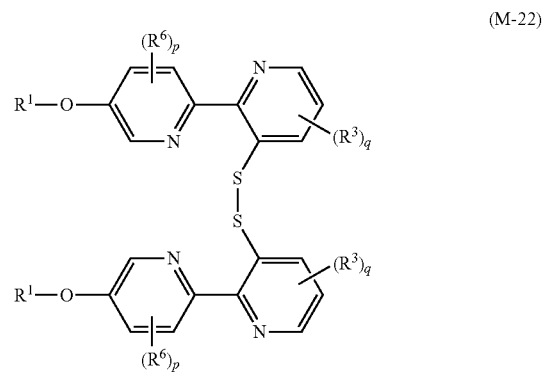

(M-22)

[wherein $R^1$, $R^3$, $R^6$, q, and p are the same as defined in formula (I)]

a compound (M-22) wherein $R^1$ represents a C2-C10 haloalkyl group, or a (C1-C5 alkoxy)C2-C5 alkyl group having one or more halogen atoms, q is 0, 1, 2 or 3, $R^3$ represents a C1-C6 chain hydrocarbon group optionally having one or more halogen atoms, a 5 or 6 membered aromatic heterocyclic group optionally having one or more substituents selected from Group D, a $OR^{12}$, a $NR^{11}R^{12}$, a $NR^{24}NR^{11}R^{12}$, or a halogen atom, p is 0, 1, 2, or 3, $R^6$ represents a C1-C6 alkyl group optionally having one or more halogen atoms, a $OR^{18}$, a $NR^{18}R^{19}$, a $C(O)OR^{25}$, a $OC(O)R^{20}$, a cyano group, a nitro group, or a halogen atom;

a compound (M-22) wherein $R^1$ represents a C2-C10 haloalkyl group, or a (C1-C5 alkoxy)C2-C5 alkyl group having one or more halogen atoms, q is 0, 1, 2 or 3, $R^3$ represents a C1-C6 chain hydrocarbon group optionally having one or more halogen atoms, or a halogen atom, p is 0, 1, 2, or 3, $R^6$ represents a C1-C6 alkyl group optionally having one or more halogen atoms, or a halogen atom; and a compound (M-22) wherein $R^1$ represents a C2-C10 haloalkyl group, q is 0, and p is 0.

Examples of the harmful arthropods on which a compound of the present invention has a control efficacy include harmful insects and harmful mites. Specific examples of the harmful arthropods are as follows:

Hemiptera Pests:

Delphacidae (for example, *Laodelphax striatellus, Nilaparvata lugens, Sogatella furcifera*, or *Peregrinus maidis*), Deltocephalidae (for example, *Nephotettix cincticeps, Nephotettix virescens, Nephotettix nigropictus* (Rice green leafhopper), *Recilia dorsalis, Empoasca onukii, Empoasca fabae, Dalbulus maidis, Mahanarva posticata* (Sugarcane froghopper), *Mahanarva fimbriolata* (Sugarcane root spittlebug), *Cofana spectra*, or *Nephotettix nigropictus, Recilia dorsalis*), Aphididae (for example, *Aphis gossypii, Myzus persicae, Brevicoryne brassicae, Aphis spiraecola, Macrosiphum euphorbiae, Aulacorthum solani, Rhopalosiphum padi, Toxoptera citricidus, Hyalopterus pruni, Aphis glycines Matsumura, Rhopalosiphum maidis, Tetraneura nigriabdominalis, Viteus vitifoliae, Daktulosphaira vitifoliae* (Grape *Phylloxera*), *Phylloxera devastatrix Pergande* (Pecan *phylloxera*), *Phylloxera notabilis pergande* (Pecan leaf *phylloxera*), or *Phylloxera russellae Stoetzel* (Southern pecan leaf *phylloxera*), Pentatomidae (for example, *Scotinophara lurida, Scotinophara coarctata* (Malayan rice black bug), *Nezara antennata, Eysarcoris parvus, Halyomorpha mista, Nezara*

*viridula*, *Euschistus heros* (Brown stink bug), *Nezara viridula* (Southern green stink bug), *Piezodorus guildinii* (Red banded stink bug), *Scaptocoris castanea* (Burrower brown bug), *Oebalus pugnax*, or *Dichelops melacanthus*), Alydidae (for example, *Riptortus clavetus*, *Leptocorisa chinensis*, *Leptocorisa acuta*, or *Leptocorisa* spp.), Miridae (for example, *Trigonotylus caelestialium*, *Stenotus rubrovittatus*, *Lygus lineolaris*, or *Blissus leucopterus leucopterus* (Chinchi bug)), Aleyrodidae (for example, *Trialeurodes vaporariorum*, *Bemisia tabaci*, *Dialeurodes citri*, or *Aleurocanthus spiniferus*), Coccoidea (for example, *Aonidiella aurantii*, *Comstockaspis perniciosa*, *Unaspis citri*, *Ceroplastes rubens*, *Icerya purchasi*, *Planococcus Kraunhiae*, *Pseudococcus longispinis*, *Pseudaulacaspis Pentagona*, or *Brevennia rehi*), Psyllidae (for example, *Diaphorina citri*, *Psylla pyrisuga*, *Bactericerca cockerelli*), Tingidae (for example, *Stephanitis nasi*), Cimicoidea (for example, *Cimex lectularius*),

*Quesada gigas* (Giant Cicada);

and the others.

Lepidoptera Pests:

Pyralidae (for example, *Chilo suppressalis*, *Chilo polychrysus* (Darkheaded stm borer), *Tryporyza incertulas*, *Chilo polychrysus*, *Scirpophaga innotata*, *Scirpophaga incertulas* (Yellow stem borer), *Sesamia inferens* (Pink borer), *Rupela albinella*, *Cnaphalocrocis medinalis*, *Marasmia patnalis*, *Marasmia exigna*, *Notarcha derogata*, *Plodia interpunctella*, *Ostrinia furnacalis*, *Hellula undalis*, *Pediasia teterrellus*, *Nymphula depunctalis*, *Marasmia* spp., *Hydraecia immanis* (Hop vine borer), *Ostrinia nubilalis* (European corn borer), *Elasmopalpus lignosellus* (Lesser cornstalk borer), *Epinotia aporema* (Bean Shoot Borer), *Diatraea saccharalis* (Sugarcane borer), *Telchin licus* (Giant Sugarcane borer)), Noctuidae (for example, *Spodoptera litura*, *Spodoptera exigua*, *Pseudaletia separata*, *Mamestra brassicae*, *Sesamia inferens*, *Spodoptera mauritia*, *Spodoptera frugiperda*, *Spodoptera exempta*, *Agrotis ipsilon*, *Plusia nigrisigna*, *Pseudoplusia includens* (Soybean looper), *Trichoplusia* spp., *Heliothis* spp. (for example, *Heliothis virescens*), *Helicoverpa* spp. (for example, *Helicoverpa armigera*), *Anticarsia gammatalis* (Velvetbean caterpillar), or *Alabama argillacea* (Cotton leafworm)), Pieridae (for example, *Pieris rapae*),

*Adokisofiesu* genus,

Tortricidae (for example, *Grapholita molesta*, *Leguminivora glycinivorella*, *Matsumuraeses azukivora*, *Adoxophyes orana fasciata*, *Adoxophyes honmai*, *Homona magnanima*, *Archips fuscocupreanus*, or *Cydia pomonella*), Gracillariidae (for example, *Caloptilia theivora*, or *Phyllonorycter ringoneella*), Carposinidae (for example, *Carposina niponensis*, *Ecdytolopha aurantiana* (Citrus fruit borer)), Lyonetiidae (for example, *Leucoptera coffeela* (Coffee Leaf miner), or *Lyonetia* spp.)), Lymantriidae (for example, *Lymantria* spp., or *Euproctis* spp.), Yponomeutidae (for example, *Plutella xylostella*), Gelechiidae (for example, *Pectinophora gossypiella*, or *Phthorimaea operculella*), Arctiidae (for example, *Hyphantria cunea*);

and the others.

Thysanoptera Pests:

Thysanopterae (for example, *Frankliniella occidentalis*, *Thrips parmi*, *Scirtothrips dorsalis*, *Thrips tabaci*, *Frankliniella intonsa*, *Frankliniella occidentalis*, *Haplothrips aculeatus*, *Stenchaetothrips biformis*);

and the others.

Diptera Pests:

Diptera:

House mosquitoes (*Culex* spp.) (for example, *Culex pipiens pallens*, *Culex tritaeniorhynchus*, or *Culex quinquefasciatus*),

*Aedes* spp. (for example, *Aedes aegypti*, or *Aedes albopictus*),

*Anopheles* spp. (for example, *Anopheles sinensis*),

Chironomidae,

Muscidae (for example, *Musca domestica*, or *Muscina stabulans*),

Anthomyiidae (for example, *Delia platura*, *Delia antiqua*, or *Tetanops myopaeformis*), Agromyzidae (for example, *Agromyza oryzae*, *Hydrellia griseola*, *Liriomyza sativae*, *Liriomyza trifolii*, or *Chromatomyia horticola*), Chloropidae (for example, *Chlorops oryzae*), Tephritidae (for example, *Dacus cucurbitae*, or *Ceratitis capitata*), Ephydridae (for example, *Hydrellia philippina*, or *Hydrellia sasakii*), Drosophilidae, Phoridae (for example, *Megaselia spiracularis*), Psychodidae (for example, *Clogmia albipunctata*), Sciaridae, Cecidomyiidae (for example, *Mayetiola destructor*, or *Orseolia oryzae*), Diopsidae (for example, Diopsis macrophthalma), Tipulidae (for example, *Tipula oleracea* (Common cranefly), or *Tipula paludosa* (European cranefly));

and the others.

Coleoptera Pests:

Chrysomelidae (for example, *Diabrotica virgifera virgifera*, *Diabrotica undecimpunctata howardi*, *Diabrotica barberi*, *Diabrotica virgifera zeae*, *Diabrotica balteata LeConte*, *Diabrotica speciosa*, *Diabrotica speciosa* (Cucurbit Beetle), *Cerotoma trifurcata*, *Oulema melanopus*, *Aulacophora femoralis*, *Phyllotreta striolata*, *Leptinotarsa decemlineata*, *Oulema oryzae*, *Colaspis brunnea*, *Chaetocnema pulicaria*, *Epitrix cucumeris*, *Dicladispa armigera*, *Stenolophus lecontei* (Seedcorn beetle), or *Clivinia impressifrons* (Slender seedcorn beetle)), Scarabaeidae (for example, *Anomala cuprea*, *Anomala rufocuprea*, *Popillia japonica*, *Rhizotrogus majalis* (European Chafer), *Bothynus gibbosus* (Carrot beetle), *Colaspis brunnea* (Grape *Colaspis*), *Myochrous denticollis* (southern Corn leaf beetle), *Holotrichia* spp., or *Phyllophaga* spp. (for example, *Phyllophaga crinita*)), Erirhinidae (for example, *Sitophilus zeamais*, *Echinocnemus squameus*, *Lissorhoptrus oryzophilus*, or *Sphenophorus venatus*), Curculionidae (for example, *Anthonomus grandis*, *Sphenophorus callosus* (Southern Corn Billbug), *Sternechus subsignatus* (Soybean stalk weevil), or *Sphenophorus* spp. (for example, *Sphenophorus levis*)), Epilachna (for example, *Epilachna vigintioctopunctata*), Scolytidae (for example, *Lyctus brunneus*, or *Tomicus piniperda*), Bostrichidae, Ptinidae, Cerambycidae (for example, *Anoplophora malasiaca*, or *Migdolus fryanus*), Elateridae (*Agriotes* sp., *Aelous* sp., *Anchastus* sp., *Melanotus* sp., *Limonius* sp., *Conoderus* sp., *Ctenicera* sp.) (for example, *Melanotus okinawensis, Agriotes ogurae fuscicollis*, or *Melanotus legatus*), Staphylinidae (for example, *Paederus fuscipes*),

*Hypothenemus hampei* (Coffee Barry Borer);

and the others.

Orthoptera Pests:

*Locusta migratoria, Gryllotalpa africana, Dociostaurus maroccanus, Chortoicetes terminifera, Nomadacris septemfasciata, Locustana pardalina* (Brown Locust), *Anacridium melanorhodon* (Tree Locust), *Calliptamus italicus* (Italian Locust), *Melanoplus differentialis* (Differential grasshopper), *Melanoplus bivittatus* (Twostriped grasshopper), *Melanoplus sanguinipes* (Migratory grasshopper), *Melanoplus femurrubrum* (Red-Legged grasshopper), *Camnula pellucida* (Clearwinged grasshopper), *Schistocerca gregaria, Gastrimargus musicus* (Yellow-winged locust), *Austracris guttulosa* (Spur-throated locust), *Oxya yezoensis, Oxya japonica, Patanga succincta, Grylloidea* (for example, *Acheta domesticus, Teleogryllus emma*, or *Anabrus simplex* (Mormon cricket));

and the others.

Hymenoptera Pests:

Tenthredinidae (for exmaple, *Athalia rosae*, or *Athalia japonica*),

*Solenopsis* spp.,

*Acromyrmex* spp. (for example, *Atta capiguara* (Brown leaf-cutting ant));

and the others.

Blattariae Pests:

*Blattella germanica, Periplaneta fuliginosa, Periplaneta americana, Periplaneta brunnea, Blatta orientalis*, and the others.

Isoptera Pests:

*Reticulitermes speratus, Coptotermes formosanus, Incisitermes minor* (*Coptotermes formosanus*), *Cryptotermes domesticus, Odontotermes formosanus, Neotermes koshunensis, Glyptotermes satsumensis, Glyptotermes nakajimai, Glyptotermes fuscus, Glyptotermes kodamai, Glyptotermes kushimensis, Hodotermopsis sjostedti, Coptotermes guangzhoensis, Reticulitermes amamianus, Reticulitermes miyatakei, Reticulitermes kanmonensis, Nasutitermes takasagoensis, Pericapritermes nitobei, Sinocapritermes mushae*, or *Cornitermes cumulans*);

and the others.

Acarina Pests:

Tetranychidae (for example, *Tetranychus urticae, Tetranychus kanzawai, Panonychus citri, Panonychus ulmi, Oligonychus* spp., or *Brevipalpus phoenicis* (Southern Turkey spider mites)), Eriophyidae (for example, *Aculops pelekassi, Phyllocoptruta citri, Aculops lycopersici, Calacarus carinatus, Acaphylla theavagrans, Eriophyes chibaensis*, or *Aculus schlechtendali*), Tarsonemidae (for example, *Polyphagotarsonemus latus*), Tenuipalpidae (for Example, *Brevipalpus phoenicis*), Tuckerellidae;

Ixodidae (for Example, *Haemaphysalis longicornis, Haemaphysalis flava, Dermacentor taiwanicus, Dermacentor variabilis, Ixodes ovatus, Ixodes persulcatus, Ixodes scapularis, Amblyomma americanum, Boophilus microplus*, or *Rhipicephalus sanguineus*), Acaridae (for example, *Tyrophagus putrescentiae*, or *Tyrophagus similis*), Pyroglyphidae (for example, *Dermatophagoides farinae*, or *Dermatophagoides ptrenyssnus*);

and the others.

The agent for controlling harmful arthropods of the present invention comprises the present compound and an inert active carrier. The agent for controlling harmful arthropods is usually prepared by mixing the present compound with an inert active carrier such as solid carrier, liquid carrier or gaseous carrier, and if necessary, adding surfactants and the other auxiliary agents for formulation, to formulate into emulsifiable concentrates, oil solutions, dust formulations, granules, wettable powders, flowables, microcapsules, aerosols, smoking agents, poison baits, resin formulations, shampoo formulations, paste-like formulations, foams, carbon dioxide formulations and tablets and the others. Such formulations may be processed into mosquito repellent coils, electric mosquito repellent mats, liquid mosquito formulations, smoking agents, fumigants, sheet formulations, spot-on formulations or formulations for oral treatment. Also, the agent for controlling harmful arthropods of the present invention may be mixed with other pesticides, miticides, nematicides, fungicides, plant growth regulators, herbicides, and synergists.

The agent for controlling harmful arthropods of the present invention comprises usually 0.01 to 95% by weight of the present compound.

Examples of the solid carrier to be used in the formulation include fine powders or granules of clays (for example, kaolin clay, diatomaceous earth, bentonite, Fubasami clay, or acid white clay), synthetic hydrated silicon oxides, talcs, ceramics, other inorganic minerals (for example, sericite, quartz, sulfur, active carbon, calcium carbonate or hydrated silica) or chemical fertilizers (for example, ammonium sulfate, ammonium phosphate, ammonium nitrate, urea or ammonium chloride) and the others; as well as synthetic resins (for Example, polyester resins such as polypropylene, polyacrylonitrile, polymethylmethacrylate and polyethylene terephthalate; nylon resins (for Example, nylon-6, nylon-11 and nylon-66); polyamide resins; polyvinyl chloride, polyvinylidene chloride, vinyl chloride-propylene copolymers, and the others).

Examples of the above-mentioned liquid carriers include water; alcohols (for example, methanol, ethanol, isopropyl alcohol, butanol, hexanol, benzyl alcohol, ethylene glycol, propylene glycol or phenoxy ethanol); ketones (for Example, acetone, methyl ethyl ketone or cyclohexanone); aromatic hydrocarbons (for example, toluene, xylene, ethyl benzene, dodecyl benzene, phenyl xylyl ethane or methylnaphthalene); aliphatic hydrocarbons (for example, hexane, cyclohexane, kerosene or light oil); esters (for example, ethyl acetate, butyl acetate, isopropyl myristate, ethyl oleate, diisopropyl adipate, diisobutyl adipate or propylene glycol monomethyl ether acetate); nitriles (for Example, acetonitrile or isobutyronitrile); ethers (for example, diisopropyl ether, 1,4-dioxane, ethyleneglycol dimethyl ether, diethyleneglycol dimethyl ether, diethylene glycol monomethyl ether, propylene glycol monomethyl ether, dipropylene glycol monomethyl ether or 3-methoxy-3-methyl-1-butanol); acid amides (for Example, dimethylformamide or dimethylacetamide); halogenated hydrocarbons (for Example, dichloromethane, trichloroethane or carbon tetrachloride); sulfoxides (for Example, dimethyl sulfoxide); propylene carbonate; and vegetable oils (for Example, soybean oil or cottonseed oil).

Examples of the above-mentioned gaseous carrier include fluorocarbon, butane gas, liquefied petroleum gas (LPG), dimethyl ether, and carbon dioxide gas.

Examples of the surfactants include nonionic surfactants such as polyoxyethylenated alkyl ethers, polyoxyethylenated alkyl aryl ethers and polyethylene glycol fatty acid esters; and anionic surfactants such as alkyl sulfonates, alkylbenzene sulfonates and alkyl sulfates.

Examples of the other auxiliary agents for formulation include a binder, a dispersant, a colorant and a stabilizer. Specific examples include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol).

Examples of base material of the resin formulation include polyvinyl chloride polymers, polyurethane and the others, and a plasticizer such as phthalate esters (for example, dimethyl phthalate, dioctyl phthalate), adipic acid esters and stearic acid may be added to these base materials, if necessary. The resin formulation can be prepared by mixing the compound of the present invention with the above-mentioned base material, kneading the mixture, followed by molding it by injection molding, extrusion molding or pressure molding and the like. The resultant resin formulation can be subjected to further molding or cutting procedure and the like, if necessary, to be processed into shapes such as a plate, film, tape, net or string shape. These resin formulations can be processed into animal collars, animal ear tags, sheet products, trap strings, gardening supports and other products.

Examples of a base material for the poison baits include bait ingredients such as grain powder, vegetable oil, saccharide and crystalline cellulose, and if necessary, with addition of antioxidants such as dibutylhydroxytoluene and nordihydroguaiaretic acid, preservatives such as dehydroacetic acid, accidental ingestion inhibitors for children and pets such as a chili powder, insect attraction fragrances such as cheese flavor, onion flavor and peanut oil.

The method for controlling harmful arthropods of the present invention is conducted by applying an effective amount of the present compound to a harmful arthropod directly and/or a habitat thereof (for example, plant bodies, soil, an interior of a house, animal bodies). In the method for controlling harmful arthropods of the present invention, the present compound is usually used in the form of a harmful arthropod controlling agent.

When an agent for controlling harmful arthropods of the present invention is used for controlling harmful arthropods in an agricultural field, the application dose as an amount of the present compound is usually within a range from 1 to 10,000 g per 10,000 m². The emulsifiable concentrate, the wettable powder, or the flowable formulation etc. of an agent for controlling harmful arthropods of the present invention is usually applied by diluting it with water in such a way that a concentration of the active ingredient is within a range from 0.01 to 10,000 ppm. The granular formulation, or the dust formulation etc., is usually applied as itself without diluting it.

These formulations or a water dilution thereof can be sparged directly to harmful arthropods or plants to be protected from harmful arthropods, and also may be applied to the soil of crop land in order to control harmful arthropods which live there.

The resin preparation which is processed into a sheet or a string may be applied by winding a crop with a sheet or a string of the resin preparation, putting a string of the resin preparation around a crop so that the crop is surrounded by the string, or laying a sheet of the resin preparation on the soil surface near the root of a crop.

When the agent for controlling harmful arthropods of the present invention is used to control pests that live inside a house, the application dose as an amount of the present compound is usually within a range from 0.01 to 1,000 mg per 1 mL of an area to be treated, in the case of using it on a planar area. In the case of using it spatially, the application dose as an amount of the present compound is usually within a range from 0.01 to 500 mg per 1 m³ of the space to be treated. When the agent for controlling harmful arthropods of the present invention is formulated into emulsifiable concentrates, wettable powders, flowables or the others, such formulations are usually applied after diluting it with water in such a way that a concentration of the active ingredient is within a range from 0.1 to 10,000 ppm, and then sparging it. In the case of being formulated into oil solutions, aerosols, smoking agents, poison baits and the others, such formulations are used as itself without diluting it.

When the agent for controlling harmful arthropods of the present invention is sued for controlling external parasites of livestock such as cows, horses, pigs, sheep, goats and chickens and small animals such as dogs, cats, rats and mice, the pest control agent of the present invention can be applied to the animals by a known method in the veterinary field. Specifically, when systemic control is intended, the pest control agent of the present invention is administered to the animals as a tablet, a mixture with feed or a suppository, or by injection (including intramuscular, subcutaneous, intravenous and intraperitoneal injections). On the other hand, when non-systemic control is intended, the pest control agent of the present invention is applied to the animals by means of spraying of the oil solution or aqueous solution, pour-on or spot-on treatment, or washing of the animal with a shampoo formulation, or by putting a collar or ear tag made of the resin formulations to the animal. In the case of administering to an animal body, the dose of the present compound is usually within a range from 0.1 to 1,000 mg per 1 kg of an animal body weight.

EXAMPLES

Hereinafter, the present invention is explained in more detail by using Preparation exmaple, Formulation example, and Test example, however, the present invention should not be limited to these examples.

First, with respect to the preparation of the present compound, the Preparation example is shown.

Preparation Example 1-1

A mixture of 2-chloro-5-hydoroxypyridine 1.0 g, potassium hydroxide 110 mg, methanol 19 mL and DMSO 19 mL was stirred at room temperature under hexafluoropropene atmosphere for 12 hours. To the resulting mixtures was added water, and the resulting mixtures are extracted with MTBE. The resulting organic layers were dried over anhydrous sodium sulfate, and the organic layers were concentrated under reduced pressure to give an intermediate compound represented by the following formula 2.0 g.

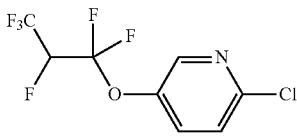 [SMILES: FC(C(F)(F)F)C(F)(F)Oc1ccc(Cl)nc1]

$^1$H-NMR (CDCl$_3$) δ: 8.32 (1H, d), 7.54 (1H, dd), 7.39 (1H, d), 5.15-4.96 (1H, m).

Preparation Example 1-2

To a mixture of 1,4-diazabicyclo[2.2.2]octane 16 g, MTBE 640 mg was added dropwise a solution of 1.6 M n-BuLi in hexane 80 mL at −45° C. under nitrogen atom. The mixtures were stirred at −45° C. for 2 hours, and to the resulting mixtures was added 3-fluoropyridine 11 mL dropwise. The mixtures were stirred at −45° C. for additional 2 hours, and cooled to −50° C., and added dropwise by (n-C4H9)3SnCl 35 mL. The mixtures were stirred at −50° C. for 1 hour, and raised to a room temperature. To the resulting mixtures was added saturated aqueous ammonium chloride solution at room temperature and the mixtures were extracted with MTBE. The resulting organic layers were washed with saturated saline and dried over anhydrous sodium sulfate. The resulting organic layers were concentrated under reduced pressure to give mixtures 50 g containing an intermediate compound 2 represented by the following formula.

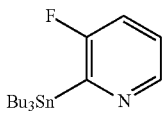

$^1$H-NMR (CDCl$_3$) δ: 8.60-8.56 (1H, m), 7.24-7.19 (1H, m), 7.18-7.12 (1H, m), 1.66-1.47 (6H, m), 1.42-1.23 (6H, m), 1.23-1.09 (6H, m), 0.97-0.80 (9H, m).

Preparation Example 1-3

A mixture containing the intermediate compound 1 1.2 g, the intermediate compound 2 2.5 g, tetrakis(triphenylphosphine) palladium(0) 500 mg, and copper iodide 160 mg, anhydrous lithium chloride 270 mg, and toluene 14 mL was stirred under reflux for 5 hours. The resulting reaction mixtures were stood to cool to a room temperature, and to the mixtures was added aqueous sodium hydrogen carbonate solution, and the mixtures were extracted with ethyl acetate. The resulting organic layers were washed with water and saturated saline successively, dried over anhydrous sodium sulfate, and the organic layers were concentrated under reduced pressure. The resulting residue was subjected to a silica gel column chromatography to give an intermediate compound 3 represented by the following formula 820 mg.

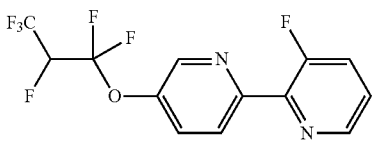 [SMILES: Fc1cccnc1-c1ccc(OC(F)(F)C(F)C(F)(F)F)cn1]

$^1$H-NMR (CDCl$_3$) δ: 8.71 (1H, d), 8.59 (1H, dd), 8.09 (1H, dd), 7.71 (1H, dd), 7.62-7.55 (1H, m), 7.43-7.37 (1H, m), 6.01 (1H, dt).

Preparation Example 1-4

To a suspension solution of sodium hydride (60%, oil) 110 mg, and dimethylformamide (hereinafter, referred to as DMF) 5 mL was added dropwise ethanethiol 200 μL under ice-cooling. The mixtures were stirred under ice-cooling for 10 minutes, and to the mixtures were added dropwise a mixed solution of the intermediate compound 820 mg and DMF 5 mL. The resulting mixtures were stirred at room temperature for 5 hours. To the resulting reaction mixtures was added at room temperature saturated aqueous sodium hydrogen carbonate solution, and the mixtures were extracted with ethyl acetate. The resulting organic layers were washed with water and saturated saline successively, dried over anhydrous sodium sulfate, and the organic layers were concentrated under reduced pressure. The resulting residues were subjected to a silica gel column chromatography to give the present compound 9 represented by the following formula 680 mg.

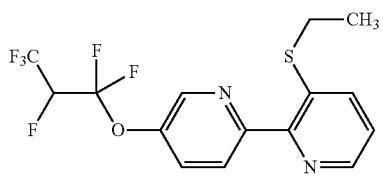 [SMILES: CCSc1cccnc1-c1ccc(OC(F)(F)C(F)C(F)(F)F)cn1]

$^1$H-NMR (CDCl$_3$) δ: 8.64 (1H, d), 8.45 (1H, dd), 8.10 (1H, d), 7.73 (1H, dd), 7.68 (1H, dd), 7.28 (1H, dd), 5.18-4.98 (1H, m), 2.92 (2H, q), 1.33 (3H, t).

Preparation Example 2

To a mixed solution of the present compound 9 530 mg and chloroform 5 mL was added mCPBA (70%) 520 mg under ice-cooling. The mixtures were stirred for 6 hours under ice-cooling, and to the mixtures were added sodium sulfite and saturated aqueous sodium hydrogen carbonate solution successively, and the mixtures were extracted with chloroform. The resulting mixtures were washed with saturated aqueous sodium hydrogen carbonate solution and saturated saline successively, dried over sodium sulfate, and the organic layers were concentrated under reduced pressure. The resulting residues were subjected to a silica gel column chromatography to give the present compound 10 represented by the following formula 210 mg and the present compound 11 represented by the following formula 340 mg.

Present compound 10

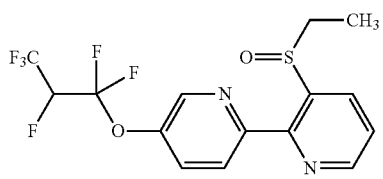 [SMILES: CCS(=O)c1cccnc1-c1ccc(OC(F)(F)C(F)C(F)(F)F)cn1]

$^1$H-NMR (CDCl$_3$) δ: 8.75 (1H, dd), 8.65 (1H, dd), 8.60-8.56 (2H, m), 7.75 (1H, dd), 7.59 (1H, dd), 5.18-4.99 (1H, m), 3.52-3.41 (1H, m), 2.96-2.86 (1H, m), 1.41 (3H, t).

Present compound 11

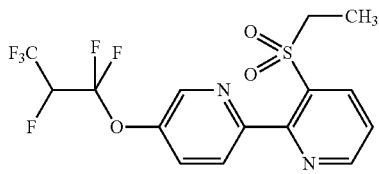 [SMILES: CCS(=O)(=O)c1cccnc1-c1ccc(OC(F)(F)C(F)C(F)(F)F)cn1]

¹H-NMR (CDCl₃) δ: 8.89 (1H, dd), 8.53 (1H, d), 8.50 (1H, dd), 7.91 (1H, d), 7.74 (1H, dd), 7.58 (1H, dd), 5.18-4.99 (1H, m), 3.87 (2H, q), 1.38 (3H, t).

Preparation Example 3-1

An intermediate compound 4 was prepared by using 2-bromo-5-methoxypyridine instead of the intermediate compound 1 according to the similar method to that described in Preparation example 1-3.

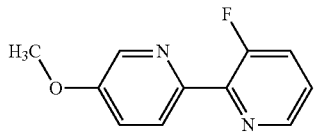

¹H-NMR (CDCl₃) δ: 8.57-8.54 (1H, m), 8.51-8.49 (1H, m), 7.96 (1H, dd), 7.56-7.49 (1H, m), 7.35-7.28 (2H, m), 3.94-3.91 (3H, m).

Preparation Example 3-2

To a mixture of the intermediate 4 510 mg, sodium hydride (oil, 60%9 110 mg, and DMF 5 mL was added dropwise ethanethiol 200 μL under ice-cooling. The mixtures were raised to room temperature and stirred for 4 hours. To the resulting mixtures was added saturated aqueous sodium hydrogen carbonate solution and the mixtures were extracted with ethyl acetate. The resulting organic layers were washed with water and saturated saline successively, dried over anhydrous sodium sulfate, and the organic layers were concentrated under reduced pressure.

To a solution of the resulting residues that was diluted with chloroform was added mCPBA (70%) 1.4 g under ice-cooling. The reaction mixtures were stirred at room temperature for 10 hours. To the resulting reaction mixtures were added sodium sulfite and saturated aqueous hydrogen carbonate solution successively, and the mixtures were extracted with chloroform. The resulting organic layers were washed with saturated aqueous sodium hydrogen carbonate, and dried over anhydrous sodium sulfate, and the organic layers were concentrated under reduced pressure. The resulting residues were subjected to a silica gel column chromatography to give an intermediate compound 5 represented by the following formula 490 mg.

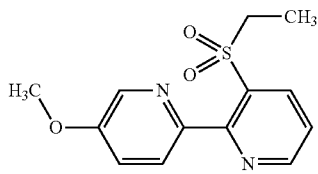 [SMILES: CCS(=O)(=O)c1cccnc1-c1ccc(OC)cn1]

¹H-NMR (CDCl₃) δ: 8.86 (1H, dd), 8.48 (1H, dd), 8.31 (1H, d), 7.83 (1H, d), 7.51 (1H, dd), 7.36 (1H, dd), 3.94-3.87 (5H, m), 1.37 (3H, t).

Preparation Example 3-3

To a solution of 1.0 M boron tribromide in dichloromethane 5.0 mL was added the intermediate compound 5 490 mg under ice-cooling. The mixtures were raised to room temperature and stirred for 2 days. To the resulting reaction mixtures was added saturated aqueous sodium hydrogen carbonate solution under ice-cooling, and the mixtures were extracted with chloroform. The resulting organic layers were washed with water and saturated saline successively, dried over anhydrous sodium sulfate, and the organic layers were concentrated under reduced pressure. The resulting residues were subjected to a silica gel column chromatography to give an intermediate compound 6 represented by the following formula 300 mg.

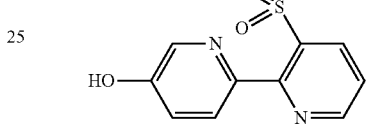

¹H-NMR (CDCl₃) δ: 8.86 (1H, dd), 8.50 (1H, dd), 8.12 (1H, d), 7.67 (1H, d), 7.54 (1H, dd), 7.08 (1H, dd), 6.64 (1H, br s), 3.94 (2H, q), 1.39 (3H, t).

Preparation Example 3-4

To a mixture of the intermediate compound 6 100 mg, cesium carbonate 190 mg and DMF 2 mL was added 2,2,3,3-tetrafluoropropyltrifluoromethanesulfonate 150 mg under ice-cooling. The mixtures were stirred at room temperature for 10 hours, and thereto was added saturated aqueous sodium hydrogen carbonate solution, and the mixtures were extracted with ethyl acetate. The resulting mixtures were washed with saturated saline, dried over anhydrous sodium sulfate, and the organic layers were concentrated under reduced pressure. The resulting residues were subjected to a silica gel column chromatography to give an intermediate compound 7 represented by the following formula 140 mg.

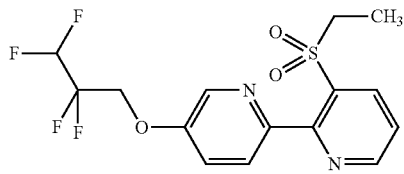 [SMILES: CCS(=O)(=O)c1cccnc1-c1ccc(OCC(F)(F)C(F)F)cn1]

¹H-NMR (CDCl₃) δ: 8.87 (1H, dd), 8.49 (1H, dd), 8.36 (1H, d), 7.87 (1H, d), 7.54 (1H, dd), 7.42 (1H, dd), 6.08 (1H, tt), 4.48 (2H, t), 3.89 (2H, q), 1.38 (3H, t).

Preparation Example 4

To a mixture of the intermediate 6 100 mg, cesium carbonate 190 mg and DMF 2 mL was added 2,2,3,3-tetrafluoropropyltrifluoromethanesulfonate 160 mg under ice-cooling. The resulting mixtures were stirred at room temperature for 10 hours, and thereto was added aqueous sodium hydrogen carbonate solution, the mixtures were extracted with ethyl acetate. The resulting organic layers were washed with saturated saline, dried over anhydrous sodium sulfate, and the organic layers were concentrated under reduced pressure. The resulting residues were subjected to a silica gel column chromatography to give an intermediate compound 8 as represented by the following formula 130 mg.

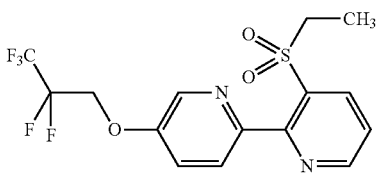 [SMILES: CCS(=O)(=O)c1cccnc1-c1ccc(OCC(F)(F)C(F)(F)F)cn1]

$^1$H-NMR (CDCl$_3$) δ: 8.87 (1H, dd), 8.49 (1H, dd), 8.37 (1H, d), 7.87 (1H, d), 7.54 (1H, dd), 7.42 (1H, dd), 4.54 (2H, t), 3.89 (2H, q), 1.38 (3H, t).

Preparation Example 5

The present compound 14 represented by the following formula was prepared by using 2,2,3,4,4,4-hexafluorobutyl-trifluoromethansulfonate instead of 2,2,3,3-tetrafluoropropyltrifluoromethansulfonate according to the similar method to that described in Preparation example 3-4.

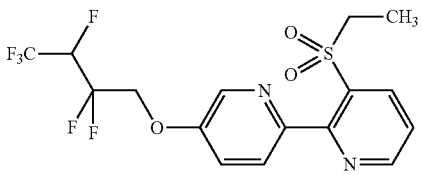 [SMILES: CCS(=O)(=O)c1cccnc1-c1ccc(OCC(F)(F)C(F)C(F)(F)F)cn1]

$^1$H-NMR (CDCl$_3$) δ: 8.87 (1H, dd), 8.49 (1H, dd), 8.36 (1H, d), 7.87 (1H, d), 7.55 (1H, dd), 7.42 (1H, dd), 5.33-5.08 (1H, m), 4.59-4.36 (2H, m), 3.89 (2H, q), 1.38 (3H, t).

Preparation Example 6-1

An intermediate compound 7 represented by the following formula was obtained by using (trifluorovinyl)(trifluoromethyl)ether instead of hexafluoropropene according to the similar method to that described in Preparation example 1-1.

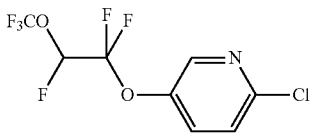

$^1$H-NMR (CDCl$_3$) δ: 8.33 (1H, d), 7.55 (1H, dd), 7.39 (1H, d), 5.97 (1H, dt).

Preparation Example 6-2

An intermediate compound 8 represented by the following formula was obtained by using the intermediate compound 7 instead of the intermediate compound 1 according to the similar method to that described in Preparation example 1-3.

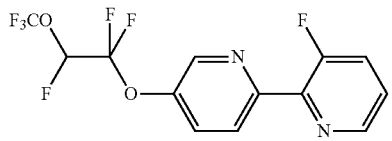 [SMILES: Fc1cccnc1-c1ccc(OC(F)(F)C(F)OC(F)(F)F)cn1]

$^1$H-NMR (CDCl$_3$) δ: 8.71 (1H, d), 8.59 (1H, dd), 8.09 (1H, d), 7.71 (1H, dd), 7.62-7.55 (1H, m), 7.43-7.37 (1H, m), 6.01 (1H, dt).

Preparation Example 6-3

The present compound 22 was obtained by using the intermediate compound 8 instead of the intermediate compound 3 according to the similar method to that described in Preparation example 1-4.

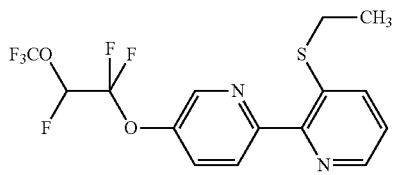 [SMILES: CCSc1cccnc1-c1ccc(OC(F)(F)C(F)OC(F)(F)F)cn1]

$^1$H-NMR (CDCl$_3$) δ: 8.65 (1H, s), 8.45 (1H, dd), 8.10 (1H, d), 7.73 (1H, d), 7.69 (1H, dd), 7.31-7.26 (1H, m), 6.00 (1H, dd), 2.92 (2H, q), 1.33 (3H, t).

Preparation Example 7

The present compound 23 represented by the following formula and the present compound 24 represented by the following formula were obtained by using the present compound 22 instead of the present compound 9 according to the similar method to that described in Preparation example 2.

Present Compound 23

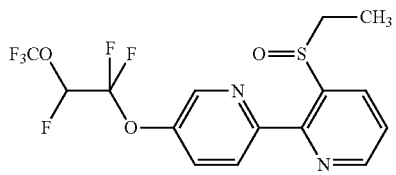 [SMILES: CCS(=O)c1cccnc1-c1ccc(OC(F)(F)C(F)OC(F)(F)F)cn1]

$^1$H-NMR (CDCl$_3$) δ: 8.75 (1H, dd), 8.65 (1H, dd), 8.61-8.56 (2H, m), 7.75 (1H, dd), 7.59 (1H, dd), 6.01 (1H, dt), 3.51-3.41 (1H, m), 2.96-2.86 (1H, m), 1.41 (3H, t).

Present Compound 24

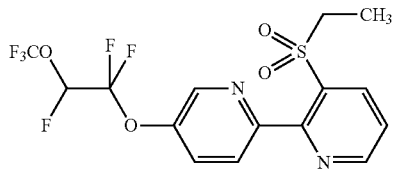 [SMILES: CCS(=O)(=O)c1cccnc1-c1ccc(OC(F)(F)C(F)OC(F)(F)F)cn1]

$^1$H-NMR (CDCl$_3$) δ: 8.89 (1H, dd), 8.54 (1H, d), 8.50 (1H, dd), 7.91 (1H, dd), 7.74 (1H, dd), 7.59 (1H, dd), 6.00 (1H, dt), 3.87 (2H, q), 1.38 (3H, t).

Preparation Example 8-1

To a mixture of 2-bromo-5-hydroxypyridine 10 g, cesium carbonate 26 g, and DMF 29 mL was added dropwise 2,2,3,3,3-pentafluoropropyltrifluoromethanesulfonate 22 g under ice-cooling. The reaction mixtures were stirred at room temperature for 2 days, and thereto was saturated aqueous ammonium chloride solution, and the mixtures were extracted with MTBE. The resulting organic layers were washed with 1M aqueous sodium hydroxide solution, and saturated saline successively, dried over anhydrous sodium sulfate, and concentrated under reduced pressure to give an intermediate compound 9 represented by the following formula 17 g.

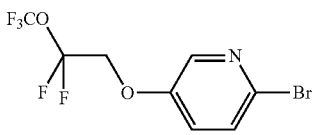 [SMILES: FC(F)(F)OC(F)(F)COc1ccc(Br)nc1]

$^1$H-NMR (CDCl$_3$) δ: 8.13 (1H, d), 7.45 (1H, d), 7.19 (1H, dd), 4.46 (2H, t).

Preparation Example 8-2

An intermediate compound 10 represented by the following formula was obtained by using the intermediate compound 9 instead of the intermediate compound 1 according to the similar method to that described in Preparation example 1-3.

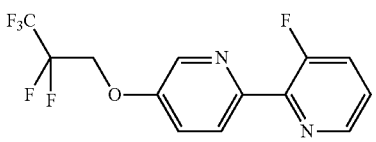

$^1$H-NMR (CDCl$_3$) δ: 8.59-8.55 (1H, m), 8.54 (1H, d), 8.01 (1H, dd), 7.58-7.52 (1H, m), 7.40 (1H, dd), 7.38-7.33 (1H, m), 4.55 (2H, t).

Preparation Example 8-3

The present compound 27 was obtained by using the intermediate compound 10 instead of the intermediate compound 3 according to the similar method to that described in Preparation example 1-4.

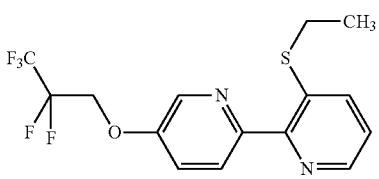 [SMILES: CCSc1cccnc1-c1ccc(OCC(F)(F)C(F)(F)F)cn1]

$^1$H-NMR (CDCl$_3$) δ: 8.47 (1H, dd), 8.43 (1H, dd), 8.02 (1H, dd), 7.70 (1H, dd), 7.41 (1H, dd), 7.28-7.23 (1H, m), 4.54 (2H, td), 2.91 (2H, q), 1.32 (3H, t).

Preparation Example 8-4

The present compound 30 represented by the following formula can be prepared by using the present compound 27 instead of the present compound 9 according to the similar method to that described in Preparation example 2.

Present Compound 30

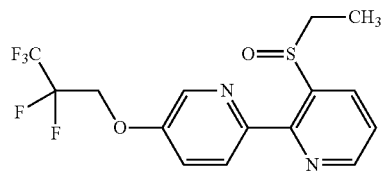 [SMILES: CCS(=O)c1cccnc1-c1ccc(OCC(F)(F)C(F)(F)F)cn1]

Preparation Example 9-1

An intermediate compound 18 was obtained by using 2,2,3,3-tetrafluoropropyltrifluoromethansulfonate instead of 2,2,3,3,3-pentafluoropropyltrifluoromethanesulfonate according to the similar method to that described in Preparation example 8-1.

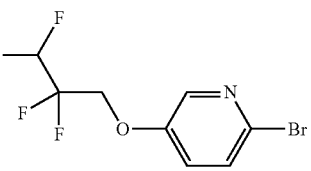

$^1$H-NMR (CDCl$_3$) δ: 8.12 (1H, d), 7.44 (1H, dd), 7.17 (1H, dd), 6.03 (1H, tt), 4.40 (2H, tt).

Preparation Example 9-2

An intermediate compound 19 represented by the following formula was obtained by using the intermediate compound 18 instead of the intermediate compound 1 according to the similar method to that described in Preparation example 1-3.

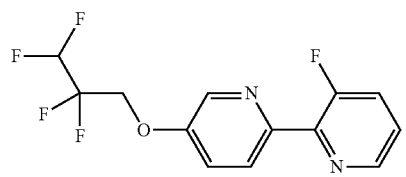 [SMILES: Fc1cccnc1-c1ccc(OCC(F)(F)C(F)F)cn1]

$^1$H-NMR (CDCl$_3$) δ: 8.59-8.52 (2H, m), 8.04-7.99 (1H, m), 7.59-7.52 (1H, m), 7.42-7.32 (2H, m), 6.25-5.93 (1H, m), 4.54-4.45 (2H, m).

Preparation Example 9-3

The present compound 26 was obtained by using the intermediate compound 19 instead of the intermediate compound 3 according to the similar method to that described in Preparation example 1-4.

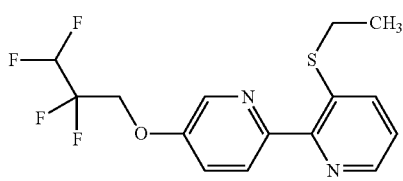

¹H-NMR (CDCl₃) δ: 8.46 (1H, d), 8.43 (1H, dd), 8.00 (1H, d), 7.70 (1H, dd), 7.39 (1H, dd), 7.28-7.23 (1H, m), 6.09 (1H, tt), 4.48 (2H, t), 2.91 (2H, q), 1.32 (3H, t).

Preparation Example 9-4

The present compound 29 represented by the following formula can be prepared by using the present compound 26 instead of the present compound 9 according to the similar method to that described in Preparation example 2.

Present Compound 29

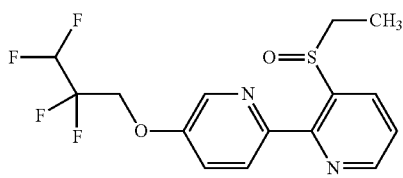 [SMILES: CCS(=O)c1cccnc1-c1ccc(OCC(F)(F)C(F)F)cn1]

Preparation Example 10-1

To a mixture of a 1.6 M solution of n-butyl lithium in hexane 100 mL and THF 160 mL was added dropwise a mixture of ethyl methyl sulfone 23 g and THF 20 mL at −78° C. The reaction mixtures were raised to 0° C. gradually, and then re-cooled to −78° C. To the reaction mixtures were added dropwise a mixture of 5-fluoro-2-cyano-pyridine 20 g and THF 20 mL at −78° C. The mixtures were raised to room temperature gradually, and then to the reaction mixtures was added 2N hydrochloric acid and the mixtures were stirred for 30 minutes. The resulting mixtures were extracted with ethyl acetate and the resulting organic layers were washed with saturated saline. The resulting mixtures were dried over anhydrous sodium sulfate, and concentrated under reduced pressure to give an intermediate compound 16 represented by the following formula 40 g.

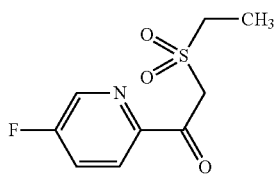

¹H-NMR (CDCl₃) δ: 8.57 (1H, d), 8.19 (1H, dd), 7.62-7.55 (1H, m), 4.97 (2H, s), 3.30 (2H, q), 1.47 (3H, t).

Preparation Example 10-2

To a mixture of oxalyl chloride 11 mL and chloroform 86 mL was added dropwise DMF 10 mL under ice-cooling. The mixtures were stirred for 30 minutes under ice-cooling, and then to the mixtures was added dropwise butyl vinyl ether 33 mL under ice-cooling. The mixtures were raised to room temperature over 2 hours, and to the mixtures were added dropwise a mixture of the intermediate 16 10 g, and triethylamine 42 mL and chloroform 30 mL under ice-cooling. The mixtures were raised to room temperature and stirred for 1 hour. The resulting mixtures were added to saturated aqueous ammonium chloride solution and the mixtures were extracted with chloroform. The resulting mixtures were washed with water and saturated saline, then dried over anhydrous sodium sulfate, and concentrated under reduced pressure. The resulting residue was diluted with ethanol 30 mL and then to the mixtures was added aqueous 28% ammonia solution 10 mL at room temperature. The mixtures were stirred with heating at 60° C. for 2.5 hours and stood to cool to room temperature, and thereto was added saturated aqueous sodium hydrogen carbonate solution and the mixtures were extracted with ethyl acetate. The resulting organic layers were dried over anhydrous sodium sulfate and concentrated under reduced pressure. The resulting residues were subjected to a silica gel column chromatography to give an intermediate compound represented by the following formula 17 9.4 g.

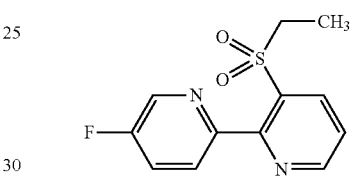

¹H-NMR (CDCl₃) δ: 8.88 (1H, dd), 8.52-8.46 (2H, m), 7.87 (1H, dd), 7.62-7.54 (2H, m), 3.86 (2H, q), 1.38 (3H, t).

Preparation Example 10-3

To a mixture of the intermediate compound 17 400 mg, sodium hydride (60%, oil) 90 mg and NMP 2 mL was added 2,2,2-trifluoroethanol 230 mg under ice-cooling. The mixtures were stirred with heating at 70° C. for 2 days. The reaction mixtures were stood to cool to room temperature, and thereto was then added water, and the mixtures were extracted with ethyl acetate. The resulting mixtures were washed with water and saturated saline, dried over anhydrous sodium sulfate, and concentrated under reduced pressure. The resulting residues were subjected to a silica gel column chromatography to give Present compound 2 represented by the following formula 170 mg.

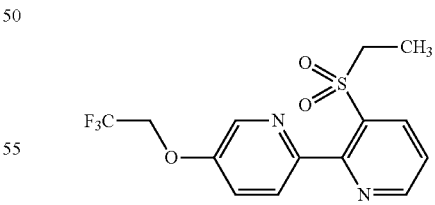

Present Compound 2

¹H-NMR (CDCl₃) δ: 8.87 (1H, dd), 8.49 (1H, dd), 8.37 (1H, d), 7.86 (1H, d), 7.54 (1H, dd), 7.42 (1H, dd), 4.48 (2H, q), 3.89 (2H, q), 1.38 (3H, t).

Preparation Example 11

To a mixture of the present compound 8 2.0 g, sulfuric acid 6 mL and water 2 mL was added aqueous 30% hydrogen peroxide solution 630 μL under ice-cooling. The mixtures were stirred at room temperature for 2 days, and the reaction mixtures were added to ice water. The resulting mixtures were extracted with chloroform, and the organic layers were washed with saturated aqueous sodium hydrogen carbonate solution and saturated saline successively, dried over anhydrous sodium sulfate, and then concentrated under reduced pressure. The resulting residues were subjected to a silica gel column chromatography to give the present compound 204 0.2 g, the present compound 214 0.6 g, and the present compound 224 0.2 g, which are represented by the following formulae.

Present Compound 204

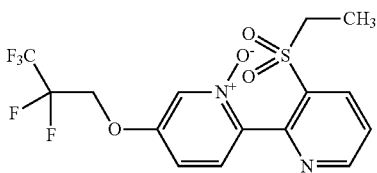

¹H-NMR (CDCl₃) δ: 8.93 (1H, dd), 8.37 (1H, dd), 8.04 (1H, d), 7.64 (1H, dd), 7.38 (1H, d), 7.05 (1H, dd), 4.50 (2H, t), 3.76-3.64 (1H, m), 3.61-3.49 (1H, m), 1.35 (3H, t).

Present Compound 214

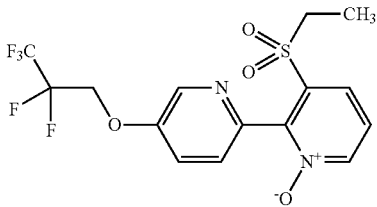

¹H-NMR (CDCl₃) δ: 8.50 (1H, dd), 8.43 (1H, d), 7.97 (1H, dd), 7.69 (1H, d), 7.50 (1H, dd), 7.43 (1H, dd), 4.54 (2H, t), 3.44 (2H, q), 1.30 (3H, t).

Present Compound 224

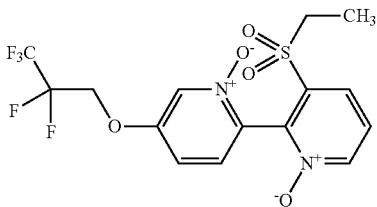

¹H-NMR (CDCl₃) δ: 8.49 (1H, dd), 8.14 (1H, d), 7.91 (1H, dd), 7.57 (1H, dd), 7.42 (1H, d), 7.07 (1H, dd), 4.51 (2H, t), 3.36-3.18 (2H, m), 1.28 (3H, t).

Preparation Example 12

To a mixture of the present compound 204 and the present compound 224 (mixed ratio, the present compound 204: the present compound 224=100:1) 6.8 g was added phosphoryl chloride 15 mL, and the mixtures were stirred with heating at 110° C. for 4 hours. The reaction mixtures were concentrated under reduced pressure, and the resulting residues were diluted with chloroform, and thereto was saturated aqueous sodium hydrogen carbonate solution. The mixtures were extracted with chloroform, and the resulting organic layers were dried over anhydrous sodium sulfate and concentrated under reduced pressure. The resulting residues were subjected to a silica gel column chromatography to give the present compound 169 6.7 g, and the present compound 194 0.07 g, which are represented by the following formulae.

Present Compound 169

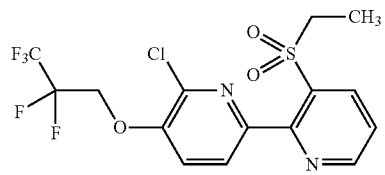 [SMILES: CCS(=O)(=O)c1cccnc1-c1ccc(OCC(F)(F)C(F)(F)F)c(Cl)n1]

¹H-NMR (CDCl₃) δ: 8.86 (1H, dd), 8.49 (1H, dd), 7.86 (1H, d), 7.56 (1H, dd), 7.42 (1H, d), 4.56 (2H, t), 3.98 (2H, q), 1.44 (3H, t).

Present Compound 194

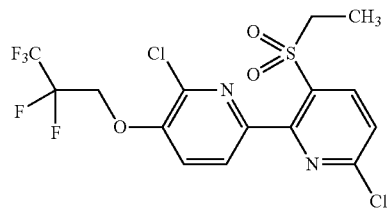 [SMILES: CCS(=O)(=O)c1ccc(Cl)nc1-c1ccc(OCC(F)(F)C(F)(F)F)c(Cl)n1]

¹H-NMR (CDCl₃) δ: 8.93 (1H, d), 7.47 (1H, d), 7.42 (1H, d), 7.39 (1H, d), 4.56 (2H, t), 3.70 (2H, q), 1.40 (3H, t).

Preparation Example 13

To the present compound 214 3.7 g was added phosphoryl chloride 10 mL, and the mixtures were stirred with heating at 110° C. for 4 hours. The reaction mixtures were concentrated under reduced pressure, and the resulting residues were diluted with chloroform, and thereto was added saturated aqueous sodium hydrogen carbonate solution. The mixtures were extracted with chloroform, and the resulting organic layers were dried over anhydrous sodium sulfate, and concentrated under reduced pressure. The resulting residues were subjected to a silica gel column chromatography to give the present compound 79 represented by the following formula 3.0 g.

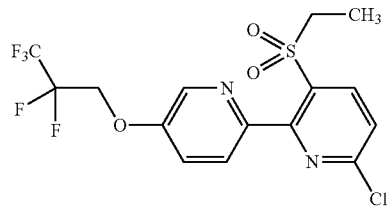 [SMILES: CCS(=O)(=O)c1ccc(Cl)nc1-c1ccc(OCC(F)(F)C(F)(F)F)cn1]

¹H-NMR (CDCl₃) δ: 8.42 (1H, dd), 8.37 (1H, d), 7.91 (1H, d), 7.54 (1H, dd), 7.41 (1H, dd), 4.54 (2H, t), 3.92 (2H, q), 1.38 (3H, t).

Preparation Example 14

To a mixture of the present compound 79 500 mg and DMF 2 mL was added aqueous 28% sodium methoxide solution 0.1 mL under ice-cooling. The mixtures were stirred at room temperature for 2 hours, and the reaction mixtures were added to saturated aqueous sodium hydrogen sodium hydrogen carbonate, and the mixtures were extracted with ethyl acetate. The resulting organic layers were dried over anhydrous sodium sulfate, and concentrated under reduced pressure. The resulting residues were subjected to a silica gel column chromatography to give the present compound 94 represented by the following formula 230 mg.

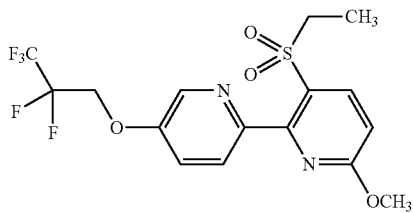 [SMILES: CCS(=O)(=O)c1ccc(OC)nc1-c1ccc(OCC(F)(F)C(F)(F)F)cn1]

$^1$H-NMR (CDCl$_3$) δ: 8.35 (1H, dd), 8.29 (1H, d), 7.83 (1H, dd), 7.40 (1H, dd), 6.88 (1H, d), 4.54 (2H, td), 4.03 (3H, s), 3.83 (2H, q), 1.36 (3H, t).

Preparation Example 15

To a mixture of the present compound 79 200 mg and DMF 2 mL were added 1H-1,2,4-triazole 39 mg and sodium hydride (60% oil) 22 mg under ice-cooling. The mixtures were stirred at room temperature for 24 hours, and the reaction mixtures were then added to saturated aqueous sodium hydrogen carbonate solution, and the mixtures were extracted with ethyl acetate. The resulting organic layers were dried over anhydrous sodium sulfate, and concentrated under reduced pressure. The resulting residues were subjected to a silica gel column chromatography to give the present compound 104 represented by the following formula 160 mg.

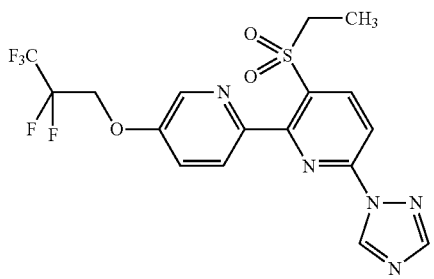 [SMILES: CCS(=O)(=O)c1ccc(-n2cncn2)nc1-c1ccc(OCC(F)(F)C(F)(F)F)cn1]

1H-NMR (CDCl$_3$) δ: 9.23 (1H, s), 8.67 (1H, d), 8.41 (1H, dd), 8.17 (1H, s), 8.10 (1H, d), 7.90 (1H, dd), 7.47 (1H, dd), 4.57 (2H, td), 3.93 (2H, q), 1.41 (3H, t).

Preparation Example 16

To a mixture of the present compound 79 200 mg, diisopropylethylamine 0.96 mL and acetonitrile 1 mL was added 2-chloro-5-(aminomethyl)thiazole hydrobromide salt 960 mg under ice-cooling. The mixtures were stirred at 80° C. for 5 days, and the reaction mixtures were added to saturated aqueous sodium hydrogen carbonate solution, and the mixtures were extracted with ethyl acetate. The resulting organic layers were dried anhydrous sodium sulfate, and concentrated under reduced pressure. The resulting residues were subjected to a silica gel column chromatography to give the present compound 89 represented by the following formula 200 mg.

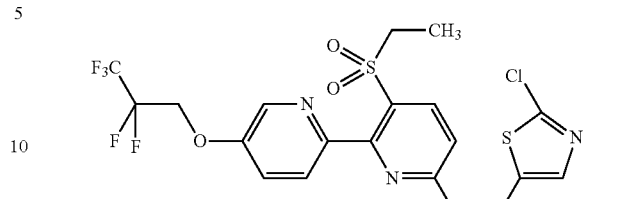

$^1$H-NMR (CDCl$_3$) δ: 8.35 (1H, d), 8.12 (1H, d), 7.77 (1H, d), 7.44 (1H, s), 7.40 (1H, dd), 6.52 (1H, d), 5.40 (1H, t), 4.77 (2H, d), 4.54 (2H, t), 3.77 (2H, q), 1.35 (3H, t).

Preparation Example 17

To a mixture of the present compound 79 200 mg and NMP 1 mL was added aqueous 28% ammonia solution 0.09 mL at room temperature. The reaction mixtures were stirred at 80° C. for 3 days. The mixtures were stood to cool to room temperature, and the reaction mixtures were added to saturated aqueous sodium hydrogen carbonate solution, and the resulting mixtures were extracted with ethyl acetate. The resulting organic layers were washed with saturated saline, dried over anhydrous sodium sulfate, and concentrated under reduced pressure. The resulting residues were subjected to a silica gel column chromatography to give the present compound 59 represented by the following formula 110 mg.

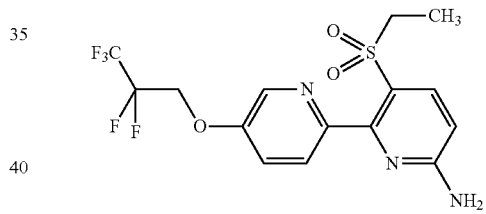

$^1$H-NMR (CDCl$_3$) δ: 8.34 (1H, d), 8.13 (1H, d), 7.71 (1H, dd), 7.38 (1H, dd), 6.58 (1H, d), 5.01 (2H, s), 4.52 (2H, td), 3.66 (2H, q), 1.32 (3H, t).

Preparation Example 18

To a mixture of the present compound 79 200 mg and DMF 1 mL was added aqueous 50% dimethylamine solution 0.13 mL at room temperature. The reaction mixtures were stirred at 60° C. for 4 hours. The mixtures were stood to cool to room temperature, and the reaction mixtures were then subjected to a silica gel column chromatography to give the present compound 69 200 mg.

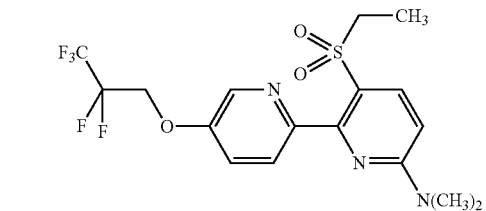 [SMILES: CCS(=O)(=O)c1ccc(N(C)C)nc1-c1ccc(OCC(F)(F)C(F)(F)F)cn1]

¹H-NMR (CDCl₃) δ: 8.80 (1H, d), 8.48 (1H, d), 8.37 (1H, d), 7.88 (1H, dd), 7.42 (1H, dd), 4.54 (2H, td), 3.94 (2H, q), 1.55 (6H, s), 1.40 (3H, t).

Preparation Example 19

To a mixture of the present compound 79 200 mg and NMP 1 mL was added 2,2,2-trifluoroethylamine 0.2 mL at room temperature. The reaction mixtures were stirred at 120° C. for 4 days. The mixtures were stood to cool to room temperature, and the reaction mixtures were then added to saturated aqueous sodium hydrogen carbonate solution, and the mixtures were extracted with ethyl acetate. The resulting organic layers were washed with saturated saline, then dried over anhydrous sodium sulfate, and concentrated under reduced pressure. The resulting residues were subjected to a silica gel column chromatography to give the present compound 74 represented by the following formula 180 mg.

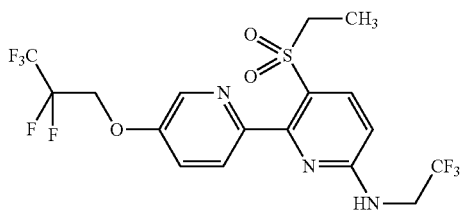

¹H-NMR (CDCl₃) δ: 8.34 (1H, d), 8.17 (1H, d), 7.75 (1H, d), 7.40 (1H, dd), 6.61 (1H, d), 5.18 (1H, t), 4.54 (2H, t), 4.28-4.16 (2H, m), 3.79 (2H, q), 1.36 (3H, t).

Preparation Example 20

To a mixture of the present compound 204 500 mg, triethylamine 240 mg, and acetonitrile 3 mL was added trimethylsilyl cyanide 360 mg at room temperature. The mixtures were stirred with heating at 80° C. for 34 hours. The reaction mixtures were concentrated under reduced pressure, and the resulting residues were diluted with ethyl acetate, and thereto was added saturated aqueous sodium hydrogen carbonate solution. The mixtures were extracted with ethyl acetate, and the resulting organic layers were washed with saturated saline, dried over anhydrous sodium sulfate, and concentrated under reduced pressure. The resulting residues were subjected to a silica gel column chromatography to give the present compound 179 represented by the following formula 180 mg.

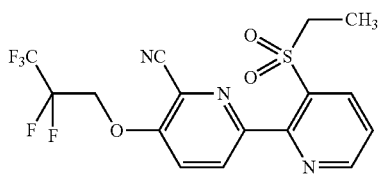 [SMILES: CCS(=O)(=O)c1cccnc1-c1ccc(OCC(F)(F)C(F)(F)F)c(C#N)n1]

¹H-NMR (CDCl₃) δ: 8.88 (1H, dd), 8.51 (1H, dd), 8.12 (1H, d), 7.61 (1H, dd), 7.55 (1H, d), 4.66 (2H, t), 3.90 (2H, q), 1.45 (3H, t).

Preparation Example 21

To the present compound 204 1.0 g was added acetic anhydride 5 mL, and the mixtures were stirred with heating at 100° C. for 20 hours. The reaction mixtures were concentrated under reduced pressure and the resulting residues were diluted with ethyl acetate, and the mixtures were added to saturated aqueous sodium hydrogen carbonate solution. The mixtures were extracted with ethyl acetate, and the resulting organic layers were washed with saturated saline, then dried over anhydrous sodium sulfate, and concentrated under reduced pressure. The resulting residues were subjected to a silica gel column chromatography to give the present invention 174 represented by the following formula 980 mg.

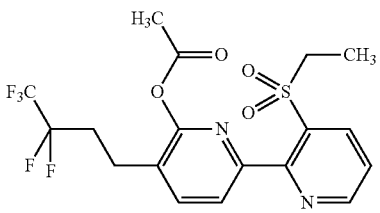 [SMILES: CCS(=O)(=O)c1cccnc1-c1ccc(CCC(F)(F)C(F)(F)F)c(OC(C)=O)n1]

¹H-NMR (CDCl₃) δ: 8.86 (1H, dd), 8.47 (1H, dd), 7.83 (1H, d), 7.55 (1H, dd), 7.47 (1H, d), 4.51 (2H, t), 3.78 (2H, q), 2.33 (3H, s), 1.36 (3H, t).

Preparation Example 22

To a mixture of the present compound 174 660 mg and methanol 17 mL was added potassium carbonate 600 mg at room temperature, and the mixtures were stirred at room temperature for 1.5 hours, and adjusted to pH 4 with 2N hydrochloric acid. The mixtures were extracted with ethyl acetate, and the organic layers were dried over anhydrous sodium sulfate, and concentrated under reduced pressure. The resulting residues were subjected to a silica gel column chromatography to give the present compound 159 represented by the following formula 530 mg.

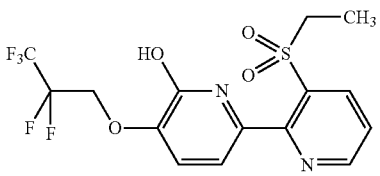 [SMILES: CCS(=O)(=O)c1cccnc1-c1ccc(OCC(F)(F)C(F)(F)F)c(O)n1]

¹H-NMR (CDCl₃) δ: 11.08 (1H, s), 8.89 (1H, dd), 8.60 (1H, d), 7.61 (1H, dd), 7.32-7.24 (1H, br m), 7.11 (1H, d), 4.71 (2H, t), 3.15 (2H, q), 1.18 (3H, t).

Preparation Example 23

To a mixture of the present compound 159 340 mg, cesium carbonate 400 mg and DMF 3 mL was added iodomethane 0.98 mL at room temperature. The mixtures were stirred at room temperature for 1 day, and the reaction mixtures were then subjected to a silica gel column chromatography to give the present compound 164 250 mg.

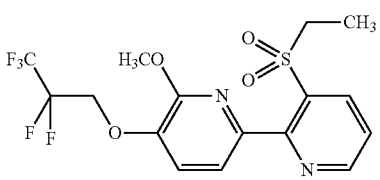 [SMILES: CCS(=O)(=O)c1cccnc1-c1ccc(OCC(F)(F)C(F)(F)F)c(OC)n1]

$^1$H-NMR (CDCl$_3$) δ: 8.88 (1H, d), 8.46 (1H, d), 7.57 (1H, dd), 7.34 (1H, d), 7.28 (1H, d), 4.52 (2H, t), 4.00 (3H, s), 3.62 (2H, q), 1.34 (3H, t).

Preparation Example 24-1

To a mixture of 2-cyano-5-fluoropyridine 30 g, 2,2,3,3-tetrafluoro-1-propanol 54 g, and NMP 90 mL was added cesium carbonate 130 g under ice-cooling, and the mixtures were then raised to room temperature, and stirred at room temperature for 1.5 hours. The resulting mixtures were warmed to 60° C. and stirred at 60° C. for additional 5 hours, and to the reaction mixtures was added water, and the mixtures were extracted with MTBE. The resulting organic layers were dried over sodium sulfate, and concentrated under reduced pressure. The resulting residues were recrystallized from isopropanol/hexane solvents to give an intermediate compound 11 represented by the following formula 47 g.

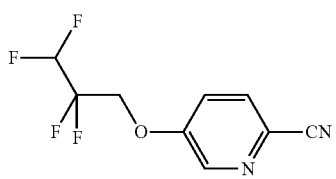 [SMILES: N#Cc1ccc(OCC(F)(F)C(F)F)cn1]

$^1$H-NMR (CDCl$_3$) δ: 8.45 (1H, d), 7.71 (1H, dd), 7.33 (1H, dd), 6.04 (1H, tt), 4.49 (2H, t).

Preparation Example 24-2

To a mixture of ethyl methyl sulfone 11 g and THF 50 L was added 1.6 M n-butyl lithium in hexane solution 59 mL under ice-cooling, and the mixtures were stirred for 15 minutes under ice-cooling. The mixtures were added to a mixture of the intermediate compound 20 g and THF 50 mL under ice-cooling, and the mixtures were stirred for 10 minutes under ice-cooling. The mixtures were added to water, and extracted with ethyl acetate. The resulting organic layers were dried over sodium sulfate, and concentrated under reduced pressure. The residues were recrystallized from ethyl acetate/hexane solution to give an intermediate compound 12 represented by the following formula 18 g.

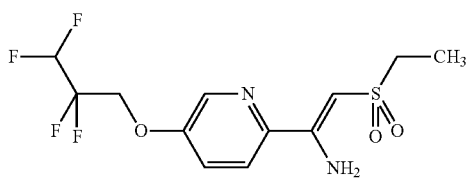

$^1$H-NMR (CDCl$_3$) δ: 8.36 (1H, d), 7.69 (1H, d), 7.33 (1H, dd), 6.79 (2H, s), 6.05 (1H, tt), 5.28 (1H, s), 4.48 (2H, t), 3.10 (2H, q), 1.40 (3H, t).

Preparation Example 24-3

A mixture of the intermediate compound 12 200 mg and 4-ethoxy-1,1,1-trifluoro-3-buten-2-one 2 mL was stirred with heating at 100° C. for 4.5 hours. The mixtures were subjected to a silica gel column chromatography to give the present compound 53 represented by the following formula 100 mg.

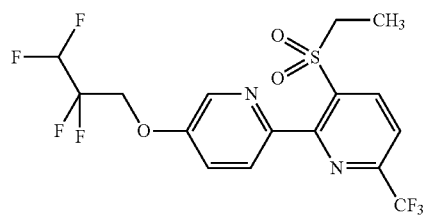 [SMILES: CCS(=O)(=O)c1ccc(C(F)(F)F)nc1-c1ccc(OCC(F)(F)C(F)F)cn1]

$^1$H-NMR (CDCl$_3$) δ: 8.69 (1H, d), 8.37 (1H, d), 7.99 (1H, d), 7.89 (1H, d), 7.43 (1H, dd), 6.08 (1H, tt), 4.49 (2H, t), 4.01 (2H, q), 1.41 (3H, t).

Preparation Example 25-1

An intermediate compound 13 represented by the following formula was obtained by using 2,2,3,3,3-pentafluoropropanol instead of 2,2,3,3-tetrafluoro-1-propanol according to the similar method to that described in Preparation example 24-1.

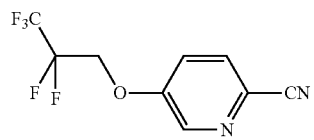 [SMILES: N#Cc1ccc(OCC(F)(F)C(F)(F)F)cn1]

$^1$H-NMR (CDCl$_3$) δ: 8.46 (1H, d), 7.73-7.71 (1H, m), 7.35 (1H, dd), 4.56 (2H, td).

Preparation Example 25-2

An intermediate compound 14 was obtained by using the intermediate compound 13 instead of the intermediate compound 11 according to the similar method to that described in Preparation example 24-2.

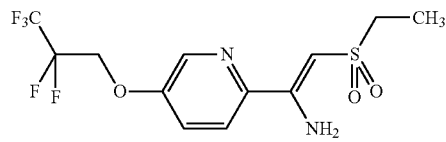

$^1$H-NMR (CDCl$_3$) δ: 8.37 (1H, d), 7.69 (1H, d), 7.34 (1H, dd), 6.79 (2H, s), 5.28 (1H, s), 4.54 (2H, t), 3.10 (2H, q), 1.40 (3H, t).

Preparation Example 25-3

The present compound 54 was obtained by using the intermediate compound 14 instead of the intermediate compound 12 according to the similar method to that described in Preparation example 24-3.

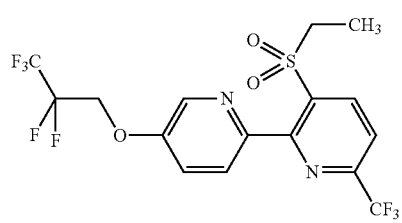 [SMILES: CCS(=O)(=O)c1ccc(C(F)(F)F)nc1-c1ccc(OCC(F)(F)C(F)(F)F)cn1]

$^1$H-NMR (CDCl$_3$) δ: 8.69 (1H, dd), 8.39 (1H, d), 7.99 (1H, dd), 7.89 (1H, d), 7.44 (1H, dd), 4.55 (2H, td), 4.01 (2H, q), 1.41 (3H, t).

Preparation Example 26

A mixture of the intermediate compound 14 3.0 g, acrolein 830 μL and ethanol 10 mL was stirred at 60° C. for 2 hours. The mixtures were concentrated under reduced pressure to the residues 3.8 g. Among the obtained residues, 500 mg part of the residue were mixed with THF 2 mL, and thereto were triethylamine 620 μL and methanesulfonyl chloride 220 μL at room temperature. The mixtures were stirred with heating at 60° C. for 1 hour. To the resulting mixtures was added 2N hydrochloric acid, and the mixtures were extracted with ethyl acetate. The resulting organic layers were dried over sodium sulfate and concentrated under reduced pressure. The resulting residues were subjected to a silica gel column chromatography to give the present compound 99 represented by the following formula 47 mg.

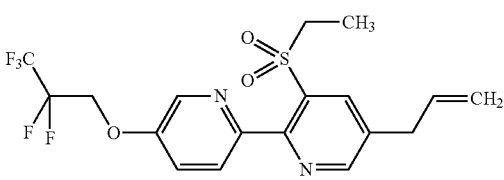 [SMILES: C=CCc1cnc(-c2ccc(OCC(F)(F)C(F)(F)F)cn2)c(S(=O)(=O)CC)c1]

$^1$H-NMR (CDCl$_3$) δ: 8.69 (1H, d), 8.36 (1H, d), 8.30 (1H, d), 7.84 (1H, d), 7.42 (1H, dd), 6.04-5.93 (1H, m), 5.23-5.18 (2H, m), 4.54 (2H, t), 3.87 (2H, q), 3.55 (2H, d), 1.37 (3H, t).

Preparation Example 27

To a mixture of the intermediate compound 14 8.5 g and chloroform 30 mL was added α-(trifluoromethyl)acryloyl chloride 9.4 g under ice-cooling, and the mixtures were stirred at room temperature for 30 minutes. To the mixtures was added hexane, and the mixtures were then filtered. The filtrates were added to saturated aqueous sodium bicarbonate solution, and the mixtures were extracted with ethyl acetate. The resulting organic layers were dried over sodium sulfate, and concentrated under reduced pressure. The residues were recrystallized from ethyl acetate/hexane solution to give an intermediate compound 15 represented by the following formula 21 g.

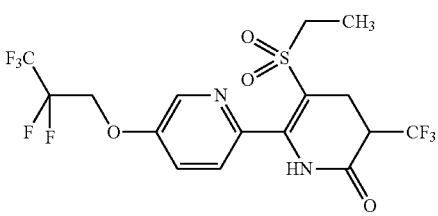 [SMILES: CCS(=O)(=O)C1=C(c2ccc(OCC(F)(F)C(F)(F)F)cn2)NC(=O)C(C(F)(F)F)C1]

$^1$H-NMR (CDCl$_3$) δ: 8.36 (1H, d), 7.81-7.78 (2H, m), 7.33 (1H, dd), 4.52 (2H, t), 3.49-3.31 (2H, m), 3.11-3.02 (3H, m), 1.29 (3H, t).

Preparation Example 28

To a mixture of the intermediate compound 15 10 g and chloroform 30 mL were added N-bromosuccinimide 4.4 g and benzoyl peroxide 10 mg, and the mixtures were stirred with heating at 60° C. for 30 minutes. The mixtures were stood to cool to room temperature, and thereto was added sodium methoxide until an exothermic reaction is stopped. To the mixtures was added water, and the mixtures were extracted with ethyl acetate, and the resulting organic layers were dried over sodium sulfate, and concentrated under reduced pressure to give the present compound 114 represented by the following formula 14 g.

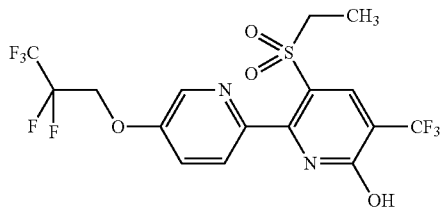

$^1$H-NMR (CDCl$_3$) δ: 8.45 (1H, d), 8.41 (1H, s), 7.92 (1H, d), 7.41 (1H, dd), 4.57 (2H, t), 3.45 (2H, q), 1.33 (3H, t).

Preparation Example 29

To the present compound 114 4.4 g was added phosphoryl chloride 23 g, and the mixtures were stirred with heating under reflux for 2 days. The mixtures were concentrated under reduced pressure, and to the residues was saturated aqueous sodium bicarbonate solution, and the mixtures were extracted with ethyl acetate. The resulting organic layers were dried over sodium sulfate, and then concentrated under reduced pressure. The resulting residues were subjected to a silica gel column chromatography to give the present compound 109 represented by the following formula 2.7 g.

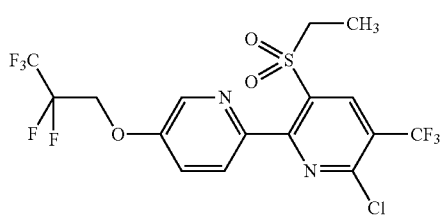 [SMILES: CCS(=O)(=O)c1cc(C(F)(F)F)c(Cl)nc1-c1ccc(OCC(F)(F)C(F)(F)F)cn1]

$^1$H-NMR (CDCl$_3$) δ: 8.75 (1H, s), 8.40 (1H, d), 8.03 (1H, d), 7.44 (1H, dd), 4.56 (2H, t), 4.01 (2H, q), 1.43 (3H, t).

Preparation Example 30

To a mixture of the present compound 109 500 mg, 1H-1,2,4-triazole 46 mg, and DMSO 2 mL was added cesium carbonate 240 mg at room temperature, and the mixtures were stirred for 30 minutes. To the mixtures was added water, and the mixtures were extracted with ethyl acetate. The resulting organic layers were dried over sodium sulfate, and concentrated under reduced pressure. The resulting residues were subjected to a silica gel column chromatography to give the present compound 154 represented by the following formula 240 mg.

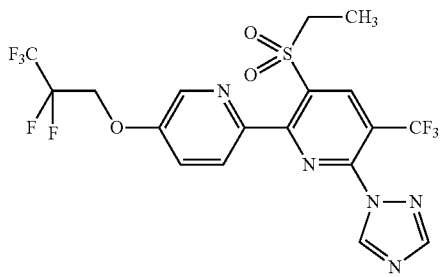 [SMILES: CCS(=O)(=O)c1cc(C(F)(F)F)c(-n2cncn2)nc1-c1ccc(OCC(F)(F)C(F)(F)F)cn1]

¹H-NMR (CDCl₃) δ: 9.02 (1H, s), 8.99 (1H, s), 8.44 (1H, d), 8.23 (1H, s), 8.01 (1H, d), 7.47 (1H, dd), 4.58 (2H, t), 4.05 (2H, q), 1.47 (3H, t).

Preparation Example 31

The present compound 124 represented by the following formula was obtained by using the present compound 109 instead of the present compound 79 according to the similar method to that described in Preparation example 17.

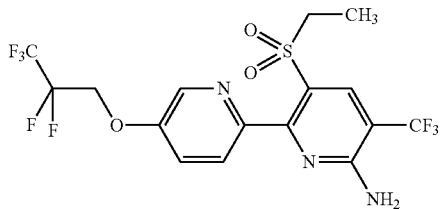 [SMILES: CCS(=O)(=O)c1cc(C(F)(F)F)c(N)nc1-c1ccc(OCC(F)(F)C(F)(F)F)cn1]

¹H-NMR (CDCl₃) δ: 8.44 (1H, s), 8.35 (1H, s), 7.78 (1H, d), 7.39 (1H, d), 5.52 (2H, s), 4.53 (2H, t), 3.79 (2H, q), 1.37 (3H, t).

Preparation Example 32

The present compound 129 represented by the following formula was obtained by using the present compound 109 instead of the present compound 79, and using 40% methylamine-methanol solution instead of aqueous 50% dimethylamine solution according to the similar method to that described in Preparation example 18.

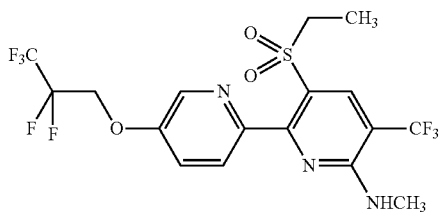

¹H-NMR (CDCl₃) δ: 8.35-8.35 (2H, m), 7.86 (1H, dd), 7.40 (1H, dd), 5.48 (1H, s), 4.54 (2H, td), 3.83 (2H, q), 3.15 (3H, d), 1.37 (3H, t).

Preparation Example 33

The present compound 139 represented by the following formula was obtained by using the present compound 109 instead of the present compound 79 according to the similar method to that described in Preparation example 19.

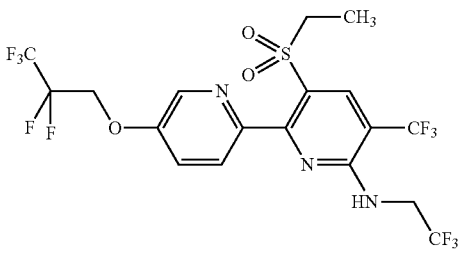

¹H-NMR (CDCl₃) δ: 8.47 (1H, d), 8.36 (1H, d), 7.81 (1H, d), 7.42 (1H, dd), 5.62 (1H, s), 4.55 (2H, t), 4.42-4.33 (2H, m), 3.89 (2H, q), 1.39 (3H, t).

Preparation Example 34

To a mixture of the present compound 109 1.0 g, diisopropylethylamine 820 μL, and THF 5 mL was added hydrazine monohydrate 160 μL, and the mixtures were stirred at room temperature for 1 hour. To the mixtures was added water, and the mixtures were extracted with ethyl acetate. The resulting organic layers were dried over sodium sulfate, and concentrated under reduced pressure. The resulting residues were subjected to a silica gel column to give the present compound 144 represented by the following formula 620 mg.

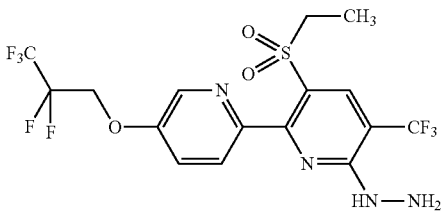

¹H-NMR (CDCl₃) δ: 8.40 (1H, d), 8.37 (1H, d), 7.82 (1H, d), 7.41 (1H, dd), 6.74 (1H, s), 4.55 (2H, t), 4.19 (2H, d), 3.80 (2H, q), 1.37 (3H, t).

Preparation Example 35

To a mixture of the present compound 144 550 mg, pyridine 110 μL, and acetonitrile 10 mL was added p-toluenesulfonyl chloride 250 mg at room temperature, and the mixtures were stirred at room temperature for 1 hour. To the mixtures was added water, and the mixtures were extracted with ethyl acetate. The resulting organic layers were dried over sodium sulfate, and concentrated under reduced pressure. The residues were subjected to a silica gel column to give the present compound 149 represented by the following formula 730 mg.

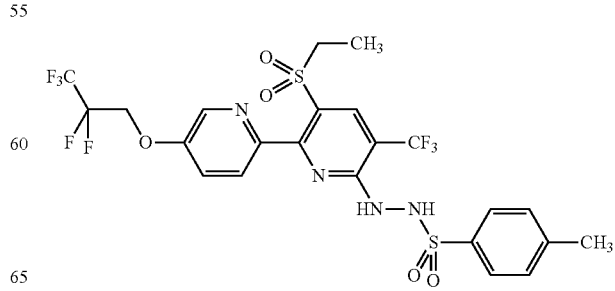

$^1$H-NMR (CDCl$_3$) δ: 8.40 (1H, d), 8.36 (1H, d), 7.71 (1H, d), 7.65 (2H, d), 7.50 (1H, t), 7.41 (1H, dd), 7.34 (1H, d), 7.00 (2H, d), 4.58 (2H, t), 3.81 (2H, q), 2.29 (3H, s), 1.33 (3H, t).

Preparation Example 36

To a mixture of the present compound 149 640 mg, water 1 mL and ethylene glycol 2 mL was added sodium hydroxide 78 mg at room temperature, and the mixtures were stirred at 90° C. for 1 hour. To the mixtures was added water, and the mixtures were extracted with ethyl acetate. The resulting mixtures were dried over sodium sulfate, and concentrated under reduced pressure. The resulting residues were subjected to a silica gel column to give the present compound 39 represented by the following formula 350 mg.

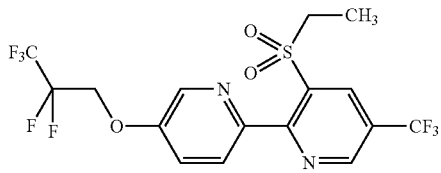 [SMILES: CCS(=O)(=O)c1cc(C(F)(F)F)cnc1-c1ccc(OCC(F)(F)C(F)(F)F)cn1]

$^1$H-NMR (CDCl$_3$) δ: 9.10 (1H, s), 8.73 (1H, s), 8.40 (1H, d), 7.97 (1H, d), 7.46-7.44 (1H, m), 4.56 (2H, t), 3.99 (2H, q), 1.42 (3H, t).

Preparation Example 37

The present compound 119 was obtained by using the present compound 109 instead of the present compound 79 according to the similar method to that described in Preparation example 14.

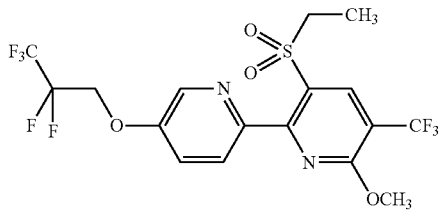

$^1$H-NMR (CDCl$_3$) δ: 8.59 (1H, d), 8.38 (1H, t), 7.90 (1H, dd), 7.42 (1H, dd), 4.55 (2H, t), 4.16 (3H, s), 3.91 (2H, q), 1.40 (3H, t).

Preparation Example 38(1)

To a mixture of the intermediate compound 10 3.4 g and NMP 36 mL was added sodium monohydrogensulfide n-hydrate (manufactured by Wako Pure Chemical Industries, Ltd.) 5.0 g at room temperature. The reaction mixtures were stirred with heating at 80° C. for 12 hours. The resulting reaction mixtures were stood to cool to room temperature, and thereto was then added water, and further added 2N hydrochloric acid to adjust to pH 4. The resulting mixtures were extracted with ethyl acetate, and dried over anhydrous sodium sulfate, and concentrated. The resulting solutions were stirred at room temperature under air atmosphere for 12 hours. The resulting solutions were subjected to a silica gel column chromatography to give the intermediate compound 20 in a trace amount and the intermediate compound 21 2.5 g, which are represented by the following formulae.

Intermediate Compound 20

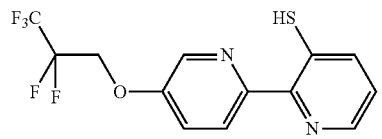 [SMILES: FC(F)(F)C(F)(F)COc1ccc(-c2ncccc2S)nc1]

LC-MS: M+H: 337

Intermediate Compound 21

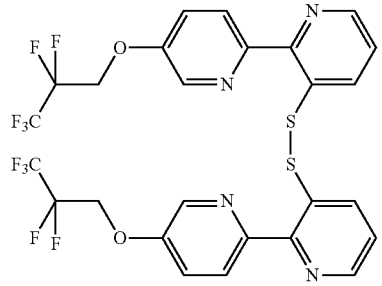 [SMILES: FC(F)(F)C(F)(F)COc1ccc(-c2ncccc2SSc2cccnc2-c2ccc(OCC(F)(F)C(F)(F)F)cn2)nc1]

$^1$H-NMR (DMSO-D$_6$) δ: 8.57 (2H, d), 8.52 (2H, dd), 8.32 (2H, d), 8.05 (2H, dd), 7.78 (2H, dd), 7.41 (2H, dd), 5.06 (4H, t).
LC-MS: M+H: 671

Preparation Example 38(2)

To a mixture of the intermediate compound 21 200 mg, potassium carbonate 240 mg, and DMF 1.2 mL were added (bromomethyl)cyclopropane 190 mg and hydroxymethanesulfinic acid sodium salt 2 hydrates 270 mg successively at room temperature. The reaction mixtures were warmed to 80° C. and stirred with heating for 10 hours. The reaction mixtures were stood to cool to room temperature, and thereto was added aqueous sodium hydrogen carbonate solution, and the mixtures were extracted with ethyl acetate. The resulting organic layers were washed with saturated saline, dried over anhydrous sodium sulfate, and concentrated under reduced pressure. The resulting residues were subjected to a silica gel column chromatography to give the present compound 279 represented by the following formula 150 mg.

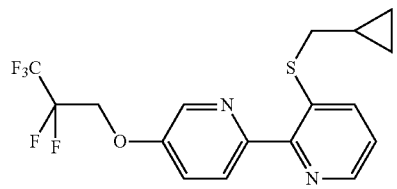 [SMILES: FC(F)(F)C(F)(F)COc1ccc(-c2ncccc2SCC2CC2)nc1]

$^1$H-NMR (CDCl$_3$) δ: 8.48 (1H, d), 8.43 (1H, dd), 8.02 (1H, dd), 7.71 (1H, dd), 7.41 (1H, dd), 7.24 (1H, dd), 4.55 (2H, td), 2.82 (2H, d), 1.07-0.97 (1H, m), 0.63-0.57 (2H, m), 0.31-0.26 (2H, m).

Preparation Example 38(3)

The present compound 280 was obtained by using the present compound 279 instead of the present compound 9 according to the similar method to that described in Preparation example 2.

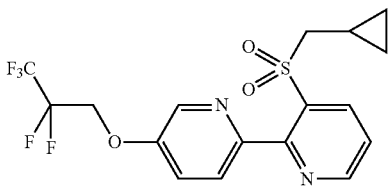 [SMILES: O=S(=O)(CC1CC1)c1cccnc1-c1ccc(OCC(F)(F)C(F)(F)F)cn1]

¹H-NMR (CDCl₃) δ: 8.86 (1H, dd), 8.56 (1H, dd), 8.34 (1H, d), 7.88 (1H, d), 7.54 (1H, dd), 7.42 (1H, dd), 4.54 (2H, td), 3.82 (2H, d), 1.20-1.08 (1H, m), 0.62-0.55 (2H, m), 0.37-0.31 (2H, m).

An intermediate compound 22 was obtained by using 5-chloro-2-cyanopyridine instead of 5-fluoro-2-cyanopyridine according to the similar method to that described in Preparation example 10-1.

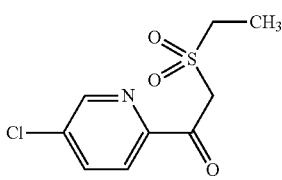

¹H NMR (CDCl₃) δ ppm: 1.47 (3H, t), 3.29 (2H, q), 4.96 (2H, s), 7.87 (1H, dd), 8.08 (1H, dd), 8.68 (1H, dd)

An intermediate compound 23 represented by the following formula was obtained by using the intermediate compound 22 instead of the intermediate compound 16 according to the similar method to that described in Preparation example 10-2.

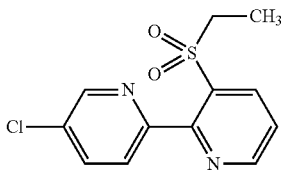 [SMILES: CCS(=O)(=O)c1cccnc1-c1ccc(Cl)cn1]

¹H NMR (CDCl₃) δ ppm: 1.38 (3H, t), 3.87 (2H, q), 7.57 (1H, dd), 7.81 (1H, dd), 7.85 (1H, dd), 8.49 (1H, dd), 8.58 (1H, dd), 8.88 (1H, dd)

An intermediate compound 24 represented by the following formula was obtained by using 2-cyano-5-bromopyridine instead of 5-fluoro-2-cyanopyridine according to the similar method to that described in Preparation example 10-1.

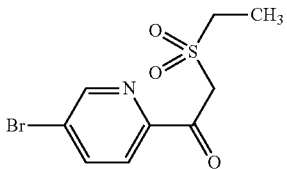

¹H-NMR (CDCl₃) δ: 8.79 (1H, d), 8.04-7.98 (2H, m), 4.97 (2H, s), 3.28 (2H, q), 1.46 (3H, t).

An intermediate compound 25 was obtained by using the intermediate compound 24 instead of the intermediate compound 16 according to the similar method to that described in Preparation example 10-2.

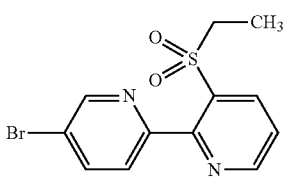

¹H-NMR (CDCl₃) δ: 8.87 (1H, dd), 8.68 (1H, d), 8.49 (1H, dd), 8.01-7.98 (1H, m), 7.74 (1H, d), 7.56 (1H, dd), 3.86 (2H, q), 1.37 (3H, t).

An intermediate compound 25 was obtained by using 2-cyano-5-(2,2,3,3-tetrafluoropropoxy)pyridine instead of 5-fluoro-2-cyanopyridine according to the similar method to that described in Preparation example 10-1.

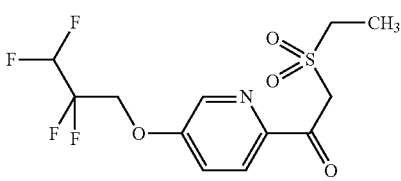 [SMILES: CCS(=O)(=O)CC(=O)c1ccc(OCC(F)(F)C(F)F)cn1]

¹H-NMR (CDCl₃) δ: 8.43 (1H, d), 8.16 (1H, d), 7.38 (1H, dd), 6.05 (1H, tt), 4.96 (2H, s), 4.52 (2H, t), 3.29 (2H, q), 1.47 (3H, t).

The present compound 7 was obtained by using the intermediate compound 25 instead of the intermediate compound 16 according to the similar method to that described in Preparation example 10-2.

An intermediate compound 26 represented by the following formula was obtained by using 2-cyano-5-(2,2,3,3,3-pentafluoropropoxy)pyridine instead of 5-fluoro-2-cyanopyridine according to the similar method to that described in Preparation example 10-1.

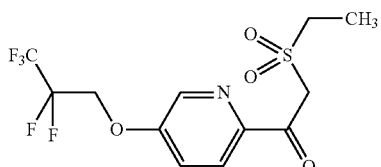

¹H-NMR (CDCl₃) δ: 8.44 (1H, t), 8.16 (1H, dd), 7.39 (1H, dd), 4.96 (2H, s), 4.58 (2H, td), 3.29 (2H, q), 1.47 (3H, t).

The present compound 8 was obtained by using the intermediate compound 26 instead of the intermediate compound 16 according to the similar method to that described in Preparation example 10-2.

A compound represented by formula (200):

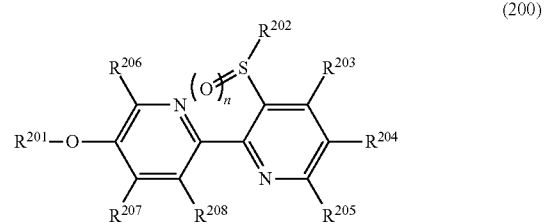

(200)

[wherein $R^{201}$, $R^{202}$, $R^{203}$, $R^{204}$, $R^{205}$, $R^{206}$, $R^{207}$, $R^{208}$, and n represent any combination of the elements indicated in the following [Table 20] to [Table 38] can be prepared according to the similar methods to those described above.

TABLE 20

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 1 | CF₂HCH₃ | CH₃CH₂ | 2 | H | H | H | H | H | H |
| 2 | CF₃CH₃ | CH₃CH₂ | 2 | H | H | H | H | H | H |
| 3 | CCl₃CH₃ | CH₃CH₂ | 2 | H | H | H | H | H | H |
| 4 | CF₂HCF₂ | CH₃CH₂ | 2 | H | H | H | H | H | H |
| 5 | CClFHCF₃ | CH₃CH₂ | 2 | H | H | H | H | H | H |
| 6 | CF₃CH₂CH₂ | CH₃CH₂ | 2 | H | H | H | H | H | H |
| 7 | CF₂HCF₂CH₃ | CH₃CH₂ | 2 | H | H | H | H | H | H |
| 8 | CF₃CF₂CH₂ | CH₃CH₂ | 2 | H | H | H | H | H | H |
| 9 | CF₃CFHCF₂ | CH₃CH₂ | 0 | H | H | H | H | H | H |
| 10 | CF₃CFHCF₂ | CH₃CH₂ | 1 | H | H | H | H | H | H |
| 11 | CF₃CFHCF₂ | CH₃CH₂ | 2 | H | H | H | H | H | H |
| 12 | CH₃CF₂CH₂ | CH₃CH₂ | 2 | H | H | H | H | H | H |
| 13 | C(CF₃)₂(CH₃)CH₂ | CH₃CH₂ | 2 | H | H | H | H | H | H |
| 14 | CF₃CFHCF₂CH₃ | CH₃CH₂ | 2 | H | H | H | H | H | H |
| 15 | CF₃CF₂CF₂CH₂ | CH₃CH₂ | 2 | H | H | H | H | H | H |
| 16 | CF₃CF₂CF₂CF₂CH₂ | CH₃CH₂ | 2 | H | H | H | H | H | H |
| 17 | CF₃CF₂CF₃CF₂CF₃CH₂ | CH₃CH₂ | 2 | H | H | H | H | H | H |
| 18 | CF₃CF₂CF₃CF₂CH₃CH₂ | CH₃CH₂ | 2 | H | H | H | H | H | H |
| 19 | CF(CF₃)₂CF₂CF₂CH₃CH₂ | CH₃CH₂ | 2 | H | H | H | H | H | H |
| 20 | CF₂HCF₂CF₂CF₂CH₂ | CH₃CH₂ | 2 | H | H | H | H | H | H |
| 21 | CF₂HCF₂CF₂CF₂CF₂CF₂CH₃ | CH₃CH₂ | 2 | H | H | H | H | H | H |
| 22 | CF₃OCFHCF₂ | CH₃CH₂ | 0 | H | H | H | H | H | H |
| 23 | CF₃OCFHCF₃ | CH₃CH₂ | 1 | H | H | H | H | H | H |
| 24 | CF₃OCFHCF₂ | CH₃CH₂ | 2 | H | H | H | H | H | H |
| 25 | CF₃CH₂OCH₂CH₂ | CH₃CH₂ | 2 | H | H | H | H | H | H |
| 26 | CF₂HCF₂CH₂ | CH₃CH₂ | 0 | H | H | H | H | H | H |
| 27 | CF₃CF₂CH₃ | CH₃CH₂ | 0 | H | H | H | H | H | H |

TABLE 21

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 28 | CF₃CFHCF₂CH₂ | CH₃CH₂ | 0 | H | H | H | H | H | H |
| 29 | CF₂HCF₂CH₂ | CH₃CH₂ | 1 | H | H | H | H | H | H |
| 30 | CF₃CF₂CH₂ | CH₃CH₂ | 1 | H | H | H | H | H | H |
| 31 | CF₃CFHCF₂CH₂ | CH₃CH₂ | 1 | H | H | H | H | H | H |
| 32 | CF₂HCH₃ | CH₃CH₂ | 2 | H | CF₃ | H | H | H | H |
| 33 | CF₃CH₂ | CH₃CH₂ | 2 | H | CF₃ | H | H | H | H |
| 34 | CCl₃CH₂ | CH₃CH₂ | 2 | H | CF₃ | H | H | H | H |
| 35 | CF₂HCF₂ | CH₃CH₂ | 2 | H | CF₃ | H | H | H | H |
| 36 | CClFHCF₂ | CH₃CH₂ | 2 | H | CF₃ | H | H | H | H |
| 37 | CF₃CH₂CH₂ | CH₃CH₂ | 2 | H | CF₃ | H | H | H | H |
| 38 | CF₂HCF₂CH₂ | CH₃CH₂ | 2 | H | CF₃ | H | H | H | H |
| 39 | CF₃CF₂CH₂ | CH₃CH₂ | 2 | H | CF₃ | H | H | H | H |
| 40 | CF₃CFHCF₂ | CH₃CH₂ | 2 | H | CF₃ | H | H | H | H |
| 41 | CH₃CF₂CH₂ | CH₃CH₂ | 2 | H | CF₃ | H | H | H | H |
| 42 | C(CF₃)₂(CH₃)CH₂ | CH₃CH₂ | 2 | H | CF₃ | H | H | H | H |
| 43 | CF₃CFHCF₂CH₂ | CH₃CH₂ | 2 | H | CF₃ | H | H | H | H |
| 44 | CF₃CF₂CF₂CH₂ | CH₃CH₂ | 2 | H | CF₃ | H | H | H | H |
| 45 | CF₃CF₂CF₂CF₂CH₂ | CH₃CH₂ | 2 | H | CF₃ | H | H | H | H |
| 46 | CF₃CF₂CF₂CF₂CF₂CH₂ | CH₃CH₂ | 2 | H | CF₃ | H | H | H | H |
| 47 | CF₃CF₂CF₂CF₂CH₂CH₂ | CH₃CH₂ | 2 | H | CF₃ | H | H | H | H |
| 48 | CF(CF₃)₂CF₂CF₂CH₂CH₂ | CH₃CH₂ | 2 | H | CF₃ | H | H | H | H |

TABLE 21-continued

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 49 | $CF_2HCF_2CF_2CF_2CH_2$ | $CH_3CH_2$ | 2 | H | $CF_3$ | H | H | H | H |
| 50 | $CF_2HCF_2CF_2CF_2CF_2CH_2$ | $CH_3CH_2$ | 2 | H | $CF_3$ | H | H | H | H |
| 51 | $CF_3OCFHCF_3$ | $CH_3CH_2$ | 2 | H | $CF_3$ | H | H | H | H |
| 52 | $CF_3CH_2OCH_2CH_2$ | $CH_3CH_2$ | 2 | H | $CF_3$ | H | H | H | H |

TABLE 22

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 53 | $CF_2HCF_2CH_2$ | $CH_3CH_2$ | 2 | H | H | $CF_3$ | H | H | H |
| 54 | $CF_3CF_2CH_2$ | $CH_3CH_2$ | 2 | H | H | $CF_3$ | H | H | H |
| 55 | $CF_3CFHCF_2$ | $CH_3CH_2$ | 2 | H | H | $CF_3$ | H | H | H |
| 56 | $CF_3CFHCF_2CH_2$ | $CH_3CH_2$ | 2 | H | H | $CF_3$ | H | H | H |
| 57 | $CF_3OCFHCF_2$ | $CH_3CH_2$ | 2 | H | H | $CF_3$ | H | H | H |
| 58 | $CF_2HCF_2CH_2$ | $CH_3CH_2$ | 2 | H | H | $NH_2$ | H | H | H |
| 59 | $CF_3CF_2CH_2$ | $CH_3CH_2$ | 2 | H | H | $NH_2$ | H | H | H |
| 60 | $CF_3CFHCF_2$ | $CH_3CH_2$ | 2 | H | H | $NH_2$ | H | H | H |
| 61 | $CF_3CFHCF_2CH_2$ | $CH_3CH_2$ | 2 | H | H | $NH_2$ | H | H | H |
| 62 | $CF_2OCFHCF_2$ | $CH_3CH_2$ | 2 | H | H | $NH_2$ | H | H | H |
| 63 | $CF_2HCF_2CH_2$ | $CH_3CH_2$ | 2 | H | H | $NHCH_3$ | H | H | H |
| 64 | $CF_3CF_2CH_2$ | $CH_3CH_2$ | 2 | H | H | $NHCH_3$ | H | H | H |
| 65 | $CF_3CFHCF_2$ | $CH_3CH_2$ | 2 | H | H | $NHCH_3$ | H | H | H |
| 66 | $CF_3CFHCF_2CH_2$ | $CH_3CH_2$ | 2 | H | H | $NHCH_3$ | H | H | H |
| 67 | $CF_3OCFHCF_2$ | $CH_3CH_2$ | 2 | H | H | $NHCH_3$ | H | H | H |
| 68 | $CF_3HCF_2CH_2$ | $CH_3CH_2$ | 2 | H | H | $N(CH_3)_2$ | H | H | H |
| 69 | $CF_3CF_2CH_2$ | $CH_3CH_2$ | 2 | H | H | $N(CH_3)_2$ | H | H | H |
| 70 | $CF_3CFHCF_2$ | $CH_3CH_2$ | 2 | H | H | $N(CH_3)_2$ | H | H | H |
| 71 | $CF_3CFHCF_2CH_2$ | $CH_3CH_2$ | 2 | H | H | $N(CH_3)_2$ | H | H | H |
| 72 | $CF_3OCFHCF_2$ | $CH_3CH_2$ | 2 | H | H | $N(CH_3)_2$ | H | H | H |
| 73 | $CF_3HCF_2CH_2$ | $CH_3CH_2$ | 2 | H | H | $NHCH_2CF_3$ | H | H | H |
| 74 | $CF_3CF_2CH_2$ | $CH_3CH_2$ | 2 | H | H | $NHCH_2CF_3$ | H | H | H |
| 75 | $CF_3CFHCF_2$ | $CH_3CH_2$ | 2 | H | H | $NHCH_2CF_3$ | H | H | H |
| 76 | $CF_3CFHCF_2CH_2$ | $CH_3CH_2$ | 2 | H | H | $NHCH_2CF_3$ | H | H | H |
| 77 | $CF_3OCFHCF_2$ | $CH_3CH_2$ | 2 | H | H | $NHCH_2CF_3$ | H | H | H |

TABLE 23

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 78 | $CF_2HCF_2CH_2$ | $CH_3CH_2$ | 2 | H | H | Cl | H | H | H |
| 79 | $CF_3CF_2CH_2$ | $CH_3CH_2$ | 2 | H | H | Cl | H | H | H |
| 80 | $CF_3CFHCF_2$ | $CH_3CH_2$ | 2 | H | H | Cl | H | H | H |
| 81 | $CF_3CFHCF_2CH_2$ | $CH_3CH_2$ | 2 | H | H | Cl | H | H | H |
| 82 | $CF_3OCFHCF_3$ | $CH_3CH_2$ | 2 | H | H | Cl | H | H | H |
| 83 | $CF_2HCF_2CH_2$ | $CH_3CH_2$ | 2 | H | Cl | H | H | H | H |
| 84 | $CF_3CF_2CH_2$ | $CH_3CH_2$ | 2 | H | Cl | H | H | H | H |
| 85 | $CF_3CFHCF_3$ | $CH_3CH_2$ | 2 | H | Cl | H | H | H | H |
| 86 | $CF_3CFHCF_2CH_2$ | $CH_3CH_2$ | 2 | H | Cl | H | H | H | H |
| 87 | $CF_3OCFHCF_2$ | $CH_3CH_2$ | 2 | H | Cl | H | H | H | H |
| 88 | $CF_2HCF_2CH_2$ | $CH_3CH_2$ | 2 | H | H | 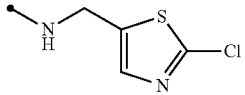 | H | H | H |
| 89 | $CF_3CF_2CH_2$ | $CH_3CH_2$ | 2 | H | H | 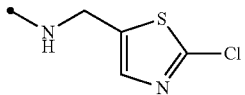 | H | H | H |
| 90 | $CF_3CFHCF_2$ | $CH_3CH_2$ | 2 | H | H | 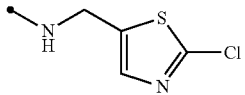 | H | H | H |

TABLE 23-continued

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 91 | $CF_3CFHCF_2CH_2$ | $CH_3CH_2$ | 2 | H | H | 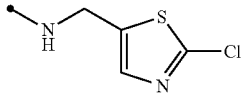 | H | H | H |
| 92 | $CF_3OCFHCF_3$ | $CH_3CH_2$ | 2 | H | H | 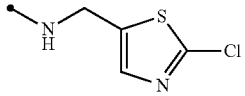 | H | H | H |
| 93 | $CF_2HCF_2CH_2$ | $CH_3CH_2$ | 2 | H | H | $OCH_3$ | H | H | H |
| 94 | $CF_3CF_2CH_2$ | $CH_3CH_2$ | 2 | H | H | $OCH_3$ | H | H | H |
| 95 | $CF_3CFHCF_2$ | $CH_3CH_2$ | 2 | H | H | $OCH_3$ | H | H | H |
| 96 | $CF_3CFHCF_2CH_2$ | $CH_3CH_2$ | 2 | H | H | $OCH_3$ | H | H | H |
| 97 | $CF_3OCFHCF_3$ | $CH_3CH_2$ | 2 | H | H | $OCH_3$ | H | H | H |
| 98 | $CF_2HCF_2CH_2$ | $CH_3CH_2$ | 2 | H | $CH_2CH=CH_2$ | H | H | H | H |
| 99 | $CF_3CF_2CH_2$ | $CH_3CH_2$ | 2 | H | $CH_2CH=CH_2$ | H | H | H | H |
| 100 | $CF_3CFHCF_2$ | $CH_3CH_2$ | 2 | H | $CH_2CH=CH_2$ | H | H | H | H |

TABLE 24

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 101 | $CF_3CFHCF_2CH_2$ | $CH_3CH_2$ | 2 | H | $CH_2CH=CH_2$ | H | H | H | H |
| 102 | $CF_3OCFHCF_2$ | $CH_3CH_2$ | 2 | H | $CH_2CH=CH_2$ | H | H | H | H |
| 103 | $CF_2HCF_2CH_2$ | $CH_3CH_2$ | 2 | H | H | 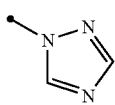 | H | H | H |
| 104 | $CF_3CF_2CH_2$ | $CH_3CH_2$ | 2 | H | H | 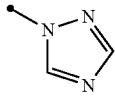 | H | H | H |
| 105 | $CF_3CFHCF_2$ | $CH_3CH_2$ | 2 | H | H | 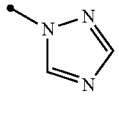 | H | H | H |
| 106 | $CF_3CFHCF_2CH_2$ | $CH_3CH_2$ | 2 | H | H | 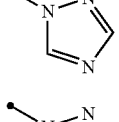 | H | H | H |
| 107 | $CF_3OCFHCF_2$ | $CH_3CH_2$ | 2 | H | H | 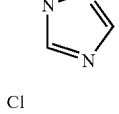 | H | H | H |
| 108 | $CF_2HCF_2CH_2$ | $CH_3CH_2$ | 2 | H | $CF_3$ | Cl | H | H | H |
| 109 | $CF_3CF_2CH_2$ | $CH_3CH_2$ | 2 | H | $CF_3$ | Cl | H | H | H |
| 110 | $CF_3CFHCF_2$ | $CH_3CH_2$ | 2 | H | $CF_3$ | Cl | H | H | H |
| 111 | $CF_3CFHCF_2CH_2$ | $CH_3CH_2$ | 2 | H | $CF_3$ | Cl | H | H | H |
| 112 | $CF_3OCFHCF_2$ | $CH_3CH_2$ | 2 | H | $CF_3$ | Cl | H | H | H |
| 113 | $CF_2HCF_2CH_2$ | $CH_3CH_2$ | 2 | H | $CF_3$ | OH | H | H | H |
| 114 | $CF_3CF_2CH_2$ | $CH_3CH_2$ | 2 | H | $CF_3$ | OH | H | H | H |
| 115 | $CF_3CFHCF_2$ | $CH_3CH_2$ | 2 | H | $CF_3$ | OH | H | H | H |
| 116 | $CF_3CFHCF_2CH_2$ | $CH_3CH_2$ | 2 | H | $CF_3$ | OH | H | H | H |
| 117 | $CF_3OCFHCF_2$ | $CH_3CH_2$ | 2 | H | $CF_3$ | OH | H | H | H |
| 118 | $CF_2HCF_2CH_2$ | $CH_3CH_2$ | 2 | H | $CF_3$ | $OCH_3$ | H | H | H |
| 119 | $CF_3CF_2CH_2$ | $CH_3CH_2$ | 2 | H | $CF_3$ | $OCH_3$ | H | H | H |
| 120 | $CF_3CFHCF_2$ | $CH_3CH_2$ | 2 | H | $CF_3$ | $OCH_3$ | H | H | H |
| 121 | $CF_3CFHCF_2CH_2$ | $CH_3CH_2$ | 2 | H | $CF_3$ | $OCH_3$ | H | H | H |
| 122 | $CF_3OCFHCF_2$ | $CH_3CH_2$ | 2 | H | $CF_3$ | $OCH_3$ | H | H | H |
| 123 | $CF_2HCF_2CH_2$ | $CH_3CH_2$ | 2 | H | $CF_3$ | $NH_2$ | H | H | H |

TABLE 25

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 124 | $CF_3CF_2CH_2$ | $CH_3CH_2$ | 2 | H | $CF_3$ | $NH_2$ | H | H | H |
| 125 | $CF_3CFHCF_2$ | $CH_3CH_2$ | 2 | H | $CF_3$ | $NH_2$ | H | H | H |
| 126 | $CF_3CFHCF_2CH_2$ | $CH_3CH_2$ | 2 | H | $CF_3$ | $NH_2$ | H | H | H |
| 127 | $CF_3OCFHCF_2$ | $CH_3CH_2$ | 2 | H | $CF_3$ | $NH_2$ | H | H | H |
| 128 | $CF_2HCF_2CH_2$ | $CH_3CH_2$ | 2 | H | $CF_3$ | $NHCH_3$ | H | H | H |
| 129 | $CF_3CF_2CH_2$ | $CH_3CH_2$ | 2 | H | $CF_3$ | $NHCH_3$ | H | H | H |
| 130 | $CF_3CFHCF_2$ | $CH_3CH_2$ | 2 | H | $CF_3$ | $NHCH_3$ | H | H | H |
| 131 | $CF_3CFHCF_2CH_2$ | $CH_3CH_2$ | 2 | H | $CF_3$ | $NHCH_3$ | H | H | H |
| 132 | $CF_3OCFHCF_2$ | $CH_3CH_2$ | 2 | H | $CF_3$ | $NHCH_3$ | H | H | H |
| 133 | $CF_2HCF_2CH_2$ | $CH_3CH_2$ | 2 | H | $CF_3$ | $N(CH_3)_2$ | H | H | H |
| 134 | $CF_3CF_2CH_2$ | $CH_3CH_2$ | 2 | H | $CF_3$ | $N(CH_3)_2$ | H | H | H |
| 135 | $CF_3CFHCF_2$ | $CH_3CH_2$ | 2 | H | $CF_3$ | $N(CH_3)_2$ | H | H | H |
| 136 | $CF_3CFHCF_2CH_2$ | $CH_3CH_2$ | 2 | H | $CF_3$ | $N(CH_3)_2$ | H | H | H |
| 137 | $CF_3OCFHCF_2$ | $CH_3CH_2$ | 2 | H | $CF_3$ | $N(CH_3)_2$ | H | H | H |
| 138 | $CF_2HCF_2CH_2$ | $CH_3CH_2$ | 2 | H | $CF_3$ | $NHCH_2CF_2$ | H | H | H |
| 139 | $CF_3CF_2CH_2$ | $CH_3CH_2$ | 2 | H | $CF_3$ | $NHCH_2CF_2$ | H | H | H |
| 140 | $CF_3CFHCF_2$ | $CH_3CH_2$ | 2 | H | $CF_3$ | $NHCH_2CF_2$ | H | H | H |
| 141 | $CF_3CFHCF_2CH_2$ | $CH_3CH_2$ | 2 | H | $CF_3$ | $NHCH_2CF_2$ | H | H | H |
| 142 | $CF_3OCFHCF_2$ | $CH_3CH_2$ | 2 | H | $CF_3$ | $NHCH_2CF_2$ | H | H | H |
| 143 | $CF_2HCF_2CH_2$ | $CH_3CH_2$ | 2 | H | $CF_3$ | $NHNH_2$ | H | H | H |
| 144 | $CF_3CF_2CH_2$ | $CH_3CH_2$ | 2 | H | $CF_3$ | $NHNH_2$ | H | H | H |
| 145 | $CF_3CFHCF_2$ | $CH_3CH_2$ | 2 | H | $CF_3$ | $NHNH_2$ | H | H | H |
| 146 | $CF_3CFHCF_2CH_2$ | $CH_3CH_2$ | 2 | H | $CF_3$ | $NHNH_2$ | H | H | H |
| 147 | $CF_3OCFHCF_2$ | $CH_3CH_2$ | 2 | H | $CF_3$ | $NHNH_2$ | H | H | H |

TABLE 26

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 148 | $CF_2HCF_2CH_2$ | $CH_3CH_2$ | 2 | H | $CF_3$ | -NH-NH-SO$_2$-C$_6$H$_4$-CH$_3$ | H | H | H |
| 149 | $CF_3CF_2CH_2$ | $CH_3CH_2$ | 2 | H | $CF_3$ | -NH-NH-SO$_2$-C$_6$H$_4$-CH$_3$ | H | H | H |
| 150 | $CF_3CFHCF_2$ | $CH_3CH_2$ | 2 | H | $CF_3$ | -NH-NH-SO$_2$-C$_6$H$_4$-CH$_3$ | H | H | H |
| 151 | $CF_3CFHCF_2CH_2$ | $CH_3CH_2$ | 2 | H | $CF_3$ | -NH-NH-SO$_2$-C$_6$H$_4$-CH$_3$ | H | H | H |
| 152 | $CF_3OCFHCF_2$ | $CH_3CH_2$ | 2 | H | $CF_3$ | -NH-NH-SO$_2$-C$_6$H$_4$-CH$_3$ | H | H | H |
| 153 | $CF_2HCF_2CH_2$ | $CH_3CH_2$ | 2 | H | $CF_3$ | 1,2,4-triazol-1-yl | H | H | H |

TABLE 26-continued

| Present compound | R²⁰¹ | R²⁰² | n | R²⁰³ | R²⁰⁴ | R²⁰⁵ | R²⁰⁶ | R²⁰⁷ | R²⁰⁸ |
|---|---|---|---|---|---|---|---|---|---|
| 154 | CF₃CF₂CH₂ | CH₃CH₂ | 2 | H | CF₃ | 1,2,4-triazol-1-yl | H | H | H |
| 155 | CF₃CFHCF₂ | CH₃CH₂ | 2 | H | CF₃ | 1,2,4-triazol-1-yl | H | H | H |
| 156 | CF₃CFHCF₂CH₂ | CH₃CH₂ | 2 | H | CF₃ | 1,2,4-triazol-1-yl | H | H | H |
| 157 | CF₃OCFHCF₂ | CH₃CH₂ | 2 | H | CF₃ | 1,2,4-triazol-1-yl | H | H | H |
| 158 | CF₂HCF₂CH₂ | CH₃CH₂ | 2 | H | H | H | OH | H | H |
| 159 | CF₃CF₂CH₂ | CH₃CH₂ | 2 | H | H | H | OH | H | H |
| 160 | CF₃CFHCF₂ | CH₃CH₂ | 2 | H | H | H | OH | H | H |
| 161 | CF₃CFHCF₂CH₂ | CH₃CH₂ | 2 | H | H | H | OH | H | H |
| 162 | CF₃OCFHCF₂ | CH₃CH₂ | 2 | H | H | H | OH | H | H |
| 163 | CF₂HCF₂CH₂ | CH₃CH₂ | 2 | H | H | H | OCH₃ | H | H |

TABLE 27

| Present compound | R²⁰¹ | R²⁰² | n | R²⁰³ | R²⁰⁴ | R²⁰⁵ | R²⁰⁶ | R²⁰⁷ | R²⁰⁸ |
|---|---|---|---|---|---|---|---|---|---|
| 164 | CF₃CF₂CH₂ | CH₃CH₂ | 2 | H | H | H | OCH₃ | H | H |
| 165 | CF₃CFHCF₂ | CH₃CH₂ | 2 | H | H | H | OCH₃ | H | H |
| 166 | CF₃CFHCF₂CH₂ | CH₃CH₂ | 2 | H | H | H | OCH₃ | H | H |
| 167 | CF₃OCFHCF₂ | CH₃CH₂ | 2 | H | H | H | OCH₃ | H | H |
| 168 | CF₂HCF₂CH₂ | CH₃CH₂ | 2 | H | H | H | Cl | H | H |
| 169 | CF₃CF₂CH₂ | CH₃CH₂ | 2 | H | H | H | Cl | H | H |
| 170 | CF₃CFHCF₂ | CH₃CH₂ | 2 | H | H | H | Cl | H | H |
| 171 | CF₃CFHCF₂CH₂ | CH₃CH₂ | 2 | H | H | H | Cl | H | H |
| 172 | CF₃OCFHCF₂ | CH₃CH₂ | 2 | H | H | H | Cl | H | H |
| 173 | CF₂HCF₂CH₂ | CH₃CH₂ | 2 | H | H | H | OC(O)CH₃ | H | H |
| 174 | CF₃CF₂CH₂ | CH₃CH₂ | 2 | H | H | H | OC(O)CH₃ | H | H |
| 175 | CF₃CFHCF₂ | CH₃CH₂ | 2 | H | H | H | OC(O)CH₃ | H | H |
| 176 | CF₃CFHCF₂CH₂ | CH₃CH₂ | 2 | H | H | H | OC(O)CH₃ | H | H |
| 177 | CF₃OCFHCF₂ | CH₃CH₂ | 2 | H | H | H | OC(O)CH₃ | H | H |
| 178 | CF₂HCF₂CH₂ | CH₃CH₂ | 2 | H | H | H | CN | H | H |
| 179 | CF₃CF₂CH₂ | CH₃CH₂ | 2 | H | H | H | CN | H | H |
| 180 | CF₃CFHCF₂ | CH₃CH₂ | 2 | H | H | H | CN | H | H |
| 181 | CF₃CFHCF₂CH₂ | CH₃CH₂ | 2 | H | H | H | CN | H | H |
| 182 | CF₃OCFHCF₂ | CH₃CH₂ | 2 | H | H | H | CN | H | H |

TABLE 28

| Present compound | R²⁰¹ | R²⁰² | n | R²⁰³ | R²⁰⁴ | R²⁰⁵ | R²⁰⁶ | R²⁰⁷ | R²⁰⁸ |
|---|---|---|---|---|---|---|---|---|---|
| 183 | CF₂HCF₂CH₂ | CH₃CH₂ | 2 | H | H | H | H | Cl | H |
| 184 | CF₃CF₂CH₂ | CH₃CH₂ | 2 | H | H | H | H | Cl | H |
| 185 | CF₃CFHCF₂ | CH₃CH₂ | 2 | H | H | H | H | Cl | H |
| 186 | CF₃CFHCF₂CH₂ | CH₃CH₂ | 2 | H | H | H | H | Cl | H |
| 187 | CF₃OCFHCF₂ | CH₃CH₂ | 2 | H | H | H | H | Cl | H |
| 188 | CF₂HCF₂CH₂ | CH₃CH₂ | 2 | H | H | H | H | CH₃ | H |
| 189 | CF₃CF₂CH₂ | CH₃CH₂ | 2 | H | H | H | H | CH₃ | H |
| 190 | CF₃CFHCF₂ | CH₃CH₂ | 2 | H | H | H | H | CH₃ | H |
| 191 | CF₃CFHCF₂CH₂ | CH₃CH₂ | 2 | H | H | H | H | CH₃ | H |
| 192 | CF₃OCFHCF₂ | CH₃CH₂ | 2 | H | H | H | H | CH₃ | H |

Note: For compounds 154–157, R²⁰⁵ is a 1,2,4-triazol-1-yl group (N-attached 1,2,4-triazole ring).

TABLE 29

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 193 | CF$_2$HCF$_2$CH$_2$ | CH$_3$CH$_2$ | 2 | H | H | Cl | Cl | H | H |
| 194 | CF$_3$CF$_2$CH$_2$ | CH$_3$CH$_2$ | 2 | H | H | Cl | Cl | H | H |
| 195 | CF$_3$CFHCF$_2$ | CH$_3$CH$_2$ | 2 | H | H | Cl | Cl | H | H |
| 196 | CF$_3$CFHCF$_2$CH$_2$ | CH$_3$CH$_2$ | 2 | H | H | Cl | Cl | H | H |
| 197 | CF$_3$OCFHCF$_2$ | CH$_3$CH$_2$ | 2 | H | H | Cl | Cl | H | H |
| 198 | CF$_2$HCF$_2$CH$_2$ | CH$_3$CH$_2$ | 2 | H | CF$_3$ | H | Cl | H | H |
| 199 | CF$_3$CF$_2$CH$_2$ | CH$_3$CH$_2$ | 2 | H | CF$_3$ | H | Cl | H | H |
| 200 | CF$_3$CFHCF$_2$ | CH$_3$CH$_2$ | 2 | H | CF$_3$ | H | Cl | H | H |
| 201 | CF$_3$CFHCF$_2$CH$_2$ | CH$_3$CH$_2$ | 2 | H | CF$_3$ | H | Cl | H | H |
| 202 | CF$_3$OCFHCF$_2$ | CH$_3$CH$_2$ | 2 | H | CF$_3$ | H | Cl | H | H |

TABLE 30

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 233 | CF$_2$HCF$_2$CH$_2$ | CH$_3$ | 2 | H | H | H | H | H | H |
| 234 | CF$_3$CF$_2$CH$_2$ | CH$_3$ | 0 | H | H | H | H | H | H |
| 235 | CF$_3$CF$_2$CH$_2$ | CH$_3$ | 2 | H | H | H | H | H | H |
| 236 | CF$_3$CFHCF$_2$ | CH$_3$ | 2 | H | H | H | H | H | H |
| 237 | CF$_3$CFHCF$_2$CH$_2$ | CH$_3$ | 2 | H | H | H | H | H | H |
| 238 | CF$_3$OCFHCF$_2$ | CH$_3$ | 2 | H | H | H | H | H | H |
| 239 | CF$_2$HCF$_2$CH$_2$ | CH$_3$ | 2 | H | CF$_3$ | H | H | H | H |
| 240 | CF$_3$CF$_2$CH$_2$ | CH$_3$ | 2 | H | CF$_3$ | H | H | H | H |
| 241 | CF$_3$CFHCF$_2$ | CH$_3$ | 2 | H | CF$_3$ | H | H | H | H |
| 242 | CF$_3$CFHCF$_2$CH$_2$ | CH$_3$ | 2 | H | CF$_3$ | H | H | H | H |
| 243 | CF$_3$OCFHCF$_2$ | CH$_3$ | 2 | H | CF$_3$ | H | H | H | H |
| 244 | CF$_2$HCF$_2$CH$_2$ | CF$_3$CH$_2$ | 2 | H | H | H | H | H | H |
| 245 | CF$_3$CF$_2$CH$_2$ | CF$_3$CH$_2$ | 0 | H | H | H | H | H | H |
| 246 | CF$_3$CF$_2$CH$_2$ | CF$_3$CH$_2$ | 1 | H | H | H | H | H | H |
| 247 | CF$_3$CF$_2$CH$_2$ | CF$_3$CH$_2$ | 2 | H | H | H | H | H | H |
| 248 | CF$_3$CFHCF$_2$ | CF$_3$CH$_2$ | 2 | H | H | H | H | H | H |
| 249 | CF$_3$CFHCF$_2$CH$_2$ | CF$_3$CH$_2$ | 2 | H | H | H | H | H | H |
| 250 | CF$_3$OCFHCF$_2$ | CF$_3$CH$_2$ | 2 | H | H | H | H | H | H |
| 251 | CF$_2$HCF$_2$CH$_2$ | CF$_3$CH$_2$ | 2 | H | CF$_3$ | H | H | H | H |
| 252 | CF$_3$CF$_2$CH$_2$ | CF$_3$CH$_2$ | 2 | H | CF$_3$ | H | H | H | H |
| 253 | CF$_3$CFHCF$_2$ | CF$_3$CH$_2$ | 2 | H | CF$_3$ | H | H | H | H |
| 254 | CF$_3$CFHCF$_2$CH$_2$ | CF$_3$CH$_2$ | 2 | H | CF$_3$ | H | H | H | H |
| 255 | CF$_3$OCFHCF$_2$ | CF$_3$CH$_2$ | 2 | H | CF$_3$ | H | H | H | H |
| 256 | CF$_2$HCF$_2$CH$_2$ | CH$_3$CH$_2$CH$_2$ | 2 | H | H | H | H | H | H |
| 257 | CF$_3$CF$_2$CH$_2$ | CH$_3$CH$_2$CH$_2$ | 0 | H | H | H | H | H | H |
| 258 | CF$_3$CF$_2$CH$_2$ | CH$_3$CH$_2$CH$_2$ | 2 | H | H | H | H | H | H |

TABLE 31

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 259 | CF$_3$CFHCF$_2$ | CH$_3$CH$_2$CH$_2$ | 2 | H | H | H | H | H | H |
| 260 | CF$_3$CFHCF$_2$CH$_2$ | CH$_3$CH$_2$CH$_2$ | 2 | H | H | H | H | H | H |
| 261 | CF$_3$OCFHCF$_2$ | CH$_3$CH$_2$CH$_2$ | 2 | H | H | H | H | H | H |
| 262 | CF$_2$HCF$_2$CH$_2$ | CH$_3$CH$_2$CH$_2$ | 2 | H | CF$_3$ | H | H | H | H |
| 263 | CF$_3$CF$_2$CH$_2$ | CH$_3$CH$_2$CH$_2$ | 2 | H | CF$_3$ | H | H | H | H |
| 264 | CF$_3$CFHCF$_2$ | CH$_3$CH$_2$CH$_2$ | 2 | H | CF$_3$ | H | H | H | H |
| 265 | CF$_3$CFHCF$_2$CH$_2$ | CH$_3$CH$_2$CH$_2$ | 2 | H | CF$_3$ | H | H | H | H |
| 266 | CF$_3$OCFHCF$_2$ | CH$_3$CH$_2$CH$_2$ | 2 | H | CF$_3$ | H | H | H | H |
| 267 | CF$_2$HCF$_2$CH$_2$ | (CH$_3$)$_2$CH | 2 | H | H | H | H | H | H |
| 268 | CF$_3$CF$_2$CH$_2$ | (CH$_3$)$_2$CH | 0 | H | H | H | H | H | H |
| 269 | CF$_3$CF$_2$CH$_2$ | (CH$_3$)$_2$CH | 2 | H | H | H | H | H | H |
| 270 | CF$_3$CFHCF$_2$ | (CH$_3$)$_2$CH | 2 | H | H | H | H | H | H |
| 271 | CF$_3$CFHCF$_2$CH$_2$ | (CH$_3$)$_2$CH | 2 | H | H | H | H | H | H |
| 272 | CF$_3$OCFHCF$_2$ | (CH$_3$)$_2$CH | 2 | H | H | H | H | H | H |
| 273 | CF$_2$HCF$_2$CH$_2$ | (CH$_3$)$_2$CH | 2 | H | CF$_3$ | H | H | H | H |
| 274 | CF$_3$CF$_2$CH$_2$ | (CH$_3$)$_2$CH | 2 | H | CF$_3$ | H | H | H | H |
| 275 | CF$_3$CFHCF$_2$ | (CH$_3$)$_2$CH | 2 | H | CF$_3$ | H | H | H | H |
| 276 | CF$_3$CFHCF$_2$CH$_2$ | (CH$_3$)$_2$CH | 2 | H | CF$_3$ | H | H | H | H |
| 277 | CF$_3$OCFHCF$_2$ | (CH$_3$)$_2$CH | 2 | H | CF$_3$ | H | H | H | H |

TABLE 32

| Present compound | R²⁰¹ | R²⁰² | n | R²⁰³ | R²⁰⁴ | R²⁰⁵ | R²⁰⁶ | R²⁰⁷ | R²⁰⁸ |
|---|---|---|---|---|---|---|---|---|---|
| 278 | CF₂HCF₂CH₂ | 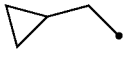 | 2 | H | H | H | H | H | H |
| 279 | CF₃CF₂CH₂ | 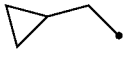 | 0 | H | H | H | H | H | H |
| 280 | CF₃CF₂CH₂ |  | 2 | H | H | H | H | H | H |
| 281 | CF₃CFHCF₂ |  | 2 | H | H | H | H | H | H |
| 282 | CF₃CFHCF₂CH₂ |  | 2 | H | H | H | H | H | H |
| 283 | CF₃OCFHCF₂ |  | 2 | H | H | H | H | H | H |
| 284 | CF₂HCF₂CH₂ |  | 2 | H | CF₃ | H | H | H | H |
| 285 | CF₃CF₂CH₂ |  | 2 | H | CF₃ | H | H | H | H |
| 286 | CF₃CFHCF₂ | 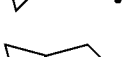 | 2 | H | CF₃ | H | H | H | H |
| 287 | CF₃CFHCF₂CH₂ | 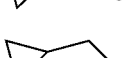 | 2 | H | CF₃ | H | H | H | H |
| 288 | CF₃OCFHCF₂ | 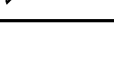 | 2 | H | CF₃ | H | H | H | H |

TABLE 33

| Present compound | R²⁰¹ | R²⁰² | n | R²⁰³ | R²⁰⁴ | R²⁰⁵ | R²⁰⁶ | R²⁰⁷ | R²⁰⁸ |
|---|---|---|---|---|---|---|---|---|---|
| 289 | CF₂HCF₂CH₂ | 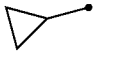 | 2 | H | H | H | H | H | H |
| 290 | CF₃CF₂CH₂ | 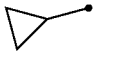 | 0 | H | H | H | H | H | H |
| 291 | CF₃CF₂CH₂ | 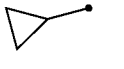 | 2 | H | H | H | H | H | H |
| 292 | CF₃CFHCF₂ |  | 2 | H | H | H | H | H | H |
| 293 | CF₃CFHCF₂CH₂ |  | 2 | H | H | H | H | H | H |
| 294 | CF₃OCFHCF₂ |  | 2 | H | H | H | H | H | H |
| 295 | CF₂HCF₂CH₂ | 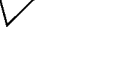 | 2 | H | CF₃ | H | H | H | H |
| 296 | CF₃CF₂CH₂ |  | 2 | H | CF₃ | H | H | H | H |
| 297 | CF₃CFHCF₂ |  | 2 | H | CF₃ | H | H | H | H |

TABLE 33-continued

| Present compound | R²⁰¹ | R²⁰² | n | R²⁰³ | R²⁰⁴ | R²⁰⁵ | R²⁰⁶ | R²⁰⁷ | R²⁰⁸ |
|---|---|---|---|---|---|---|---|---|---|
| 298 | CF₃CFHCF₂CH₂ | cyclopropyl | 2 | H | CF₃ | H | H | H | H |
| 299 | CF₃OCFHCF₂ | cyclopropyl | 2 | H | CF₃ | H | H | H | H |

TABLE 34

| Present compound | R²⁰¹ | R²⁰¹ | n | R²⁰³ | R²⁰⁴ | R²⁰⁵ | R²⁰⁶ | R²⁰⁷ | R²⁰⁸ |
|---|---|---|---|---|---|---|---|---|---|
| 300 | (CF₃)(CH₃)CH– | CH₃CH₂ | 2 | H | H | H | H | H | H |
| 301 | (CF₃)(CH₃)CHCH₂– | CH₃CH₂ | 2 | H | H | H | H | H | H |
| 302 | (CF₃)(CH₃)CHCH(CH₃)– | CH₃CH₂ | 2 | H | H | H | H | H | H |
| 303 | CF₃CF₂CH(CH₃)– | CH₃CH₂ | 2 | H | H | H | H | H | H |
| 304 | CF₃CF₂CH(CH₃)CH₂– | CH₃CH₂ | 2 | H | H | H | H | H | H |
| 305 | CH₂=CHCH₂CH(CF₃)– | CH₃CH₂ | 2 | H | H | H | H | H | H |
| 306 | 4,4-difluorocyclohexyl | CH₃CH₂ | 2 | H | H | H | H | H | H |
| 307 | (2,2-difluorocyclopropyl)methyl | CH₃CH₂ | 2 | H | H | H | H | H | H |
| 308 | (2-trifluoromethylcyclopropyl)methyl | CH₃CH₂ | 2 | H | H | H | H | H | H |
| 309 | 4-trifluoromethylcyclohexyl | CH₃CH₂ | 2 | H | H | H | H | H | H |

TABLE 34-continued

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 310 | 3-(trifluoromethyl)cyclohexyl | $CH_3CH_2$ | 2 | H | H | H | H | H | H |

TABLE 35

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 311 | $CF_3CF_2CF_2CF_2CF_2CF_2CH_2$ | $CH_3CH_2$ | 2 | H | H | H | H | H | H |
| 312 | $CH_3OCH_2CF_2CH_2$ | $CH_3CH_2$ | 2 | H | H | H | H | H | H |

TABLE 36

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 313 | $CH(CF_3)_2$ | $CH_3CH_2$ | 2 | H | H | H | H | H | H |
| 314 | 2-fluoro-3,3,3-trifluoro-1-propenyl | $CH_3CH_2$ | 2 | H | H | H | H | H | H |
| 315 | $CBrH_2CH_2$ | $CH_3CH_2$ | 2 | H | H | H | H | H | H |
| 316 | $CF_3CF_2CH_2$ | $CH_3CH_2$ | 2 | H | H | $NHNH_2$ | H | H | H |
| 317 | $CF_3CF_2CH_2$ | $CH_3CH_2$ | 2 | H | H | $NHNHCH_3$ | H | H | H |
| 318 | $CF_3CF_2CH_2$ | $CH_3CH_2$ | 2 | H | H | $N(CH_3)NH_2$ | H | H | H |
| 319 | $CF_3CF_2CH_2$ | $CH_3CH_2$ | 2 | H | H | $NHNHCH(CH_3)_2$ | H | H | H |
| 320 | $CF_3CF_2CH_2$ | $CH_3CH_2$ | 2 | H | H | $N[CH(CH_3)_2]NH_2$ | H | H | H |
| 321 | $CF_3CF_2CH_2$ | $CH_3CH_2$ | 2 | H | H | $NHNHC(O)CH_3$ | H | H | H |
| 322 | $CF_3CF_2CH_2$ | $CH_3CH_2$ | 2 | H | H | 1H-pyrazol-1-yl | H | H | H |
| 323 | $CF_3CF_2CH_2$ | $CH_3CH_2$ | 2 | H | H | $SCH_3$ | H | H | H |
| 324 | $CF_3CF_2CH_2$ | $CH_3CH_2$ | 2 | H | H | $S(O)_2CH_2CH_3$ | H | H | H |

TABLE 37

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 325 | $CF_3CF_2CH_2$ | $CH_3CH_2$ | 2 | H | $CF_3$ | $NHCH_2CH_2NH_2$ | H | H | H |
| 326 | $CF_3CF_2CH_2$ | $CH_3CH_2$ | 2 | H | $CF_3$ | $NHCH_2CH_2OH$ | H | H | H |
| 327 | $CF_3CF_2CH_2$ | $CH_3CH_2$ | 2 | H | $CF_3$ | CN | H | H | H |
| 328 | $CF_3CF_2CH_2$ | $CH_3CH_2$ | 2 | H | $CF_3$ | $SCH_3$ | H | H | H |
| 329 | $CF_3CF_2CH_2$ | $CH_3CH_2$ | 2 | H | $CF_3$ | $NHNHCH_2$ | H | H | H |
| 330 | $CF_3CF_2CH_2$ | $CH_3CH_2$ | 2 | H | $CF_3$ | $N(CH_3)NH_2$ | H | H | H |
| 331 | $CF_3CF_2CH_2$ | $CH_3CH_2$ | 2 | H | $CF_3$ | $N(CH_2CH_3)NH_2$ | H | H | H |
| 332 | $CF_3CF_2CH_2$ | $CH_3CH_2$ | 2 | H | $CF_3$ | $NHNHCH(CH_3)_2$ | H | H | H |
| 333 | $CF_3CF_2CH_2$ | $CH_3CH_2$ | 2 | H | $CF_3$ | $N[CH(CH_3)_2]NH_2$ | H | H | H |
| 334 | $CF_3CF_2CH_2$ | $CH_3CH_2$ | 2 | H | $CF_3$ | $N(CH_2CH_3)NHCH_2CH_3$ | H | H | H |
| 335 | $CF_3CF_2CH_2$ | $CH_3CH_2$ | 2 | H | $CF_3$ | $NHNHC(O)CH_3$ | H | H | H |

TABLE 38

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 336 | $CF_3CF_2CH_2$ | $CH_3CH_2$ | 2 | H | $CF_3$ | piperazin-1-yl | H | H | H |
| 337 | $CF_3CF_2CH_2$ | $CH_3CH_2$ | 2 | H | $CF_3$ | morpholin-4-yl | H | H | H |
| 338 | $CF_3CF_2CH_2$ | $CH_3CH_2$ | 2 | H | $CF_3$ | pyrrolidin-1-yl | H | H | H |
| 339 | $CF_3CF_2CH_2$ | $CH_3CH_2$ | 2 | H | $CF_3$ | pyrazol-1-yl | H | H | H |
| 340 | $CF_3CF_2CH_2$ | $CH_3CH_2$ | 2 | H | $CF_3$ | 3-amino-1,2,4-triazol-1-yl | H | H | H |
| 341 | $CF_3CF_2CH_2$ | $CH_3CH_2$ | 2 | H | $CF_3$ | 5-amino-1,2,4-triazol-1-yl | H | H | H |
| 342 | $CF_3CF_2CH_2$ | $CH_3CH_2$ | 2 | H | Br | H | H | H | H |
| 343 | $CF_3CF_2CH_2$ | $CH_3CH_2$ | 2 | H | Br | OH | H | H | H |
| 344 | $CF_3CF_2CH_2$ | $CH_3CH_2$ | 2 | H | Br | $NH_2$ | H | H | H |
| 345 | $CF_3CF_2CH_2$ | $CH_3CH_2$ | 2 | H | Cl | OH | H | H | H |
| 346 | $CF_3CF_2CH_2$ | $CH_3CH_2$ | 2 | H | Cl | $NH_2$ | H | H | H |
| 347 | $CF_3CF_2CH_2$ | $CH_3CH_2$ | 2 | H | H | phenyl | H | H | H |

A compound represented by formula (201):

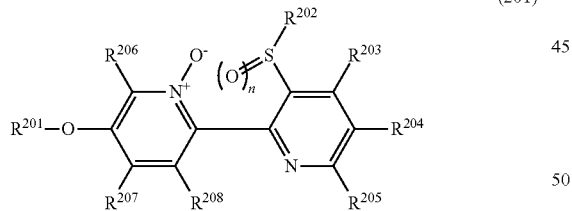

(201)

[wherein $R^{201}$, $R^{202}$, $R^{203}$, $R^{204}$, $R^{205}$, $R^{206}$, $R^{207}$, $R^{208}$, and n represent any combination of the elements indicated in the following [Table 39]]
can be prepared according to the similar methods to those described above.

TABLE 39

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 203 | $CF_3HCF_2CH_2$ | $CH_3CH_2$ | 2 | H | H | H | H | H | H |
| 204 | $CF_3CF_2CH_2$ | $CH_3CH_2$ | 2 | H | H | H | H | H | H |
| 205 | $CF_3CFHCF_2$ | $CH_3CH_2$ | 2 | H | H | H | H | H | H |
| 206 | $CF_3CFHCF_2CH_2$ | $CH_3CH_2$ | 2 | H | H | H | H | H | H |
| 207 | $CF_3OCFHCF_2$ | $CH_3CH_2$ | 2 | H | H | H | H | H | H |

TABLE 39-continued

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 208 | $CF_2HCF_2CH_2$ | $CH_3CH_2$ | 2 | H | $CF_3$ | H | H | H | H |
| 209 | $CF_3CF_2CH_2$ | $CH_3CH_2$ | 2 | H | $CF_3$ | H | H | H | H |
| 210 | $CF_3CFHCF_2$ | $CH_3CH_2$ | 2 | H | $CF_3$ | H | H | H | H |
| 211 | $CF_3CFHCF_2CH_2$ | $CH_3CH_2$ | 2 | H | $CF_2$ | H | H | H | H |
| 212 | $CF_3OCFHCF_2$ | $CH_3CH_2$ | 2 | H | $CF_3$ | H | H | H | H |

A compound represented by formula (202):

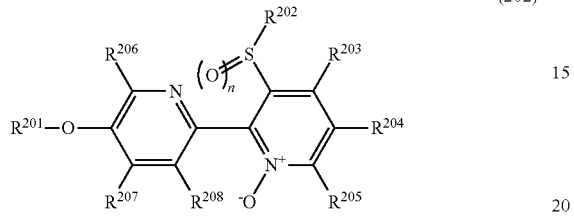

(202)

[wherein $R^{201}$, $R^{202}$, $R^{203}$, $R^{204}$, $R^{205}$, $R^{206}$, $R^{207}$, $R^{208}$, and n represent any combination of the elements indicated in the following [Table 40]] can be prepared according to the similar methods to those described above.

TABLE 40

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 213 | $CF_2HCF_2CH_2$ | $CH_3CH_2$ | 2 | H | H | H | H | H | H |
| 214 | $CF_3CF_2CH_2$ | $CH_3CH_2$ | 2 | H | H | H | H | H | H |
| 215 | $CF_3CFHCF_2$ | $CH_3CH_2$ | 2 | H | H | H | H | H | H |
| 216 | $CF_3CFHCF_2CH_2$ | $CH_3CH_2$ | 2 | H | H | H | H | H | H |
| 217 | $CF_3OCFHCF_2$ | $CH_3CH_2$ | 2 | H | H | H | H | H | H |
| 218 | $CF_2HCF_3CH_2$ | $CH_3CH_2$ | 2 | H | $CF_3$ | H | H | H | H |
| 219 | $CF_3CF_2CH_2$ | $CH_3CH_2$ | 2 | H | $CF_3$ | H | H | H | H |
| 220 | $CF_3CFHCF_2$ | $CH_3CH_2$ | 2 | H | $CF_3$ | H | H | H | H |
| 221 | $CF_3CFHCF_2CH_2$ | $CH_3CH_2$ | 2 | H | $CF_3$ | H | H | H | H |
| 222 | $CF_3OCFHCF_2$ | $CH_3CH_2$ | 2 | H | $CF_3$ | H | H | H | H |

A compound represented by formula (203):

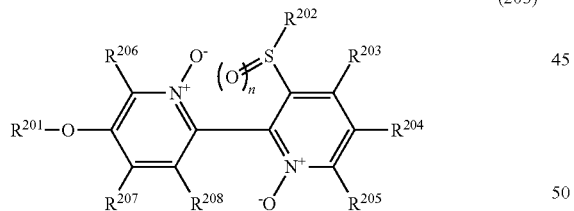

(203)

[wherein $R^{201}$, $R^{202}$, $R^{203}$, $R^{204}$, $R^{205}$, $R^{206}$, $R^{207}$, $R^{208}$, and n represent any combination of the elements indicated in the following [Table 41]] can be prepared according to the similar methods to those described above.

TABLE 41

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 223 | $CF_2HCF_2CH_2$ | $CH_3CH_2$ | 2 | H | H | H | H | H | H |
| 224 | $CF_3CF_2CH_2$ | $CH_3CH_2$ | 2 | H | H | H | H | H | H |
| 225 | $CF_3CFHCF_2$ | $CH_3CH_2$ | 2 | H | H | H | H | H | H |
| 226 | $CF_3CFHCF_2CH_2$ | $CH_3CH_2$ | 2 | H | H | H | H | H | H |
| 227 | $CF_3OCFHCF_2$ | $CH_3CH_2$ | 2 | H | H | H | H | H | H |

TABLE 41-continued

| Present compound | $R^{201}$ | $R^{202}$ | n | $R^{203}$ | $R^{204}$ | $R^{205}$ | $R^{206}$ | $R^{207}$ | $R^{208}$ |
|---|---|---|---|---|---|---|---|---|---|
| 228 | $CF_3HCF_2CH_2$ | $CH_3CH_2$ | 2 | H | $CF_3$ | H | H | H | H |
| 229 | $CF_4CF_2CH_2$ | $CH_3CH_2$ | 2 | H | $CF_3$ | H | H | H | H |
| 230 | $CF_3CFHCF_2$ | $CH_3CH_2$ | 2 | H | $CF_3$ | H | H | H | H |
| 231 | $CF_3CFHCF_2CH_2$ | $CH_3CH_2$ | 2 | H | $CF_3$ | H | H | H | H |
| 232 | $CF_3OCFHCF_2$ | $CH_3CH_2$ | 2 | H | $CF_3$ | H | H | H | H |

The physical properties of Present compounds are shown below.

TABLE 42

| Present compound | Physical properties |
|---|---|
| 2 | $^1$H-NMR (CDCl$_3$) δ: 8.87 (1H, dd), 8.49 (1H, dd), 8.37 (1H, d), 7.86 (1H, d), 7.54 (1H, dd), 7.42 (1H, dd), 4.48 (2H, q), 3.89 (2H, q), 1.38 (3H, t). |
| 7 | $^1$H-NMR (CDCl$_3$) δ: 8.87 (1H, dd), 8.49 (1H, dd), 8.36 (1H, d), 7.87 (1H, d), 7.54 (1H, dd), 7.42 (1H, dd), 6.08 (1H, tt), 4.48 (2H, t), 3.89 (2H, q), 1.38 (3H, t). |
| 8 | $^1$H-NMR (CDCl$_3$) δ: 8.87 (1H, dd), 8.49 (1H, dd), 8.37 (1H, d), 7.87 (1H, d), 7.54 (1H, dd), 7.42 (1H, dd), 4.54 (2H, t), 3.89 (2H, q), 1.38 (3H, t). |
| 9 | $^1$H-NMR (CDCl$_3$) δ: 8.64 (1H, d), 8.45 (1H, dd), 8.10 (1H, d), 7.73 (1H, dd), 7.68 (1H, dd), 7.28 (1H, dd), 5.18-4.98 (1H, m), 2.92 (2H, q), 1.33 (3H, t). |
| 10 | $^1$H-NMR (CDCl$_3$) δ: 8.75 (1H, dd), 8.65 (1H, dd), 8.60-8.56 (2H, m), 7.75 (1H, dd), 7.59 (1H, dd), 5.18-4.99 (1H, m), 3.52-3.41 (1H, m), 2.96-2.86 (1H, m), 1.41 (3H, t). |
| 11 | $^1$H-NMR (CDCl$_3$) δ: 8.89 (1H, dd), 8.53 (1H, d), 8.50 (1H, dd), 7.91 (1H, d), 7.74 (1H, dd), 7.58 (1H, dd), 5.18-4.99 (1H, m), 3.87 (2H, q), 1.38 (3H, t). |
| 12 | $^1$H-NMR (CDCl$_3$) δ: 8.85 (1H, dd), 8.48 (1H, dd), 8.34 (1H, d), 7.84 (1H, d), 7.52 (1H, dd), 7.39 (1H, dd), 4.22 (2H, t), 3.89 (2H, q), 1.81 (3H, t), 1.37 (3H, t). |
| 14 | $^1$H-NMR (CDCl$_3$) δ: 8.87 (1H, dd), 8.49 (1H, dd), 8.36 (1H, d), 7.87 (1H, d), 7.55 (1H, dd), 7.42 (1H, dd), 5.33-5.08 (1H, m), 4.59-4.36 (2H, m), 3.89 (2H, q), 1.38 (3H, t). |
| 15 | $^1$H-NMR (CDCl$_3$) δ: 8.86 (1H, dd), 8.49 (1H, dd), 8.37 (1H, d), 7.87 (1H, d), 7.53 (1H, dd), 7.42 (1H, dd), 4.58 (2H, t), 3.87 (2H, q), 1.37 (3H, t). |
| 16 | $^1$H-NMR (CDCl$_3$) δ: 8.93 (1H, dd), 8.48-8.42 (2H, m), 7.83 (1H, dd), 7.76-7.72 (2H, m), 5.12 (2H, t), 3.89 (2H, q), 1.23 (3H, t). |
| 22 | $^1$H-NMR (CDCl$_3$) δ: 8.65 (1H, s), 8.45 (1H, dd), 8.10 (1H, d), 7.73 (1H, dd), 7.69 (1H, dd), 7.31-7.26 (1H, m), 6.00 (1H, tt), 2.92 (2H, q), 1.33 (3H, t). |
| 23 | $^1$H-NMR (CDCl$_3$) δ: 8.75 (1H, dd), 8.65 (1H, dd), 8.61-8.56 (2H, m), 7.75 (1H, dd), 7.59 (1H, dd), 6.01 (1H, dt), 3.51-3.41 (1H, m), 2.96-2.86 (1H, m), 1.41 (3H, t). |

TABLE 43

| Present compound | Physical properties |
|---|---|
| 24 | $^1$H-NMR (CDCl$_3$) δ: 8.89 (1H, dd), 8.54 (1H, d), 8.50 (1H, dd), 7.91 (1H, dd), 7.74 (1H, dd), 7.59 (1H, dd), 6.00 (1H, dt), 3.87 (2H, q), 1.38 (3H, t). |
| 26 | $^1$H-NMR (CDCl$_3$) δ: 8.46 (1H, d), 8.43 (1H, dd), 8.00 (1H, d), 7.70 (1H, dd), 7.39 (1H, dd), 7.28-7.23 (1H, m), 6.09 (1H, tt), 4.48 (2H, t), 2.91 (2H, q), 1.32 (3H, t). |
| 27 | $^1$H-NMR (CDCl$_3$) δ: 8.47 (1H, dd), 8.43 (1H, dd), 8.02 (1H, dd), 7.70 (1H, dd), 7.41 (1H, dd), 7.28-7.23 (1H, m), 4.54 (2H, td), 2.91 (2H, q), 1.32 (3H, t). |
| 39 | $^1$H-NMR (CDCl$_3$) δ: 9.10 (1H, s), 8.73 (1H, s), 8.40 (1H, d), 7.97 (1H, d), 7.46-7.44 (1H, m), 4.56 (2H, t), 3.99 (2H, q), 1.42 (3H, t). |
| 53 | $^1$H-NMR (CDCl$_3$) δ: 8.69 (1H, d), 8.37 (1H, d), 7.99 (1H, d), 7.89 (1H, d), 7.43 (1H, dd), 6.08 (1H, tt), 4.49 (2H, t), 4.01 (2H, q), 1.41 (3H, t). |

TABLE 43-continued

| Present compound | Physical properties |
|---|---|
| 54 | $^1$H-NMR (CDCl$_3$) δ: 8.69 (1H, dd), 8.39 (1H, d), 7.99 (1H, dd), 7.89 (1H, d), 7.44 (1H, dd), 4.55 (2H, td), 4.01 (2H, q), 1.41 (3H, t). |
| 59 | 1H-NMR (CDCl3) δ: 8.34 (1H, d), 8.13 (1H, d), 7.71 (1H, dd), 7.38 (1H, dd), 6.58 (1H, d), 5.01 (2H, s), 4.52 (2H, td), 3.66 (2H, q), 1.32 (3H, t). |
| 69 | $^1$H-NMR (CDCl$_3$) δ: 8.80 (1H, d), 8.48 (1H, d), 8.37 (1H, d), 7.88 (1H, dd), 7.42 (1H, dd), 4.54 (2H, td), 3.94 (2H, q), 1.55 (6H, s), 1.40 (3H, t). |
| 74 | $^1$H-NMR (CDCl$_3$) δ: 8.34 (1H, d), 8.17 (1H, d), 7.75 (1H, d), 7.40 (1H, dd), 6.61 (1H, d), 5.18 (1H, t), 4.54 (2H, t), 4.28-4.16 (2H, m), 3.79 (2H, q), 1.36 (3H, t). |
| 79 | $^1$H-NMR (CDCl$_3$) δ: 8.42 (1H, dd), 8.37 (1H, d), 7.91 (1H, d), 7.54 (1H, dd), 7.41 (1H, dd), 4.54 (2H, t), 3.92 (2H, q), 1.38 (3H, t). |
| 89 | $^1$H-NMR (CDCl$_3$) δ: 8.35 (1H, d), 8.12 (1H, d), 7.77 (1H, d), 7.44 (1H, s), 7.40 (1H, dd), 6.52 (1H, d), 5.40 (1H, t), 4.77 (2H, d), 4.54 (2H, t), 3.77 (2H, q), 1.35 (3H, t). |
| 94 | $^1$H-NMR (CDCl$_3$) δ: 8.35 (1H, dd), 8.29 (1H, d), 7.83 (1H, dd), 7.40 (1H, dd), 6.88 (1H, d), 4.54 (2H, td), 4.03 (3H, s), 3.83 (2H, q), 1.36 (3H, t). |
| 99 | $^1$H-NMR (CDCl$_3$) δ: 8.69 (1H, d), 8.36 (1H, d), 8.30 (1H, d), 7.84 (1H, d), 7.42 (1H, dd), 6.04-5.93 (1H, m), 5.23-5.18 (2H, m), 4.54 (2H, t), 3.87 (2H, q), 3.55 (2H, d), 1.37 (3H, t). |

TABLE 44

| Present compound | Physical properties |
|---|---|
| 104 | $^1$H-NMR (CDCl$_3$) δ: 9.23 (1H, s), 8.67 (1H, d), 8.41 (1H, dd), 8.17 (1H, s), 8.10 (1H, d), 7.90 (1H, dd), 7.47 (1H, dd), 4.57 (2H, td), 3.93 (2H, q), 1.41 (3H, t). |
| 109 | $^1$H-NMR (CDCl$_3$) δ: 8.75 (1H, s), 8.40 (1H, d), 8.03 (1H, d), 7.44 (1H, dd), 4.56 (2H, t), 4.01 (2H, q), 1.43 (3H, t). |
| 114 | $^1$H-NMR (CDCl$_3$) δ: 8.45 (1H, d), 8.41 (1H, s), 7.92 (1H, d), 7.41 (1H, dd), 4.57 (2H, t), 3.45 (2H, q), 1.33 (3H, t). |
| 119 | $^1$H-NMR (CDCl$_3$) δ: 8.59 (1H, d), 8.38 (1H, t), 7.90 (1H, dd), 7.42 (1H, dd), 4.55 (2H, t), 4.16 (3H, s), 3.91 (2H, q), 1.40 (3H, t). |
| 124 | $^1$H-NMR (CDCl$_3$) δ: 8.44 (1H, s), 8.35 (1H, s), 7.78 (1H, d), 7.39 (1H, d), 5.52 (2H, s), 4.53 (2H, t), 3.79 (2H, q), 1.37 (3H, t). |
| 129 | $^1$H-NMR (CDCl$_3$) δ: 8.35-8.35 (2H, m), 7.86 (1H, dd), 7.40 (1H, dd), 5.48 (1H, s), 4.54 (2H, td), 3.83 (2H, q), 3.15 (3H, d), 1.37 (3H, t). |
| 139 | $^1$H-NMR (CDCl$_3$) δ: 8.47 (1H, d), 8.36 (1H, d), 7.81 (1H, d), 7.42 (1H, dd), 5.62 (1H, s), 4.55 (2H, t), 4.42-4.33 (2H, m), 3.89 (2H, q), 1.39 (3H, t). |
| 144 | $^1$H-NMR (CDCl$_3$) δ: 8.40 (1H, s), 8.37 (1H, d), 7.82 (1H, d), 7.41 (1H, dd), 6.74 (1H, s), 4.55 (2H, t), 4.19 (2H, d), 3.80 (2H, q), 1.37 (3H, t). |
| 149 | $^1$H-NMR (CDCl$_3$) δ: 8.40 (1H, d), 8.36 (1H, d), 7.71 (1H, d), 7.65 (2H, d), 7.50 (1H, t), 7.41 (1H, dd), 7.34 (1H, d), 7.00 (2H, d), 4.58 (2H, t), 3.81 (2H, q), 2.29 (3H, s), 1.33 (3H, t). |
| 154 | $^1$H-NMR (CDCl$_3$) δ: 9.02 (1H, s), 8.99 (1H, s), 8.44 (1H, d), 8.23 (1H, s), 8.01 (1H, d), 7.47 (1H, dd), 4.58 (2H, t), 4.05 (2H, q), 1.47 (3H, t). |

TABLE 44-continued

| Present compound | Physical properties |
| --- | --- |
| 159 | ¹H-NMR (CDCl₃) δ: 11.08 (1H, s), 8.89 (1H, dd), 8.60 (1H, d), 7.61 (1H, dd), 7.32-7.24 (1H, m), 7.11 (1H, d), 4.71 (2H, t), 3.15 (2H, q), 1.18 (3H, t). |
| 164 | ¹H-NMR (CDCl₃) δ: 8.88 (1H, d), 8.46 (1H, d), 7.57 (1H, dd), 7.34 (1H, d), 7.28 (1H, d), 4.52 (2H, t), 4.00 (3H, s), 3.62 (2H, q), 1.34 (3H, t). |
| 169 | ¹H-NMR (CDCl₃) δ: 8.86 (1H, dd), 8.49 (1H, dd), 7.86 (1H, d), 7.56 (1H, dd), 7.42 (1H, d), 4.56 (2H, t), 3.98 (2H, q), 1.44 (3H, t), |

TABLE 45

| Present compound | Physical properties |
| --- | --- |
| 174 | ¹H-NMR (CDCl₃) δ: 8.86 (1H, dd), 8.47 (1H, dd), 7.83 (1H, d), 7.55 (1H, dd), 7.47 (1H, dd), 4.51 (2H, t), 3.78 (2H, q), 2.33 (3H, s), 1.36 (3H, t). |
| 179 | ¹H-NMR (CDCl₃) δ: 8.88 (1H, dd), 8.51 (1H, dd), 8.12 (1H, d), 7.61 (1H, dd), 7.55 (1H, d), 4.66 (2H, t), 3.90 (2H, q), 1.45 (3H, t). |
| 184 | ¹H-NMR (CDCl₃) δ: 8.88 (1H, dd), 8.49 (1H, dd), 8.30 (1H, s), 7.97 (1H, s), 7.57 (1H, dd), 4.64 (2H, t), 3.90 (2H, q), 1.39 (3H, t). |
| 194 | ¹H-NMR (CDCl₃) δ: 8.93 (1H, d), 7.47 (1H, d), 7.42 (1H, d), 7.39 (1H, d), 4.56 (2H, t), 3.70 (2H, q), 1.40 (3H, t). |
| 234 | ¹H-NMR (CDCl₃) δ: 8.46-8.42 (2H, m), 8.08 (1H, d), 7.66 (1H, dd), 7.41 (1H, dd), 7.28 (1H, dd), 4.54 (2H, t), 2.42 (3H, s). |
| 235 | ¹H-NMR (CDCl₃) δ: 8.88 (1H, dd), 8.55 (1H, dd), 8.39 (1H, d), 7.89 (1H, d), 7.55 (1H, dd), 7.43 (1H, dd) 4.55 (2H, t), 3.64 (3H, s). |
| 245 | ¹H-NMR (CDCl₃) δ: 8.54 (1H, s), 8.45 (1H, s), 8.06 (1H, d), 7.86 (1H, dd), 7.43 (1H, dd), 7.30 (1H, dd), 4.55 (2H, t), 3.51 (2H, q). |
| 246 | ¹H-NMR (CDCl₃) δ: 8.79 (1H, dd), 8.74 (1H, dd), 8.53 (1H, d), 8.38 (1H, d), 7.61 (1H, dd), 7.49 (1H, dd), 4.57 (2H, t), 4.33-4.22 (1H, m), 3.33-3.22 (1H, m). |
| 257 | ¹H-NMR (CDCl₃) δ: 8.42-8.42 (2H, m), 8.00 (1H, d), 7.70 (1H, dd), 7.40 (1H, dd), 7.25 (1H, dd), 4.54 (2H, t), 2.85 (2H, t), 1.73-1.64 (2H, m), 1.02 (3H, t). |
| 258 | ¹H-NMR (CDCl₃) δ: 8.87 (1H, dd), 8.49 (1H, dd), 8.38 (1H, d), 7.87 (1H, d), 7.54 (1H, dd), 7.41 (1H, dd), 4.54 (2H, t), 3.83 (2H, t), 1.90-1.80 (2H, m), 1.09 (3H, t). |
| 279 | ¹H-NMR (CDCl₃) δ: 8.48 (1H, d), 8.43 (1H, dd), 8.02 (1H, dd), 7.71 (1H, dd), 7.41 (1H, dd), 7.24 (1H, dd), 4.55 (2H, t), 2.82 (2H, d), 1.07-0.97 (1H, m), 0.63-0.57 (2H, m), 0.31-0.26 (2H, m). |
| 280 | ¹H-NMR (CDCl₃) δ: 8.86 (1H, dd), 8.56 (1H, dd), 8.34 (1H, d), 7.88 (1H, d), 7.54 (1H, dd), 7.42 (1H, dd), 4.54 (2H, t), 3.82 (2H, d), 1.19-1.07 (1H, m), 0.62-0.55 (2H, m), 0.37-0.31 (2H, m). |

TABLE 46

| Present compound | Physical properties |
| --- | --- |
| 300 | ¹H-NMR (CDCl₃)δ: 8.86 (1H, dd), 8.56 (1H, dd), 8.6 (1H, d), 7.85 (d, J = 8.7 Hz, 1H), 7.52 (dd, J = 4.8 and 8.1 Hz, 1H), 7.42 (dd, J = 3 and 9 Hz, 1H), 4.79-4.71 (m, 1H), 3.88 (q, J = 7.6 Hz, 2H), 1.57 (d, J = 6.6 Hz, 3H), 1.77 (t, J = 7.5 Hz, 3H). |
| 301 | ¹H-NMR (CDCl₃)δ: 8.86 (1H, dd), 8.49 (2H, dd), 7.85 (1H, d), 7.53 (1H, dd), 7.45 (1H, dd), 4.52 (1H, d), 3.88 (2H, q), 1.99 (2H, dd), 1.37 (3H, t), 1.13 (3H, t). |
| 302 | ¹H-NMR (CDCl₃)δ: 8.86 (1H, dd), 8.49 (1H, dd), 8.39 (1H, d), 7.85 (1H, d), 7.52 (1H, dd), 7.45 (1H, dd), 4.42-4.36 (1H, m), 3.95 (2H, q), 2.36-2.28 (1H, m), 1.36 (3H, t), 1.14 (6H, t). |

TABLE 46-continued

| Present compound | Physical properties |
| --- | --- |
| 303 | ¹H-NMR (CDCl₃)δ: 8.86 (1H, dd), 8.49 (1H, dd), 8.34 (1H, d), 7.86 (1H, d), 7.53 (1H, dd), 7.4 (1H, dd), 4.88-4.85 (1H, m), 3.88 (2H, q), 1.59 (3H, d), 1.37 (3H, t), |
| 304 | ¹H-NMR (CDCl₃)δ: 8.85 (1H, dd), 8.49 (1H, dd), 8.36 (1H, d), 7.85 (1H, d), 7.55 (1H, dd), 7.45 (1H, dd), 4.7-4.66 (1H, m), 3.87 (2H, q), 2.01 (2H, dd), 1.37 (3H, t), 1.13 (3H, t). |
| 305 | ¹H-NMR (CDCl₃)δ: 8.85 (1H, dd), 8.47 (1H, dd), 8.37 (1H, d), 7.83 (1H, d), 7.52 (1H, dd), 7.44 (1H, dd), 5.89-5.78 (1H, m), 5.3-5.19 (2H, m), 4.63 (1H, q), 3.84 (2H, q), 2.69 (2H, t), 1.36 (3H, t). |
| 306 | ¹H-NMR (CDCl₃)δ: 8.84 (1H, dd), 8.48 (1H, dd), 8.3 (1H, dd), 7.8 (1H, d), 7.5 (1H, dd), 7.32 (1H, dd), 4.61 (1H, d), 3.89 (2H, q), 2.24-1.95 (8H, m), 1.39 (3H, t). |
| 307 | ¹H-NMR (CDCl₃) δ: 8.85 (1H, dd), 8.48 (1H, dd), 8.31 (1H, d), 7.82 (1H, d), 7.51 (1H, dd), 7.31 (1H, dd), 4.22-4.10 (2H, m), 3.89 (2H, q), 2.16-2.08 (1H, m), 1.69-1.60 (1H, m), 1.39-1.3 (4H, m). |
| 308 | ¹H-NMR (CDCl₃)δ: 8.85 (1H, dd), 8.47 (1H, dd), 8.3 (1H, d), 7.82 (1H, d), 7.51 (1H, dd), 7.34 (1H, dd), 4.19 (2H, s), 3.89 (2H, q), 1.37 (3H, t), 1.19 (2H, t), 0.97 (2H, brs). |
| 309 | ¹H-NMR (CDCl₃) δ: 8.84 (1H, dd), 8.47 (1H, d), 8.29 (1H, dd), 7.81 (1H, d), 7.5 (1H, dd), 7.34-7.26 (1H, m), 4.68 (1H, d), 3.94-3.86 (2H, m), 2.29-2.11 (5H, m), 1.83-1.8 (2H, m), 1.36 (3H, t), 1.34-1.25 (2H, m). |
| 310 | ¹H-NMR (CDCl₃) δ: 8.85 (1H, dd), 8.48 (1H, dd), 8.28 (1H, dd), 7.82 (1H, dd), 7.53 (1H, dd), 7.36-7.31 (1H, m), 4.82 (1H, brs), 4.3-4.29 (1H, m), 3.68 (2H, q), 2.61-1.95 (5H, m), 1.74-1.68 (1H, m), 1.58-1.42 (2H, m), 1.36 (3H, t). |

TABLE 47

| Present compound | Physical properties |
| --- | --- |
| 311 | ¹H-NMR (CDCl₃) δ: 8.93 (1H, dd), 8.48-8.42 (2H, m), 7.83 (1H, d), 7.76-7.72 (2H, m), 5.12 (2H, t), 3.89 (2H, q), 1.23 (3H, t). |
| 312 | ¹H-NMR (CDCl₃) δ: 8.85 (1H, dd), 8.48 (1H, dd), 8.35 (1H, d), 7.8 (1H, d), 7.52 (1H, dd), 7.42 (1H, dd), 4.35 (2H, t), 3.89 (2H, q), 3.79 (2H, t), 3.47 (3H, s), 1.37 (3H, t). |

TABLE 48

| Present compound | Physical properties |
| --- | --- |
| 1 | ¹H-NMR (CDCl₃) δ: 8.87 (1H, dd), 8.49 (1H, dd), 8.34 (1H, d), 7.85 (1H, d), 7.53 (1H, dd), 7.39 (1H, dd), 6.28-6.01 (1H, m), 4.31 (2H, td), 3.89 (2H, q), 1.38 (3H, t). |
| 29 | ¹H-NMR (CDCl₃) δ: 8.72 (1H, dd), 8.61 (1H, dd), 8.49 (1H, d), 8.41 (1H, d), 7.54 (1H, dd), 7.45 (1H, dd), 4.57 (2H, td), 3.51-3.39 (1H, m), 2.94-2.84 (1H, m), 1.40 (3H, t). |
| 30 | ¹H-NMR (CDCl₃) δ: 8.72 (1H, dd), 8.61 (1H, dd), 8.49 (1H, dd), 8.40 (1H, d), 7.54 (1H, dd), 7.44 (1H, dd), 6.08 (1H, tt), 4.51 (2H, tt), 3.54-3.38 (1H, m), 2.96-2.81 (1H, m), 1.40 (3H, t). |
| 64 | ¹H-NMR (CDCl₃) δ: 8.32 (1H, d), 8.10 (1H, d), 7.71 (1H, d), 7.36 (1H, dd), 6.44 (1H, d), 5.27 (1H, s), 4.51 (2H, t), 3.68 (2H, q), 2.98 (3H, d), 1.32 (3H, t). |
| 84 | ¹H-NMR (CDCl₃) δ: 8.80 (1H, d), 8.48 (1H, dd), 8.37 (1H, d), 7.88 (1H, d), 7.42 (1H, dd), 4.54 (2H, t), 3.94 (2H, q), 1.40 (3H, t). |
| 134 | ¹H-NMR (CDCl₃) δ: 8.46 (1H, s), 8.34 (1H, d) 7.87 (1H, d), 7.39 (1H, d), 4.54 (2H, t), 3.86 (2H, q), 3.24 (6H, s), 1.39 (3H, t). |
| 313 | ¹H-NMR (CDCl₃) δ: 8.96 (1H, s), 8.90 (1H, dd), 8.25 (1H, dd), 8.20 (1H, d), 7.93 (1H, d), 7.61 (1H, dd), 4.93 (1H, br s), 3.88 (2H, q), 1.37 (3H, t). |

TABLE 48-continued

| Present compound | Physical properties |
|---|---|
| 314 | $^1$H-NMR (CDCl$_3$) δ: 8.88 (1H, dd), 8.52-8.46 (2H, m), 7.91 (1H, dd), 7.60-7.54 (2H, m), 6.95 (1H, dd), 3.88 (2H, q), 1.38 (3H, t). |
| 315 | $^1$H NMR (CDCl$_3$) δ: 8.84 (1H, dd), 8.47 (1H, dd), 8.32 (1H, d), 7.83 (1H, d), 7.53 (1H, dd), 7.36 (1H, dd), 4.41 (2H, t), 3.85 (2H, q), 3.68 (2H, t), 1.36 (3H, t). |
| 316 | $^1$H-NMR (CDCl$_3$) δ: 8.34 (1H, d), 8.17 (1H, d), 7.70 (1H, d), 7.38 (1H, dd), 6.89 (1H, d), 6.40 (1H, s), 4.52 (2H, t), 3.93 (2H, s), 3.66 (2H, q), 1.32 (3H, t). |

TABLE 49

| Present compound | Physical properties |
|---|---|
| 317 | $^1$H-NMR (CDCl$_3$) δ: 8.72 (1H, d), 8.35 (1H, d), 8.15 (1H, d), 7.71 (1H, dd), 7.18 (1H, d), 4.65 (2H, t), 3.31-3.26 (2H, m), 3.04 (3H, s), 1.26 (3H, t). |
| 318 | $^1$H-NMR (CDCl$_3$) δ: 8.32 (1H, d), 8.11 (1H, d), 7.73 (1H, d), 7.37 (1H, dd), 7.07 (1H, d), 4.52, (2H, t), 4.15 (2H, s), 3.71 (2H, q), 3.41 (3H, s), 1.33 (3H, t). |
| 319 | $^1$H-NMR (CDCl$_3$) δ: 8.33 (1H, s), 8.14 (1H, d), 7.68 (1H, d), 7.37 (1H, dd), 7.06 (1H, d), 6.41 (1H, s), 4.52 (2H, t), 3.63 (2H, q), 3.11 (1H, t), 1.32 (3H, t), 1.11 (6H, d). |
| 320 | $^1$H-NMR (CDCl$_3$) δ: 8.32 (1H, d), 8.09 (1H, d), 7.72 (1H, dd), 7.37 (1H, dd), 7.10 (1H, d), 4.93 (1H, s), 4.52 (2H, td), 3.75-3.69 (4H, m), 1.34 (3H, t), 1.22 (6H, d). |
| 321 | $^1$H-NMR (CDCl$_3$) δ: 8.34 (1H, d), 8.19 (1H, s), 7.75 (2H, d), 7.38 (1H, dd), 7.06 (1H, s), 6.67 (1H, s), 4.53 (2H, t), 3.76 (2H, q), 2.10 (3H, s), 1.34 (3H, t). |
| 322 | $^1$H-NMR (CDCl$_3$) δ: 8.61 (1H, t), 8.57 (1H, d), 8.39 (1H, d), 8.15 (1H, d), 7.89 (1H, d), 7.82 (1H, d), 7.44 (1H, dd), 6.52 (1H, dd), 4.56 (2H, td), 3.91 (2H, q), 1.40 (3H, t). |
| 323 | $^1$H-NMR (CDCl$_3$) δ: 8.36 (1H, s), 8.19 (1H, d), 7.87 (1H, d), 7.41 (1H, dd), 7.34 (1H, d), 4.54 (2H, t), 3.87 (2H, q), 2.62 (3H, s), 1.37 (3H, t). |
| 324 | $^1$H-NMR (CDCl$_3$) δ: 8.77 (1H, dd), 8.40 (1H, d), 8.28 (1H, dd), 7.95 (1H, d), 7.44 (1H, dd), 4.56 (2H, t), 4.01 (2H, q), 3.50 (2H, q), 1.44-1.36 (6H, m). |
| 325 | $^1$H-NMR (CDCl$_3$) δ: 8.35 (2H, s), 7.80 (1H, d), 7.38 (1H, d), 6.14 (1H, s), 4.54 (2H, t), 3.82 (2H, q), 3.64 (2H, q), 2.99 (2H, t), 1.37 (3H, t). |
| 326 | $^1$H-NMR (CDCl$_3$) δ: 8.38 (1H, s), 8.35 (1H, d), 7.78 (1H, d), 7.39 (1H, dd), 5.90 (1H, s), 4.53 (2H, t), 3.87 (2H, q), 3.83-3.78 (4H, m), 1.37 (3H, t). |

TABLE 50

| Present compound | Physical properties |
|---|---|
| 327 | $^1$H-NMR (CDCl$_3$) δ: 8.88 (1H, d), 8.43 (1H, dd), 8.10 (1H, d), 7.48 (1H, dd), 4.58 (2H, t), 4.08 (2H, q), 1.46 (3H, t). |
| 328 | $^1$H-NMR (CDCl$_3$) δ: 8.50 (1H, s), 8.39 (1H, d), 7.95 (1H, d), 7.44 (1H, dd), 4.56 (2H, t), 3.95 (2H, q), 2.67 (3H, s), 1.41 (3H, t). |
| 329 | $^1$H-NMR (CDCl$_3$) δ: 8.40 (1H, s), 8.36 (1H, d), 7.80 (1H, d), 7.42 (1H, dd), 7.00 (1H, s), 4.95 (1H, s), 4.55 (2H, t), 3.84 (2H, q), 2.75 (3H, s), 1.39 (3H, t). |
| 330 | $^1$H-NMR (CDCl$_3$) δ: 8.52 (1H, s), 8.35 (1H, d), 7.82 (1H, dd), 7.38 (1H, dd), 4.54 (2H, td), 4.14 (2H, s), 3.84 (2H, q), 3.47 (3H, s), 1.38 (3H, t). |
| 331 | $^1$H-NMR (CDCl$_3$) δ: 8.50 (1H, s), 8.34 (1H, d), 7.80 (1H, dd), 7.39 (1H, dd), 4.54 (2H, td), 4.03 (2H, s), 3.92 (2H, q), 3.85 (2H, q), 1.39 (3H, t), 1.29 (3H, dd). |
| 332 | $^1$H-NMR (CDCl$_3$) δ: 8.39 (1H, s), 8.36 (1H, d), 7.77 (1H, d), 7.42 (1H, dd), 6.96 (1H, s), 5.00 (1H, s), 4.55 (2H, t), 3.86 (2H, q), 3.28-3.22 (1H, m), 1.39 (3H, t), 1.10 (6H, d). |

TABLE 50-continued

| Present compound | Physical properties |
|---|---|
| 333 | $^1$H-NMR (CDCl$_3$) δ: 8.49 (1H, s), 8.34 (1H, d), 7.80 (1H, d), 7.39 (1H, dd), 5.15-5.08 (1H, m), 4.54 (2H, t), 3.85 (2H, q), 3.77 (2H, s), 1.39 (3H, t), 1.24 (6H, d). |
| 334 | $^1$H-NMR (CDCl$_3$) δ: 8.49 (1H, s), 8.34 (1H, d), 7.81 (1H, d), 7.38 (1H, dd), 4.53 (2H, t), 3.94-3.79 (5H, m), 2.96-2.86 (2H, m), 1.39 (3H, t), 1.25 (3H, t), 1.05 (3H, t). |
| 335 | $^1$H-NMR (CDCl$_3$) δ: 8.51 (1H, s), 8.39 (1H, d), 8.01 (1H, s), 7.75 (1H, d), 7.69 (1H, s), 7.39 (1H, dd), 4.57 (2H, t), 3.88 (2H, q), 2.14 (3H, s), 1.47-1.39 (3H, m). |
| 336 | $^1$H-NMR (CDCl$_3$) δ: 8.47 (1H, s), 8.35 (1H, d), 7.86 (1H, d), 7.40 (1H, dd), 4.54 (2H, t), 3.88 (2H, q), 3.67 (4H, t), 3.00 (4H, t), 1.40 (3H, t). |

TABLE 51

| Present compound | Physical properties |
|---|---|
| 337 | $^1$H-NMR (CDCl$_3$) δ: 8.51 (1H, s), 8.36 (1H, s), 7.85 (1H, d), 7.40 (1H, dd), 4.54 (2H, t), 3.89 (2H, q), 3.83 (4H, t), 3.69 (4H, t), 1.40 (3H, t). |
| 338 | $^1$H-NMR (CDCl$_3$) δ: 8.46 (1H, s), 8.34 (1H, d), 7.85 (1H, d), 7.37 (1H, dd), 4.53 (2H, t), 3.84 (2H, q), 3.73-3.73 (4H, m), 2.01-2.00 (4H, m), 1.38 (3H, t). |
| 339 | $^1$H-NMR (CDCl$_3$) δ: 8.92 (1H, s), 8.45 (1H, dd), 8.42 (1H, d), 8.00 (1H, d), 7.89 (1H, dd), 7.45 (1H, dd), 6.55 (1H, dd), 4.60-4.54 (2H, m), 4.01 (2H, q), 1.45 (3H, t). |
| 340 | $^1$H-NMR (CDCl$_3$) δ: 8.90 (1H, d), 8.78 (1H, s), 8.42 (1H, d), 7.97 (1H, d), 7.45 (1H, dd), 4.57 (2H, t), 4.45 (2H, s), 4.01 (2H, q), 1.45 (3H, t). |
| 341 | $^1$H-NMR (CDCl$_3$) δ: 8.94 (1H, s), 8.45 (1H, d), 7.91 (1H, d), 7.68 (1H, s), 7.48 (1H, dd), 6.16 (2H, s), 4.58 (2H, t), 3.94 (2H, q), 1.45 (3H, t). |
| 342 | $^1$H-NMR (CDCl$_3$) δ: 8.90 (1H, d), 8.62 (1H, d), 8.36 (1H, d), 7.88 (1H, d), 7.41 (1H, dd), 4.54 (2H, t), 3.94 (2H, q), 1.40 (3H, t). |
| 343 | $^1$H-NMR (CDCl$_3$) δ: 8.46 (1H, d), 8.40 (1H, s), 7.99 (1H, d), 7.43 (1H, dd), 4.57 (2H, t), 3.31 (2H, q), 1.30 (3H, t). |
| 344 | $^1$H-NMR (CDCl$_3$) δ: 8.37 (1H, s), 8.33 (1H, d), 7.72 (1H, dd), 7.37 (1H, dd), 5.48 (2H, s), 4.52 (2H, t), 3.73 (2H, q), 1.35 (3H, t). |
| 345 | $^1$H-NMR (CDCl$_3$) δ: 8.80 (1H, d), 8.48 (1H, d), 8.37 (1H, d), 7.88 (1H, d), 7.42 (1H, dd), 4.54 (2H, t), 3.94 (2H, q), 4.01 (3H, t). |
| 346 | $^1$H-NMR (CDCl$_3$) δ: 8.33 (1H, d), 8.23 (1H, s), 7.72 (1H, d), 7.37 (1H, dd), 5.43 (2H, s), 4.52 (2H, t), 3.73 (2H, q), 1.35 (3H, t). |
| 347 | $^1$H-NMR (CDCl$_3$) δ: 8.52 (1H, d), 8.38 (1H, d), 8.14-8.12 (2H, m), 8.01 (1H, d), 7.93 (1H, d), 7.55-7.49 (3H, m), 7.45 (1H, dd), 4.56 (2H, td), 3.95 (2H, q), 1.41 (3H, t). |

A compound represented by formula (300):

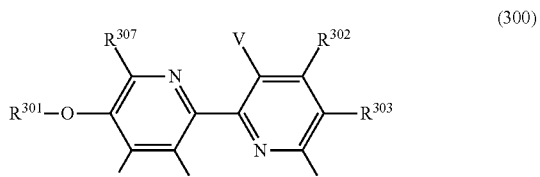

[wherein $R^{301}$, $R^{302}$, $R^{303}$, $R^{304}$, $R^{305}$, $R^{306}$, $R^{307}$, and V represent any combination of the elements indicated in the following [Table 52]]

can be prepared according to the similar method to those described above.

TABLE 52

| Intermediate compound | $R^{301}$ | V | $R^{302}$ | $R^{303}$ | $R^{304}$ | $R^{305}$ | $R^{306}$ | $R^{307}$ |
|---|---|---|---|---|---|---|---|---|
| 3 | $CF_3CFHCF_2$ | F | H | H | H | H | H | H |
| 8 | $CF_3OCFHCF_2$ | F | H | H | H | H | H | H |
| 10 | $CF_3CF_2CH_2$ | F | H | H | H | H | H | H |
| 19 | $CF_2HCF_2CH_2$ | F | H | H | H | H | H | H |
| 100 | $CF_3CFHCF_2CH_2$ | F | H | H | H | H | H | H |
| 101 | $CF_3CFHCF_2$ | F | H | $CF_3$ | H | H | H | H |
| 102 | $CF_3OCFHCF_2$ | F | H | $CF_3$ | H | H | H | H |
| 103 | $CF_3CF_2CH_2$ | F | H | $CF_3$ | H | H | H | H |
| 104 | $CF_3HCF_2CH_2$ | F | H | $CF_3$ | H | H | H | H |
| 105 | $CF_3CFHCF_2CH_2$ | F | H | $CF_3$ | H | H | H | H |

A compound represented by formula (400):

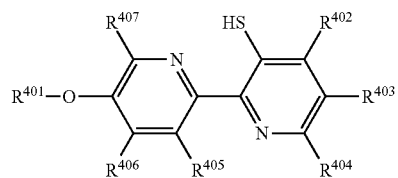

(400)

[wherein $R^{401}$, $R^{402}$, $R^{403}$, $R^{404}$, $R^{405}$, $R^{406}$, and $R^{407}$ represent any combination of the elements indicated in the following [Table 53]]
can be prepared according to the similar method to those described above.

TABLE 53

| Intermediate compound | $R^{401}$ | $R^{402}$ | $R^{403}$ | $R^{404}$ | $R^{405}$ | $R^{406}$ | $R^{407}$ |
|---|---|---|---|---|---|---|---|
| 106 | $CF_3CFHCF_2$ | H | H | H | H | H | H |
| 107 | $CF_2OCFHCF_2$ | H | H | H | H | H | H |
| 20 | $CF_3CF_2CH_2$ | H | H | H | H | H | H |
| 108 | $CF_2HCF_2CH_2$ | H | H | H | H | H | H |
| 109 | $CF_3CFHCF_2CH_2$ | H | H | H | H | H | H |
| 110 | $CF_3CFHCF_2$ | H | $CF_3$ | H | H | H | H |
| 111 | $CF_3OCFHCF_2$ | H | $CF_3$ | H | H | H | H |
| 112 | $CF_3CF_2CH_2$ | H | $CF_3$ | H | H | H | H |
| 113 | $CF_2HCF_2CH_2$ | H | $CF_3$ | H | H | H | H |
| 114 | $CF_3CFHCF_2CH_2$ | H | $CF_3$ | H | H | H | H |

A compound represented by formula (500):

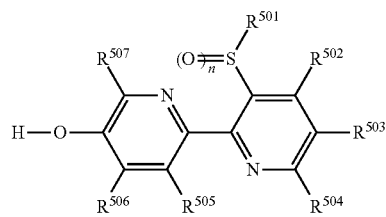

(500)

[wherein $R^{501}$, $R^{502}$, $R^{503}$, $R^{504}$, $R^{505}$, $R^{506}$, and $R^{507}$ represent any combination of the elements indicated in the following [Table 54] to [Table 56]]
can be prepared according to the similar method to those described above.

TABLE 54

| Intermediate compound | $R^{501}$ | n | $R^{502}$ | $R^{503}$ | $R^{504}$ | $R^{505}$ | $R^{506}$ | $R^{507}$ |
|---|---|---|---|---|---|---|---|---|
| 115 | $CH_3$ | 0 | H | H | H | H | H | H |
| 116 | $CH_3CH_2$ | 0 | H | H | H | H | H | H |
| 117 | $CH_3CH_2CH_2$ | 0 | H | H | H | H | H | H |
| 118 | $(CH_3)_2CH$ | 0 | H | H | H | H | H | H |
| 119 | $CF_3CH_2$ | 0 | H | H | H | H | H | H |
| 120 | $CH_3$ | 0 | H | $CF_3$ | H | H | H | H |
| 121 | $CH_3CH_2$ | 0 | H | $CF_3$ | H | H | H | H |
| 122 | $CH_3CH_2CH_2$ | 0 | H | $CF_3$ | H | H | H | H |
| 123 | $(CH_3)_2CH$ | 0 | H | $CF_3$ | H | H | H | H |
| 124 | $CF_3CH_2$ | 0 | H | $CF_3$ | H | H | H | H |

TABLE 55

| Intermediate compound | $R^{501}$ | n | $R^{502}$ | $R^{503}$ | $R^{504}$ | $R^{505}$ | $R^{506}$ | $R^{507}$ |
|---|---|---|---|---|---|---|---|---|
| 125 | $CH_3$ | 1 | H | H | H | H | H | H |
| 126 | $CH_3CH_2$ | 1 | H | H | H | H | H | H |
| 127 | $CH_3CH_2CH_2$ | 1 | H | H | H | H | H | H |
| 128 | $(CH_3)_2CH$ | 1 | H | H | H | H | H | H |
| 129 | $CF_3CH_2$ | 1 | H | H | H | H | H | H |
| 130 | $CH_3$ | 1 | H | $CF_3$ | H | H | H | H |
| 131 | $CH_3CH_2$ | 1 | H | $CF_3$ | H | H | H | H |
| 132 | $CH_3CH_2CH_2$ | 1 | H | $CF_3$ | H | H | H | H |
| 133 | $(CH_3)_2CH$ | 1 | H | $CF_3$ | H | H | H | H |
| 134 | $CF_3CH_2$ | 1 | H | $CF_3$ | H | H | H | H |

TABLE 56

| Intermediate compound | $R^{501}$ | n | $R^{502}$ | $R^{503}$ | $R^{504}$ | $R^{505}$ | $R^{506}$ | $R^{507}$ |
|---|---|---|---|---|---|---|---|---|
| 135 | $CH_3$ | 2 | H | H | H | H | H | H |
| 6 | $CH_3CH_2$ | 2 | H | H | H | H | H | H |
| 136 | $CH_3CH_2CH_2$ | 2 | H | H | H | H | H | H |
| 137 | $(CH_3)_2CH$ | 2 | H | H | H | H | H | H |
| 138 | $CF_3CH_2$ | 2 | H | H | H | H | H | H |
| 139 | $CH_3$ | 2 | H | $CF_3$ | H | H | H | H |
| 140 | $CH_3CH_2$ | 2 | H | $CF_3$ | H | H | H | H |
| 141 | $CH_3CH_2CH_2$ | 2 | H | $CF_3$ | H | H | H | H |
| 142 | $(CH_3)_2CH$ | 2 | H | $CF_3$ | H | H | H | H |
| 143 | $CF_3CH_2$ | 2 | H | $CF_3$ | H | H | H | H |

A compound represented by formula (600):

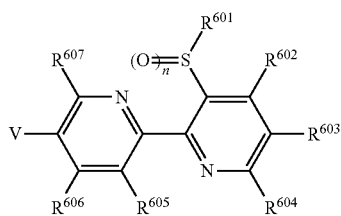

(600)

[wherein $R^{601}$, $R^{602}$, $R^{603}$, $R^{604}$, $R^{605}$, $R^{606}$, $R^{607}$, n, and V represent any combination of the elements indicated in the following [Table 57] to [Table 60]]
can be prepared according to the similar method to those described above.

TABLE 57

| Intermediate compound | $R^{601}$ | n | V | $R^{602}$ | $R^{603}$ | $R^{604}$ | $R^{605}$ | $R^{606}$ | $R^{607}$ |
|---|---|---|---|---|---|---|---|---|---|
| 144 | $CH_3$ | 2 | F | H | H | H | H | H | H |
| 17 | $CH_3CH_2$ | 2 | F | H | H | H | H | H | H |
| 145 | $CH_3CH_2CH_2$ | 2 | F | H | H | H | H | H | H |
| 146 | $(CH_3)_2CH$ | 2 | F | H | H | H | H | H | H |
| 147 | $CF_3CH_2$ | 2 | F | H | H | H | H | H | H |
| 148 | $CH_3$ | 2 | F | H | $CF_3$ | H | H | H | H |
| 149 | $CH_3CH_2$ | 2 | F | H | $CF_3$ | H | H | H | H |
| 150 | $CH_3CH_2CH_2$ | 2 | F | H | $CF_3$ | H | H | H | H |
| 151 | $(CH_3)_2CH$ | 2 | F | H | $CF_3$ | H | H | H | H |
| 152 | $CF_3CH_2$ | 2 | F | H | $CF_3$ | H | H | H | H |

TABLE 58

| Intermediate compound | $R^{601}$ | n | V | $R^{602}$ | $R^{603}$ | $R^{604}$ | $R^{605}$ | $R^{606}$ | $R^{607}$ |
|---|---|---|---|---|---|---|---|---|---|
| 153 | $CH_3$ | 2 | Cl | H | H | H | H | H | H |
| 23 | $CH_3CH_2$ | 2 | Cl | H | H | H | H | H | H |
| 154 | $CH_3CH_2CH_2$ | 2 | Cl | H | H | H | H | H | H |
| 155 | $(CH_3)_2CH$ | 2 | Cl | H | H | H | H | H | H |
| 156 | $CF_3CH_2$ | 2 | Cl | H | H | H | H | H | H |
| 157 | $CH_3$ | 2 | Cl | H | $CF_3$ | H | H | H | H |
| 158 | $CH_3CH_2$ | 2 | Cl | H | $CF_3$ | H | H | H | H |
| 159 | $CH_3CH_2CH_2$ | 2 | Cl | H | $CF_3$ | H | H | H | H |
| 160 | $(CH_3)_2CH$ | 2 | Cl | H | $CF_3$ | H | H | H | H |
| 161 | $CF_3CH_2$ | 2 | Cl | H | $CF_3$ | H | H | H | H |

TABLE 59

| Intermediate compound | $R^{601}$ | n | V | $R^{602}$ | $R^{603}$ | $R^{604}$ | $R^{605}$ | $R^{606}$ | $R^{607}$ |
|---|---|---|---|---|---|---|---|---|---|
| 162 | $CH_3$ | 2 | Br | H | H | H | H | H | H |
| 25 | $CH_3CH_2$ | 2 | Br | H | H | H | H | H | H |
| 163 | $CH_3CH_2CH_2$ | 2 | Br | H | H | H | H | H | H |
| 164 | $(CH_3)_2CH$ | 2 | Br | H | H | H | H | H | H |
| 165 | $CF_3CH_2$ | 2 | Br | H | H | H | H | H | H |
| 166 | $CH_3$ | 2 | Br | H | $CF_3$ | H | H | H | H |
| 167 | $CH_3CH_2$ | 2 | Br | H | $CF_3$ | H | H | H | H |
| 168 | $CH_3CH_2CH_2$ | 2 | Br | H | $CF_3$ | H | H | H | H |
| 169 | $(CH_3)_2CH$ | 2 | Br | H | $CF_3$ | H | H | H | H |
| 170 | $CF_3CH_2$ | 2 | Br | H | $CF_3$ | H | H | H | H |

TABLE 60

| Intermediate compound | $R^{601}$ | n | V | $R^{602}$ | $R^{603}$ | $R^{604}$ | $R^{605}$ | $R^{606}$ | $R^{607}$ |
|---|---|---|---|---|---|---|---|---|---|
| 171 | $CH_3$ | 2 | I | H | H | H | H | H | H |
| 172 | $CH_3CH_2$ | 2 | I | H | H | H | H | H | H |
| 173 | $CH_3CH_2CH_2$ | 2 | I | H | H | H | H | H | H |
| 174 | $(CH_3)_2CH$ | 2 | I | H | H | H | H | H | H |
| 175 | $CF_3CH_2$ | 2 | I | H | H | H | H | H | H |
| 176 | $CH_3$ | 2 | I | H | $CF_3$ | H | H | H | H |
| 177 | $CH_3CH_2$ | 2 | I | H | $CF_3$ | H | H | H | H |
| 178 | $CH_3CH_2CH_2$ | 2 | I | H | $CF_3$ | H | H | H | H |
| 179 | $(CH_3)_2CH$ | 2 | I | H | $CF_3$ | H | H | H | H |
| 180 | $CF_3CH_2$ | 2 | I | H | $CF_3$ | H | H | H | H |

A compound represented by formula (700):

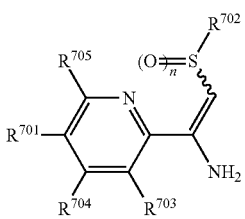

(700)

[wherein $R^{701}$, $R^{702}$, $R^{703}$, $R^{704}$, $R^{705}$, n represent any combination of the elements indicated in the following [Table 61] to [Table 63]]
can be prepared according to the similar method to those described above.

TABLE 61

| Intermediate compound | $R^{701}$ | n | $R^{702}$ | $R^{703}$ | $R^{704}$ | $R^{705}$ |
|---|---|---|---|---|---|---|
| 181 | $CF_3CFHCF_2O$ | 2 | $CH_3$ | H | H | H |
| 182 | $CF_3OCFHCF_2O$ | 2 | $CH_3$ | H | H | H |
| 183 | $CF_3CF_2CH_2O$ | 2 | $CH_3$ | H | H | H |
| 184 | $CF_2HCF_2CH_2O$ | 2 | $CH_3$ | H | H | H |
| 185 | $CF_3CFHCF_2CH_2O$ | 2 | $CH_3$ | H | H | H |
| 186 | F | 2 | $CH_3$ | H | H | H |
| 187 | Cl | 2 | $CH_3$ | H | H | H |
| 188 | Br | 2 | $CH_3$ | H | H | H |
| 189 | I | 2 | $CH_3$ | H | H | H |
| 190 | $CF_3CFHCF_2O$ | 2 | $CH_3CH_2$ | H | H | H |
| 191 | $CF_3OCFHCF_2O$ | 2 | $CH_3CH_2$ | H | H | H |
| 14 | $CF_3CF_2CH_2O$ | 2 | $CH_3CH_2$ | H | H | H |
| 12 | $CF_2HCF_2CH_2O$ | 2 | $CH_3CH_2$ | H | H | H |
| 192 | $CF_3CFHCF_2CH_2O$ | 2 | $CH_3CH_2$ | H | H | H |
| 193 | F | 2 | $CH_3CH_2$ | H | H | H |
| 194 | Cl | 2 | $CH_3CH_2$ | H | H | H |
| 195 | Br | 2 | $CH_3CH_2$ | H | H | H |
| 196 | I | 2 | $CH_3CH_2$ | H | H | H |

TABLE 62

| Intermediate compound | $R^{701}$ | n | $R^{702}$ | $R^{703}$ | $R^{704}$ | $R^{705}$ |
|---|---|---|---|---|---|---|
| 197 | $CF_3CFHCF_2O$ | 2 | $CH_3CH_2CH_2$ | H | H | H |
| 198 | $CF_3OCFHCF_2O$ | 2 | $CH_3CH_2CH_2$ | H | H | H |
| 199 | $CF_3CF_2CH_2O$ | 2 | $CH_3CH_2CH_2$ | H | H | H |
| 200 | $CF_2HCF_2CH_2O$ | 2 | $CH_3CH_2CH_2$ | H | H | H |
| 201 | $CF_3CFHCF_2CH_2O$ | 2 | $CH_3CH_2CH_2$ | H | H | H |
| 202 | F | 2 | $CH_3CH_2CH_2$ | H | H | H |
| 203 | Cl | 2 | $CH_3CH_2CH_2$ | H | H | H |
| 204 | Br | 2 | $CH_3CH_2CH_2$ | H | H | H |

TABLE 62-continued

| Intermediate compound | $R^{701}$ | n | $R^{702}$ | $R^{703}$ | $R^{704}$ | $R^{705}$ |
|---|---|---|---|---|---|---|
| 205 | I | 2 | $CH_3CH_2CH_2$ | H | H | H |
| 206 | $CF_3CFHCF_2O$ | 2 | $(CH_3)_2CH$ | H | H | H |
| 207 | $CF_3OCFHCF_2O$ | 2 | $(CH_3)_2CH$ | H | H | H |
| 208 | $CF_3CF_2CH_2O$ | 2 | $(CH_3)_2CH$ | H | H | H |
| 209 | $CF_2HCF_2CH_2O$ | 2 | $(CH_3)_2CH$ | H | H | H |
| 210 | $CF_3CFHCF_2CH_2O$ | 2 | $(CH_3)_2CH$ | H | H | H |
| 211 | F | 2 | $(CH_3)_2CH$ | H | H | H |
| 212 | Cl | 2 | $(CH_3)_2CH$ | H | H | H |
| 213 | Br | 2 | $(CH_3)_2CH$ | H | H | H |
| 214 | I | 2 | $(CH_3)_2CH$ | H | H | H |

TABLE 63

| Intermediate compound | $R^{701}$ | n | $R^{702}$ | $R^{703}$ | $R^{704}$ | $R^{705}$ |
|---|---|---|---|---|---|---|
| 215 | $CF_3CFHCF_2O$ | 2 | $CH_3CH_2$ | H | H | H |
| 216 | $CF_3OCFHCF_2O$ | 2 | $CH_3CH_2$ | H | H | H |
| 217 | $CF_3CF_2CH_2O$ | 2 | $CH_3CH_2$ | H | H | H |
| 218 | $CF_2HCF_2CH_2O$ | 2 | $CH_3CH_2$ | H | H | H |
| 219 | $CF_3CFHCF_2CH_2O$ | 2 | $CH_3CH_2$ | H | H | H |
| 220 | F | 2 | $CH_3CH_2$ | H | H | H |
| 221 | Cl | 2 | $CH_3CH_2$ | H | H | H |
| 222 | Br | 2 | $CH_3CH_2$ | H | H | H |
| 223 | I | 2 | $CH_3CH_2$ | H | H | H |

A compound represented by formula (800):

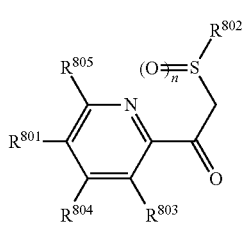

(800)

[wherein $R^{801}$, $R^{802}$, $R^{803}$, $R^{804}$, $R^{805}$, n represent any combination of the elements indicated in the following [Table 64] to [Table 66]]
can be prepared according to the similar method to those described above.

TABLE 64

| Intermediate compound | $R^{801}$ | n | $R^{802}$ | $R^{803}$ | $R^{804}$ | $R^{805}$ |
|---|---|---|---|---|---|---|
| 224 | $CF_3CFHCF_2O$ | 2 | $CH_3$ | H | H | H |
| 225 | $CF_3OCFHCF_2O$ | 2 | $CH_3$ | H | H | H |
| 226 | $CF_3CF_2CH_2O$ | 2 | $CH_3$ | H | H | H |
| 227 | $CF_2HCF_2CH_2O$ | 2 | $CH_3$ | H | H | H |
| 228 | $CF_3CFHCF_2CH_2O$ | 2 | $CH_3$ | H | H | H |
| 229 | F | 2 | $CH_3$ | H | H | H |
| 230 | Cl | 2 | $CH_3$ | H | H | H |
| 231 | Br | 2 | $CH_3$ | H | H | H |
| 232 | I | 2 | $CH_3$ | H | H | H |
| 233 | $CF_3CFHCF_2O$ | 2 | $CH_3CH_2$ | H | H | H |
| 234 | $CF_3OCFHCF_2O$ | 2 | $CH_3CH_2$ | H | H | H |
| 26 | $CF_3CF_2CH_2O$ | 2 | $CH_3CH_2$ | H | H | H |
| 25 | $CF_2HCF_2CH_2O$ | 2 | $CH_3CH_2$ | H | H | H |
| 235 | $CF_3CFHCF_2CH_2O$ | 2 | $CH_3CH_2$ | H | H | H |
| 16 | F | 2 | $CH_3CH_2$ | H | H | H |
| 22 | Cl | 2 | $CH_3CH_2$ | H | H | H |
| 24 | Br | 2 | $CH_3CH_2$ | H | H | H |
| 236 | I | 2 | $CH_3CH_2$ | H | H | H |

TABLE 65

| Intermediate compound | $R^{801}$ | n | $R^{802}$ | $R^{803}$ | $R^{804}$ | $R^{805}$ |
|---|---|---|---|---|---|---|
| 237 | $CF_3CFHCF_2O$ | 2 | $CH_3CH_2CH_2$ | H | H | H |
| 238 | $CF_3OCFHCF_2O$ | 2 | $CH_3CH_2CH_2$ | H | H | H |
| 239 | $CF_3CF_2CH_2O$ | 2 | $CH_3CH_2CH_2$ | H | H | H |
| 240 | $CF_2HCF_2CH_2O$ | 2 | $CH_3CH_2CH_2$ | H | H | H |
| 241 | $CF_3CFHCF_2CH_2O$ | 2 | $CH_3CH_2CH_2$ | H | H | H |
| 242 | F | 2 | $CH_3CH_2CH_2$ | H | H | H |
| 243 | Cl | 2 | $CH_3CH_2CH_2$ | H | H | H |
| 244 | Br | 2 | $CH_3CH_2CH_2$ | H | H | H |
| 245 | I | 2 | $CH_3CH_2CH_2$ | H | H | H |
| 246 | $CF_3CFHCF_2O$ | 2 | $(CH_3)_2CH$ | H | H | H |
| 247 | $CF_3OCFHCF_2O$ | 2 | $(CH_3)_2CH$ | H | H | H |
| 248 | $CF_3CF_2CH_2O$ | 2 | $(CH_3)_2CH$ | H | H | H |
| 249 | $CF_2HCF_2CH_2O$ | 2 | $(CH_3)_2CH$ | H | H | H |
| 250 | $CF_2CFHCF_2CH_2O$ | 2 | $(CH_3)_2CH$ | H | H | H |
| 251 | F | 2 | $(CH_3)_2CH$ | H | H | H |
| 252 | Cl | 2 | $(CH_3)_2CH$ | H | H | H |
| 253 | Br | 2 | $(CH_3)_2CH$ | H | H | H |
| 254 | I | 2 | $(CH_3)_2CH$ | H | H | H |

TABLE 66

| Intermediate compound | $R^{801}$ | n | $R^{802}$ | $R^{803}$ | $R^{804}$ | $R^{805}$ |
|---|---|---|---|---|---|---|
| 255 | $CF_3CFHCF_2O$ | 2 | $CH_3CH_2$ | H | H | H |
| 256 | $CF_3OCFHCF_2O$ | 2 | $CH_3CH_2$ | H | H | H |
| 257 | $CF_3CF_2CH_2O$ | 2 | $CH_3CH_2$ | H | H | H |
| 258 | $CF_2HCF_2CH_2O$ | 2 | $CH_3CH_2$ | H | H | H |
| 259 | $CF_3CFHCF_2CH_2O$ | 2 | $CH_3CH_2$ | H | H | H |
| 260 | F | 2 | $CH_3CH_2$ | H | H | H |
| 261 | Cl | 2 | $CH_3CH_2$ | H | H | H |
| 262 | Br | 2 | $CH_3CH_2$ | H | H | H |
| 263 | I | 2 | $CH_3CH_2$ | H | H | H |

A compound represented by formula (900):

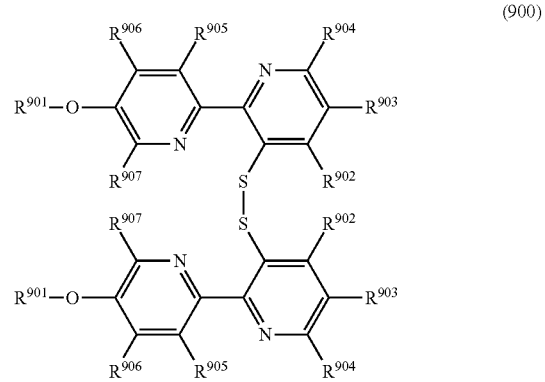

(900)

[wherein $R^{901}$, $R^{902}$, $R^{903}$, $R^{904}$, $R^{905}$, $R^{906}$, and $R^{907}$ represent any combination of the elements indicated in the following [Table 67]]
can be prepared according to the similar method to those described above.

TABLE 67

| Intermediate compound | $R^{901}$ | $R^{902}$ | $R^{903}$ | $R^{909}$ | $R^{905}$ | $R^{906}$ | $R^{907}$ |
|---|---|---|---|---|---|---|---|
| 264 | $CF_3CFHCF_2$ | H | H | H | H | H | H |
| 265 | $CF_3OCFHCF_2$ | H | H | H | H | H | H |
| 21 | $CF_3CF_2CH_2$ | H | H | H | H | H | H |
| 266 | $CF_2HCF_2CH_2$ | H | H | H | H | H | H |

TABLE 67-continued

| Intermediate compound | $R^{901}$ | $R^{902}$ | $R^{903}$ | $R^{909}$ | $R^{905}$ | $R^{906}$ | $R^{907}$ |
|---|---|---|---|---|---|---|---|
| 267 | $CF_3CFHCF_2CH_2$ | H | H | H | H | H | H |
| 268 | $CF_3CFHCF_2$ | H | $CF_3$ | H | H | H | H |
| 269 | $CF_3OCFHCF_2$ | H | $CF_3$ | H | H | H | H |
| 270 | $CF_3CF_2CH_2$ | H | $CF_3$ | H | H | H | H |
| 271 | $CF_2HCF_2CH_2$ | H | $CF_3$ | H | H | H | H |
| 272 | $CF_3CFHCF_2CH_2$ | H | $CF_3$ | H | H | H | H |

Next, the formulation examples of the present compound are shown below. The "parts" represents "part by weight" unless otherwise specified.

Formulation Example 1

Into a mixture of 35 parts of xylene and 35 parts of DMF, 10 parts of each of the present compounds 1 to 347 is dissolved, and then 14 parts of polyoxyethylene styryl phenyl ether and 6 parts of calcium dodecylbenzene sulfonate are added, followed by mixing them to obtain each formulation.

Formulation Example 2

Four (4) parts of sodium lauryl sulfate, 2 parts of calcium lignin sulfonate, 20 parts of synthetic hydrated silicon oxide fine powder and 54 parts of diatomaceous earth are mixed, and further 20 parts of each of the present compounds 1 to 347 is added, followed by mixing them to obtain each wettable powders.

Formulation Example 3

To 2 parts of each of the present compounds 1 to 347, 1 part of synthetic hydrated silicon oxide fine powder, 2 parts of calcium lignin sulfonate, 30 parts of bentonite and 65 parts of kaolin clay are added, followed by mixing, granulation with a granulator and forced-air drying to obtain each granular formulation.

Formulation Example 4

Into an appropriate amount of acetone, 1 part of each the present compounds 1 to 347 is mixed, and then 5 parts of synthetic hydrous silicon oxide fine powder, 0.3 parts of isopropyl acid phosphate and 93.7 parts of kaolin clay are added, followed by mixing with stirring thoroughly and removal of acetone from the mixture by evaporation to obtain each of powder formulation.

Formulation Example 5

A mixture of 35 parts of polyoxyethylene alkyl ether sulfate ammonium salt and white carbon (weight ratio of 1:1), 10 parts of each of the present compounds 1 to 347, and 55 parts of water are mixed, followed by finely grounding by a wet grinding method to obtain each flowable formulation.

Formulation Example 6

Into a mixture of 5 parts of xylene and 5 parts of trichloroethane, 0.1 parts of each of the present compounds 1 to 347 is dissolved, and the resulting mixture is then mixed with 89.9 parts of kerosene to obtain each oil solution.

Formulation Example 7

Into 0.5 mL of acetone, 10 mg of each of the present compounds 1 to 347 is dissolved and the solution is added dropwise to 5 g of a solid feed powder for an animal (solid feed powder for rearing and breeding CE-2, manufactured by CLEA Japan, Inc.), followed by mixing the resulting mixture uniformly, and then by drying them by evaporation of acetone to obtain each poison bait.

Formulation Example 8

Into an aerosol can, 0.1 part of each of the present compound 1 to 347 and 49.9 parts of Neothiozole (Chuo Kasei Co., Ltd.) are placed. After mounting an aerosol valve, 25 parts of dimethylether and 25 parts of LPG are filled, followed by shaking and further mounting an actuator to obtain an oily aerosol.

Formulation Example 9

A mixture of 0.6 part of each of the present compounds 1 to 347, 0.01 part of BHT (2,6-di-tert-butyl-4-methylphenol), 5 parts of xylene, 3.39 parts of deodorized kerosine and 1 part of an emulsifier {Rheodol MO-60 (registered trademark of Kao Corporation)} and 50 parts of distilled water are filled into an aerosol container, and a valve part is attached. Then, 40 parts of a propellant (LPG) is filled therein through the valve under pressure to obtain an aqueous aerosol.

Formulation Example 10

Zero point one (0.1) parts of each of the present compounds 1 to 347 are mixed into 2 mL of propylene glycol, and the resulting solution is impregnated into a ceramic plate having a size of 4.0 cm×4.0 cm and a thickness of 1.2 cm, to obtain thermal fumigants.

Formulation Example 11

Five (5) parts of each of the present compounds 1 to 347, and 95 parts of ethylene-methyl methacrylate copolymer (the ratio of the methyl methacrylate in the copolymer: 10 weight %), Acryft (registered by trademark) WD 301, manufactured by Sumitomo Chemical Co. Ltd.) are melted and kneaded with a closed type pressure kneader, and the resulting kneaded product is extruded from an extrusion molding machine through a molding die to obtain a rod-shaped molded product having a length of 15 cm and a diameter of 3 mm.

Formulation Example 12

Five (5) parts of each of the present compounds 1 to 347, and 95 parts of plasticized polyvinyl chloride resin are melted and kneaded with a closed type pressure kneader, and the resulting kneaded product is extruded from an extrusion molding machine through a molding die to obtain a rod-shaped molded product having a length of 15 cm and a diameter of 3 mm.

Formulation Example 13

One hundred (100) mg of each of the present compounds 1 to 347, 68.75 mg of lactose, 237.5 mg of corn starch, 43.75 mg of microcrystalline cellulose, 18.75 mg of polyvinylpyrrolidone, 28.75 mg of sodium carbomethyl starch and 25 mg of magnesium stearate are mixed, and the resulting mixture was compressed to an appropriate size to obtain a tablet.

Formulation Example 14

Twenty five (25) mg of each of the present compounds 1 to 347, 60 mg of lactose, 25 mg of corn starch, 6 mg of carmellose calcium and an appropriate amount of 5% of hydroxypropyl methylcellulose are mixed, and the resulting mixture are filled into a hard shell gelatin capsule or a hydroxypropyl methylcellulose capsule to obtain capsules.

Formulation Example 15

To 100 mg of each of the present compounds 1 to 347, 500 mg of fumaric acid, 2,000 mg of granulated sugar, 13,000 mg of sorbitol (70% solution), 100 mg of Veegum K (manufactured by Vanderbilt Co.), 35 mg of perfume and 500 mg of coloring agent, a distilled water is added so that a final volume is set to be 100 mL, followed by mixing them to obtain a suspension for oral administration.

Formulation Example 16

Into a mixture of 5% by weight of an emulsifier, 3% by weight of benzyl alcohol and 30% by weight of propylene glycol, 5% by weight of each of the present compounds 1 to 347 is dissolved, and phosphate buffer is added thereto so that a pH of the solution is set to be 6.0 to 6.5, and water is added as the rest parts to obtain the solution for oral administration.

Formulation Example 17

To a mixture of 57% by weight of fractional distillated palm oil and 3% by weight of polysorbate 85, 5% by weight of aluminum distearate is added, and heated to disperse it. The resulting mixture is cooled to room temperature, and 25% by weight of saccharin is dispersed in an oil vehicle. Ten (10) % by weight of each of the present compounds 1 to 346 is divided thereto to obtain a paste for oral administration.

Formulation Example 18

Five (5) % by weight of each of the present compounds 1 to 346 is mixed with 95% by weight of limestone filler, followed by a wet granulation of the resulting mixture to obtain a granule for oral administration.

Formulation Example 19

Into 80 parts of diethylene glycol monomethyl ether, 5 parts of each of the present compounds 1 to 347 is dissolved, and 15 parts of propylene carbonate is added thereto, and the resulting mixture is mixed to obtain a spot-on solution.

Formulation Example 20

Into 70 parts of diethylene glycol monomethyl ether, 10 parts of each of the present compounds 1 to 347 is dissolved, and 20 parts of 2-octyldodecanol is added thereto, and the resulting mixture is mixed to obtain a pour-on solution.

Formulation Example 21

To 0.5 parts of each of the present compounds 1 to 347, 60 parts of Nikkol (registered by trademark) TEALS-42 (manufactured by Nikko Chemical Co. Ltd.: 42% of aqueous solution of lauryl sulfuric acid triethanol amine) and 20 parts of propylene glycol are added, and the resulting mixture is mixed with stirring thoroughly, and 19.5 parts of water is then added thereto and the resulting mixture is further mixed with stirring thoroughly to obtain a hydrogenous solution of shampoo formulation.

Formulation Example 22

Zero point fifteen (0.15)% by weight of each of the present compounds 1 to 347, 95% by weight of animal feed, as well as 4.85% by weight of a mixture of dibasic calcium phosphate, diatomaceous earth, aerosol and carbonate (or chalk) are mixed with stirring thoroughly to obtain a premix for animal feed.

Formulation Example 23

Seven point two (7.2) g of each of the present compounds 1 to 347, and 92.8 g of Hosco (registered trademark) S-55 (manufactured by Maruishi Pharmaceuticals) are melted and mixed at 100° C., and the resulting mixture was poured into a suppository mold, followed by performing a cooling solidification to obtain a suppository.

Next, Test Examples are used to show an efficacy of the present compound on controlling harmful arthropods.

Test Example 1

Each of the present compounds 1, 2, 9, 10, 12, 16, 22, 26, 27, 39, 59, 64, 69, 74, 79, 89, 94, 104, 124, 129, 144, 154, 159, 164, 169, 174, 179, 184, 204, 214, 224, 280, 300, 301, 302, 303, 304, 305, 306, 307, 308, 309, 311, 314, 315, 318, 320, 323, 325, 326, 328, 330, 331, 336, 339, 341, 344, and 346 was made to a formulation according to a similar method to that described in the Formulation Example 5 and was then diluted with water so that the active ingredient concentration was set to 500 ppm to prepare each of the diluted solution.

Cucumber seedling (on the developmental stage of the first true leaf) was planted in a polyethylene cup and 30 heads of cotton aphid (*Aphis gossypii*) (all stages of life) were released onto the leaves of the cucumber and allowed to stand for 1 day. The diluted solutions 20 mL were sprayed into the seedling.

Cucumber (cv; *Sagami-hanjiro-fushinari*) was grown in a polyethylene cup until the first true leaf was developed. Approximately 30 heads of cotton aphid (*Aphis gossypii*) (including the adults and the larvae) was released onto the leaves of the cabbage and next day, the above-mentioned testing drug dilutions 20 mL were sprayed.

After 6 days, the number of the surviving insects that were parasitic on the leaves of the cucumber was examined and the controlling value was calculated by the following equation.

Controlling value (%)={1−($Cb×Tai$)/($Cai×Tb$)}×100 wherein the symbols in the formula represent the following descriptions.

Cb: Number of the insects before treatment in untreated area;

Cai: Number of the surviving parasitic insects at the time of the investigation in untreated area;

Tb: Number of the insects before treatment in treated area;

Tai: Number of the surviving parasitic insects at the time of the investigation in treated area;

Here the "untreated area" represents an area that was sprayed by a diluted solution of the formulation described in the Formulation Example 5 without the present compound with water in the same amount as that of the treated area.

As a result, the treated area that was treated with each of the diluted solutions of the present compounds 1, 2, 9, 10, 12, 16, 22, 26, 27, 39, 59, 64, 69, 74, 79, 89, 94, 104, 124, 129, 144, 154, 159, 164, 169, 174, 179, 184, 204, 214, 224, 280, 300, 301, 302, 303, 304, 305, 306, 307, 308, 309, 311, 314, 315, 318, 320, 323, 325, 326, 328, 330, 331, 336, 339, 341, 344, and 346 respectively showed 90% or greater as the controlling value.

Test Example 2

Each of the present compounds 1, 2, 7, 8, 9, 10, 11, 12, 14, 15, 22, 23, 24, 26, 27, 29, 30, 39, 59, 64, 69, 74, 79, 89, 94, 99, 104, 124, 129, 144, 169, 174, 179, 184, 204, 214, 224, 235, 280, 300, 301, 302, 303, 304, 305, 306, 307, 308, 309, 314, 316, 318, 319, 320, 325, 329, 332, 335, 344, and 346 was made to a formulation according to a similar method to that described in the Formulation example 5 and was then diluted with water so that each of the active ingredient concentration was set to 200 ppm to prepare each of the diluted solution.

Cucumber seedling (on the developmental stage of the first true leaf) was planted in a polyethylene cup and 30 heads of cotton aphid (*Aphis gossypii*) (all stages of life) were released onto the leaves of the cucumber and allowed to stand for 1 day. The diluted solutions 20 mL were sprayed into the seedling.

Cucumber (cv; *Sagami-hanjiro-fushinari*) was grown in a polyethylene cup until the first true leaf was developed. Approximately 30 heads of cotton aphid (*Aphis gossypii*) (including the adults and the larvae) was released onto the leaves of the cabbage and next day, the above-mentioned testing drug dilutions 20 mL were sprayed.

After 6 days, the number of the surviving insects that were parasitic on the leaves of the cucumber was examined and the controlling value was calculated by the following equation.

Controlling value (%)={1−(*Cb*×*Tai*)/(*Cai*×*Tb*)}×100 wherein the symbols in the formula represent the following descriptions.

Cb: Number of the insects before treatment in untreated area;

Cai: Number of the surviving parasitic insects at the time of the investigation in untreated area;

Tb: Number of the insects before treatment in treated area;

Tai: Number of the surviving parasitic insects at the time of the investigation in treated area; Here the "untreated area" represents an area that was sprayed by a diluted solution of the formulation described in the Formulation Example 5 without the present compound with water in the same amount as that of the treated area.

As a result, the treated area that was treated with each of the diluted solutions of the present compounds 1, 2, 7, 8, 9, 10, 11, 12, 14, 15, 22, 23, 24, 26, 27, 29, 30, 39, 59, 64, 69, 74, 79, 89, 94, 99, 104, 124, 129, 144, 169, 174, 179, 184, 204, 214, 224, 235, 280, 300, 301, 302, 303, 304, 305, 306, 307, 308, 309, 314, 316, 318, 319, 320, 325, 329, 332, 335, 344, and 346 respectively showed 90% or greater as the controlling value.

Test Example 3

Each of the present compounds 7, 8, 11, 12, 14, 15, 26, 27, 29, 30, 59, 64, 69, 74, 79, 89, 94, 99, 104, 124, 169, 184, 204, 224, 235, 300, 301, 302, 303, 306, 309, 314, 316, 318, 319, 320, 335, 344, and 346 was made to a formulation according to a similar method to that described in the Formulation example 5 and was then diluted with water so that the active ingredient concentration was set to 200 ppm to prepare the diluted solution.

Cucumber seedling (on the developmental stage of the second true leaf) was planted in a polyethylene cup, and the diluted solutions 5 mL were irrigated into the plant foot, and the plants were held at 25° C. in a greenhouse for 7 days. Approximately 30 heads of cotton aphid (*Aphis gossypii*) (all stages of life) were inoculated onto the cucumber leaves and the plants were held in a greenhouse for additional 6 days, and then the number of the surviving insects that were parasitic on the cucumber leaves was examined and the controlling value was calculated by the following equation.

Controlling value (%)={1−(*Cb*×*Tai*)/(*Cai*×*Tb*)}×100 wherein the symbols in the formula represent the following descriptions.

Cb: Number of the insects before treatment in untreated area;

Cai: Number of the surviving parasitic insects at the time of the investigation in untreated area;

Tb: Number of the insects before treatment in treated area;

Tai: Number of the surviving parasitic insects at the time of the investigation in treated area; Here the "untreated area" represents an area that was sprayed by a diluted solution of the formulation described in the Formulation Example 5 without the present compound with water in the same amount as that of the treated area.

As a result, the treated area that was treated with each of the diluted solutions of the present compounds 7, 8, 11, 12, 14, 15, 26, 27, 29, 30, 59, 64, 69, 74, 79, 89, 94, 99, 104, 124, 169, 184, 204, 224, 235, 300, 301, 302, 303, 306, 309, 314, 316, 318, 319, 320, 335, 344, and 346 respectively showed 90% or greater as the controlling value.

Test Example 4

Each of the present compounds 1, 2, 9, 10, 12, 26, 27, 39, 59, 64, 69, 89, 94, 144, 169, 184, 204, 214, 224, 280, 300, 301, 303, 304, 305, 308, 314, 318, 320, 344, 346, 320, 335, 344, and 346 was made to a formulation according to a similar method to that described in the Formulation example 5 and was then diluted with water so that each of the active ingredient concentration was set to 500 ppm to prepare each of the diluted solution.

Rice seedling (on the developmental stage of the second true leaf) was planted in a polyethylene cup, and the diluted solutions 10 mL were sprayed. After air drying, 20 heads of 3rd to 4th instar larvae of brown planthopper (*Nilaparvata lugens*) were released onto the rice leaves and the plants were held at 25° C. in a greenhouse.

After 6 days, the number of the surviving insects that were parasitic on the leaves of the rice was examined and the controlling value was calculated by the following equation.

Controlling value (%)={1−(*Cb*×*Tai*)/(*Cai*×*Tb*)}×100 wherein the symbols in the formula represent the following descriptions.

Cb: Number of the insects before treatment in untreated area;

Cai: Number of the surviving parasitic insects at the time of the investigation in untreated area;

Tb: Number of the insects before treatment in treated area;

Tai: Number of the surviving parasitic insects at the time of the investigation in treated area;

Here the "untreated area" represents an area that was sprayed by a diluted solution of the formulation described in the Formulation Example 5 without the present compound with water in the same amount as that of the treated area.

As a result, the treated area that was treated with each of the diluted solutions of the present compounds 1, 2, 9, 10, 12, 26, 27, 39, 59, 64, 69, 89, 94, 144, 169, 184, 204, 214, 224, 280, 300, 301, 303, 304, 305, 308, 314, 318, 320, 344, 346, 320, 335, 344, and 346 respectively showed 90% or greater as the controlling value.

Test Example 5

Each of the present compounds 1, 2, 7, 8, 9, 10, 11, 12, 15, 24, 26, 27, 29, 30, 39, 59, 64, 69, 144, 169, 184, 204, 235, 300, 301, 303, 314, 316, 318, 319, 320, 335, 344, and 346 was made to a formulation according to a similar method to that described in the Formulation example 5 and was then diluted with water so that each of the active ingredient concentration was set to 200 ppm to prepare each of the diluted solution.

Rice seedling (on the developmental stage of the second true leaf) was planted in a polyethylene cup, and the diluted solutions 10 mL were sprayed. After air drying, 20 heads of 3rd to 4th instar larvae of brown planthopper (*Nilaparvata lugens*) were released onto the rice leaves and the plants were held at 25° C. in a greenhouse.

After 6 days, the number of the surviving insects that were parasitic on the leaves of the rice was examined and the controlling value was calculated by the following equation.

Controlling value (%)={1−(Cb×Tai)/(Cai×Tb)}×100 wherein the symbols in the formula represent the following descriptions.

Cb: Number of the insects before treatment in untreated area;

Cai: Number of the surviving parasitic insects at the time of the investigation in untreated area;

Tb: Number of the insects before treatment in treated area;

Tai: Number of the surviving parasitic insects at the time of the investigation in treated area;

Here the "untreated area" represents an area that was sprayed by a diluted solution of the formulation described in the Formulation Example 5 without the present compound with water in the same amount as that of the treated area.

As a result, the treated area that was treated with each of the diluted solutions of the present compounds 1, 2, 7, 8, 9, 10, 11, 12, 15, 24, 26, 27, 29, 30, 39, 59, 64, 69, 144, 169, 184, 204, 235, 300, 301, 303, 314, 316, 318, 319, 320, 335, 344, and 346 respectively showed 90% or greater as the controlling value.

Test Example 6

Each of the present compounds 2, 7, 8, 11, 12, 14, 15, 24, 29, 30, 59, 64, 69, 74, 94, 99, 144, 169, 184, 204, 214, 235, 280, 300, 303, 316, 318, 319, 320, 335, and 346 was made to a formulation according to a similar method to that described in the Formulation example 5 and was then diluted with water so that each of the active ingredient concentration was set to 200 ppm to prepare each of the diluted solution.

Rice seedling (two weeks after sowing, on the developmental stage of the second true leaf) was planted in a polyethylene cup, and the diluted solutions 5 mL were irrigated into the plant foot, and the plants were held at 25° C. in a greenhouse for 7 days. Twenty (20) heads of 3rd to 4th instar larvae of brown planthopper (*Nilaparvata lugens*) were released onto the rice leaves and the plants were held at 25° C. in a greenhouse for additional 6 days, and then the number of the surviving insects that were parasitic on rice leaves was examined and the controlling value was calculated by the following equation.

Controlling value (%)={1−(Cb×Tai)/(Cai×Tb)}×100 wherein the symbols in the formula represent the following descriptions.

Cb: Number of the insects before irrigation in untreated area;

Cai: Number of the surviving parasitic insects at the time of the investigation in untreated area;

Tb: Number of the insects before irrigation in treated area;

Tai: Number of the surviving parasitic insects at the time of the investigation in treated area;

Here the "untreated area" represents an area that was sprayed by a diluted solution of the formulation described in the Formulation Example 5 without the present compound with water in the same amount as that of the treated area.

As a result, the treated area that was treated with each of the diluted solutions containing the present compounds 2, 7, 8, 11, 12, 14, 15, 24, 29, 30, 59, 64, 69, 74, 94, 99, 144, 169, 184, 204, 214, 235, 280, 300, 303, 316, 318, 319, 320, 335, and 346 respectively showed 90% or greater as the controlling value.

Test Example 7

Each of the present compounds 2, 9, 10, 12, 16, 26, 27, 39, 53, 54, 59, 64, 69, 74, 79, 89, 94, 104, 119, 124, 129, 134, 144, 149, 154, 159, 164, 169, 174, 179, 184, 204, 214, 280, 300, 301, 302, 303, 304, 305, 306, 307, 308, 309, 311, 314, 315, 318, 320, 323, 325, 326, 328, 330, 331, 333, 336, 339, 341, 344, and 346 was made to a formulation according to a similar method to that described in the Formulation example 5 and was then diluted with water so that each of the active ingredient concentration was set to 500 ppm to prepare each of the diluted solution.

A cabbage in the third leaf stage was planted in a polyethylene cup, and thereto was sprayed the diluted solution in a ratio of 20 mL/cup. After the above-mentioned dilutions were dried, and the stem and leaf thereof was cut and then was installed in a 50 mL cup, and five heads of cabbage moth (*Plutella xylostella*) at the second instar larval stages were released into the cup and the cup was covered with the lid. The cup was held at 25° C. and after 5 days, the number of died insects was counted and the mortality of insects was calculated by the following equation.

Mortality of insects (%)=(Number of dead insects/Number of tested insects)×100

As a result, the treated area that was treated with each of the diluted solutions of the present compounds 2, 9, 10, 12, 16, 26, 27, 39, 53, 54, 59, 64, 69, 74, 79, 89, 94, 104, 119, 124, 129, 134, 144, 149, 154, 159, 164, 169, 174, 179, 184, 204, 214, 280, 300, 301, 302, 303, 304, 305, 306, 307, 308, 309, 311, 314, 315, 318, 320, 323, 325, 326, 328, 330, 331, 333, 336, 339, 341, 344, and 346 respectively showed 80% or greater as the mortality of insects.

Test Example 8

Each of the present compounds 2, 7, 8, 9, 10, 11, 12, 14, 15, 16, 24, 26, 27, 29, 30, 39, 53, 54, 59, 64, 69, 79, 89, 94, 99, 104, 124, 129, 134, 144, 149, 154, 169, 179, 184, 204, 235, 246, 258, 280, 300, 301, 302, 303, 304, 305, 306, 307, 308, 309, 314, 315, 316, 318, 319, 320, 325, 326, 329, 330, 332, 335, 336, 339, 340, 341, 344, and 346 was made to a formulation according to a similar method to that described in the Formulation example 5 and was then diluted with water so that each of the active ingredient concentration was set to 200 ppm to prepare each of the diluted solution.

A cabbage in the third leaf stage was planted in a polyethylene cup, and thereto was sprayed the diluted solution in a ratio of 20 mL/cup. After the above-mentioned dilutions were dried, and the stem and leaf thereof was cut and then was installed in a 50 mL cup, and five heads of cabbage moth (*Plutella xylostella*) at the second instar larval stages were released into the cup and the cup was covered with the lid. The cup was held at 25° C. and after 5 days, the number of died insects was counted and the mortality of insects was calculated by the following equation.

Mortality of insects (%)=(Number of dead insects/Number of tested insects)×100

As a result, the treated area that was treated with each of the diluted solutions of the present compounds 2, 7, 8, 9, 10, 11, 12, 14, 15, 16, 24, 26, 27, 29, 30, 39, 53, 54, 59, 64, 69, 79, 89, 94, 99, 104, 124, 129, 134, 144, 149, 154, 169, 179, 184, 204, 235, 246, 258, 280, 300, 301, 302, 303, 304, 305, 306, 307, 308, 309, 314, 315, 316, 318, 319, 320, 325, 326, 329, 330, 332, 335, 336, 339, 340, 341, 344, and 346 respectively showed 80% or greater as the mortality of insects.

Test Example 9

Each of the present compounds 9, 10, 12, 59, 64, 94, 104, 184, 204, 214, 235, 300, 301, 303, 305, 318, 331, and 346 was made to a formulation according to a similar method to that described in the Formulation example 5 and was then diluted with water so that each of the active ingredient concentration was set to 500 ppm to prepare each of the diluted solution.

The bottom of the polyethylene cup having 5.5 cm diameter was matted with the same size of a filter paper, and 0.7 mL of the diluted solution was added dropwise to the filter paper and 30 mg sucrose as bait was placed in the cup uniformly. Ten (10) heads of female adult housefly (*Musca domestica*) were released into the polyethylene cup and the cup was covered with the lid. After 24 hours, the life and death of housefly was examined and the number of died insects was counted and the mortality of insects was calculated by the following equation.

Mortality of insects (%)=(Number of dead insects/Number of tested insects)×100

As a result, the treated area that was treated with each of the diluted solutions of the present compounds 9, 10, 12, 59, 64, 94, 104, 184, 204, 214, 235, 300, 301, 303, 305, 318, 331, and 346 respectively showed 100% as the mortality of insects.

Test Example 10

Each of the present compounds 7, 8, 9, 10, 11, 14, 22, 23, 24, 53, and 69 was made to a formulation according to a similar method to that described in the Formulation example 1 and was then diluted with water so that each of the active ingredient concentration was set to 500 ppm to prepare each of the diluted solution.

A cucumber in the third leaf stage was planted in a polyethylene cup, and thereto were sprayed each of the above-mentioned diluted solutions in a ratio of 30 mL/cup. After the above-mentioned dilutions were dried, the second leaf was cut, and then was installed in a 200 mL cup, and ten heads of cucurbit leaf beetle (*Aulacophora femoralis*) at the second instar larval stages were released into the cup and the cup was covered with the lid. The cup was held at 25° C. and after 5 days, the number of died insects was counted and the mortality of insects was calculated by the following equation.

Mortality of insects (%)=(Number of dead insects/Number of tested insects)×100

As a result, the treated area that was treated with each of the diluted solutions of the present compounds 7, 8, 9, 10, 11, 14, 22, 23, 24, 53, and 69 respectively showed 80% or greater as the mortality of insects.

Test Example 11

The present compound 2 was mixed with a mixed solution of acetone and polyoxyethylene sorbitan mono-cocoate (acetone and polyoxyethylene sorbitan mono-cocoate=95:5 (weight ratio)) in a ratio of 50 µL of the mixed solution per 1 mg of the present compound, and the resulting mixtures were then diluted with ion-exchange water containing 0.03% by volume of shindain (registered trademark, manufactured by Sumitomo Chemical Co. Ltd.) so that the concentration of the present compound was set to 500 ppm to prepare the diluted solution of the present compound.

Corns (Xea mays) were sown on a tray overlaid with damped KimWipes (registered trademark). After corns were grown for 5 days, the entire seedling of the corn was immersed into the diluted solution for 30 seconds. After the seedling was dried, two grains of the seedling were installed in a plastic petri dish (90 mm radius), and ten heads of western corn rootworm (*Diabrotica virgifera virgifera*) at the second instar larval stages were released onto the petri dish and the petri dish was covered with the lid. The petri dish was held at 25° C. and after 5 days, the number of died insects was counted and the mortality of insects was calculated by the following equation.

Mortality of insects (%)=(Number of dead insects/Number of tested insects)×100

Similarly, using the present compounds 1, 15, 16, 29, 30, 39, 54, 59, 64, 69, 74, 89, 119, 124, 129, 134, 144, 149, 154, 169, 184, 204, 235, 246, 280, 301, 307, 308, 313, 314, 318, 320, 325, 333, 336, and 344 instead of the present compound 2, the tests were carried out.

As a result, the following present compounds respectively showed 80% or greater as the mortality of insects.

Present compounds to be tested: 1, 15, 16, 29, 30, 39, 54, 59, 64, 69, 74, 89, 119, 124, 129, 134, 144, 149, 154, 169, 184, 204, 235, 246, 280, 301, 307, 308, 313, 314, 318, 320, 325, 333, 336, and 344.

INDUSTRIAL APPLICABILITY

The present compound shows an excellent control effect against a harmful arthropod.

The invention claimed is:

1. A bipyridine compound of formula (I) or an N-oxide thereof:

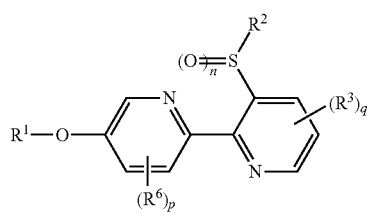

wherein:
- $R^1$ represents a C2-C10 haloalkyl group, a C3-C10 haloalkenyl group, a C3-C10 haloalkynyl group, a (C1-C5 alkoxy)C2-C5 alkyl group substituted with one or more halogen atoms, a (C1-C5 alkylsulfanyl)C2-C5 alkyl group substituted with one or more halogen atoms, a (C1-C5 alkylsulfinyl)C2-C5 alkyl group substituted with one or more halogen atoms, a (C1-C5 alkylsulfonyl)C2-C5 alkyl group substituted with one or more halogen atoms, a (C3-C7 cycloalkyl)C1-C3 alkyl group substituted with one or more substituents selected from Group G, or a C3-C7 cycloalkyl group substituted with one or more substituents selected from Group G;
- $R^2$ represents a C1-C6 alkyl group optionally substituted with one or more halogen atoms, a cyclopropylmethyl group, or a cyclopropyl group;
- $R^3$ represents a C1-C6 chain hydrocarbon group optionally substituted with one or more substituents selected from Group B, a phenyl group optionally substituted with one or more substituents selected from Group D, a 5 or 6 membered aromatic heterocyclic group optionally substituted with one or more substituents selected from Group D, a $OR^{12}$, a $NR^{11}R^{12}$, a $NR^{11a}R^{12a}$, a $NR^{24}NR^{11}R^{12}$, a $NR^{11}C(O)R^{13}$, a $NR^{24}NR^{11}C(O)R^{13}$, a $NR^{11}C(O)OR^{14}$, a $NR^{24}NR^{11}C(O)OR^{14}$, a $NR^{11}C(O)NR^{15}R^{16}$, a $NR^{24}NR^{11}C(O)NR^{15}R^{16}$, a $N=CHNR^{15}R^{16}$, a $N=S(O)_xR^{15}R^{16}$, a $S(O)_yR^{15}$, a $C(O)OR^{17}$, a $C(O)NR^{11}R^{12}$, a cyano group, a nitro group, or a halogen atom;
- $R^6$ represents a C1-C6 alkyl group optionally substituted with one or more halogen atoms, a $OR^{18}$, a $NR^{18}R^{19}$, a $C(O)OR^{25}$, a $OC(O)R^{20}$, a cyano group, a nitro group, or a halogen atom;
- $R^{11}$, $R^{17}$, $R^{18}$, $R^{19}$, $R^{20}$, $R^{24}$ and $R^{25}$ represent independently of each other a hydrogen atom, or a C1-C6 chain hydrocarbon group optionally substituted with one or more halogen atoms;
- $R^{12}$ represents a hydrogen atom, a C1-C6 chain hydrocarbon group optionally substituted with one or more halogen atoms, a C1-C6 alkyl group substituted with one substituent selected from Group F, or a $S(O)_2R^{23}$;
- $R^{23}$ represents a C1-C6 chain hydrocarbon group optionally substituted with one or more halogen atoms, or a phenyl group optionally substituted with one or more substituents selected from Group D,
- $R^{11a}$ and $R^{12a}$ combine together with a nitrogen atom to which they are attached to form a 3 to 7 membered nonaromatic heterocyclic group, wherein the 3 to 7 membered nonaromatic heterocyclic group represents aziridine, azetidine, pyrrolidine, imidazoline, imidazolidine, piperidine, tetrahydropyrimidine, hexahydropyrimidine, piperazine, azepane, oxazolidine, isooxazolidine, 1,3-oxazinane, morpholine, 1,4-oxazepane, thiazolidine, isothiazolidine, 1,3-thiazinane, thiomorpholine, or 1,4-thiazepane, and the 3 to 7 membered nonaromatic heterocyclic group is optionally substituted with one or more substituents selected from Group E;
- $R^{13}$ represents a hydrogen atom, a C1-C6 chain hydrocarbon group optionally substituted with one or more halogen atoms, a C3-C7 cycloalkyl group optionally substituted with one or more halogen atoms, a (C3-C6 cycloalkyl)C1-C3 alkyl group optionally substituted with one or more halogen atoms, a phenyl group optionally substituted with one or more substituents selected from Group D, or a 5 or 6 membered aromatic heterocyclic group optionally substituted with one or more substituents selected from Group D;
- $R^{14}$ represents a C1-C6 chain hydrocarbon group optionally substituted with one or more halogen atoms, a C3-C7 cycloalkyl group optionally substituted with one or more halogen atoms, a (C3-C6 cycloalkyl)C1-C3 alkyl group optionally substituted with one or more halogen atoms, or a phenylC1-C3 alkyl group, wherein the phenyl group in the group is optionally substituted with one or more substituents selected from Group D;
- $R^{15}$ and $R^{16}$ represent independently of each other, a C1-C6 alkyl group optionally substituted with one or more halogen atoms;
- n and y represent independently of each other 0, 1 or 2;
- x represents 0 or 1;
- p and q represent independently of each other 0, 1, 2, or 3, and when p is 2 or 3, a plurality of $R^6$ can be identical or different, and when q is 2 or 3, a plurality of $R^3$ can be identical or different;
- Group B is selected from the group consisting of a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a C1-C6 alkylsulfanyl group optionally substituted with one or more halogen atoms, a C1-C6 alkylsulfinyl group optionally substituted with one or more halogen atoms, a C1-C6 alkylsulfonyl group optionally substituted with one or more halogen atoms, a C3-C6 cycloalkyl group optionally substituted with one or more halogen atoms, a cyano group, a hydroxy group, and a halogen atom;
- Group D is selected from the group consisting of a C1-C6 chain hydrocarbon group optionally substituted with one or more halogen atoms, a hydroxy group, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a sulfanyl group, a C1-C6 alkylsulfanyl group optionally substituted with one or more halogen atoms, a C1-C6 alkylsulfinyl group optionally substituted with one or more halogen atoms, a C1-C6 alkylsulfonyl group optionally hsubstituted with one or more halogen atoms, an amino group, a $NHR^{21}$, a $NR^{21}R^{22}$, a $C(O)R^{21}$, a $OC(O)R^{21}$, a $C(O)OR^{21}$, a cyano group, a nitro group, and a halogen atom, wherein $R^{21}$ and $R^{22}$ represent independently of each other a C1-C6 alkyl group optionally substituted with one or more halogen atoms;

Group E is selected from the group consisting of a C1-C6 chain hydrocarbon group optionally substituted with one or more halogen atoms, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a halogen atom, an oxo group, a hydroxy group, a cyano group, and a nitro group;

Group F is selected from the group consisting of a C1-C6 alkoxy group optionally substituted with one or more halogen atoms, a $NHR^{21}$, a $NR^{21}R^{22}$, a cyano group, a phenyl group optionally substituted with one or more substituents selected from Group D, a 5 or 6 membered aromatic heterocyclic group optionally substituted with one or more substituents selected from Group D, a C3-C7 cycloalkyl group optionally substituted with one or more halogen atoms, and a 3 to 7 membered non-aromatic heterocyclic group optionally substituted with one or more substituents selected from Group C;

Group C is selected from the group consisting of a C1-C6 chain hydrocarbon group optionally substituted with one or more halogen atoms, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, and a halogen atom;

Group G is selected from the group consisting of a halogen atom, and a C1-C6 haloalkyl group.

2. The bipyridine compound according to claim 1, wherein q is 0, 1, 2 or 3, $R^3$ represents a C1-C6 chain hydrocarbon group optionally substituted with one or more halogen atoms, a 5 or 6 membered aromatic heterocyclic group optionally substituted with one or more substituents selected from Group D, a $OR^{12}$, a $NR^{11}R^{12}$, a $NR^{24}NR^{11}R^{12}$, or a halogen atom.

3. The bipyridine compound according to claim 1, wherein q is 0, 1, 2 or 3, $R^3$ represents a C1-C6 chain hydrocarbon group optionally substituted with one or more halogen atoms, or a 5 membered aromatic heterocyclic group containing one to four nitrogen atoms, wherein the 5 membered aromatic heterocyclic group is optionally substituted with one or more substituents selected from Group D, a $OR^{12}$, a $NR^{11}R^{12}$, a $NR^{24}NR^{11}R^{12}$, or a halogen atom.

4. The bipyridine compound according to claim 1, wherein q is 0, 1 or 2, $R^3$ represents a C1-C6 alkyl group optionally substituted with one or more halogen atoms, a 1,2,4-triazol-1-yl group optionally substituted with one or more halogen atoms, a $NR^{11}R^{12}$, or a halogen atom, and $R^{11}$ and $R^{12}$ represent independently of each other a hydrogen atom, or a C1-C3 alkyl group optionally substituted with one or more halogen atoms.

5. The bipyridine compound according to claim 1, wherein p is 0 or 1, and $R^6$ represents a C1-C6 alkyl group optionally substituted with one or more halogen atoms, or a halogen atom.

6. The bipyridine compound according to claim 1, wherein $R^1$ represents a C2-C10 haloalkyl group, or a (C1-C5 alkoxy)C2-C5 alkyl group substituted with one or more halogen atoms.

7. The bipyridine compound according to claim 1, wherein $R^1$ represents a C2-C10 fluoroalkyl group, or a (C1-C5 alkoxy)C2-C5 alkyl group substituted with one or more fluorine atoms.

8. The bipyridine compound according to claim 1, wherein $R^1$ represents a C2-C10 alkyl group substituted with two or more fluorine atoms, or a (C1-C5 alkoxy)C2-C5 alkyl group substituted with two or more fluorine atoms.

9. The bipyridine compound according to claim 1, wherein $R^1$ represents a C3-C5 alkyl group substituted with four or more fluorine atoms.

10. The bipyridine compound according to claim 1, wherein $R^2$ represents a C1-C6 alkyl group optionally substituted with one or more halogen atoms.

11. The bipyridine compound according to claim 1, wherein $R^2$ represents an ethyl group.

12. The bipyridine compound according to claim 1, wherein $R^1$ represents a C2-C10 haloalkyl group, or a (C1-C5 alkoxy)C2-C5 alkyl group substituted with one or more halogen atoms;

$R^2$ represents a C1-C6 alkyl group optionally substituted with one or more halogen atoms;

q is 0, 1 or 2, $R^3$ represents a halogen atom, or a C1-C6 alkyl group optionally substituted with one or more halogen atoms, p is 0 or 1, and $R^6$ represents a halogen atom, or a C1-C6 alkyl group optionally substituted with one or more halogen atoms.

13. The bipyridine compound according to claim 1, wherein $R^1$ represents a C3-C5 alkyl group substituted with four or more fluorine atoms, or a 1,1,2-trifluoro-2-(trifluoromethoxy)ethyl group;

$R^2$ represents an ethyl group;

q is 0, 1 or 2, $R^3$ represents a C1-C6 alkyl group optionally substituted with one or more halogen atoms, a 1,2,4-triazol-1-yl group optionally substituted with one or more halogen atoms, a $NR^{11}R^{12}$, or a halogen atom, and $R^{11}$ and $R^{12}$ represent independently of each other a hydrogen atom, or a C1-C3 alkyl group optionally substituted with one or more halogen atoms; and p is 0 or 1, and $R^6$ represents a halogen atom.

14. The bipyridine compound according to claim 1, wherein $R^1$ represents a C3-C5 alkyl group substituted with four or more fluorine atoms;

$R^2$ represents an ethyl group, q is 0 or 1, $R^3$ represents a halogen atom, or a C1-C6 alkyl group optionally substituted with one or more halogen atoms, and p is 0.

15. A composition for controlling a harmful arthropod comprising the bipyridine compound according to claim 1 and an inert carrier.

16. A method for controlling a harmful arthropod which comprises applying an effective amount of the bipyridine compound according to claim 1 to a harmful arthropod or a habitat where a harmful arthropod lives.

* * * * *